United States Patent
Crudden et al.

(10) Patent No.: US 11,008,291 B2
(45) Date of Patent: May 18, 2021

(54) METHODS OF FORMING CARBENE-FUNCTIONALIZED COMPOSITE MATERIALS

(71) Applicant: Queen's University at Kingston, Kingston (CA)

(72) Inventors: Cathleen M. Crudden, Kingston (CA); J. Hugh Horton, Kingston (CA); Mina Raafat Ryad Narouz, Kingston (CA); Joseph Daniel Padmos, Kingston (CA)

(73) Assignee: Queen's University at Kingston, Kingston (CA)

( * ) Notice: Subject to any disclaimer, the term of this patent is extended or adjusted under 35 U.S.C. 154(b) by 23 days.

(21) Appl. No.: 15/773,811

(22) PCT Filed: Nov. 2, 2016

(86) PCT No.: PCT/CA2016/051275
§ 371 (c)(1),
(2) Date: May 4, 2018

(87) PCT Pub. No.: WO2017/075704
PCT Pub. Date: May 11, 2017

(65) Prior Publication Data
US 2019/0169132 A1 Jun. 6, 2019

Related U.S. Application Data

(60) Provisional application No. 62/344,718, filed on Jun. 2, 2016, provisional application No. 62/266,950, filed (Continued)

(51) Int. Cl.
*C07D 235/08* (2006.01)
*C07D 471/04* (2006.01)
*C07D 233/56* (2006.01)
*C07D 403/12* (2006.01)
*C07D 487/04* (2006.01)
(Continued)

(52) U.S. Cl.
CPC ......... *C07D 235/08* (2013.01); *C07D 233/56* (2013.01); *C07D 403/12* (2013.01); *C07D 471/04* (2013.01); *C07D 487/04* (2013.01); *C23C 22/02* (2013.01); *G01N 21/554* (2013.01);
(Continued)

(58) Field of Classification Search
CPC .................................................. C07D 235/08
See application file for complete search history.

(56) References Cited

PUBLICATIONS

Vignolle et al., "N-Heterocyclic carbene-stabilized gold nanoparticles and their assembly into 3D superlattices," 2009, Chem. Comm., pp. 7230-7232. (Year: 2009).*
(Continued)

*Primary Examiner* — Robert A Vetere
(74) *Attorney, Agent, or Firm* — Angela Lyon

(57) ABSTRACT

Deposition of carbene monolayers that excluded starting anions, such as iodide ions, has been achieved. Anions such as iodide are a typical contaminant in carbene hydrogen carbonate salts when synthesized using the state-of-the-art method. A method is described for eliminating substantially all starting anion (e.g., iodide) contamination from the monolayer. Air stable, purified carbenes precursors were used to deposit an intact monolayer on the surface of some industrially relevant metals. The monolayer's ability to protect these metals against, for example, oxidation has been demonstrated.

3 Claims, 47 Drawing Sheets

Related U.S. Application Data on Dec. 14, 2015, provisional application No. 62/252,299, filed on Nov. 6, 2015.

(51) Int. Cl.
    *C23C 22/02* (2006.01)
    *G01N 21/552* (2014.01)
    *G01N 33/543* (2006.01)
    *B82Y 30/00* (2011.01)

(52) U.S. Cl.
    CPC ........ *G01N 33/54353* (2013.01); *B82Y 30/00* (2013.01)

(56) References Cited

PUBLICATIONS

Crudden et al., "Ultra stable self-assembled monolayers of N-heterocyclic carbenes on gold," Mar. 23, 2014, Nature Chem. 6, pp. 409-414. (Year: 2014).*

Fevre et al., "Imidazol(in)ium Hydrogen Carbonates as a Genuine Source of N-Heterocyclic Carbenes (NHCs): Applications to the Facile Preparation of NHC Metal Complexes and to NHC-Organocatalyzed Molecular and Macromolecular Syntheses," 2012, J. Am. Chem. Soc. 134, pp. 6776-6784. (Year: 2012).*

Gautier et al., "Chiral Gold Nanoparticles," 2009, ChemPhysChem 10, pp. 483-492. (Year: 2009).*

International Search Report and Written Opinion of International Application No. PCT/CA2016/051275 filed on Nov. 2, 2016.

Arduengo, A.J., III, et al., "A Stable Crystalline Carbene", American Chemical Society, vol. 91, pp. 361-363, (1991).

Fevre, M. et al., "Imidazol(in)ium Hydrogen Carbonates as a Genuine Source of N-Heterocyclic Carbenes (NHCs): Applications to the Facile Preparation of NHC Metal Complexes and to NHC-Organocatalyzed Molecular and Macromolecular Syntheses", JACS, vol. 134, pp. 6776-6784, (2012).

Huang, R.T.W., et al., "Liquid crystals of gold(I) N-heterocyclic carbene complexes", Dalton Transactions, pp. 7121-7131, (2009).

Hurst, E.C., et al., "N-Heterocyciic carbene coated metal nanoparticles", New Journal of Chemistry, vol. 33, pp. 1837-1840, (2009).

McKenzie, L.C. et al., "Structurally Similar Triphenylphosphine-Stabilized Undecagolds, Au11(PPh3_Cl3 and [Au11(PPh3)8Cl2]Cl, Exhibit Distinct Ligand Exchange Pathways with Glutathione", JACS, vol. 136, pp. 113426-13435, (2014).

Vignolle, J. et al., "N-Heterocyclic carbene-stabilized gold nanoparticles and their assembly into 3D superlattices", Chem. Communication, pp. 7230-7232, (2009).

Wang, Z.J. et al., "A simple and practical preparation of an efficient water soluble olefin metathesis catalyst", Green Chemistry, vol. 17, pp. 3407-3414, (2015).

Weidner, T. et al., "NHC-Based Self-Assembled Monolayers on Solid Gold Substrates", Aust. J. Chem, vol. 64, pp. 1177-1179, (2011).

Zhukhoviskly, A.V., et al.., "Addressable Carbene Anchors for Gold Surfaces", JACS, vol. 135, pp. 7418-7421, (2013).

* cited by examiner

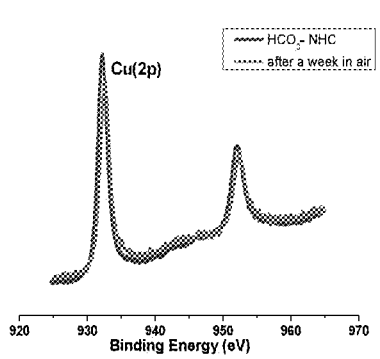
Fig. 10a
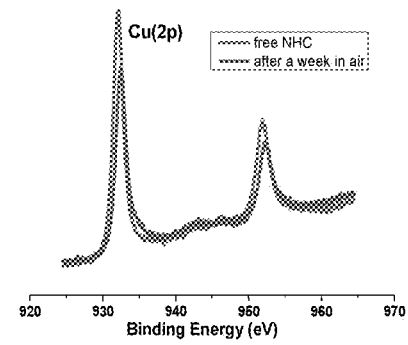
Fig. 10b
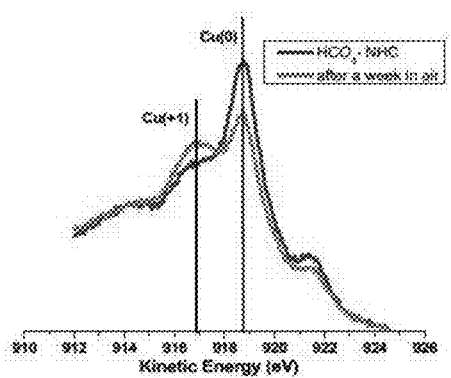
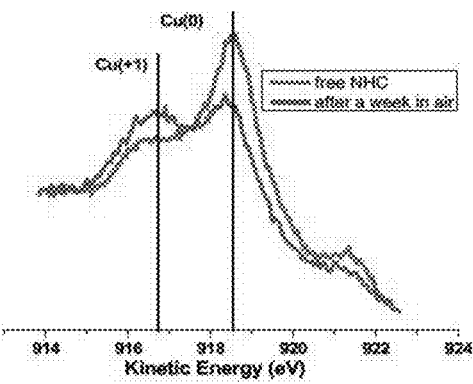
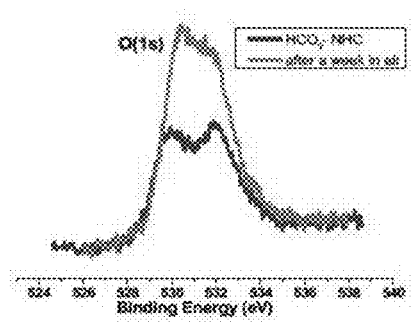
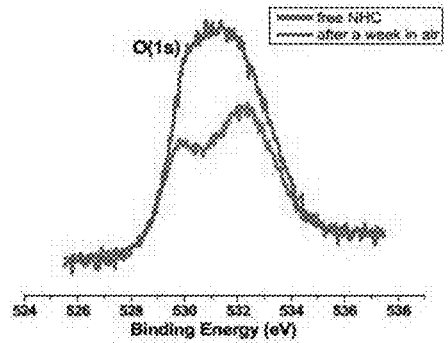
Fig. 10c

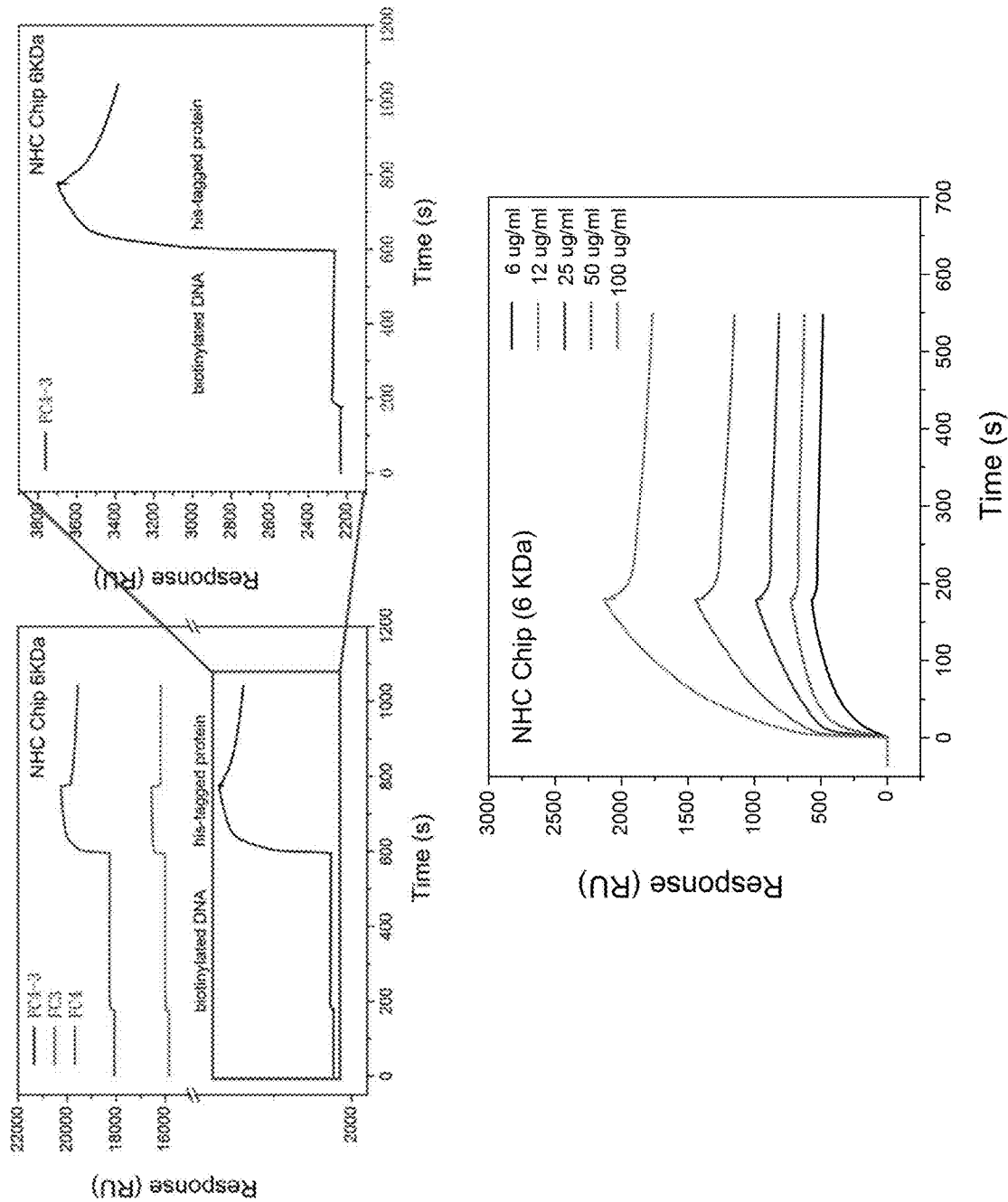
Fig. 16A-C

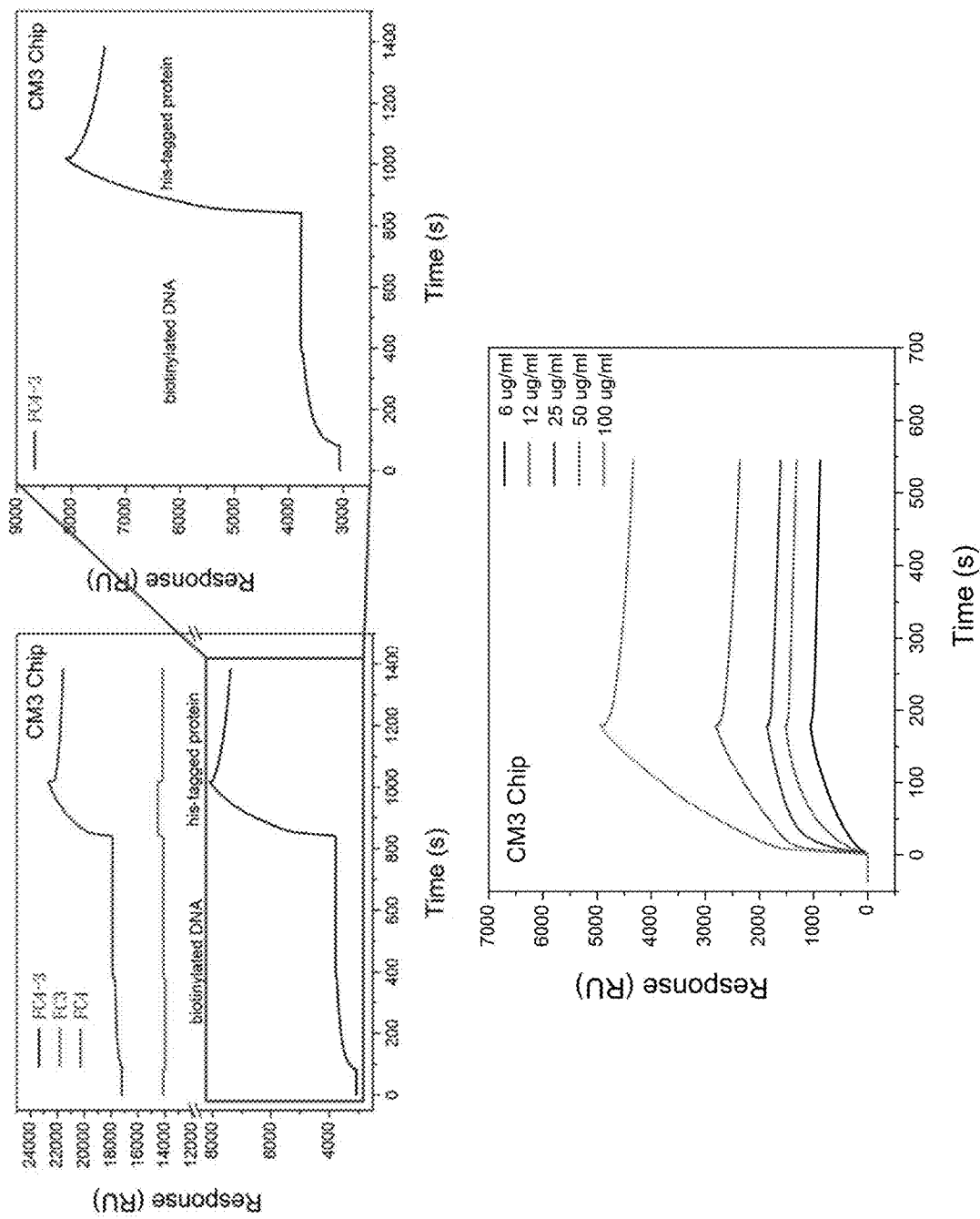
Fig. 17 A-C

METHODS OF FORMING CARBENE-FUNCTIONALIZED COMPOSITE MATERIALS

FIELD OF THE INVENTION

The present application pertains to the field of materials science. More particularly, the present application relates to methods of forming carbene-functionalized composite materials.

INTRODUCTION

Use of self-assembled monolayers (SAMs) on gold (R. G. Nuzzo et al., J. Am. Chem. Soc. 105, 4481-4483 (1983), C. D. Bain et al., J. Am. Chem. Soc. 111, 321-335 (1989), and J. C. Love, et al., Chem. Rev. 105, 1103-1169 (2005)) as an interface between metal surfaces and organics has had significant impact on molecular electronics, surface patterning techniques and biosensing. Thiol-based thin-film-on-metal biosensors employing surface plasmon resonance effects (SPR) are routinely used for detection of nanogram quantities of biomolecules without a need for fluorescent labeling, although challenges with film stability lead to low shelf life, poor bilayer film quality and increased non-specific adsorption.

Self-assembled monolayers (SAMs) on metals such as gold have potential application in sensing, electrochemistry, drug delivery, surface protection, microelectronics and microelectromechanical systems, among others (R. G. Nuzzo, et al., J. Am. Chem. Soc. 105, 4481 (1983); B. D. Gates, et al., Chem. Rev. 105, 1171 (2005); J. C. Love, et al., Chem. Rev. 105,1103 (2005); U. Drechsler, et al., Chem.—Eur. J. 10, 5570 (2004)). Since sulfur-based SAMs on gold were discovered (C. D. Bain et al., J. Am. Chem. Soc. 111, 321 (1989)), suitable alternatives for these ligands have not been found. This lack of alternatives, despite thiol-based SAMs' oxidative and thermal instability on gold, is an impediment to their widespread use (C. Vericat, et al., Chem. Soc. Rev. 39, 1805 (2010)). Thiol-based SAMs are stable when stored in ultra-high vacuum in an absence of light (J. Noh, et al., J. Phys. Chem. B 110, 2793 (2006)), however degradation has been observed after as little as one to two weeks at room temperature in air (C. Vericat, et al., J. Phys. Condens. Matter 20, 184004 (2008); Y. Li, et al., J. Am. Chem. Soc. 114, 2428 (1992); M. H. Schoenfisch, et al., J. Am. Chem. Soc. 120, 4501 (1998); J. B. Schlenoff, et al., J. Am. Chem. Soc. 117, 12528 (1995)). Improvements in stability can be accomplished by changing the gold surface's nature (C. Vericat, et al., J. Phys. Condens. Matter 20, 184004 (2008)), through use of additives (G. Yang, et al., Langmuir 20, 3995 (2004)), or through use of multi-dentate thio-adsorbates (P. Chinwangso, A. C. Jamison, T. R. Lee, Accounts of Chemical Research, 44, 511 (2011)). Phosphine-based ligands have also been examined, but offer weaker bonds to surfaces (A. D. Jewell, et al., Phys. Rev. B 82, 205401 (2010)).

Carbon-based ligands known as N-heterocyclic carbenes (NHCs) have played an important role in the field of transition metal complexes (W. A. Herrmann, Angew. Chem. Int. Ed. 41, 1290 (2002); E. Peris, et al., Coord. Chem. Rev. 248, 2239 (2004)). These ligands are part of catalysts such as the Grubbs second generation metathesis catalyst (R. M. Thomas, et al., Organometallics 30, 6713 (2011)), and NHC-based cross-coupling catalysts (E. A. B Kantchev, et al., Angew. Chem. Int. Ed. 46, 2768 (2007)). Unlike most carbenes, which are reactive with limited stability, NHCs typically have one or two heteroatoms adjacent to a carbene carbon (A. Igau, et al., J. Am. Chem. Soc. 110, 6463 (1988); A. J. Arduengo, et al., J. Am. Chem. Soc. 113, 361 (1991)). These heteroatoms increase NHCs' stability such that they can usually be prepared on a gram scale (M. Niehues, et al., Organometallics 21, 2905 (2002)), crystallized (A. J. Arduengo, R. L. Harlow, M. Kline, J. Am. Chem. Soc. 113, 361 (1991)), distilled (M. Niehues, et al., Organometallics 21, 2905 (2002)), and stored for longer periods of time (4 years, when stored under $N_2$ in a freezer). An Au—NHC bond was estimated to be on an order of 90 kJ/mol stronger than a corresponding Au-phosphine bond, and twice as strong as metal sulfide bonds in molecular complexes (P. Pyykkö, et al., Chem. Asian J. 1, 623 (2006)). As such, NHCs have potential to be valuable ligands for protecting and functionalizing gold and other metal surfaces. Application of these carbenes in materials science, and other fields outside of homogeneous catalysis, has been limited (L. Mercs, et al., Chem. Soc. Rev. 39, 1903 (2010)).

The above information was provided for the purpose of making known information believed by the applicant to be of possible relevance to the present invention. No admission is necessarily intended, nor should be construed, that any of the preceding information constitutes prior art against the present invention.

SUMMARY OF THE INVENTION

In an aspect of the application, a carbene-functionalized composite material is provided, which comprises a material having at least a metal surface, and a carbene monolayer substantially free of contamination sourced from an air stable carbene salt, wherein said carbene monolayer interacts with the metal surface and is uniform, stable and/or substantially free of contamination. In some embodiments, the contamination includes iodide.

In another aspect, there is provided a carbene-functionalized composite material, comprising a material having at least a metal surface; and a carbene monolayer sourced from an air stable carbene salt that is substantially free of iodide; wherein said carbene monolayer interacts with the metal surface and is uniform, stable and/or substantially free of contamination.

In another aspect, the application provides a method for forming a carbene-functionalized composite material, comprising placing a material having at least a metal surface in fluid communication with a carbene hydrogen carbonate salt (i.e., a hydrogen carbonate carbene precursor), thermally decomposing a carbene hydrogen carbonate salt in the presence of a material having at least a metal surface, or vacuum depositing a carbene hydrogen carbonate salt in the presence of a material having at least a metal surface, wherein the salt is substantially free of contamination (e.g., starting anion iodide), a carbene monolayer is formed on the metal surface, and the monolayer is uniform, stable and/or substantially free of contamination.

In another aspect, the application provides a method of protecting a metal surface from corrosion or oxidation, comprising applying to a metal surface a carbene monolayer that is substantially free of contamination (e.g., starting anion iodide) that is sourced from an air stable carbene salt. In some embodiments, the carbene salt is a carbene hydrogen carbonate salt. In some embodiments, the carbene salt is a carbene hydrogen carbonate salt and is substantially free of contamination (e.g., starting anion iodide).

In another aspect, the application includes use of the composite material of the above aspect or its embodiments, or of a composite material prepared by the forming method of the above aspect.

In embodiments of the above aspects, the material having a metal surface is a metal film on a support, metal nanoparticles, metal nanoworms, or solid metal (e.g., metal sheet, metal film, single crystal metal). In other embodiments wherein the metal surface is a metal film on a support, the support is mica, alumina, silica, titania, silicon, glass, indium tin oxide, or any combination thereof. In other embodiments, the metal surface comprises Fe, Rh, Ir, Ni, Pd, Pt, Cr, Cu, Ag, Au, W, an alloy such as steel (e.g., stainless steel), brass, bronze, tungsten carbide, calcium carbide, or any combination thereof.

In other embodiments of the above aspects, the carbene salt (i.e., purified carbene precursor) is a compound of formula I, Ia, III or IIIa:

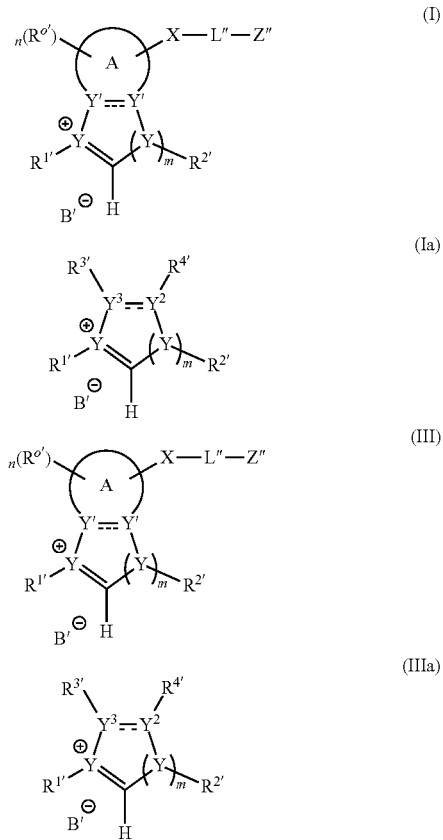

wherein n is an integer from 1 to 8, or alternatively from 1 to 4;

m is an integer from 0 to 4;

ring A is a cyclic aliphatic moiety, a heterocycle, an aromatic ring, a fused aromatic ring system, a heteroaromatic ring, a fused heteroaromatic ring system, each of which is optionally substituted;

B' is a counter ion that may act as a base with a $pKa_H$ of about 4 to about 6 (e.g., $[HCO_3]^-$ or $[RCO_2]^-$).

L" is a divalent moiety, such as $C_1$-$C_{20}$ alkylene, $C_{10}$-$C_{20}$ alkylene, branched $C_1$-$C_{10}$ alkylene, branched $C_{10}$-$C_{20}$ alkylene, $C_1$-$C_{10}$ alkenylene, $C_{10}$-$C_{20}$ alkenylene, $C_1$-$C_{20}$ alkynylene, $C_{10}$-$C_{20}$ alkynylene, dextran, a simple sugar, complex sugar, carbohydrate, ether, thioether, polyether, or polythioether, each of which is optionally substituted; polyether, and/or polythioether, each of which is optionally substituted;

Z" is H or L, as defined above;

X is C or a heteroatom;

Y is C or a heteroatom, optionally wherein at least one of the Y's located adjacent to the C(H) is not carbon;

$Y^2$ and $Y^3$ are independently C or a heteroatom, and the dashed line is an optional double bond;

Z" is H, or a chemically derivatizable group, such as azide, amino acid, nucleic acid, alkene, conjugated diene, thiol, alkyl thiol, or thioester, each of which is optionally substituted;

$R_{o'}$ is independently H, halogen, the substituent X-L"-Z" as defined above, $C_1$-$C_{20}$ aliphatic moiety (e.g., $C_1$-$C_{10}$ alkyl, $C_{10}$-$C_{20}$ alkyl, branched $C_1$-$C_{10}$ alkyl, branched $C_{10}$-$C_{20}$ alkyl, $C_1$-$C_{10}$ alkenyl, $C_{10}$-$C_{20}$ alkenyl, $C_1$-$C_{10}$ alkynyl, or $C_{10}$-$C_{20}$ alkynyl), $C_1$-$C_{10}$ alkoxyl, $C_{10}$-$C_{20}$ alkoxyl, $C_3$-$C_{20}$ cyclic aliphatic, aryl, heteroaryl, polyether, or polythiol, each of which is optionally substituted; or, two of $R^o$, together with the atoms to which they are attached, are connected to form a cycle, or heterocycle, each of which is optionally substituted; or, $R^o$ is independently the substituent XL"Z"; and $R^{1'}$ and $R^{2'}$ are independently H, $C_1$-$C_{20}$ aliphatic moiety (e.g., $C_1$-$C_{10}$ alkyl, $C_{10}$-$C_{20}$ alkyl, branched $C_1$-$C_{10}$ alkyl, branched $C_{10}$-$C_{20}$ alkyl, $C_1$-$C_{10}$ alkenyl, $C_{10}$-$C_{20}$ alkenyl, $C_1$-$C_{10}$ alkynyl, or $C_{10}$-$C_{20}$ alkynyl), $C_3$-$C_{20}$ cyclic aliphatic, aryl, heteroaryl, polyether, or polythiol, each of which is optionally substituted; or, one of $R^1$ or $R^2$, with one of $R^o$, together with the atoms to which they are attached, are connected to form a cycle, or heterocycle, each of which is optionally substituted;

$R^{3'}$ and $R^{4'}$ are independently H, halogen, $C_1$-$C_{10}$ alkyl, $C_{10}$-$C_{20}$ alkyl, branched $C_1$-$C_{10}$ alkyl, branched $C_{10}$-$C_{20}$ alkyl, $C_1$-$C_{10}$ alkenyl, $C_{10}$-$C_{20}$ alkenyl, $C_{10}$ alkynyl, $C_{10}$-$C_{20}$ alkynyl, $C_1$-$C_{10}$ alkoxyl, ester-$C_1$-$C_{20}$, $C_{10}$-$C_{20}$ alkoxyl, alkoxyl, ester-$C_1$-$C_{10}$, $C_3$-$C_{20}$ cyclic aliphatic, aryl, heteroaryl, ether, thioether, polyether, polythioether or polythiol, each of which is optionally substituted; or, any one of $R^3$ or $R^4$, with any one of $R^1$ or $R^2$, together with the atoms to which they are attached, are connected to form a cycle, or heterocycle, each of which is optionally substituted.

In embodiments of this aspect, $R^{1'}$ to $R^{2'}$ are independently methyl, ethyl, propyl, butyl, isopropyl, phenyl, mesityl, or 1,3-diisopropylphenyl, each of which may be optionally substituted.

In other embodiments, the compound of formula I, Ia, III or IIIc is as defined above, or is any subset thereof.

In embodiments of the above aspects, there is provided a hydrogen carbonate salt prepared from an iodide salt that had its iodide anions removed by oxidative removal of iodide in the presence of base and $CO_2$ and water, and/or by exposure to ion exchange resin. In other embodiments, there is provided a hydrogen carbonate salt prepared from an iodide salt that had its iodide anions removed by oxidative removal of iodide in the presence of hydrogen peroxide and $CO_2$ and water, and/or by exposure to ion exchange resin.

In embodiments of the above aspects, the metal surface is functionalized with a chemical species that can be displaced by a carbene and/or is functionalized with a thiol group (e.g., alkylthiol compounds, dodecanethiol), or a sulfide group (e.g., dialkylsulfide compounds, dodecyl sulfide).

In embodiments of the above aspects, the carbene salt comprises a hydrogen carbonate counterion and is substantially free of contamination (e.g., starting anions iodide, bromide, triflate). Methods of removing iodide from such NHC salts are presented in Example 1. Alternative methods of producing such hydrogen carbonate salts by starting with triflate salts instead of iodide salts are presented in Example 16. In embodiments of the above aspects, the metal surface comprises Mg, Al, Ti, Fe, Rh, Ir, Ni, Pd, Pt, Cr, Cu, Ag, Au, W, Ta, Nb, Re, Mo, Ru, Co, or any combination or alloy thereof; and/or an alloy such as steel (e.g., stainless steel), brass, bronze, tungsten carbide, calcium carbide, or any combination thereof. In embodiments of any of the above aspects, the metal surface is a metal film on a support and the support is mica, alumina, silica, titania, silicon, glass, indium tin oxide, gallium arsenide, lead sulfide, cadmium selenide, or any combination thereof.

In embodiments of the above aspects, the carbene salt is 1,3-Diisopropylbenzimidazolium hydrogen carbonate (3a), 1,3-Dimethylbenzimidazolium hydrogen carbonate (3b), 5-((12-(4-(Ferrocenyl)-1H-1,2,3-triazol-1-yl)dodecyl)oxy)-1,3-diisopropyl-1H-benzo[d]imidazol-3-ium hydrogen carbonate (3c), or 5-(Dodecyloxy)-1,3-diisopropyl-1H-benzo[d]imidazol-3-ium hydrogen carbonate (3d).

In embodiments of any of the above aspects, the carbene-functionalized composite material is for making nano-patterns on semi-conducting surfaces, fabricating electronic or microelectronic devices, adherence to a substrate (e.g., an optionally coated second metal surface), protecting a metal surface from corrosion or oxidation, drug delivery, electrochemically detecting molecules, surface plasmon resonance for detecting molecules, making electrochemical sensors, sensing applications, detecting molecules (e.g., biomolecules), or colourimetric analysis of molecules (e.g., biomolecules).

In other embodiments, the sensing application includes use of a carboxymethyldextran-coated NHC-based biosensing SPR chip. In other embodiments, the carbene-functionalized composite material is for lithography; or microcontact printing, wherein a solution of a herein described NHC is adsorbed onto a surface of a patterned PDMS stamp, and the NHC is mechanically transferred to the metal surface.

In certain embodiments of this aspect, the composite material is used for detecting biomolecules, such as DNA, proteins, lipids or carbohydrates (e.g., glucose). In other embodiments of this aspect, the composite material is used for colourimetric analysis or quantitation of biomolecules such as DNA, RNA, proteins, lipids or carbohydrates (e.g., glucose).

In yet another aspect, the application provides carbene structures and their corresponding carbene metal complexes. In some embodiments, such carbene metal complexes are nanoparticles, nanoworms, nanoparticles comprising carbene and gold, nanoworms comprising carbene and gold.

In another aspect, there is provided compounds of the following structure and metal complexes thereof:

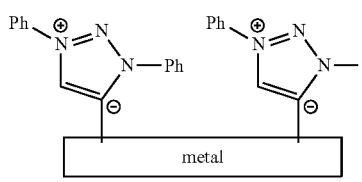

-continued

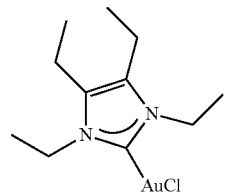

1

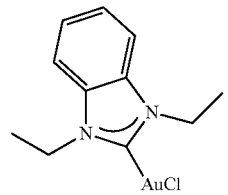

2

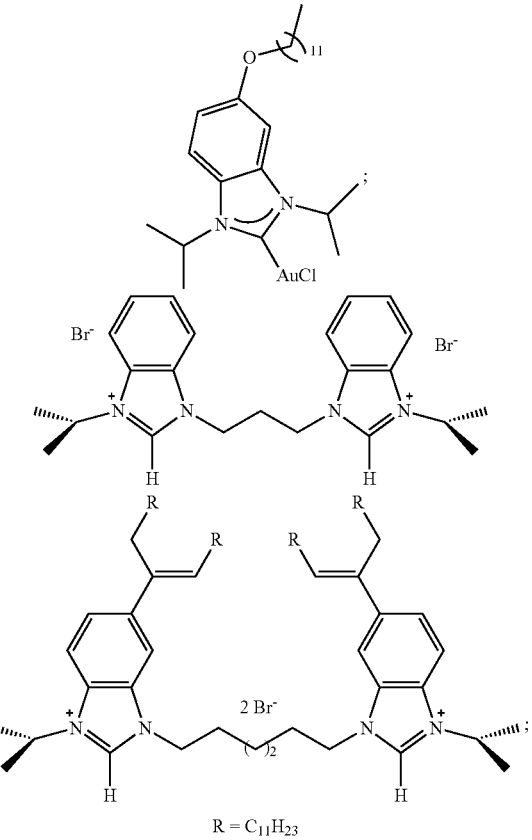

3

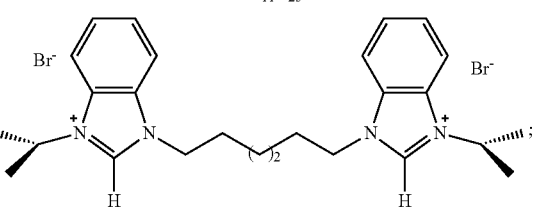

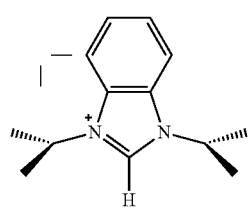

1a

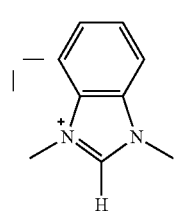
1b
1c
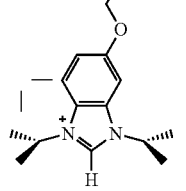
1d
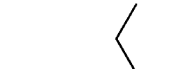
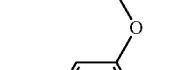
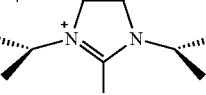
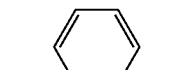
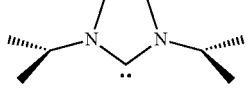
2a
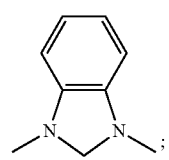
2b
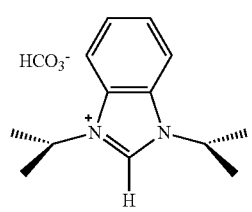
3a
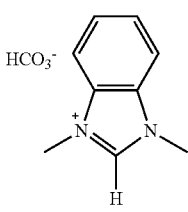
3b
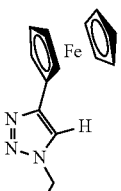
3c
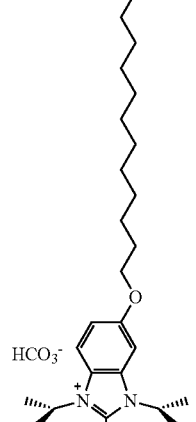

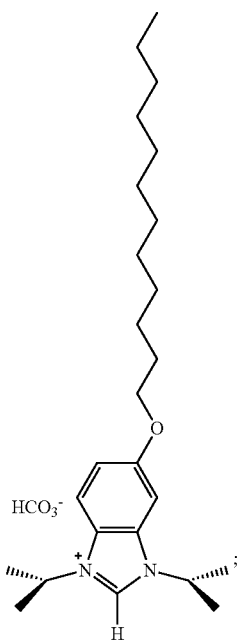

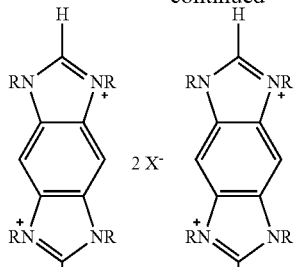

R = $^n$Pr, $^i$Pr, $^i$Bu, Bu, $C_6H_{13}$, $C_{12}H_{23}$, Bn
X = I, Br

R = $^n$Pr, $^i$Pr, $^i$Bu, Bu, $C_6H_{13}$, $C_{12}H_{23}$, Bn

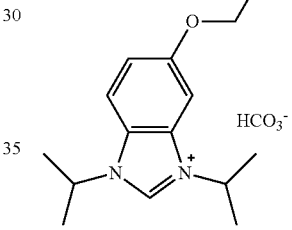

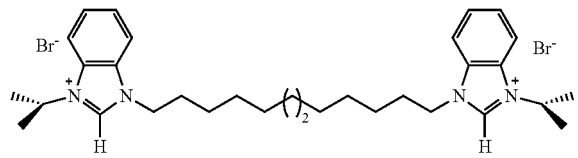

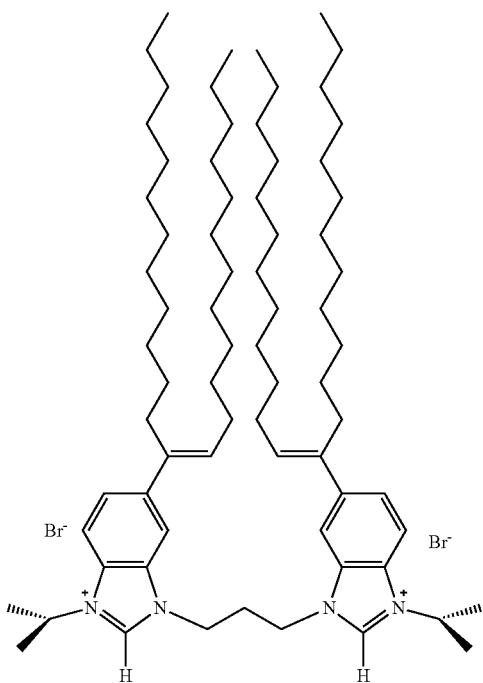

In an aspect of the present application, there is provided a method, comprising oxidizing a starting anion of a carbene precursor in the presence of water and $CO_2$; or exchanging a starting anion of a carbene precursor via a hydrogen carbonate-anion exchange resin; and forming a purified carbene precursor comprising hydrogen carbonate as a final anion, the purified carbene precursor being substantially free of the starting anion.

In another aspect of the present application, there is provided a method for forming a carbene-functionalized composite material, comprising forming a carbene precursor by (i) oxidizing an anion of a carbene precursor in the presence of water and $CO_2$, or (ii) exchanging an anion of a carbene salt via a hydrogen carbonate-anion exchange resin, and forming a purified carbene precursor comprising a hydrogen carbonate anion that is substantially free of the anion; placing a material having at least a metal surface in fluid communication with the purified carbene precursor, thermally decomposing the purified precursor in the presence of a material having at least a metal surface, or vacuum depositing the purified carbene precursor in the presence of a material having at least a metal surface; and forming a carbene monolayer on the metal surface, the monolayer being uniform, stable, substantially free of contamination, and substantially free of the anion.

In another aspect, there is provided a method for forming a carbene-functionalized composite material, comprising forming a carbene precursor by (i) oxidizing a starting anion of a carbene precursor in the presence of water and $CO_2$, or (ii) exchanging a starting anion of a carbene salt via a hydrogen carbonate-anion exchange resin, and forming a purified carbene precursor comprising a final hydrogen carbonate anion that is substantially free of the starting anion; placing a material having at least a metal surface in fluid communication with the purified carbene precursor, thermally decomposing the purified precursor in the presence of a material having at least a metal surface, or vacuum depositing the purified carbene precursor in the presence of a material having at least a metal surface; and forming a carbene monolayer on the metal surface, the monolayer being uniform, stable, substantially free of contamination, and substantially free of the starting anion.

In embodiments of the above aspects, there is provided a method wherein the purified carbene precursor comprises ≤10% of the starting anion; or, ≤5%; or, ≤2%; or, ≤1%; or, ≤0.5%; or, ≤0.1%. In other embodiments, there is provided a method wherein the monolayer comprises ≤55% contamination; or, ≤52%.

In other embodiments, there is provided a method wherein forming a carbene precursor by oxidizing comprises exposing the starting anion to hydrogen peroxide. In other embodiments, oxidizing may also comprise oxidizing means known in the art.

In other embodiments, there is provided a method wherein the starting anion comprises chloride, bromide, iodide, tetrafluoroborate, triflate, or hexafluorophosphate. In other embodiments, the starting anion is an anion of the formula $MX_n^-$.

In other embodiments of the above aspects, there is provided a method wherein the purified carbene precursor is a compound of (i) Formula II:

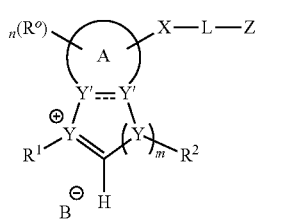

(II)

wherein:
n is an integer from 1 to 8, or from 1 to 4;
m is an integer from 0 to 4;
each Y or Y' is independently C or a heteroatom;
B is hydrogen carbonate;
A is absent, an aliphatic cycle, a heterocycle, an aromatic ring, a fused aromatic ring system, a heteroaromatic ring, and/or a fused heteroaromatic ring system, each of which is optionally substituted;
X-L-Z is absent, or
X is C or a heteroatom,
L is a divalent moiety, such as $C_1$-$C_{10}$ alkylene, $C_{10}$-$C_{20}$ alkylene, $C_1$-$C_{10}$ alkenylene, $C_{10}$-$C_{20}$ alkenylene, $C_1$-$C_{10}$ alkynylene, $C_{10}$-$C_{20}$ alkynylene, or dextran, a simple sugar, complex sugar, carbohydrate, ether, thioether, amine, polyamine, polyether, and/or polythioether, each of which is optionally substituted;
Z is H, an aliphatic cycle, a heterocycle, an aromatic ring, a fused aromatic ring system, a heteroaromatic ring, a fused heteroaromatic ring system, an N-heterocyclic carbene precursor, an organometallic complex, a transition-metal catalyst, a metal-oxide catalyst, a simple sugar, a complex sugar, a carbohydrate, or a chemically derivatizable group, such as hydroxyl (—OH), azide, carboxylic acid, carbonyl chloride, anhydride, ester, aldehyde, alcohol, amine, halogen, epoxide, thiirane, aziridine, amino acid, nucleic acid, alkene, alkyne, conjugated diene, thiol, or thioester, each of which is optionally substituted;
each $R^o$ is independently H, halogen, the substituent X-L-Z as defined above, $C_1$-$C_{10}$ alkyl, $C_{10}$-$C_2O$ alkyl, $C_1$-$C_{10}$ alkenyl, $C_{10}$-$C_{20}$ alkenyl, $C_1$-$C_{10}$ alkynyl, $C_{10}$-$C_{20}$ alkynyl, $C_1$-$C_{10}$ alkoxyl, $C_{10}$-$C_{20}$ alkoxyl, $C_3$-$C_{20}$ cyclic aliphatic moiety, aryl, heteroaryl, ether, thioether, amine, polyamine, polyether, or polythioether, each of which is optionally substituted; or, two of $R^o$, together with the atoms to which they are attached, are connected to form a cycle, heterocycle, or an N-heterocyclic carbene precursor, each of which is optionally substituted; and
$R^1$ and $R^2$ are independently absent, at least one lone pair of electrons, H, the substituent X-L-Z as defined above, $C_1$-$C_{10}$ alkyl, $C_{10}$-$C_{20}$ alkyl, $C_1$-$C_{10}$ alkenyl, $C_{10}$-$C_{20}$ alkenyl, $C_1$-$C_{10}$ alkynyl, $C_{10}$-$C_{20}$ alkynyl, $C_3$-$C_{20}$ cyclic aliphatic moiety, aryl, benzyl, polycyclic aryl, polycyclic benzyl, heteroaryl, ether, thiol, thioether, amine, polyamine, polyether, polythioether, or polythiol, each of which is optionally substituted; or, one of $R^1$ or $R^2$, with one of $R^o$, together with the atoms to which they are attached, are connected to form a cycle, or heterocycle, each of which is optionally substituted;
wherein, when A is absent or non-aromatic, the dashed line represents an optional double bond; and
when A is absent, each Y' is independently bonded to $R^o$ or X-L-Z, as defined above;

(ii) Formula IIa

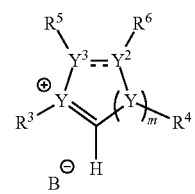

(IIa)

wherein:
m and B are as defined above;
each Y is independently C or a heteroatom;
$Y^2$ and $Y^3$ are independently C or a heteroatom, and the dashed line is an optional double bond;
$R^3$ and $R^4$ are independently absent, at least one lone pair of electrons, H, the substituent X-L-Z as defined for Formula II, $C_1$-$C_{10}$ alkyl, $C_{10}$-$C_{20}$ alkyl, $C_1$-$C_{10}$ alkenyl, $C_{10}$-$C_2O$ alkenyl, $C_1$-$C_{10}$ alkynyl, $C_{10}$-$C_{20}$ alkynyl), cycloalkyl, aryl, benzyl, polycyclic aryl, polycyclic benzyl, heteroaryl, ether, thiol, thioether, amine, polyamine, polyether, polythioether, or polythiol, each of which is optionally substituted; and
$R^5$ and $R^6$ are independently H, halogen, the substituent X-L-Z as defined for Formula II, $C_1$-$C_{10}$ alkyl, $C_{10}$-$C_{20}$ alkyl, $C_1$-$C_{10}$ alkenyl, $C_{10}$-$C_{20}$ alkenyl, $C_1$-$C_{10}$ alkynyl, $C_{10}$-$C_{20}$ alkynyl, $C_1$-$C_{10}$ alkoxyl, $C_{10}$-$C_{20}$ alkoxyl, $C_3$-$C_{20}$ cyclic aliphatic, aryl, heteroaryl, ether, thiol, thioether, amine, polyamine, polyether, polythioether, or polythiol, each of which is optionally substituted; or, any one of $R^5$ or $R^6$, with any one of $R^3$ or $R^4$, together with the atoms to which they are attached, are connected to form a cycle, or heterocycle, each of which is optionally substituted; or, any one of $R^5$ or $R^6$, together with the atoms to which they are attached, are connected to form a cycle, heterocycle, or an N-heterocyclic carbene precursor, each of which is optionally substituted;

(iii) Formula V

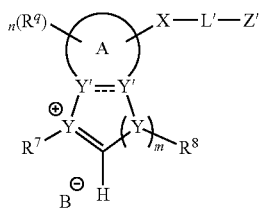

(V)

wherein:

n, m, Y or Y', B, and A are as defined for Formula (II);

X-L'-Z' is absent, or

X is C or a heteroatom,

L' is a divalent moiety, such as $C_{10}$-$C_{20}$ alkylene, $C_{10}$-$C_{20}$ alkenylene, $C_{10}$-$C_{20}$ alkynylene, dextran, a simple sugar, complex sugar, carbohydrate, ether, thioether, polyether, and/or polythioether, each of which is optionally substituted;

Z' is H, or L', as defined above;

each $R^q$ is independently H, halogen, the substituent X-L'-Z' as defined above, $C_{10}$-$C_{20}$ alkyl, $C_{10}$-$C_{20}$ alkenyl, $C_{10}$-$C_{20}$ alkynyl, $C_{10}$-$C_{20}$ alkoxyl, $C_6$-$C_{20}$ cyclic aliphatic moiety, aryl, ether, thioether, polyether, or polythioether, each of which is optionally substituted; or, two of $R^q$, together with the atoms to which they are attached, are connected to form a cycle, which is optionally substituted; and $R^7$ and $R^8$ are independently absent, at least one lone pair of electrons, H, the substituent X-L'-Z' as defined above, $C_1$-$C_{10}$ alkyl, $C_{10}$-$C_{20}$ alkyl, $C_1$-$C_{10}$ alkenyl, $C_{10}$-$C_{20}$ alkenyl, $C_1$-$C_{10}$ alkynyl, $C_{10}$-$C_{20}$ alkynyl, $C_6$-$C_{20}$ cyclic aliphatic moiety, aryl, benzyl, polycyclic aryl, polycyclic benzyl, ether, thiol, thioether, polyether, polythioether, or polythiol, each of which is optionally substituted; or, one of $R^7$ or $R^8$, with one of $R^q$, together with the atoms to which they are attached, are connected to form a cycle, which is optionally substituted;

wherein, when A is absent or non-aromatic, the dashed line represents an optional double bond; and when A is absent, each Y' is independently bonded to $R^q$ or X-L'-Z', as defined above; or (iv) Formula Va

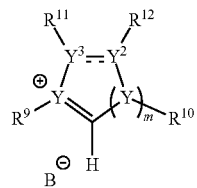

(Va)

wherein:

m, Y, $Y^2$ and $Y^3$, and B are as defined for Formula (IIa);

the dashed line is an optional double bond;

$R^9$ and $R^{10}$ are independently absent, at least one lone pair of electrons, H, the substituent X-L'-Z' as defined above, $C_1$-$C_{10}$ alkyl, $C_{10}$-$C_{20}$ alkyl, $C_1$-$C_{10}$ alkenyl, $C_{10}$-$C_{20}$ alkenyl, $C_1$-$C_{10}$ alkynyl, $C_{10}$-$C_{20}$ alkynyl, $C_6$-$C_{20}$ cyclic aliphatic moiety, aryl, benzyl, polycyclic aryl, polycyclic benzyl, ether, thiol, thioether, polyether, polythioether, or polythiol, each of which may be optionally substituted;

$R^{11}$ and $R^{12}$ are independently H, the substituent X-L'-Z' as defined for Formula V, $C_{10}$-$C_{20}$ alkyl, $C_{10}$-$C_{20}$ alkenyl, $C_{10}$-$C_{20}$ alkynyl, $C_6$-$C_{20}$ cyclic aliphatic moiety, $C_{10}$-$C_{20}$ alkoxyl, aryl, ether, thioether, polyether, or polythioether, each of which is optionally substituted; or, any one of $R^{11}$ or $R^{12}$, with any one of $R^9$ or $R^{10}$, together with the atoms to which they are attached, are connected to form a cycle, which is optionally substituted.

In other embodiments, there is provided a method wherein when the purified carbene precursor is a compound of Formula (II) or Formula (V): n is 3 or 4; m is 1; each Y is N; each Y' is C; A is an aromatic ring; X-L-Z or X-L'-Z' is absent when n is 4; X-L-Z or X-L'-Z' is present when n is 3; $R^o$ or $R^q$ is H; and, $R^1$ and $R^2$ or $R^7$ and $R^8$ are independently methyl, ethyl, propyl, isopropyl, butyl, isobutyl, hexyl, phenyl, benzyl, mesityl, or 1,3-diisopropylphenyl. In other embodiments, when the purified carbene precursor is a compound of Formula (IIa) or Formula (Va): m is 1; each Y is N; $Y^2$ and $Y^3$ are C; $R^5$ and $R^6$ or $R^{11}$ and $R^{12}$ are independently H or, X-L-Z or X-L'-Z'; and, $R^3$ and $R^4$ or $R^9$ and $R^{10}$ are independently methyl, ethyl, propyl, isopropyl, butyl, isobutyl, hexyl, phenyl, benzyl, mesityl, or 1,3-diisopropylphenyl. In other embodiments, the compound of formula II, IIa, V or Va is as defined above, or is any subset thereof.

In other embodiments of the above aspects, there is provided a method wherein the material having at least a metal surface comprises a (i) metal film on a support; (ii) metal nanoparticles; (iii) metal nanoclusters; (iv) metal nanoworms; (v) a metal chip; (vi) metal coating; or (vii) solid metal. In other embodiments, when the material comprises a solid metal, the solid metal is a metal sheet; a metal wire; or a single crystal metal. In other embodiments, when the material comprises a metal film on a support, the support comprises mica, alumina, silica, titania, silicon, glass, indium tin oxide, gallium arsenide, PbS, CdSe, or any combination thereof. In other embodiments, when the material comprises a metal chip, the metal chip is a surface plasmon resonance (SPR) detector chip.

In other embodiments of the above aspects, there is provided a method wherein the metal surface comprises Mg, Al, Ti, Ga, Fe, Rh, Ir, Ni, Pd, Pt, Ru, Co, Cr, Cu, Ag, Au, W, Ta, Nb, Re, Mo, or any combination or alloy thereof. In other embodiments, the metal surface comprises a steel alloy, brass alloy, bronze alloy, tungsten carbide alloy, or any combination thereof.

In other embodiments of the above aspects, there is provided a method wherein the metal surface is functionalized with a chemical species that can be displaced by a carbene. In some embodiments the chemical species comprises a phosphine group (e.g., triphenylphosphine), a sulfide group (e.g., dialkylsulfide compounds, didodecyl sulfide), a thiol group (e.g., alkylthiol compounds, dodecanethiol), a selenolate group, or an alkynyl group.

In other embodiments of the above aspects, wherein when oxidizing comprises exposing the starting anion to hydrogen peroxide, the starting anion is iodide and the purified carbene precursor is relatively water soluble; or, relatively hydrophilic.

In another aspect of the present application, there is provided a method for forming a carbene-functionalized composite material, comprising forming a carbene precursor by (i) oxidizing a starting anion of a carbene precursor in the presence of water and $CO_2$, or (ii) exchanging a starting anion of a carbene precursor via a hydrogen carbonate-anion exchange resin, and forming a purified carbene precursor comprising a final hydrogen carbonate anion that is substantially free of the starting anion; reducing a metal salt in the presence of the purified carbene precursor; and forming a carbene-functionalized composite material, the composite material comprising carbene-functionalized nanoparticles or nanoclusters. In an embodiment, the purified carbene precursor comprises ≤10% of the starting anion; or, ≤5%; or, ≤2%; or, ≤1%; or, ≤0.5%; or, ≤0.1%.

In other embodiments of the above aspect, there is provided a method wherein reducing a metal salt comprises (i) reducing the metal salt in the presence of a reducing agent; (ii) reducing the metal salt at an elevated temperature; (iii) electrochemically reducing the metal salt; or (iv) photochemically reducing the metal salt. In other embodiments, reducing a metal salt may also comprise reducing means known in the art.

In other embodiments, reducing the metal salt in the presence of a reducing agent further comprises reducing the metal salt in the presence of at least two solvents. In other embodiments, the at least two solvents comprise tetrahydrofuran and water.

In other embodiments, wherein when reducing a metal salt comprises reducing the metal salt in the presence of a reducing agent, the reducing agent is $NaBH_4$. In other embodiments, wherein reducing the metal salt at an elevated temperature further comprises reducing the metal salt in the presence of at least one solvent. In other embodiments, the at least one solvent comprises toluene, 1,2-dichlorobenzene, xylenes, or bromobenzene. In other embodiments reducing the metal salt at an elevated temperature comprises a temperature of ≥0.80° C.; or, ≥100° C.; or, ≥120° C.; or, ≥140° C.; or, ≥160° C.; or, ≥180° C.; or, ≥200° C.; or, ≥210° C.; or, ≥220° C.; or, ≥240° C.; or, ≥260° C.

In other embodiments of the above aspect, there is provided a method wherein the starting anion is chloride, bromide, iodide, tetrafluoroborate, triflate, or hexafluorophosphate. In other embodiments of the above aspect, metal salt comprises Mg, Al, Ti, Fe, Rh, Ir, Ni, Pd, Pt, Ru, Co, Cr, Cu, Ag, Au, W, Ta, Nb, Re, Mo, or any combination thereof.

In other embodiments of the above aspect, there is provided a method wherein the purified carbene precursor is a compound of (v) Formula II:

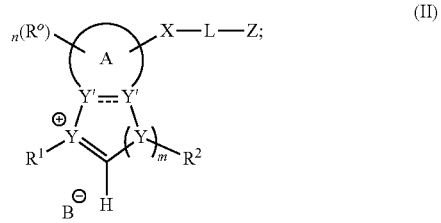

(vi) Formula IIa

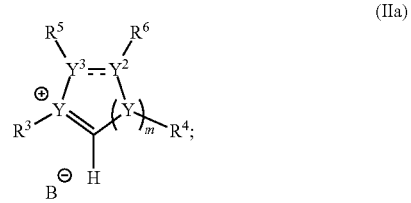

(vii) Formula V

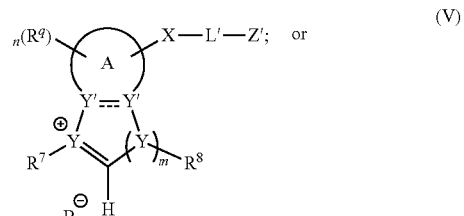

(viii) Formula Va

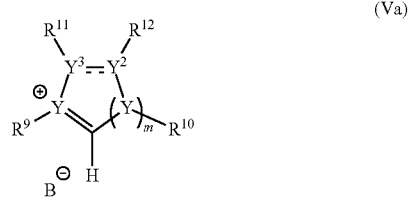

as defined above.

In other embodiments, there is provided a method wherein when the purified carbene precursor is a compound of Formula (II) or Formula (V): n is 3 or 4; m is 1; each Y is N; each Y' is C; A is an aromatic ring; X-L-Z or X-L'-Z' is absent when n is 4; X-L-Z or X-L'-Z' is present when n is 3; $R^o$ or $R^q$ is H; and, $R^1$ and $R^2$ or $R^7$ and $R^8$ are independently methyl, ethyl, propyl, isopropyl, butyl, isobutyl, hexyl, phenyl, benzyl, mesityl, or 1,3-diisopropylphenyl. In other embodiments, the purified carbene precursor is a compound of Formula (IIa) or Formula (Va): m is 1; each Y is N; $Y^2$ and $Y^3$ are C; $R^5$ and $R^6$ or $R^{11}$ and $R^{12}$ are independently H or, X-L-Z or X-L'-Z'; and, $R^3$ and $R^4$ or $R^9$ and $R^{10}$ are independently methyl, ethyl, propyl, isopropyl, butyl, isobutyl, hexyl, phenyl, benzyl, mesityl, or 1,3-diisopropylphenyl. In other embodiments, the compound of formula II, IIa, V or Va is as defined above, or is any subset thereof.

In other embodiments of the above aspect, the metal salt, the reducing agent, the purified carbene precursor, the carbene generated from the purified carbene precursor, or the solvent, or any combination thereof, may act as reductant in reducing the metal salt.

In another aspect of the present application, there is provided a carbene-functionalized composite material, comprising a material having at least a metal surface; and a carbene monolayer that is uniform, stable, and substantially free of contamination, the monolayer being sourced from a purified carbene precursor; wherein the monolayer interacts with the metal surface; and the purified precursor is sourced from a carbene precursor having a starting anion that is exchanged for a final hydrogen carbonate anion such that the purified precursor and the monolayer is substantially free of the starting anion. In embodiments of the above aspect, there is provided a composite material wherein the purified carbene precursor and carbene monolayer comprise ≤10% of the starting anion; or, ≤5%; or, ≤2%; or, ≤1%; or, ≤0.5%; or, ≤0.1%. In other embodiments, the monolayer comprises ≤5% contamination; or, ≤2%.

In other embodiments of the above aspect, there is provided a composite material wherein the starting anion is chloride, bromide, iodide, tetrafluoroborate, triflate, or hexafluorophosphate. In other embodiments the purified carbene precursor is a compound of (i) Formula II:

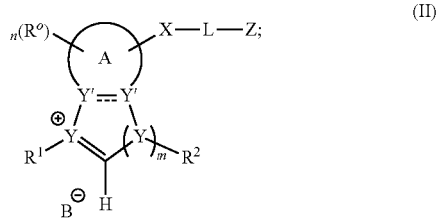

(II)

(ii) Formula IIa

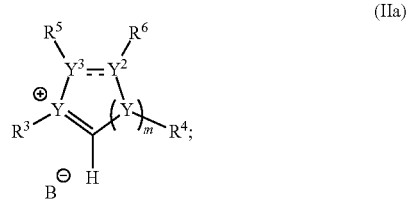

(IIa)

(iii) Formula V

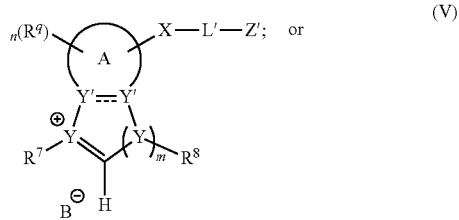

(V)

(iv) Formula Va

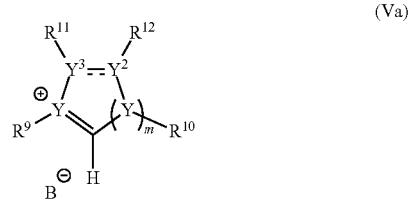

(Va)

as defined above.

In other embodiments, there is provided a composite material wherein when the purified carbene precursor is a compound of Formula (II) or Formula (V): n is 3 or 4; m is 1; each Y is N; each Y' is C; A is an aromatic ring; X-L-Z or X-L'-Z' is absent when n is 4; X-L-Z or X-L'-Z' is present when n is 3; $R^o$ or $R^q$ is H; and, $R^1$ and $R^2$ or $R^7$ and $R^8$ are independently methyl, ethyl, propyl, isopropyl, butyl, isobutyl, hexyl, phenyl, benzyl, mesityl, or 1,3-diisopropylphenyl. In other embodiments, the purified carbene precursor is a compound of Formula (IIa) or Formula (Va): m is 1; each Y is N; $Y^2$ and $Y^3$ are C; $R^5$ and $R^6$ or $R^{1'}$ and $R^{12}$ are independently H or, X-L-Z or X-L'-Z'; and, $R^3$ and $R^4$ or $R^9$ and $R^{10}$ are independently methyl, ethyl, propyl, isopropyl, butyl, isobutyl, hexyl, phenyl, benzyl, mesityl, or 1,3-diisopropylphenyl.

In other embodiments, the compound of formula II, IIa, V or Va is as defined above, or is any subset thereof.

In other embodiments of the above aspect, there is provided a composite material wherein the material having at least a metal surface comprises a (i) metal film on a support; (ii) metal nanoparticles; (iii) metal nanoclusters; (iv) metal nanoworms; (v) a metal chip; (vi) metal coating; or (vii) solid metal. In other embodiments, when the material comprises a solid metal, the solid metal is a metal sheet; a metal wire; or a single crystal metal. In other embodiments, when the material comprises a metal film on a support, the support comprises mica, alumina, silica, titania, silicon, glass, indium tin oxide, gallium arsenide, PbS, CdSe, or any combination thereof. In other embodiments, when the material comprises a metal chip, the metal chip is a surface plasmon resonance (SPR) detector chip.

In other embodiments of the above aspect, there is provided a method wherein the metal surface comprises Mg, Al, Ti, Ga, Fe, Rh, Ir, Ni, Pd, Pt, Ru, Co, Cr, Cu, Ag, Au, W, Ta, Nb, Re, Mo, or any combination or alloy thereof. In other embodiments, the metal surface comprises Cu, Ag, Au, Ni, or any combination or alloy thereof. In yet other embodiments, the metal surface comprises a steel alloy, brass alloy, bronze alloy, tungsten carbide alloy, or any combination thereof.

In other embodiments of the above aspect, there is provided a composite material that comprises carbene-functionalized nanoclusters or carbene-functionalized nanoparticles. In some embodiments, the nanoclusters consist essentially of $[Au_{11}(PPh_3)_7(NHC-iPr)Cl_2]Cl$, $[Au_{11}(PPh_3)_{6-7}(NHC-Et)_{1-2}Cl_2]Cl$, or 1,3-diisopropylbenzimidazolylidene-functionalized Cu nanoclusters. In other embodiments, the nanoparticles consist essentially of 1,3-diisopropylbenzimidazolylidene-functionalized Cu nanoparticles; 1,3-diisopropylbenzimidazolylidene-functionalized Ag nanoparticles; 1,3-diisopropylbenzimidazolylidene-functionalized Au nanoparticles; monodentate N-heterocyclic carbene-functionalized Au nanoparticles; or bidentate N-heterocyclic carbene-functionalized Au nanoparticles.

In other embodiments of the above aspect, there is provided a composite material wherein the metal surface is functionalized with a chemical species that can be displaced by a carbene. In other embodiments, the chemical species comprises a phosphine group (e.g., triphenylphosphine), a sulfide group (e.g., dialkylsulfide compounds, didodecyl sulfide), a thiol group (e.g., alkylthiol compounds, dodecanethiol), a selenolate group, or an alkynyl group.

In another aspect of the present application, there is provided a carbene-functionalized composite material comprising a lipid layer or a polysaccharide matrix; a material having at least one metal surface; a carbene monolayer that is uniform, stable, and substantially free of contamination, the monolayer being sourced from a purified carbene precursor; wherein the monolayer interacts with the metal surface and the lipid layer or polysaccharide matrix, the monolayer being located between the lipid layer or polysaccharide matrix and the metal surface; and the purified precursor is sourced from a carbene precursor having a starting anion that is exchanged for a final hydrogen carbonate anion such that the purified precursor and the monolayer is substantially free of the starting anion. In an embodiment of the above aspect, there is provided a composite material the purified carbene precursor and carbene monolayer comprise ≤0.10% of the starting anion; or, ≤5%; or, ≤2%; or, ≤1%; or, ≤0.5%; or, ≤0.1%. In other embodiments, the monolayer comprises 55% contamination; or, ≤2%.

In other embodiments of the above aspect, the starting anion is chloride, bromide, iodide, tetrafluoroborate, triflate, or hexafluorophosphate. In other embodiments, the polysaccharide matrix is a dextran matrix. In yet other embodiments, the dextran matrix is a carboxymethylated dextran matrix.

In other embodiments of the above aspect, there is provided a composite material wherein the purified carbene precursor is a compound of (i) Formula II:

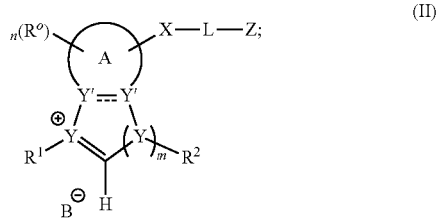
(II)

(ii) Formula IIa

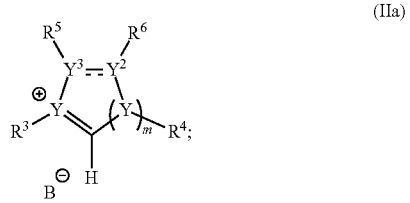
(IIa)

(iii) Formula V

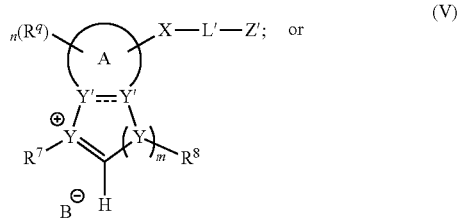
(V)

(iv) Formula Va

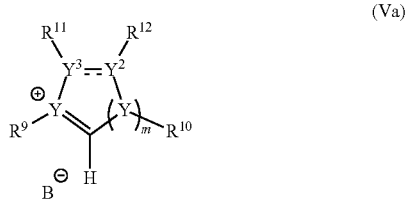
(Va)

as defined above.

In other embodiments, there is provided a composite material wherein when the purified carbene precursor is a compound of Formula (II) or Formula (V): n is 3; m is 1; each Y is N; each Y' is C; A is an aromatic ring; X-L-Z or X-L'-Z' are as defined in claim 6; $R^o$ or $R^q$ is H; and, $R^1$ and $R^2$ or $R^7$ and $R^8$ are independently methyl, ethyl, propyl, isopropyl, butyl, isobutyl, hexyl, phenyl, benzyl, mesityl, or 1,3-diisopropylphenyl. In other embodiments, the purified carbene precursor is a compound of Formula (IIa) or Formula (Va): m is 1; each Y is N; $Y^2$ and $Y^3$ are C; $R^5$ and $R^6$ or $R^{11}$ and $R^{12}$ are independently H or, X-L-Z or X-L'-Z'; and, $R^3$ and $R^4$ or $R^9$ and $R^{10}$ are independently methyl, ethyl, propyl, isopropyl, butyl, isobutyl, hexyl, phenyl, benzyl, mesityl, or 1,3-diisopropylphenyl.

In other embodiments, the compound of formula II, IIa, V or Va is as defined above, or is any subset thereof.

In other embodiments of the above aspect, there is provided a composite material wherein the material having at least a metal surface comprises a metal chip. In other embodiments, the metal chip comprises a metal film and all connections necessary for incorporation into an analytical instrument as a detector. In yet other embodiments, the analytical instrument is a surface plasmon resonance (SPR) system.

In other embodiments of the above aspect, there is provided a composite material wherein the monolayer interacting polysaccharide matrix comprises van der Waals interactions, hydrogen bonding, electrostatic interactions, and/or forming a covalent bond between the monolayer and the matrix. In other embodiments, monolayer interacts with the lipid layer comprising van der Waals interactions, hydrogen bonding, and/or electrostatic interactions.

In embodiments of the above aspects, there is provided a composite material wherein the purified precursor is sourced from a carbene precursor having a starting anion that is exchanged for a final hydrogen carbonate anion, wherein having the starting anion exchanged comprises (i) oxidizing a starting anion of a carbene precursor in the presence of water and $CO_2$, or (ii) exchanging a starting anion of a carbene precursor via a hydrogen carbonate-anion exchange resin, and forming a purified carbene precursor comprising a final hydrogen carbonate anion that is substantially free of the starting anion. In other embodiments, oxidizing a starting anion comprises exposing the starting anion to hydrogen peroxide. In yet other embodiments, when oxidizing comprises exposing the starting anion to hydrogen peroxide, the starting anion is iodide and the purified carbene precursor is relatively water soluble; or, relatively hydrophilic.

In another aspect of the present application, there is provided a use of the herein described carbene-functionalized composite materials for: making nano-patterns on semiconducting surfaces; fabricating electronic or microelectronic devices; altering properties of a metal surface (e.g., altering electronic properties of a metal surface); adherence to a substrate (e.g., an optionally coated second metal surface); protecting a metal surface from corrosion or oxidation; biomedical applications (e.g., drug delivery); electrochemically detecting molecules; electrochemical biosensing; surface plasmon resonance for detecting molecules; making electrochemical sensors; sensing applications; detecting molecules (e.g., biomolecules); antibacterial/antimicrobial applications; generating a catalyst; catalysis; or colourimetric analysis of molecules (e.g., biomolecules).

In another aspect of the present application, there is provided a method for modifying a metal surface comprising utilizing the carbene-functionalized materials described herein. In an embodiment, modifying a metal surface comprises surface functionalization, altering properties of a metal surface (e.g., altering electronic properties of a metal surface); adhering to a substrate (e.g., an optionally coated second metal surface); protecting a metal surface from corrosion or oxidation; generating a catalyst; displacing a chemical species from the metal surface; or changing a surface property of the metal surface. In other embodiments, there is provided a method wherein the carbene-functionalized composite material is utilized for making nano-patterns on semi-conducting surfaces; fabricating electronic or microelectronic devices; altering properties of a metal surface (e.g., altering electronic properties of a metal surface); adherence to a substrate (e.g., an optionally coated second metal surface); protecting a metal surface from corrosion or oxidation; biomedical applications (e.g., drug delivery); electrochemically detecting molecules; electrochemical biosensing; surface plasmon resonance for detecting molecules; making electrochemical sensors; sensing applications; detecting molecules (e.g., biomolecules); antibacterial/antimicrobial applications; generating a catalyst; catalysis; or colourimetric analysis of molecules (e.g., biomolecules).

In embodiments of the above aspect, there is provided a use wherein the composite material is used for detecting biomolecules, such as DNA, proteins, lipids or carbohydrates (e.g., glucose). In other embodiments, the composite material is used for colourimetric analysis or quantitation of biomolecules such as DNA, RNA, proteins, lipids or carbohydrates (e.g., glucose). In other embodiments, the composite material is used for protecting a metal surface from corrosion or oxidation. In an embodiment, the metal surface comprises a (i) metal film on a support; (ii) metal nanoparticles; (iii) metal nanoclusters; (iv) metal nanoworms; (v) a metal chip; (vi) metal coating; or (vii) solid metal. In other embodiments, when the metal surface comprises a solid metal, the solid metal is a metal sheet; a metal wire; or a single crystal metal.

In other embodiments of the above aspect, there is provided a use wherein the composite material is used for altering properties of a metal surface (e.g., altering electronic properties of a metal surface). In other embodiments, wherein the composite material is used in sensing applications, the sensing applications include use of a carboxymethyl-dextran-coated NHC-based biosensing SPR chip.

In embodiments of all above aspects, a carbene monolayer may be formed from two or more purified carbene precursors.

In embodiments of all above aspects, carbene monolayers or carbene-functionalized composite materials can be prepared directly from herein described purified carbene precursors without pre-generation of the carbene by thermal or other methods.

In an embodiment, a purified carbene precursor comprising a final hydrogen carbonate anion may be formed by reacting a carbene precursor having a starting anion with $Ag_2CO_3$ in the presence of $CO_2$.

In another embodiment, B is a counter ion that acts as a base. In other embodiments, the base has a $pKa_H$ of about 4 to about 6.

In an embodiment of compounds of Formulae (II), (IIa), (V), and (Va), the compounds are mesoionic. In another embodiment, any one of Y, Y', $Y^2$, and $Y^3$ may charged. In yet another embodiment, any one of Y, Y', $Y^2$, and $Y^3$ may be positively or negatively charged.

In an embodiment of compounds of Formulae (II), (IIa), (V), and (Va), optionally at least one of the Y's located adjacent to the C(H) is not carbon. In an embodiment of Formulae (V) and (Va), L' is a divalent moiety such as $C_1$-$C_{10}$ alkyl, $C_{10}$-$C_{20}$ alkyl, $C_1$-$C_{10}$ alkenyl, $C_{10}$-$C_{20}$ alkenyl, $C_1$-$C_{10}$ to alkynyl, $C_{10}$-$C_{20}$ alkynyl, each of which is optionally substituted. In another embodiment of Formulae (V) and (Va), Z' is H, L' as defined above, or a monovalent moiety of L'.

In another embodiment, the herein described carbene-functionalized composite materials may be derived from a diamidocarbene (DAC), a non-limiting example of which comprises a compound of Formula (X), or any analogue thereof:

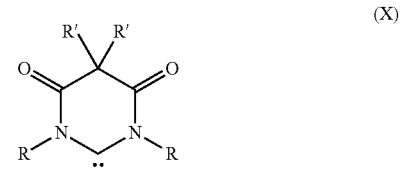

wherein R' and R are independently aliphatic groups, each of which is optionally substituted.

In another embodiment, the herein described carbene-functionalized composite materials may be derived from purified NHC precursors having extended backbone it conjugation, such as but not limited to precursors having the structures:

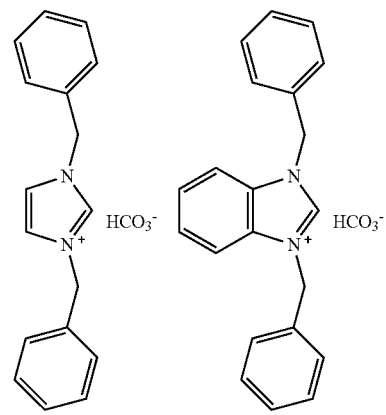

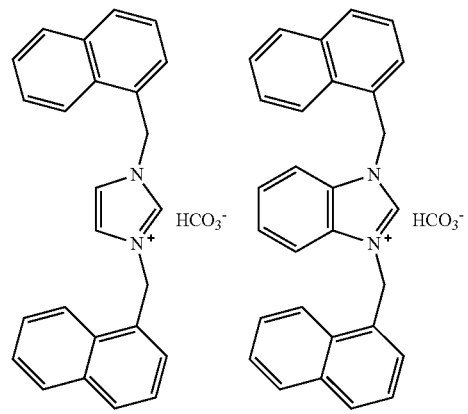

-continued

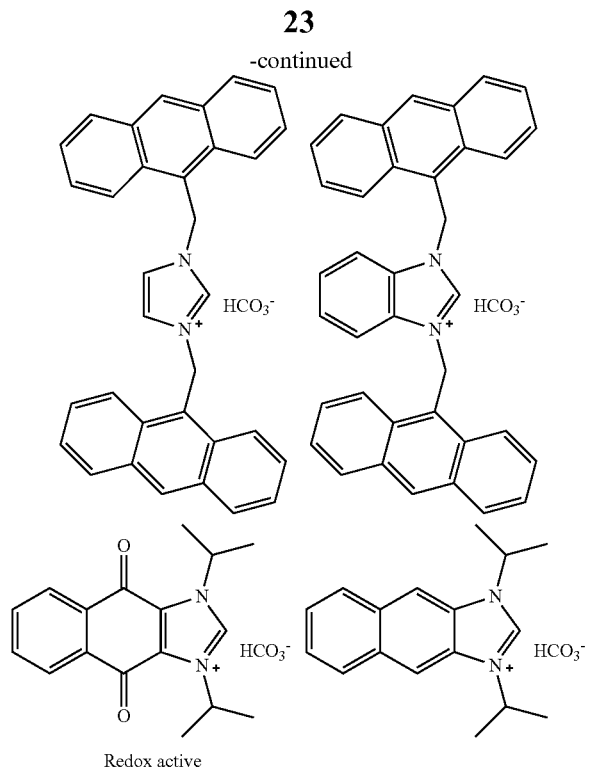

Redox active

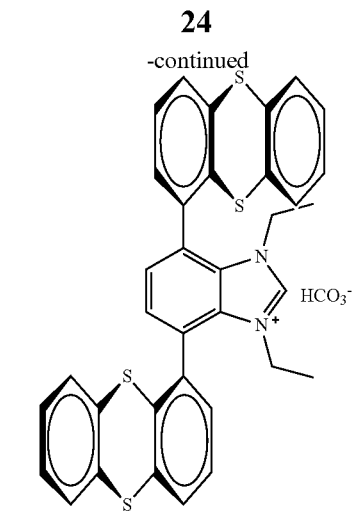

-continued

BRIEF DESCRIPTION OF FIGURES

For a better understanding of the present invention, as well as other aspects and further features thereof, reference is made to the following description which is to be used in conjunction with the accompanying tables and drawings, where:

FIG. 4c depicts results of run-to-run variability in BSA adsorption on both chips from FIG. 4a.

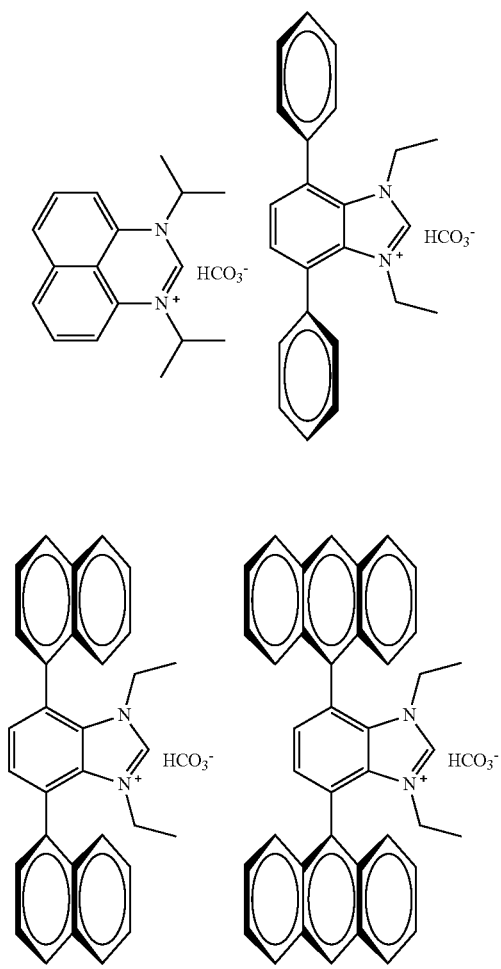

from iPr₂bimy(H)[HCO₃] (3a) before ("starting") and after ("pH 2") exposure to pH 2 at RT for 24 h.

Figure 7A:
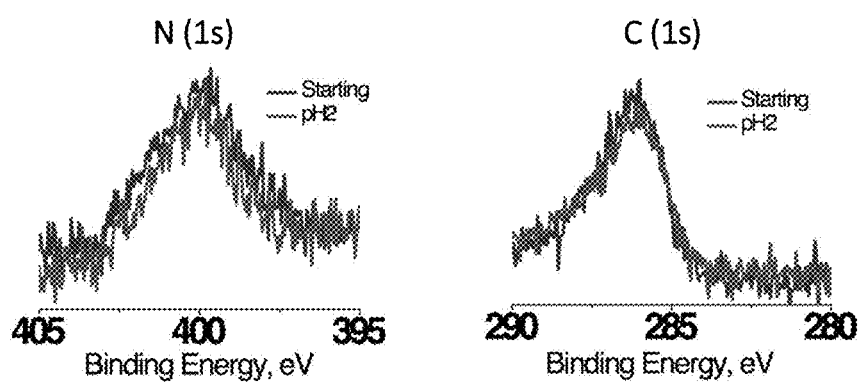
FIG. 7a shows N(1s) and C(1s) regions of an XPS spectrum for 3a-based NHC films deposited on Au(111)
Figure 7B:
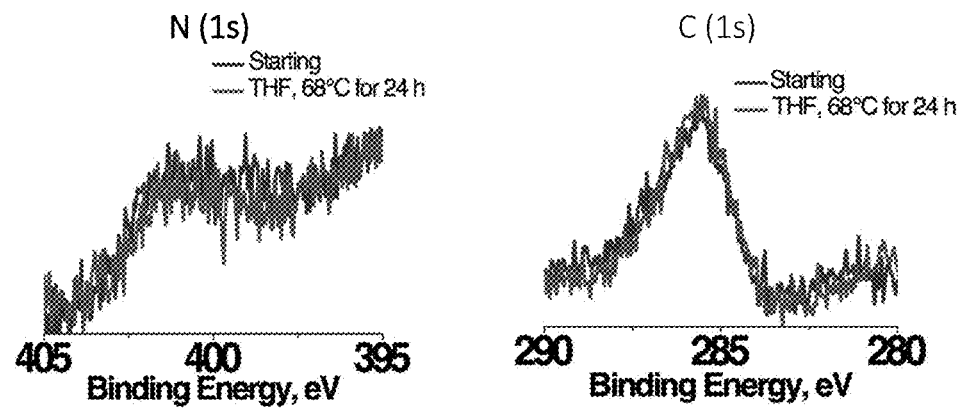

FIG. 7b shows N(1s) and C(1s) regions of an XPS spectrum for NHC films deposited on Au(111) from iPr₂bimy(H)[HCO₃] (3a) before and after treatment in THF at 68° C. for 24 h.

Figure 7C:
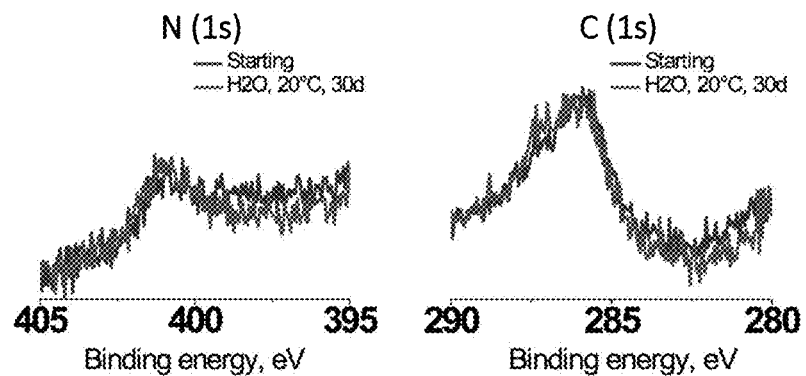

FIG. 7c shows NO s) and C(1s) regions of an XPS spectrum for NHC films deposited on Au(111) from iPr₂bimy(H)[HCO₃] (3a) before and after exposure to deionized water at RT for 1 month.

Figure 7D:
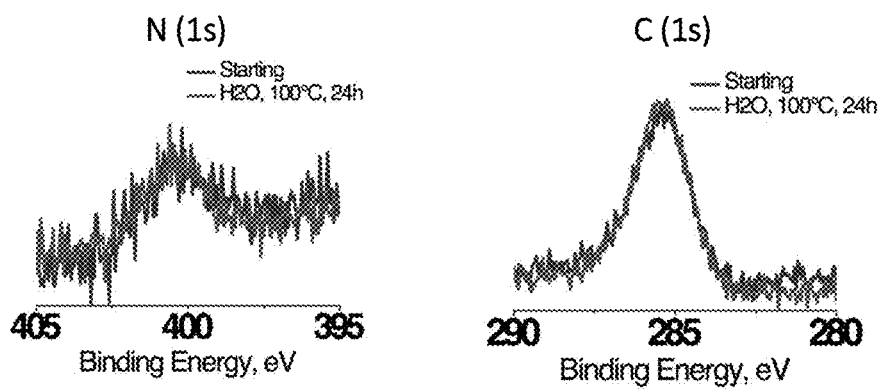

FIG. 7d shows N(1s) and C(1s) regions of an XPS spectrum for NHC films deposited on Au(111) from iPr₂bimy(H)[HCO₃] (3a) before and after treatment in deionized water at 100° C. for 24 h.

Figure 7E:
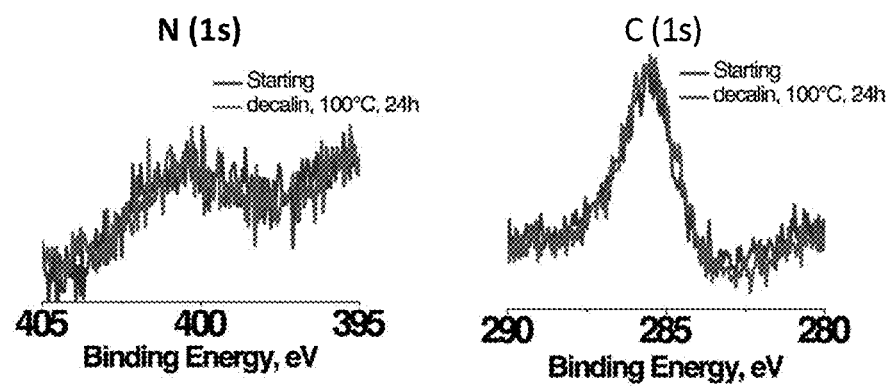

FIG. 7e shows N(1s) and C(1s) regions of an XPS spectrum for NHC films deposited on Au(111) from iPr₂bimy(H)[HCO₃] (3a) before and after treatment in decalin at 100° C. for 24 h.

Figure 7F:
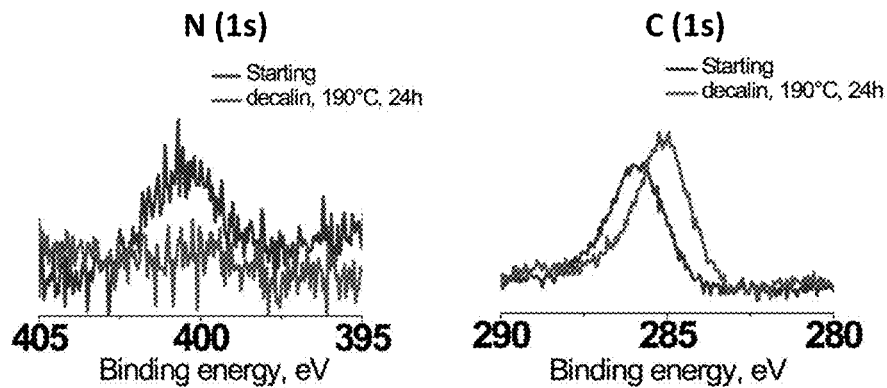

FIG. 7f shows N(1s) and C(1s) regions of an XPS spectrum for NHC films deposited on Au(111) from iPr₂bimy(H)[HCO₃] (3a) before and after treatment in decalin at 186° C. for 24 h.

Figure 7G:
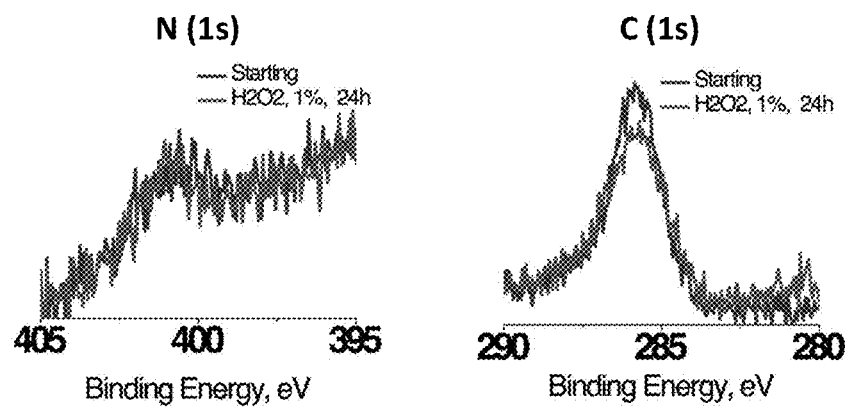

FIG. 7g shows N(1s) and CO s) regions of an XPS spectrum for NHC films deposited on Au(111) from iPr₂bimy(H)[HCO₃] (3a) before and after treatment in hydrogen peroxide (1% solution in water) at RT for 24 h. On the C(1s) peaks, the lower one is after $H_2O_2$ treatment.

Figures 8A, 8B:
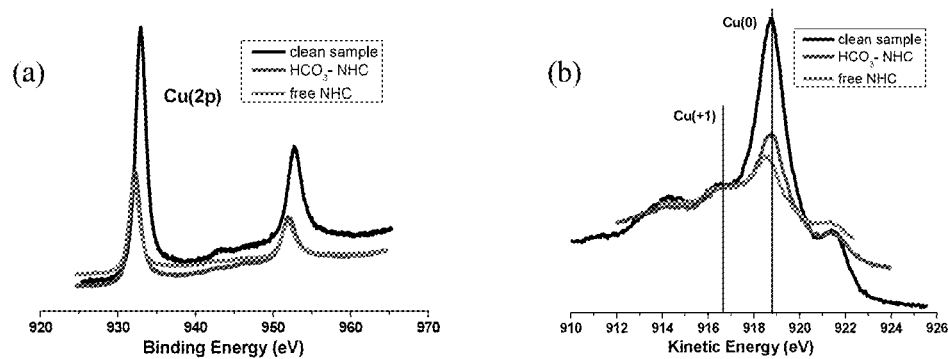

FIG. 8a shows Cu(2p) region of an XPS spectra of blank Cu, and NHC SAMs from 3a and 2a on Cu.

FIG. 8b shows Cu(LMM) region of an XPS spectra of blank Cu, and NHC SAMs from 3a and 2a on Cu.

Figures 9A, 9B:
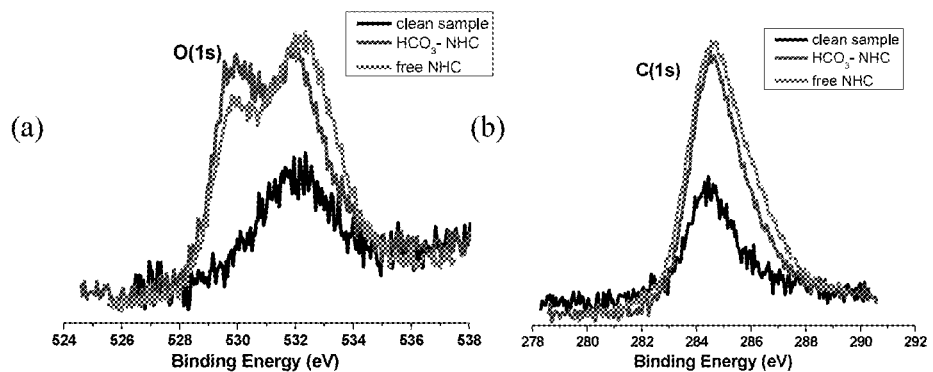

FIG. 9a shows O (1s) region of an XPS spectra of blank Cu, and NHC SAMs from 3a and 2a on Cu.

FIG. 9b shows C(1s) region of an XPS spectra of blank Cu, and NHC SAMs from 3a and 2a on Cu.

Figure 9C:
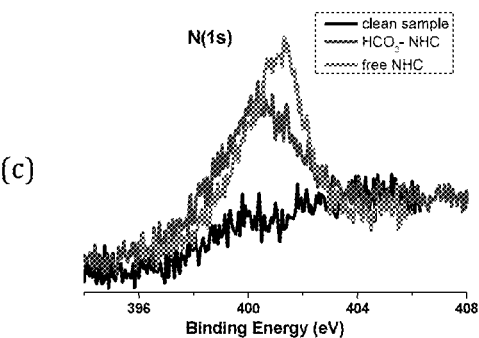

FIG. 9c shows N(1s) region of an XPS spectra of blank Cu (clean sample), and NHC SAMs from 3a (HCO₃—NHC) and 2a (free NHC) on Cu.

FIGS. 10a and 10b show Cu(2p) regions of XPS spectra for freshly prepared Cu coated with NHC via 3a and 2a, respectively, as well as an overlay of spectra of these samples after a week in air.

Figure 10C:
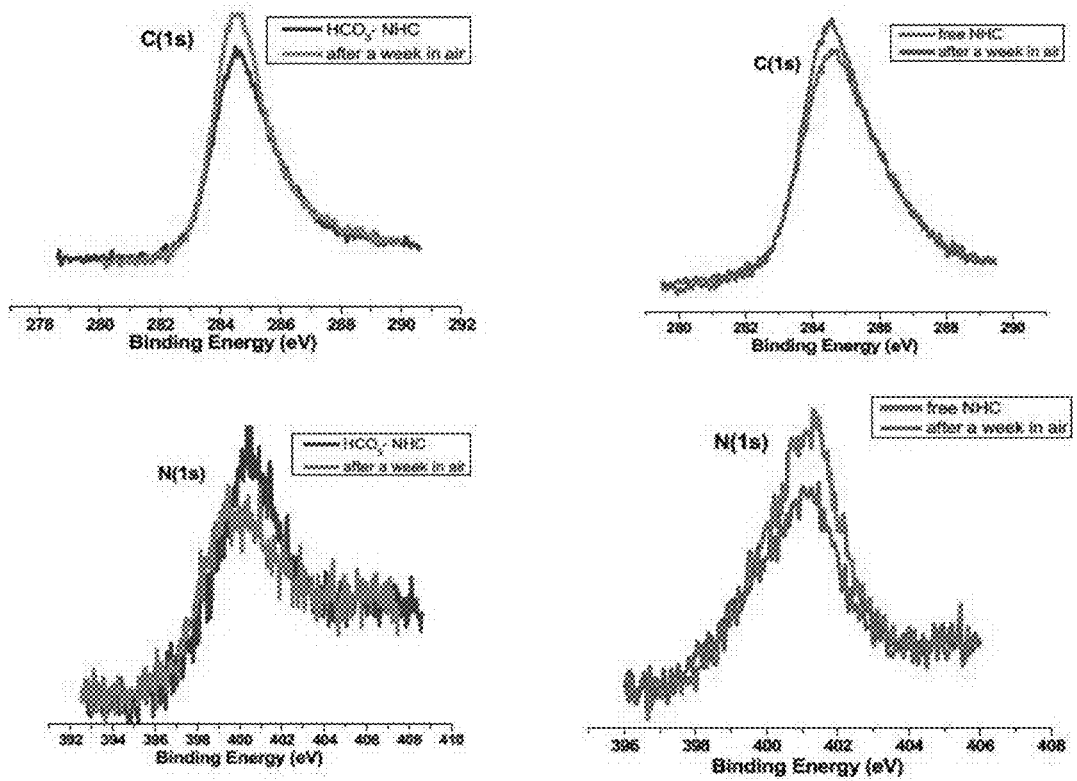

FIG. 10c depicts Cu(LMM), O(1s), C(1s), and N(1s) regions of XPS spectra for freshly prepared Cu coated with NHC via 3a and 2a, respectively, as well as an overlay of spectra of these samples after a week in air.

Figure 11A:
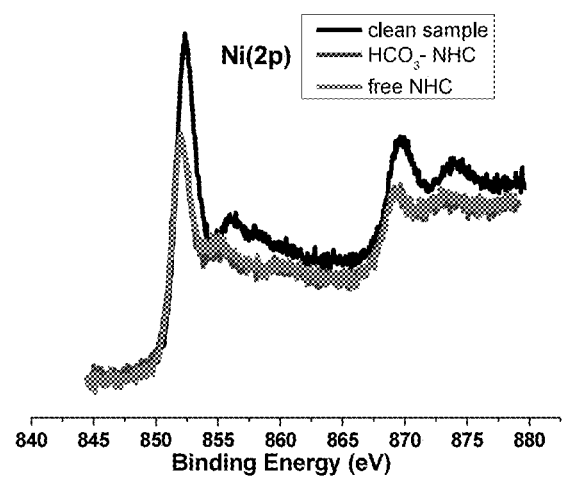

FIG. 11a shows Ni(2p) region of an XPS spectra of blank Ni, and NHC SAMs from 3a and 2a on Ni.

Figure 11B:
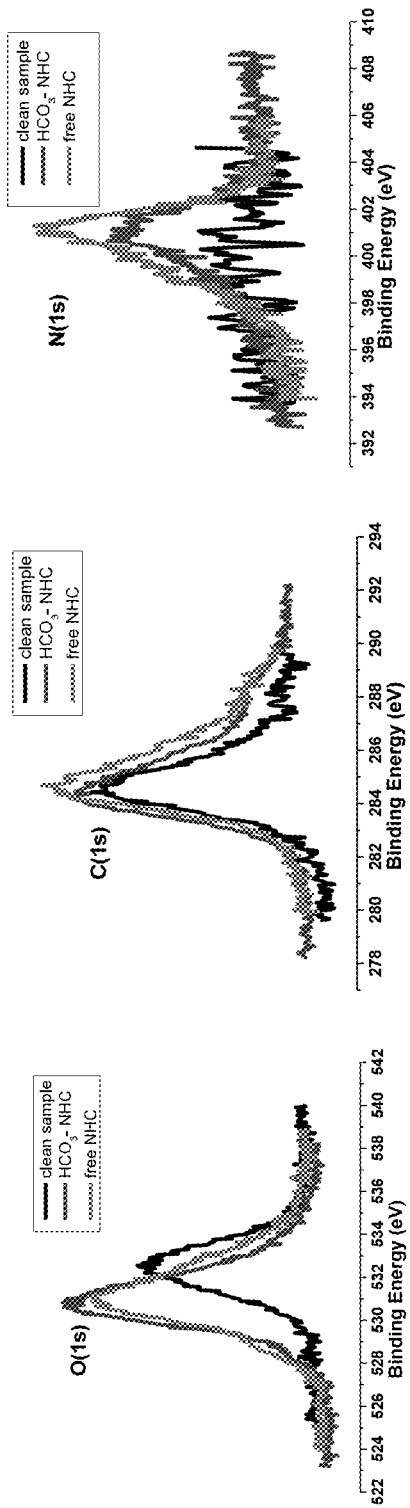

FIG. 11b shows O (1s), C(1s), and N(1s) regions of an XPS spectra of blank Ni, and NHC SAMs from 3a and 2a on Ni.

Figure 11C:
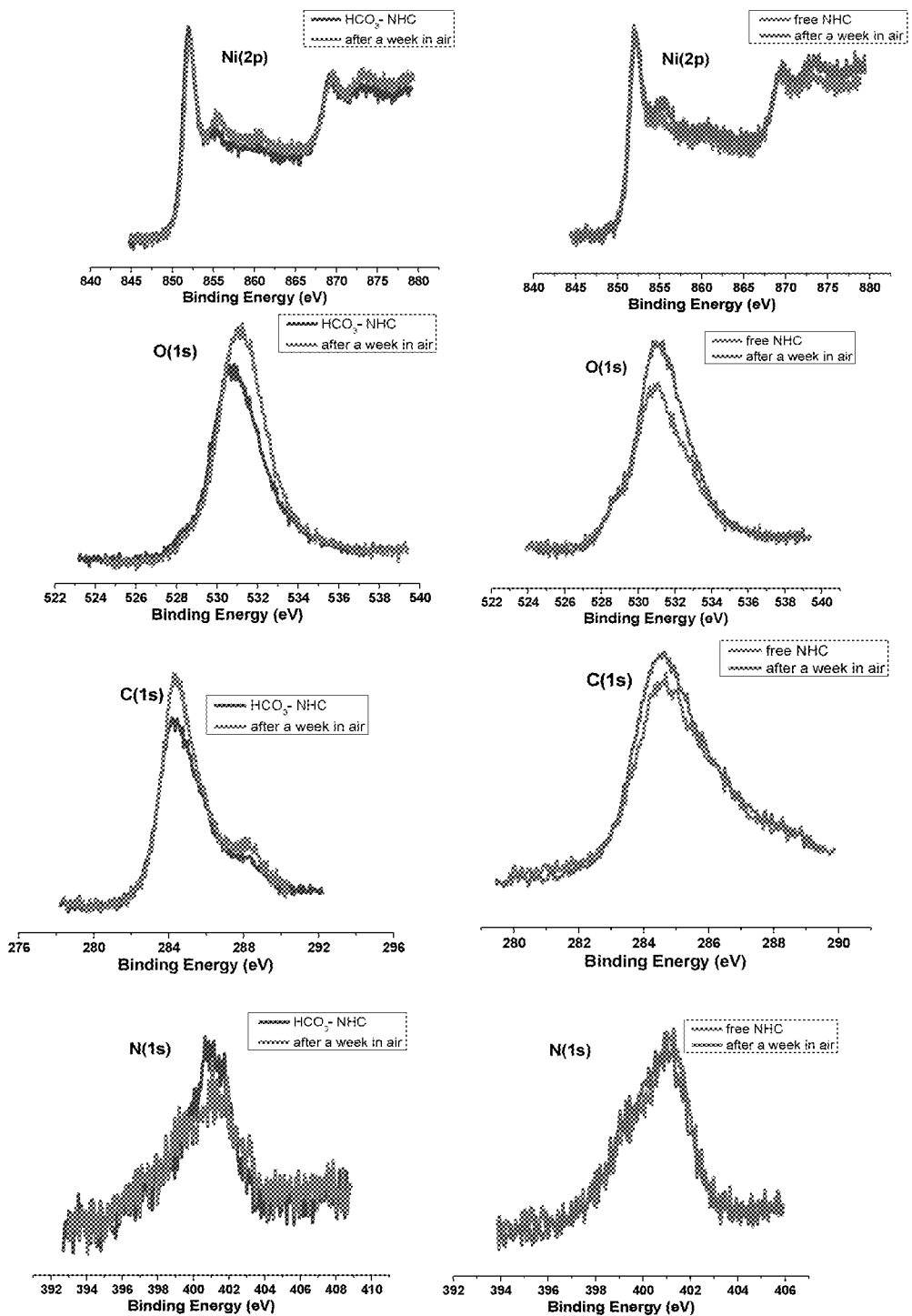

FIG. 11c shows Ni(2p), O(1s), s), and N(1s) regions of an XPS spectra of freshly prepared and after a week in air for blank Ni, and NHC SAMs from 3a and 2a on Ni.

Figure 12:
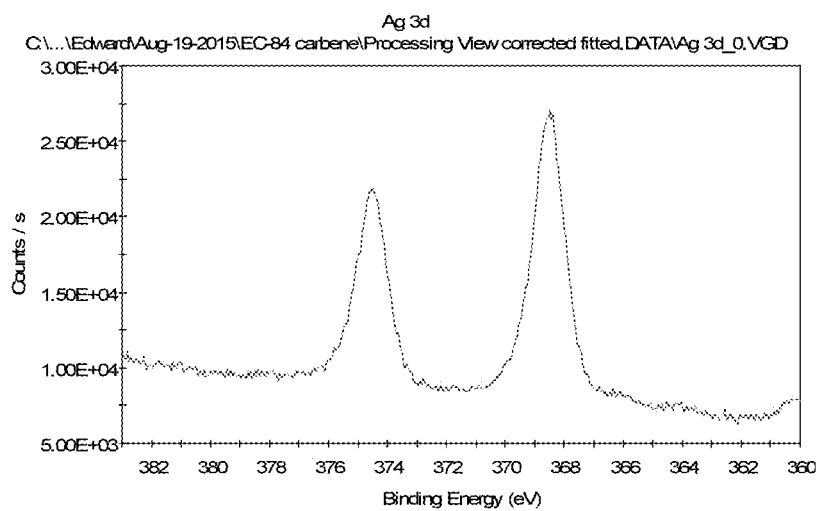

FIG. 12 shows Ag(3d) region of an XPS spectra of NHC SAMs from 3a on Ag.

Figure 13:
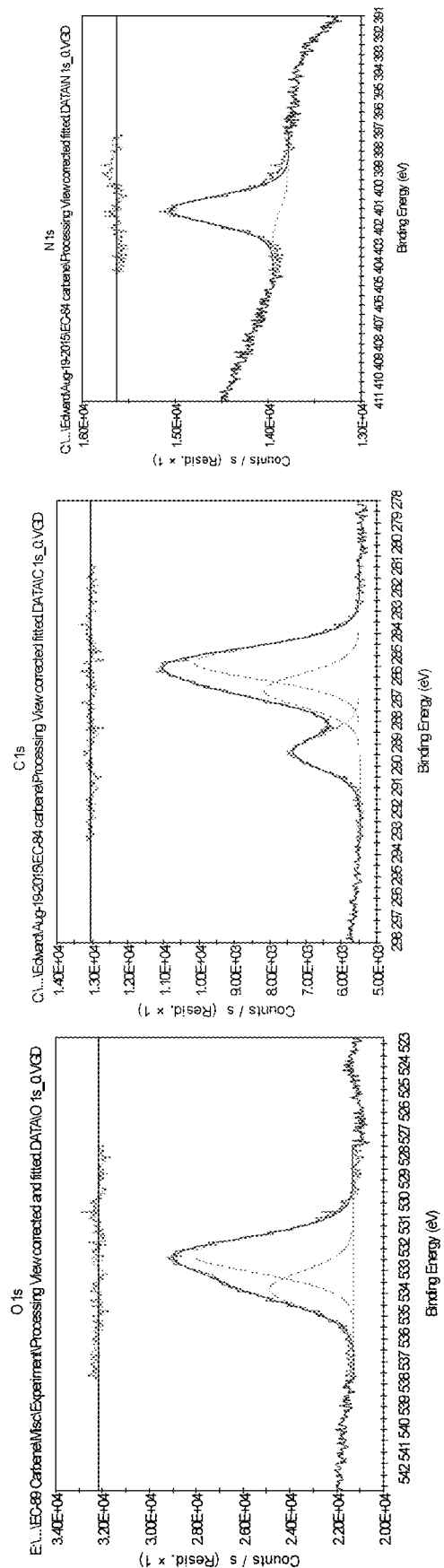

FIG. 13 shows O (1s), C(1s), and N(1s) regions of an XPS spectra of NHC SAMs from 3a on Ag.

Figure 14:
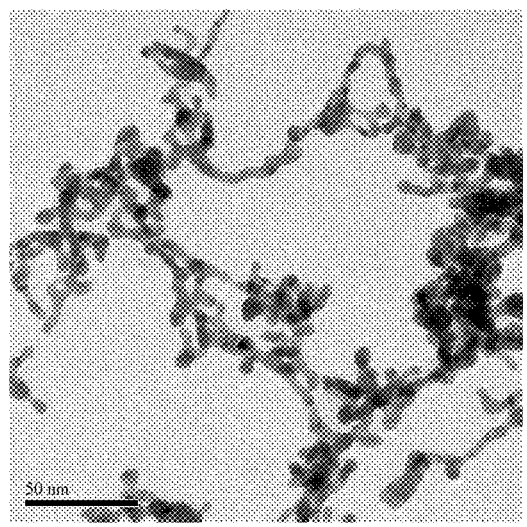

FIG. 14 depicts a Transmission Electron Microscopy (TEM) image of NHC nanoworms formed through the reduction of gold complex 1 (see structural formula in Example 11) under mild conditions using hydrazine hydrate as the reducing agent at room temperature (200,000 times magnification).

Figure 15A:
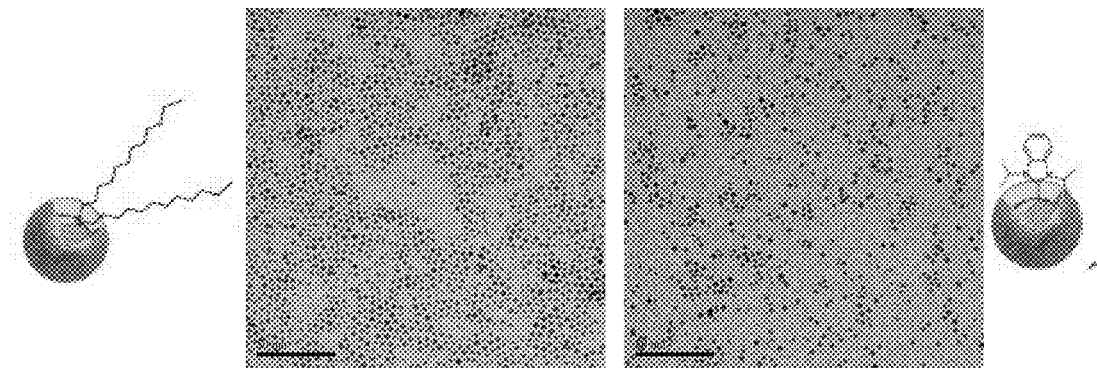

FIG. 15A depicts a TEM image of docecylsulfide (DDS)- and 2a-protected nanoparticles.

Figure 15B:
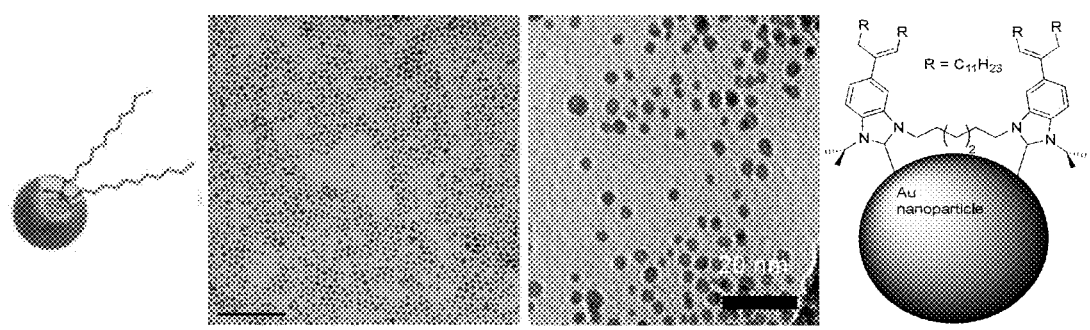

FIG. 15B depicts a TEM image of docecylsulfide (DDS)-nanoparticles and olefinic tail-equipped $C_6H_{12}$-linked di-NHC-protected Au nanoparticles. No drastic etching/recombination of nanoparticles was observed. For the left hand side TEM image, average nanoparticle (NP) size 2.27 nm, polydispersity 22%. For the right hand side image, average NP size 2.4 nm, polydispersity 25%.

FIGS. 16A-C show sensorgrams of different concentrations of his-tagged protein interacting with biotinylated DNA on NHC-SA chip surface.

FIG. 17A-C show sensorgram of different concentrations of his-tagged protein interacting with biotinylated DNA on CM3-SA chip surface.

Figure 18A:
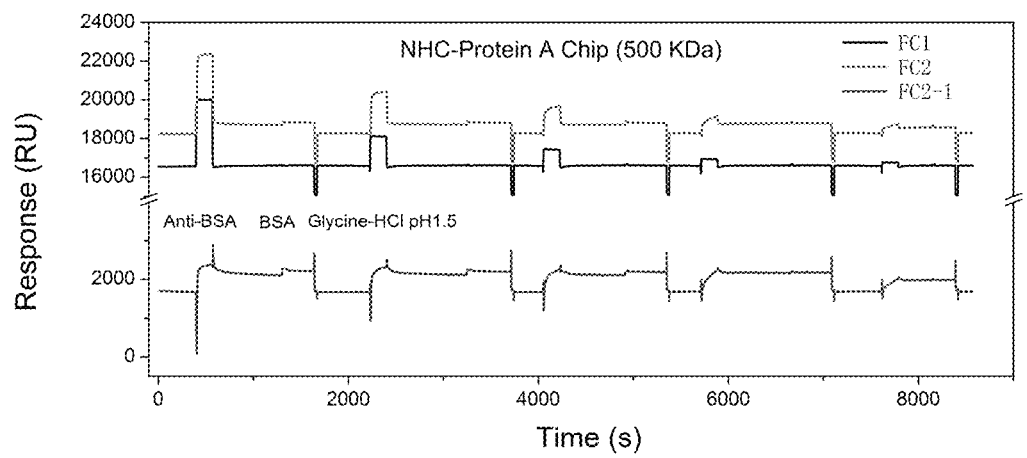

FIG. 18A shows sensorgrams for injection of anti-BSA on NHC-Protein A chip surface, followed by BSA injection, two interactions are shown: (1) Protein A interacted with IgG type anti-body (anti-BSA), and (2) anti-body (anti-BSA) interacted with antigen (BSA).

Figure 18B:
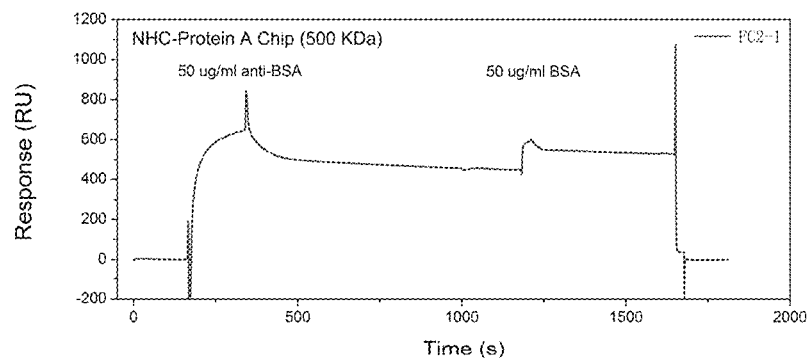
Figure 18C:
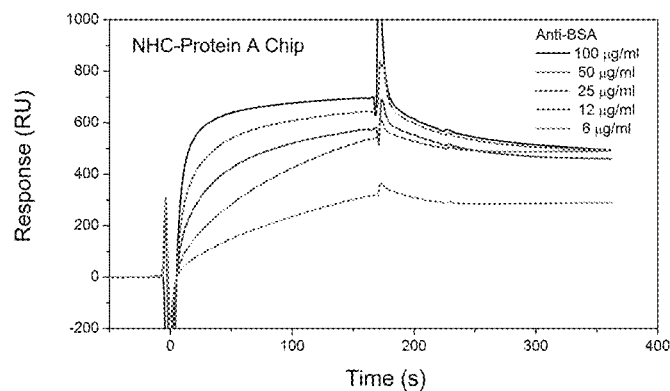
Figure 18D:
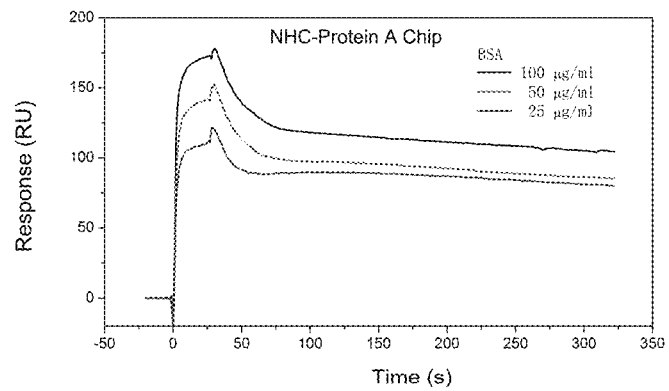

FIG. 18B shows 1 cycle example of Protein A—anti-BSA—BSA FIGS. 18C and 18D show concentration dependent sensorgrams monitored during injection of anti-BSA on NHC-Protein A chip surface.

Figure 18E:
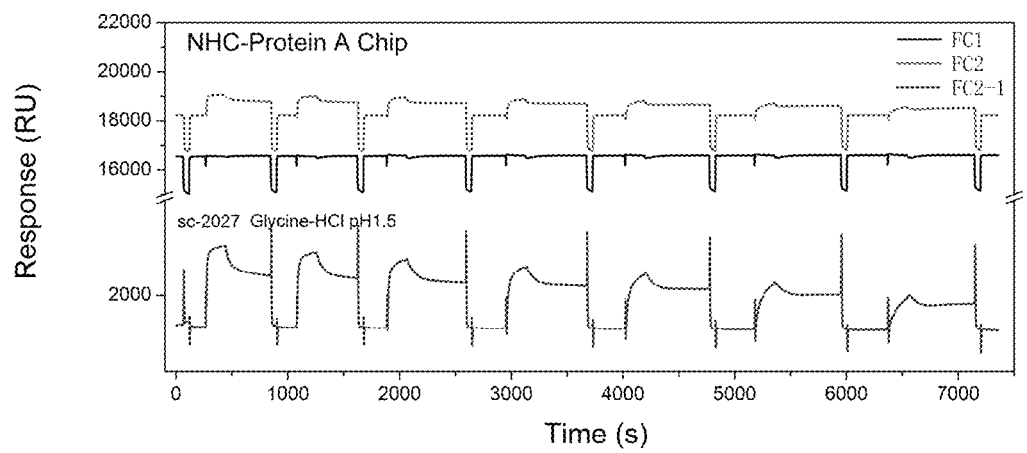

FIG. 18E shows NHC-Protein A Chip interacting with normal rabbit IgG sc-2027 using a flow rate of 5 μL/min, and injecting different concentrations (1 to 80 μg/ml) of normal sc-2027 for 3 min on FC2 and FC1, one injection of 1-min 10 mM Glycine-HCl pH1.5 was used as regeneration solution to disrupt the interaction between protein and IgG sc-2027.

Figure 18F:
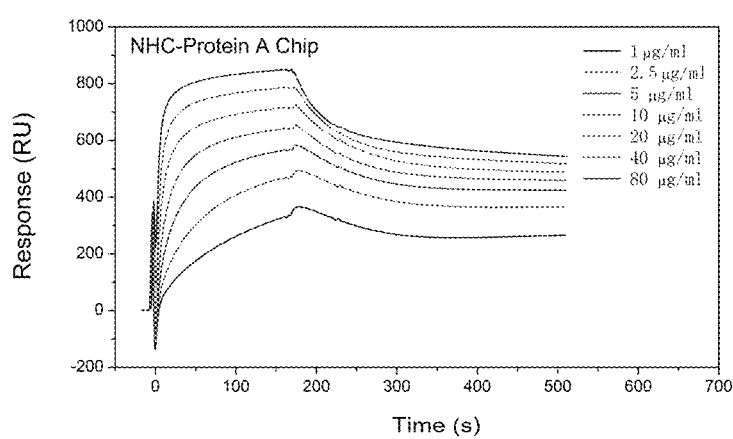

FIG. 18F shows a plot of Response versus Time for 7 cycles of different concentrations of sc-2027, which demonstrate a potential application of the NHC-Protein A chip.

Figure 19A:
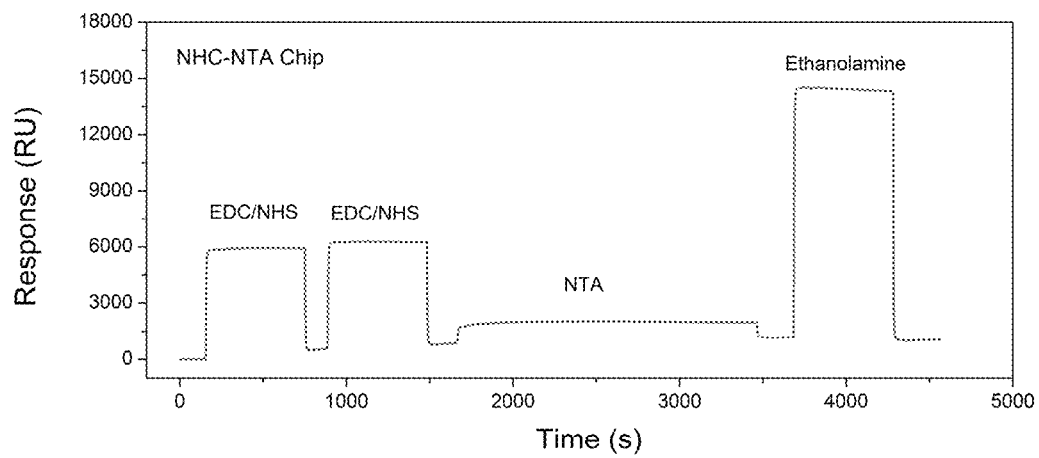

FIG. 19A shows a plot of response versus time and validates NHC-NTA chip with his-tagged protein.

Figures 19B, 19C:
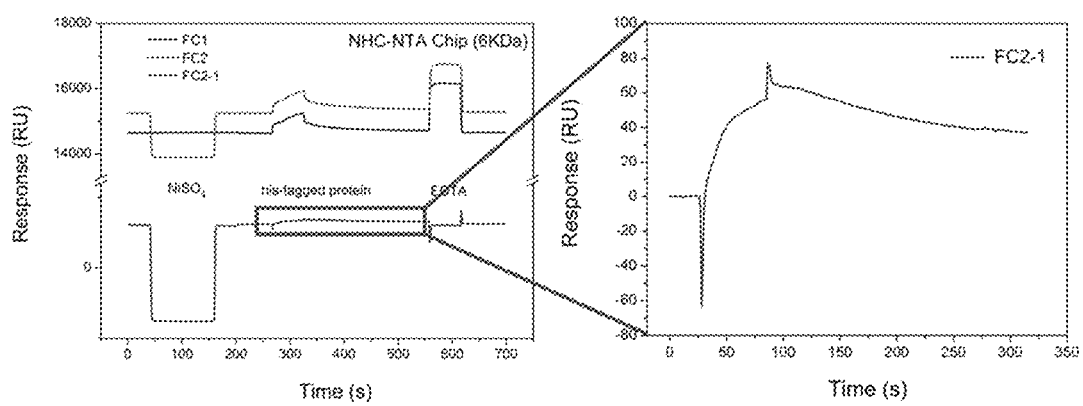

FIGS. 19B and 19C show plots of Response versus time for His-tagged protein (35 KDa, from synechocystis) 25 μg/mL.

Figure 19D:
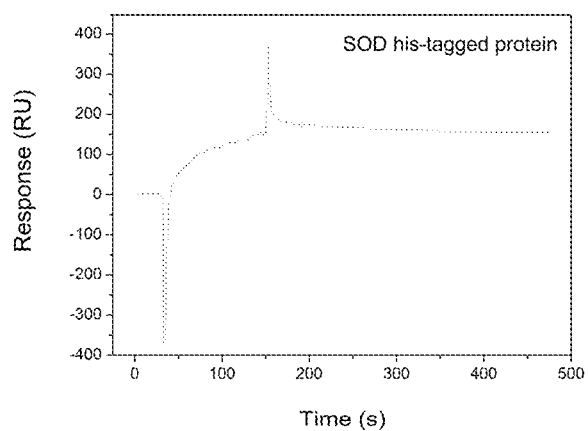

FIG. 19D shows a plot of Response versus time for a SOD protein that has been tagged with a his (histadine) peptide (SOD his-tagged protein) (32 Kda) 50 μg/mL.

Figure 20:
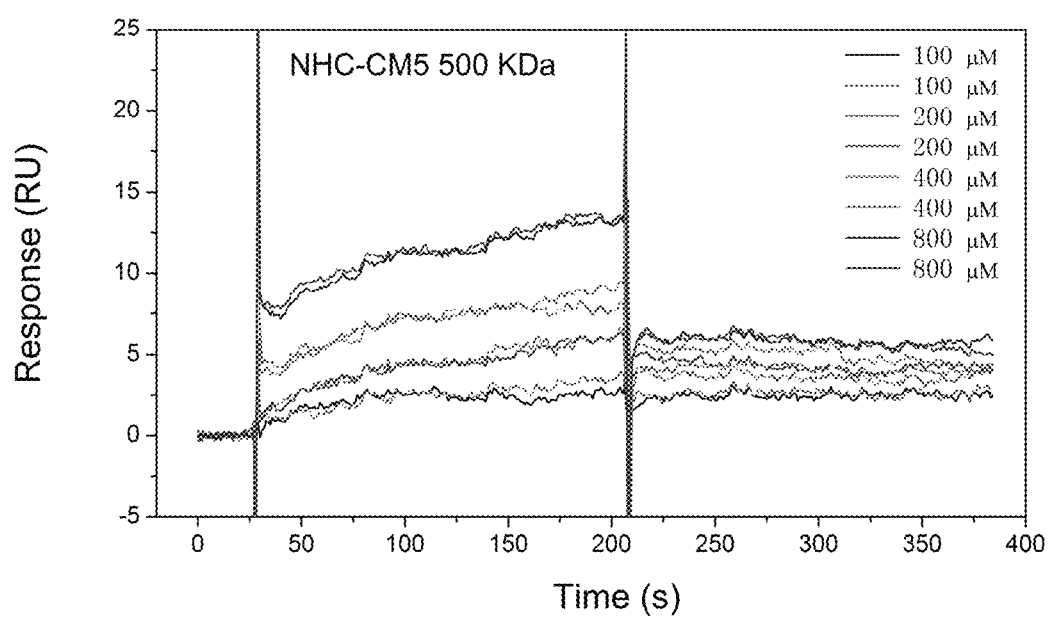

FIG. 20 is a plot of Response versus Time and indicates good reproducibility of replicate tests.

FIGS. 21A-D depict plots of Response versus time for detection of the indicated opioids (narcotic drugs/human serum albumin interactions) at a concentration of approximately 10 ug/L by an NHC-CM5 chip.

Figure 22:
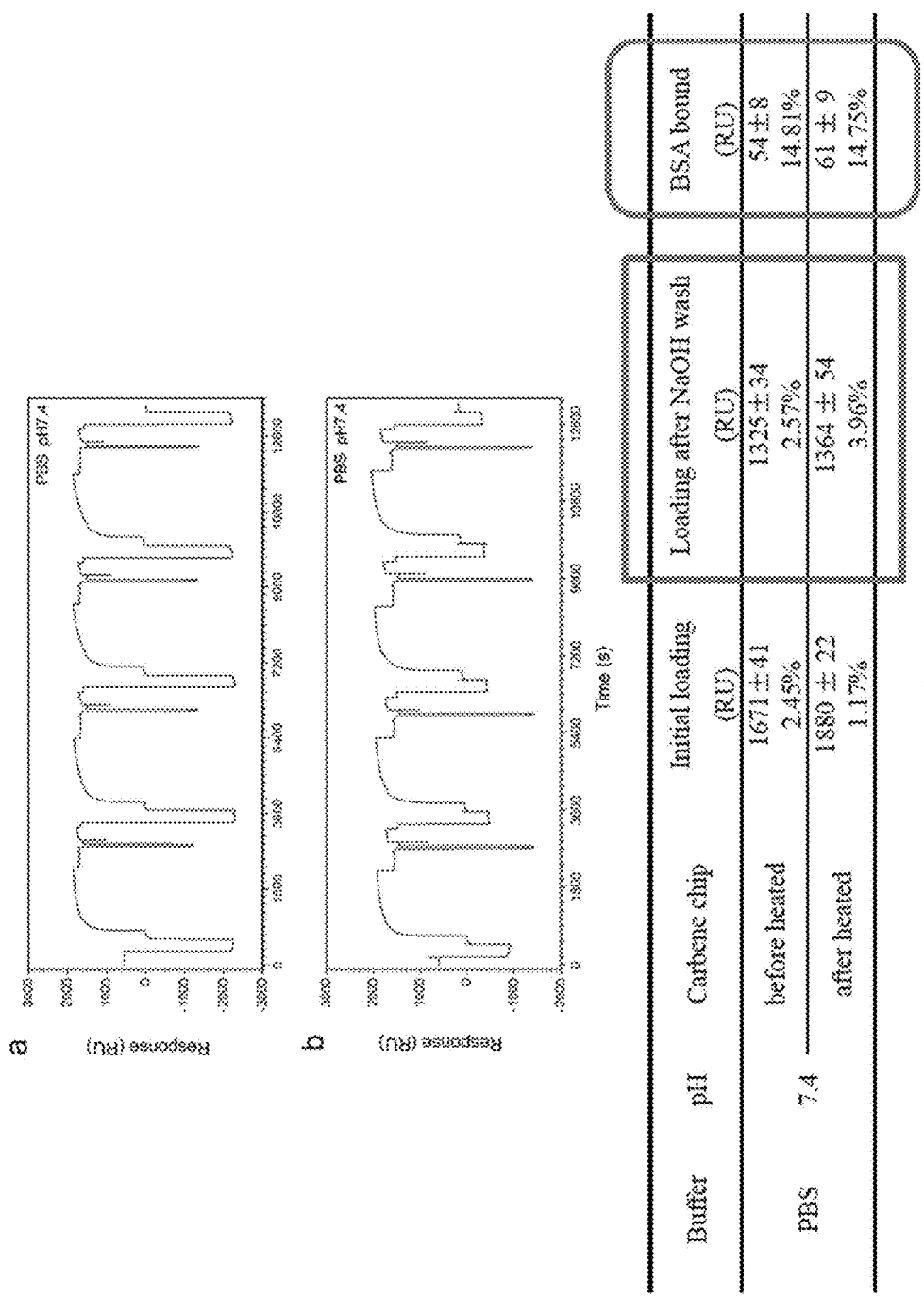

FIG. 22 is a plot of Response versus Time for an NHC-CM chip showing thermal stability after 65° C. for 24 h.

Figure 23:
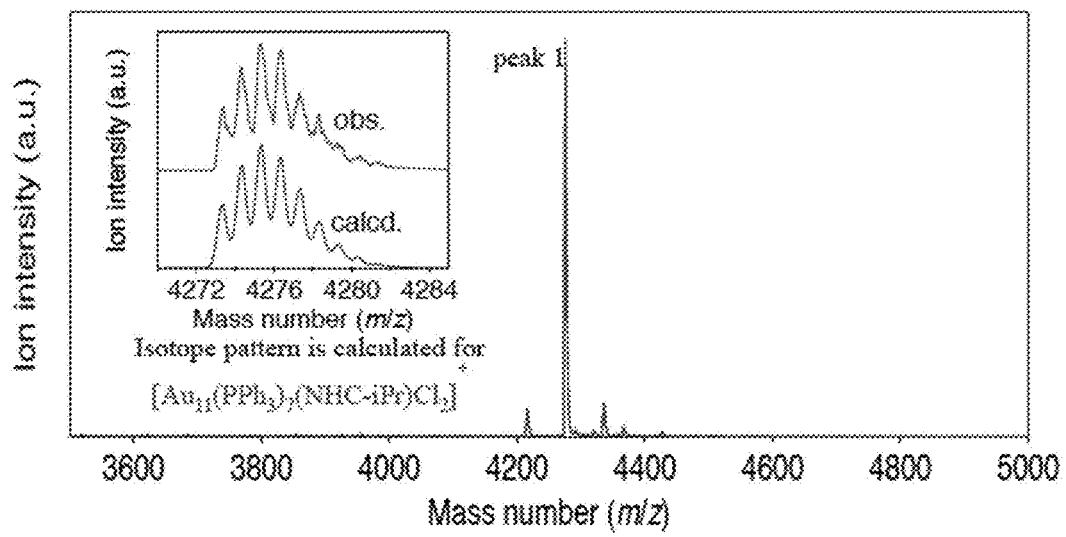

FIG. 23 depicts an ESI-MS spectrum and analysis of Au11-NHC(iPr).

Figure 24:
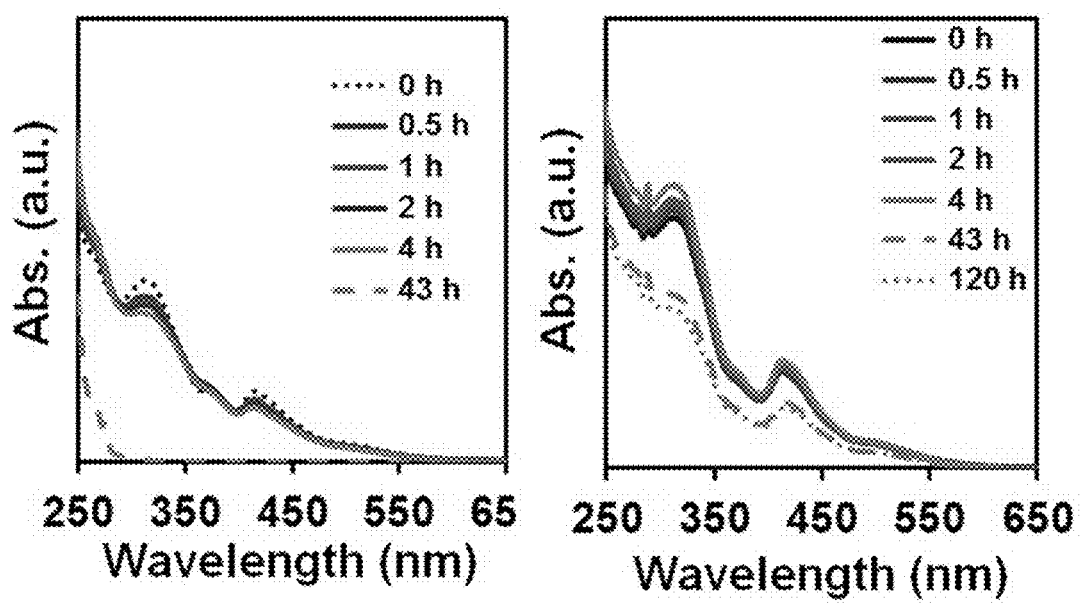

FIG. 24 depicts UV-visible spectra showing higher stability of $Au_{11}$—NHC(iPr) (right) relative to $Au_{11}$-TPP (left) under oxidation conditions in boiling DCM at room temperature.

Figure 25:
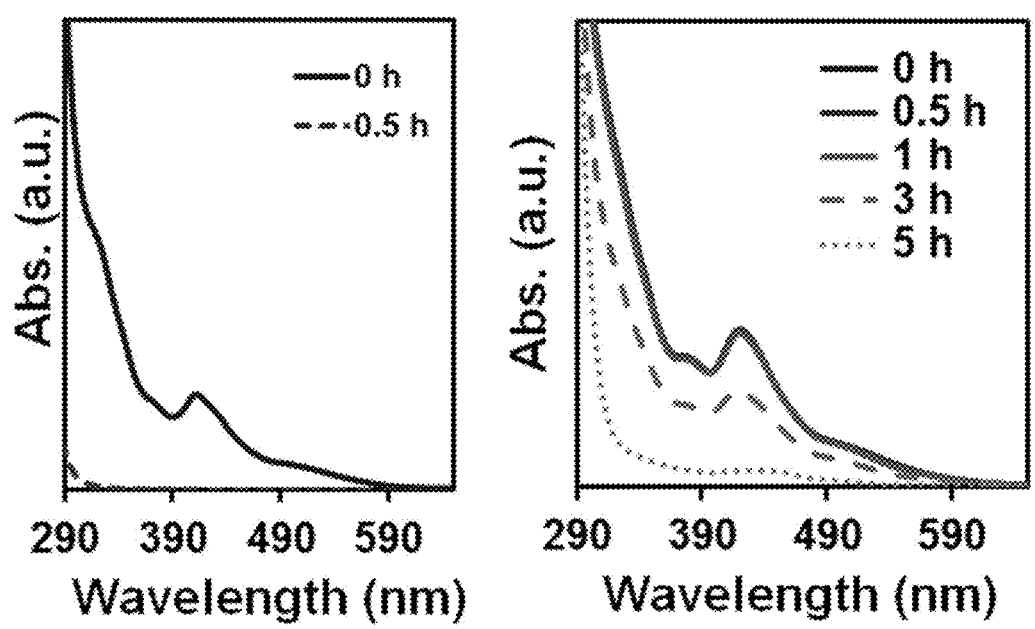

FIG. 25 depicts UV-visible spectra showing higher stability of Au11-NHC(iPr) (right) relative to Au11-TPP8 (left) under PPh₃ etching conditions in boiling THF.

Figure 26:
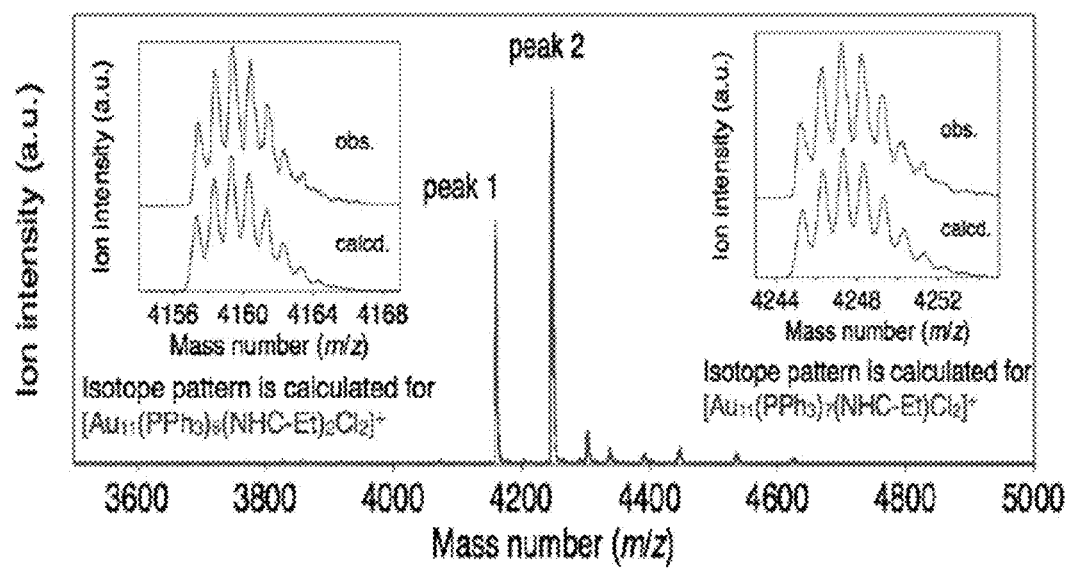

FIG. 26 depicts an ESI-MS spectrum of Au11-NHC(Et).

Figure 27:
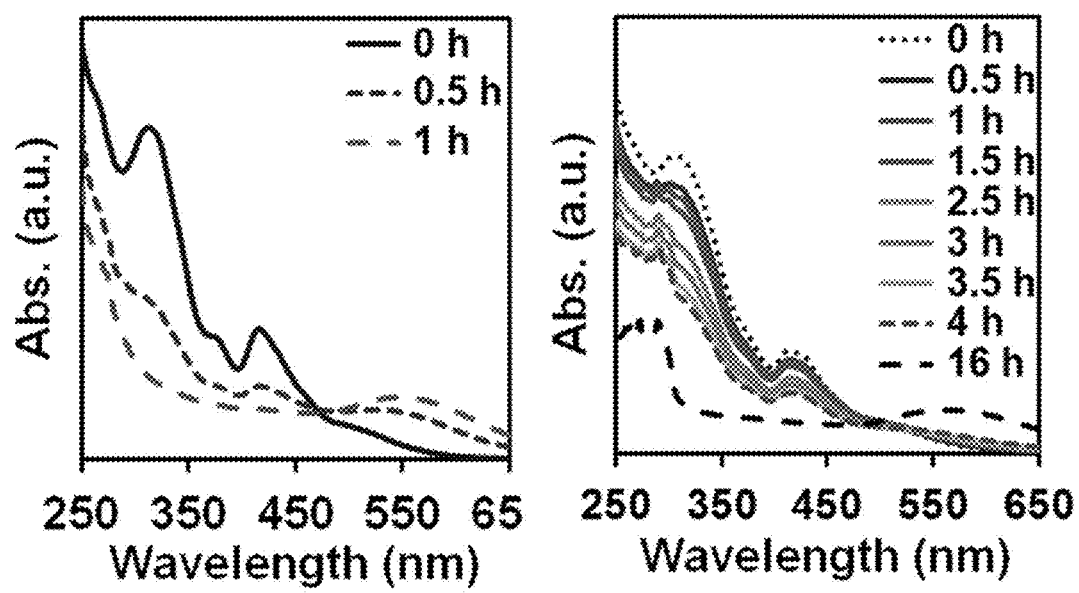

FIG. 27 depicts UV-Vis spectra indicating a higher thermal stability of Au11-NHC(Et) (right) relative to Au11-TPP8 (left) in pentanol at 90° C.

Figure 28:
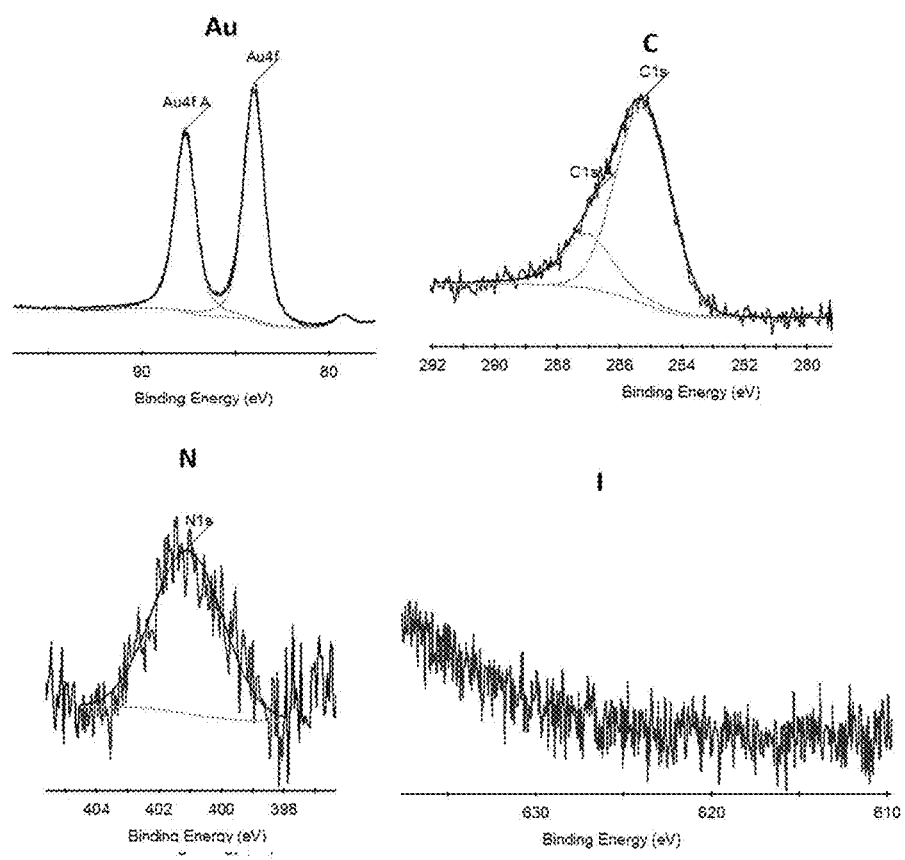

FIG. 28 depicts XPS spectra for an Au SAM made from NHC(iPr)HCO₃ that was in turn prepared from an iodode precursor.

Figure 29:
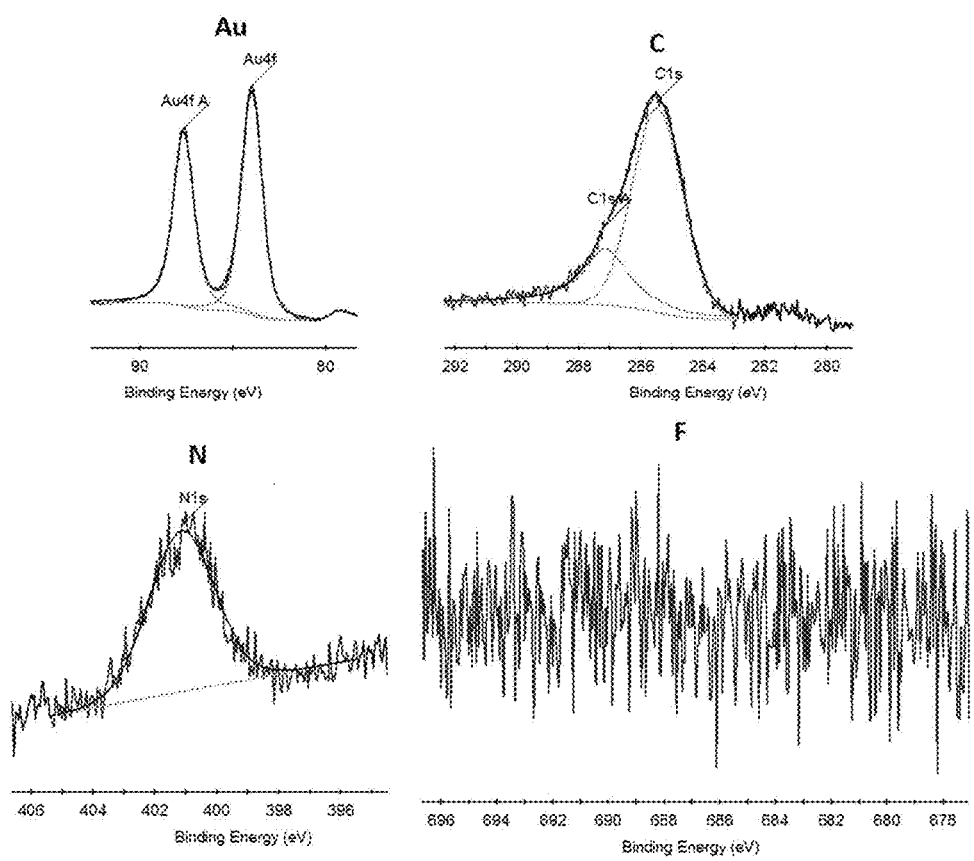

FIG. 29 depicts XPS spectra of an Au SAM made from NHC(iPr)HCO₃ that was in turn prepared from a triflate precursor.

Figure 30:
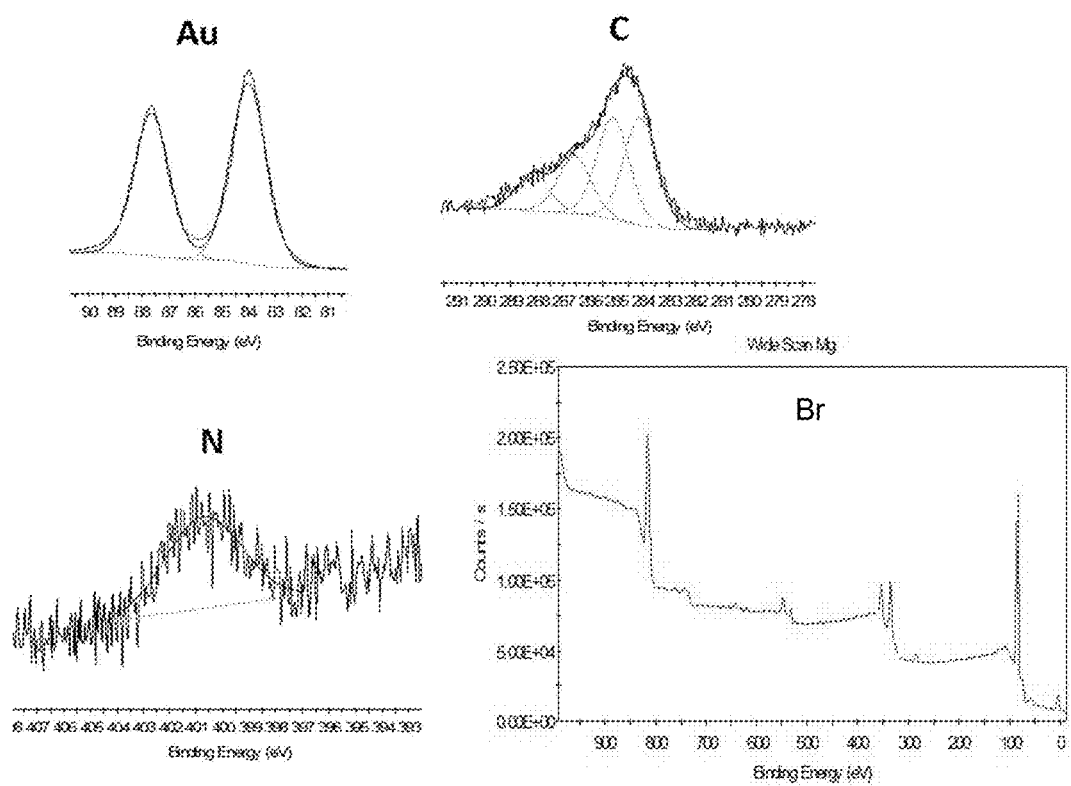

FIG. 30 depicts XPS spectra for an Au SAM made from NHC(Bn)HCO$_3$ that was in turn prepared from a bromide precursor.

Figure 31:
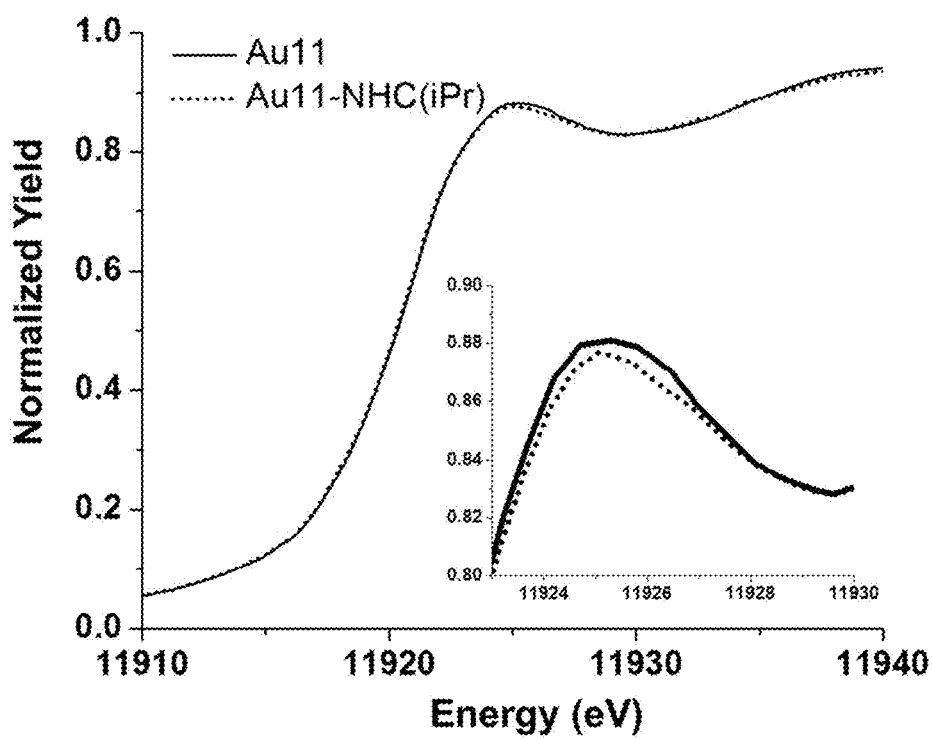

FIG. 31 depicts Au L$_3$-edge XANES data of Au11-TPP8 (Au11) and Au11-NHC(iPr) clusters; a first feature of the XANES spectra depicts a slight decrease from Au11(–) to Au11-NHC(iPr) ( . . . ), indicating small electronic and potentially structural differences.

Figure 32:
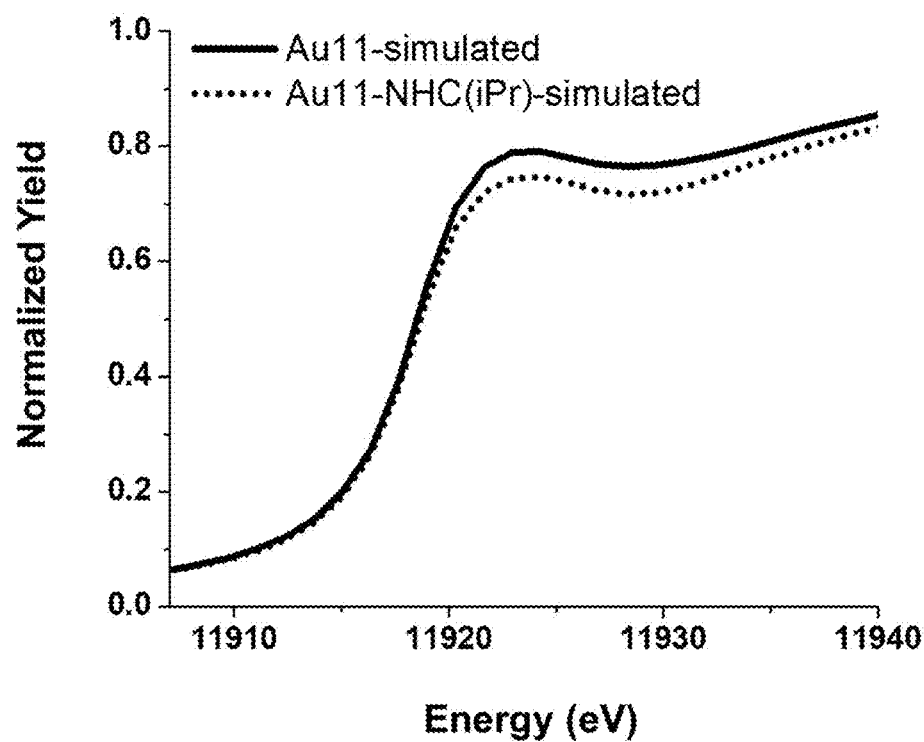

FIG. 32 depicts simulated Au L$_3$-edge XANES spectra which demonstrate a decrease in a first feature with replacement of one phosphine with NHC as in Au11-NHC(iPr).

Figure 33:
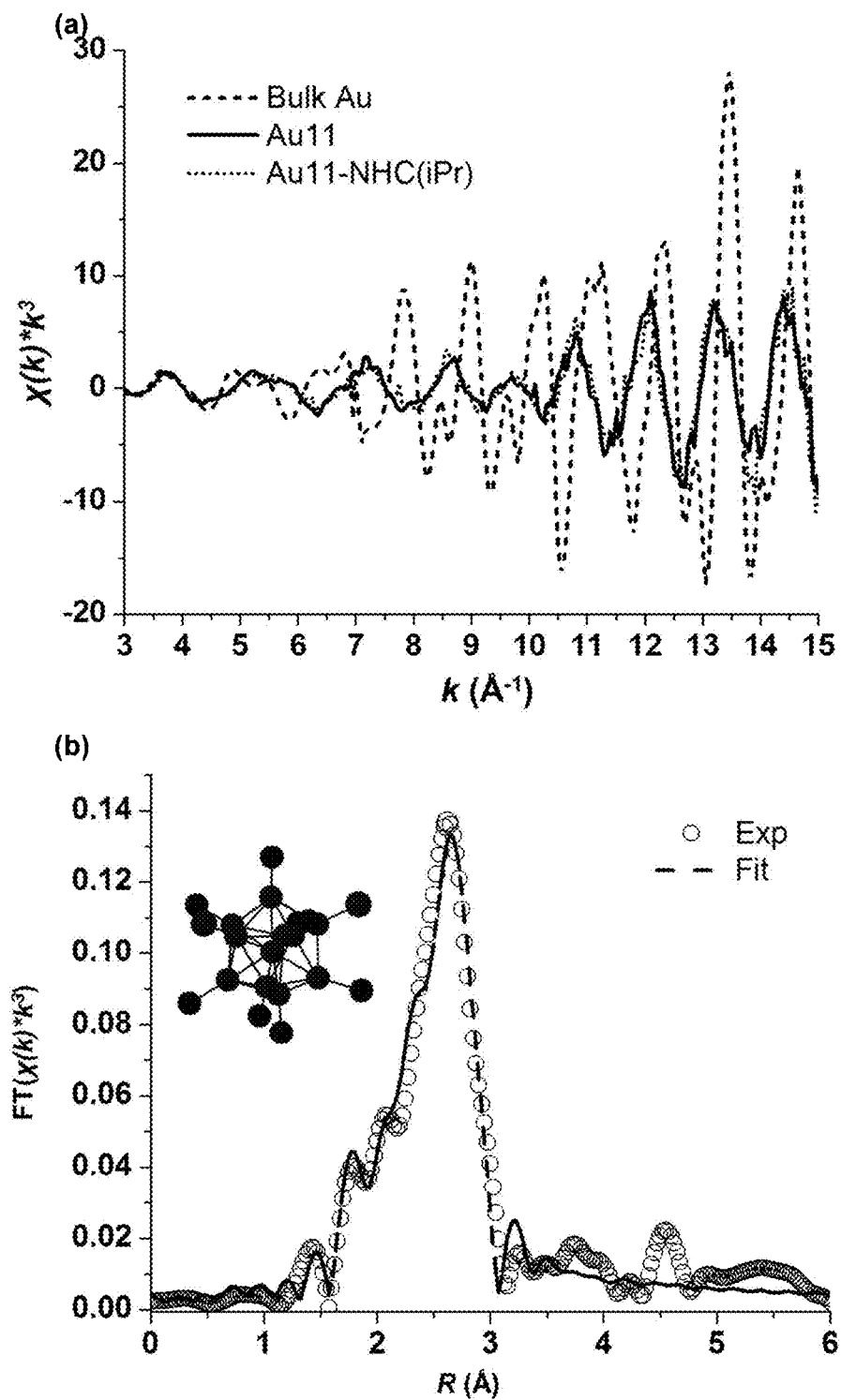
Figure 33:
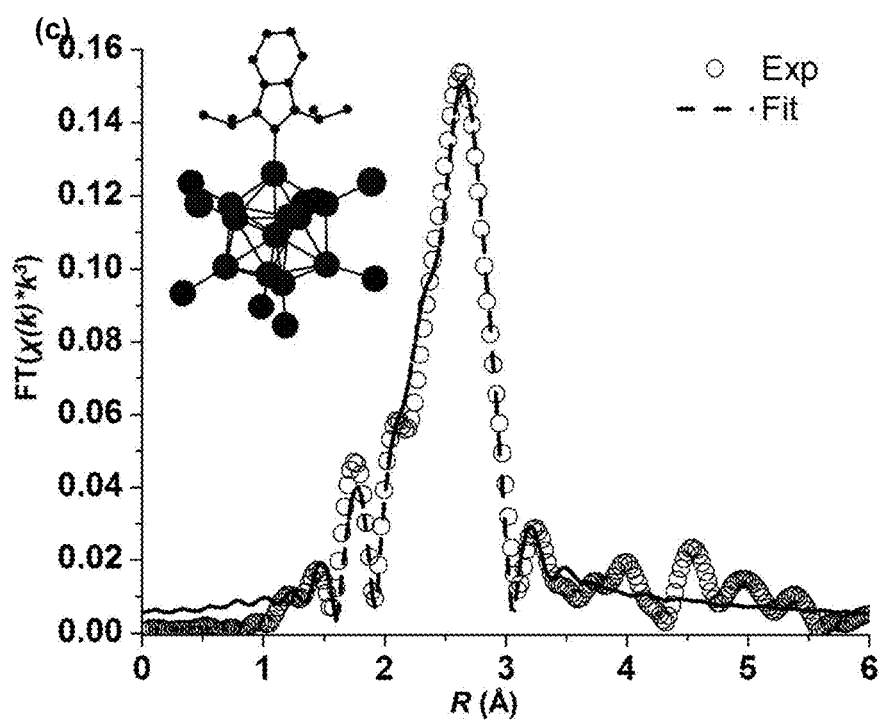

FIG. 33 depicts (a) Au L$_3$-edge EXAFS data of Au11-TPP8 and Au11-NHC(iPr) nanoclusters (NCs); k-spaces shown in (a) show a similarity between Au11 (–) and Au11-NHC(iPr) ( . . . ) and a difference of both NCs to the fcc bulk Au ( - - - ); (b) the R-space refinement of the Au11-TPP8 EXAFS data where experimental data (o) is compared to refinement data ( - - ); the inset figure shows the predicted structure of Au11-TPP8 NCs; (c) the R-space refinement of the Au11-NHC(iPr) EXAFS data where experimental data (°) is compared to refinement data ( - - ); the inset figure shows the predicted structure of Au11-NHC (iPr) NCs.

Figure 34:
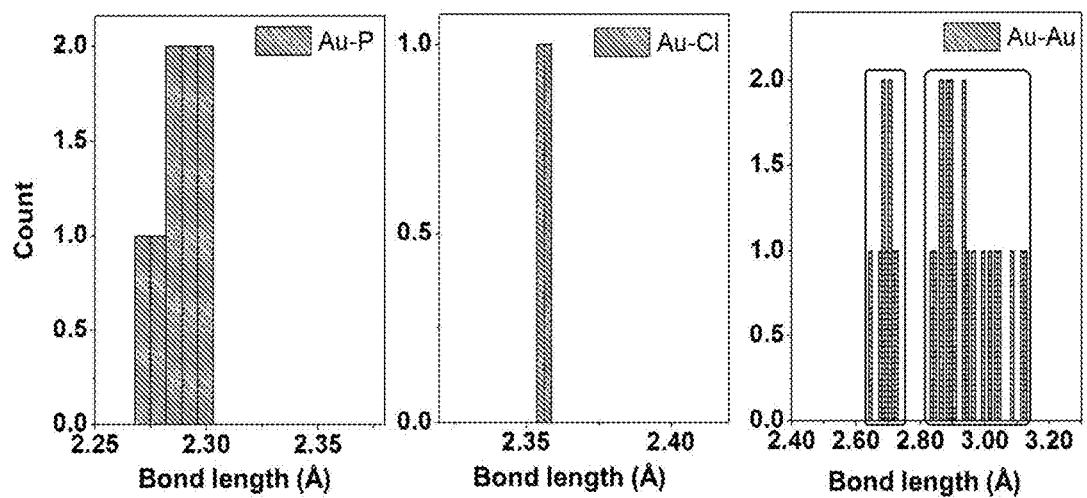

FIG. 34 depicts Au—P, Au—Cl, and Au—Au bond lengths plotted as histograms; histogram showing Au—Au bond lengths indicates that there were two main groupings of Au—Au bond lengths which were denoted as Au—Au$_1$ and Au—Au$_2$.

Figure 35:
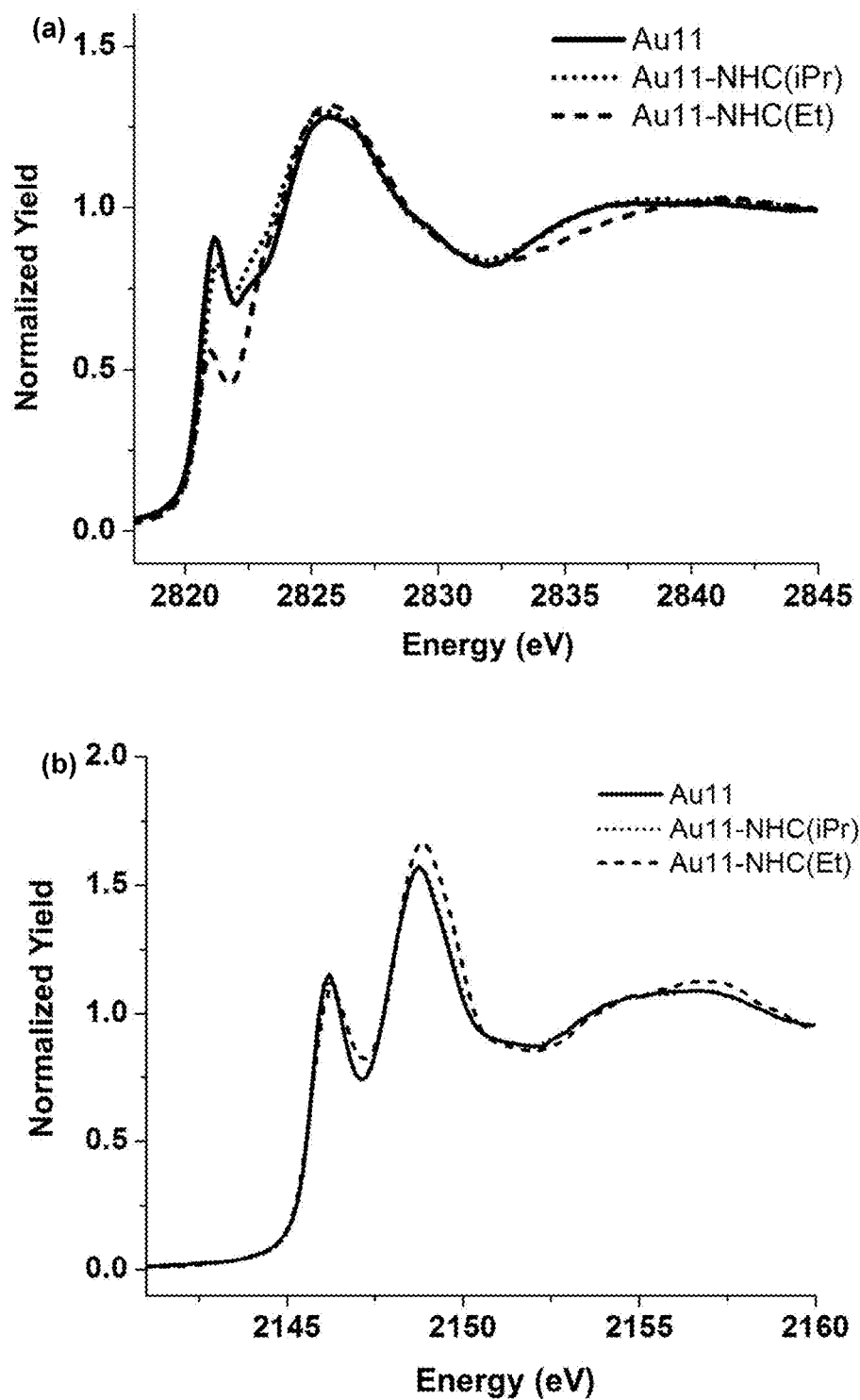

FIG. 35 depicts (a) C$_1$ K-edge XANES data of Au11-TPP8 (Au11; –), Au11-NHC(iPr)( - - - ), and Au11-Et ( - - - ); pre-edge feature demonstrates electronic mixing between C$_1$ and Au as well as depicts overall donating effect of NHC as number of substitutions increased from Au11→Au-iPr→Au11-Et; (b) P K-edge XANES data of Au11-TPP8 (Au11; –), Au11-NHC(iPr)( . . . ), and Au11-Et ( - - - ); Au11-NHC(iPr) and Au11-NHC(Et) demonstrated a decrease in pre-edge feature, albeit less intense, potentially as a result of Au—P donation/back donation mechanism.

Figure 36:
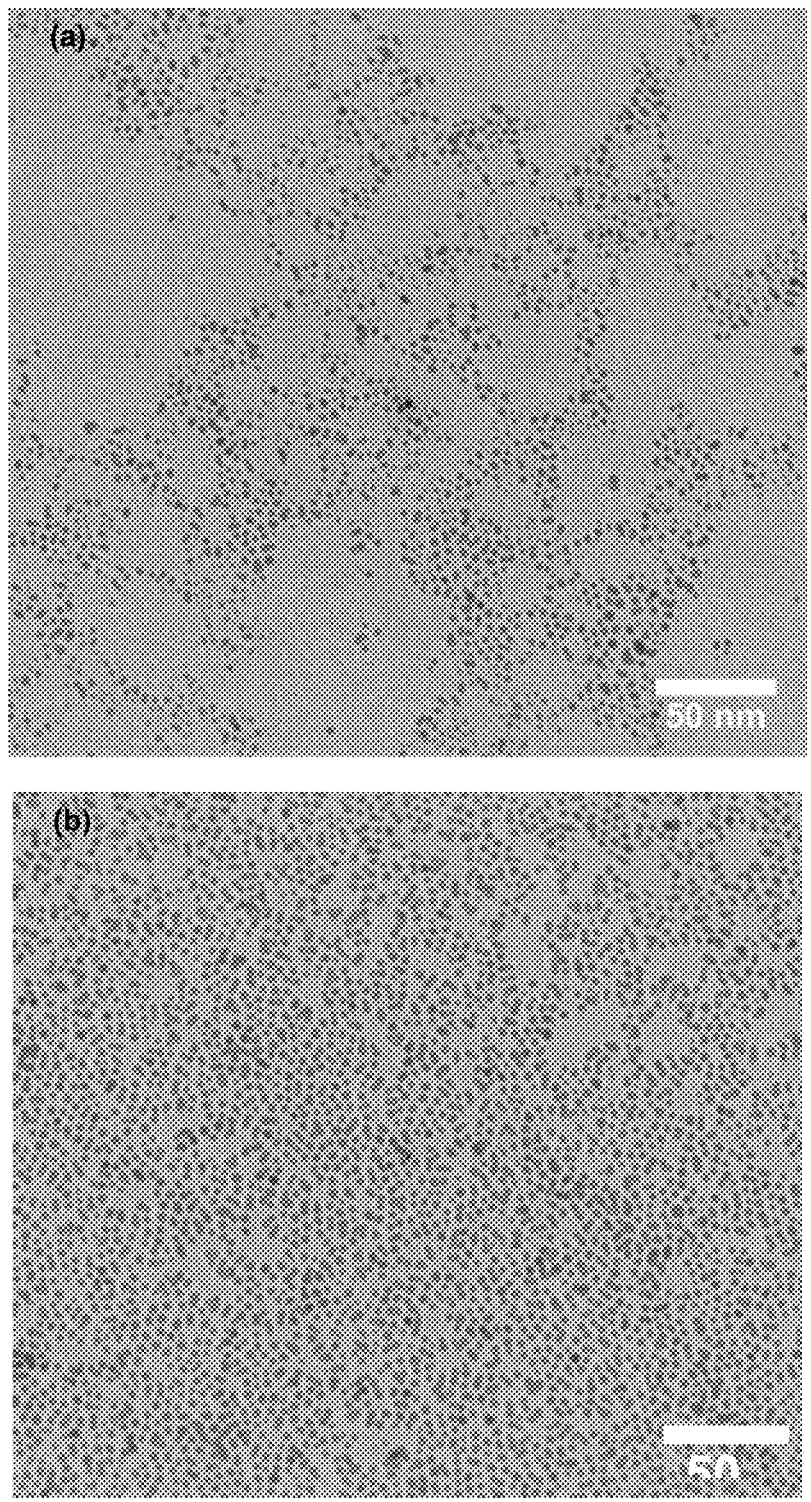

FIG. 36 depicts (a) TEM results of Au-DDS NPs and indicates that Au-DDS NPs have an average diameter of 2.0±0.5 nm; (b) TEM results of Au—NHC NPs and indicates that Au—NHC NPs have an average diameter of 2.4 f 0.6 nm.

Figure 37:
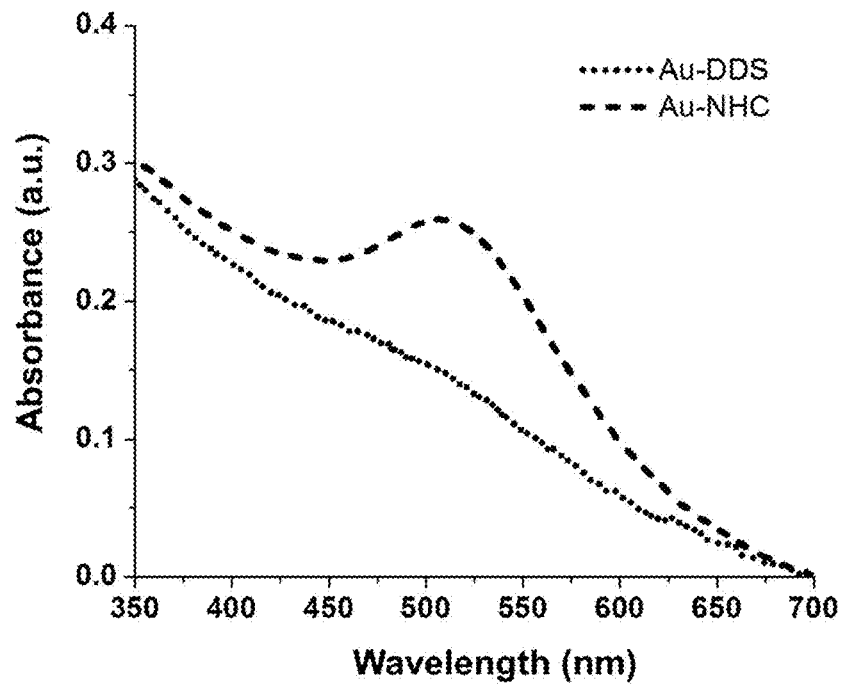

FIG. 37 depicts a more intense SPR peak of Au—NHC NPs ( - - - ) compared to Au-DDS NPs ( . . . ) which was considered to be from a combination of removal of the less electronegative S on the surface of the Au NPs and a slight increase in size.

Figure 38:
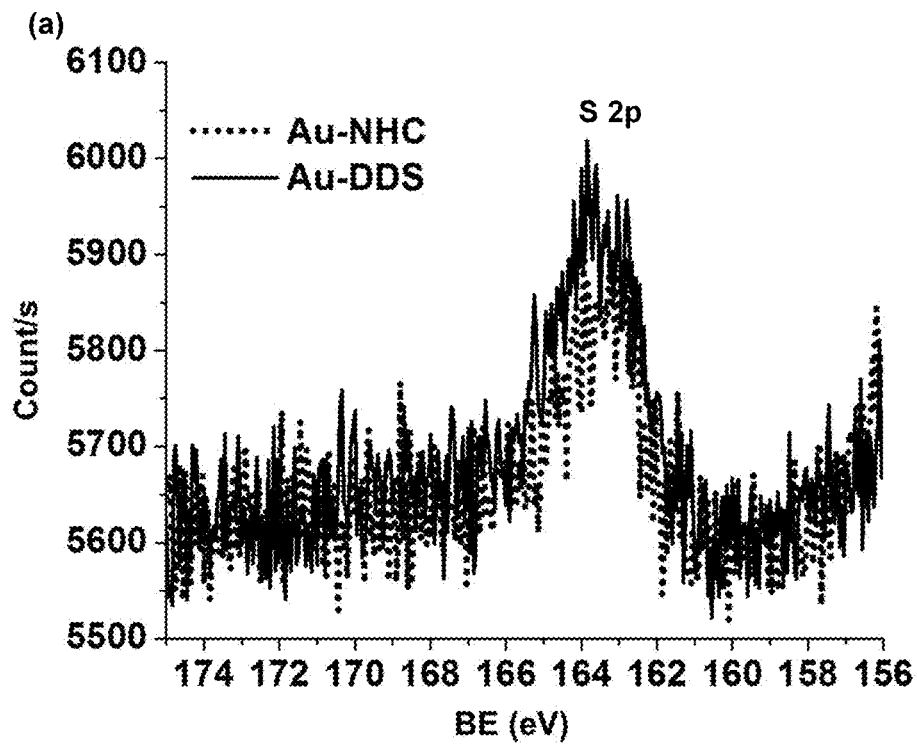
Figure 38:
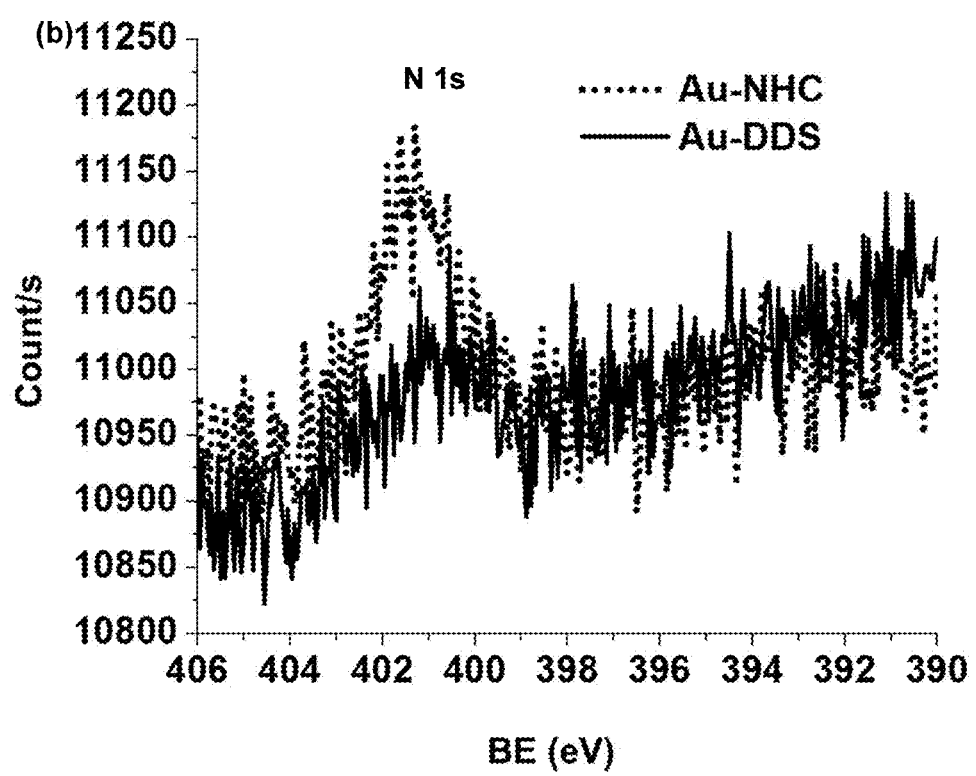

FIG. 38 depicts XPS spectra of (a) the S 2p peaks of Au-DDS (–) and Au—NHC NPs ( . . . ); and depicts a decrease in S with addition of NHC; (b) the N 1s peaks of Au-DDS (–) and Au—NHC NPs ( . . . ); and shows an increase in N with addition of NHC.

Figure 39:
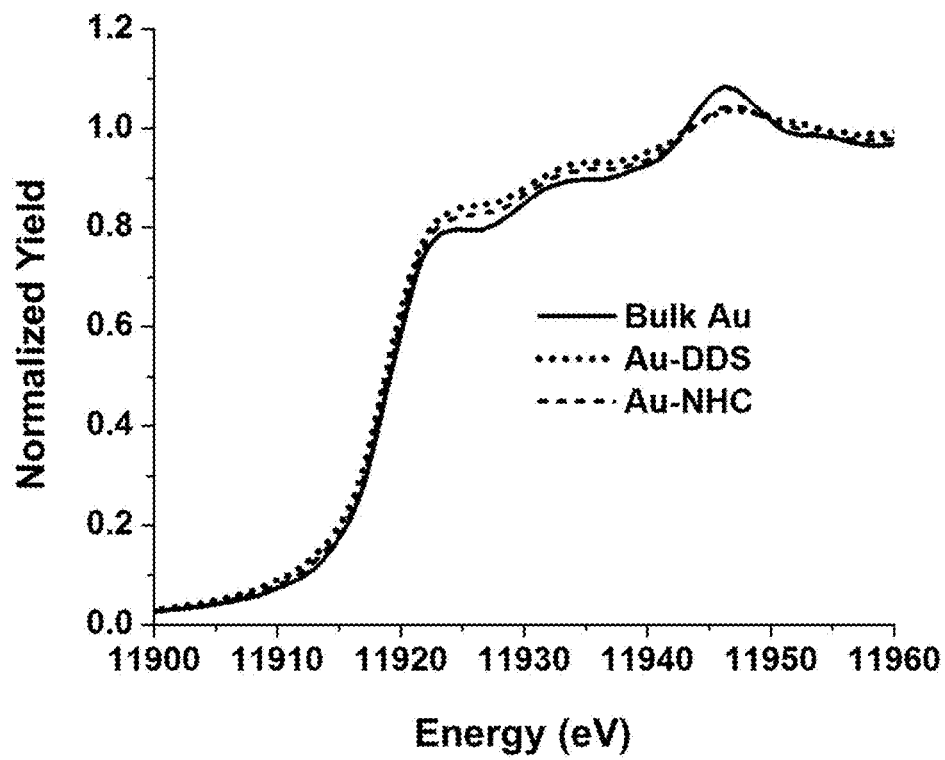

FIG. 39 depicts Au L$_3$-edge XANES of Au-DDS and Au—NHC NPs; XANES spectrum of Au—NHC NPs ( - - - ) indicated a less intense near-edge feature compared to Au-DDS NPs ( . . . ), and was more similar to bulk Au (–), consistent with replacement of DDS ligands with NHC.

Figure 40:
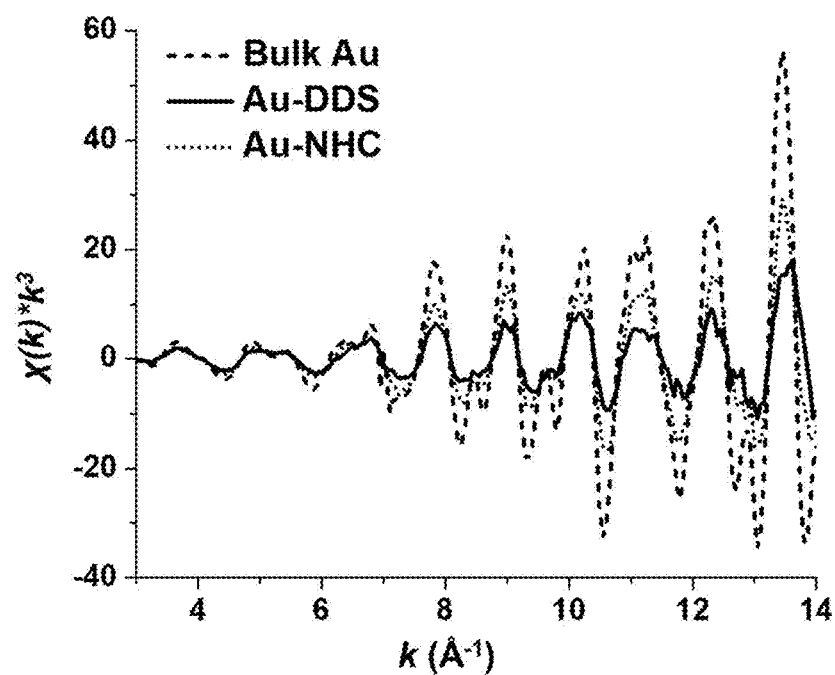

FIG. 40 depicts k-space EXAFS data for Au-DDS and Au—NHC NPs; k-space spectra of Au-DDS (–) and Au—NHC NPs ( . . . ) indicated similar bonding as bulk Au ( - - - ) but with lower coordination as represented by lower intensity oscillations.

Figure 41:
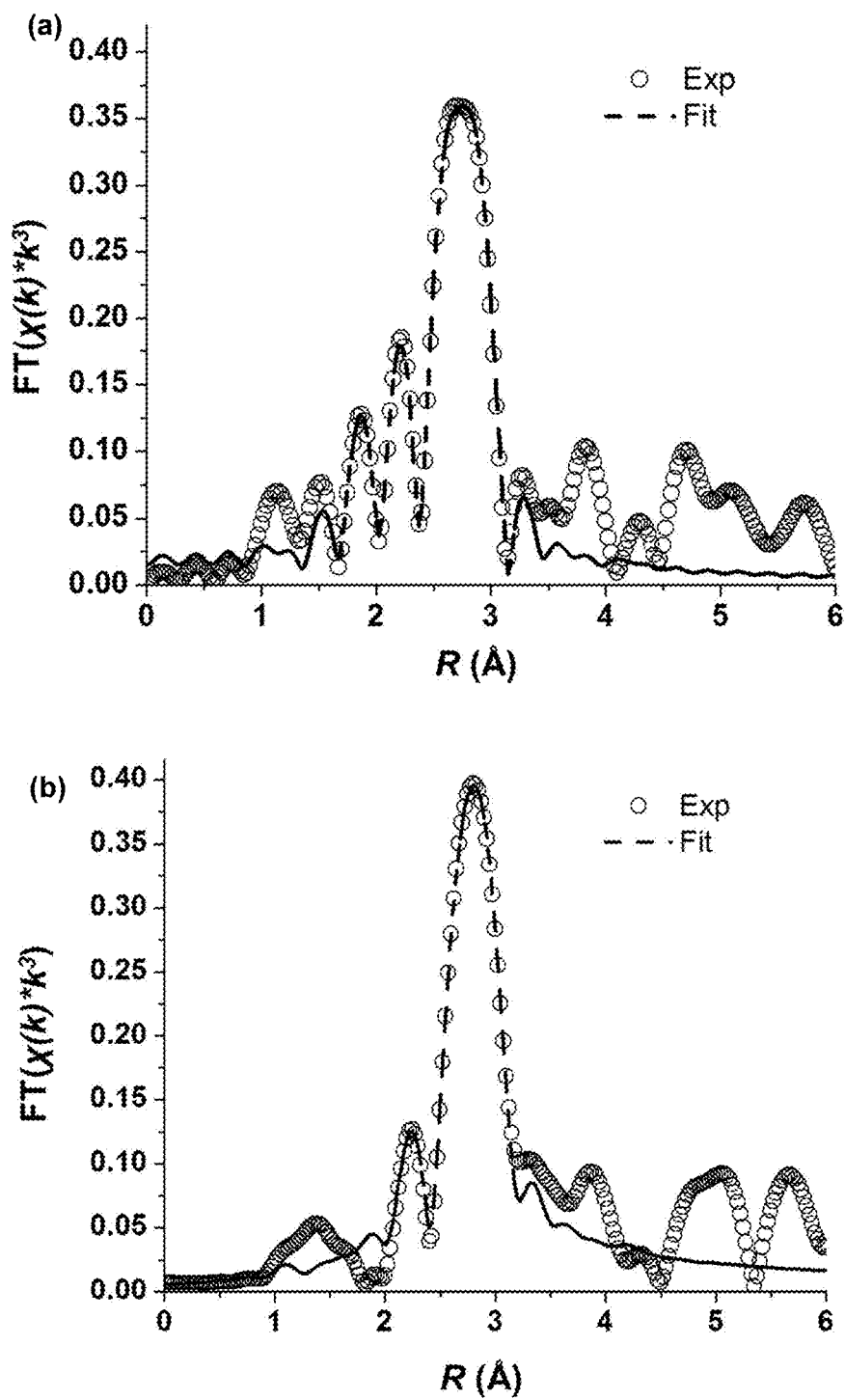

FIG. 41 depicts (a) refinement spectrum and experimental data for Au-DDS where experimental data)(° is compared to the refinement data ( - - ); (b) refinement spectrum and experimental data for Au—NHC where experimental data)(° is compared to the refinement data ( - - ).

Figure 42:
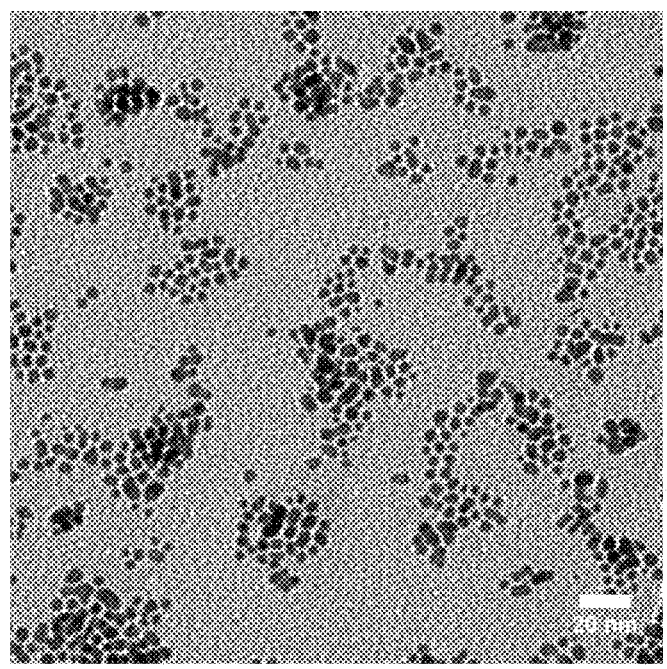

FIG. 42 depicts a TEM image of NHC-protected Au NPs prepared by a direct synthesis method using a THF and water/NaBH$_4$ combination; the Au NPs had an average diameter of 3.5±0.5 nm.

Figure 43:
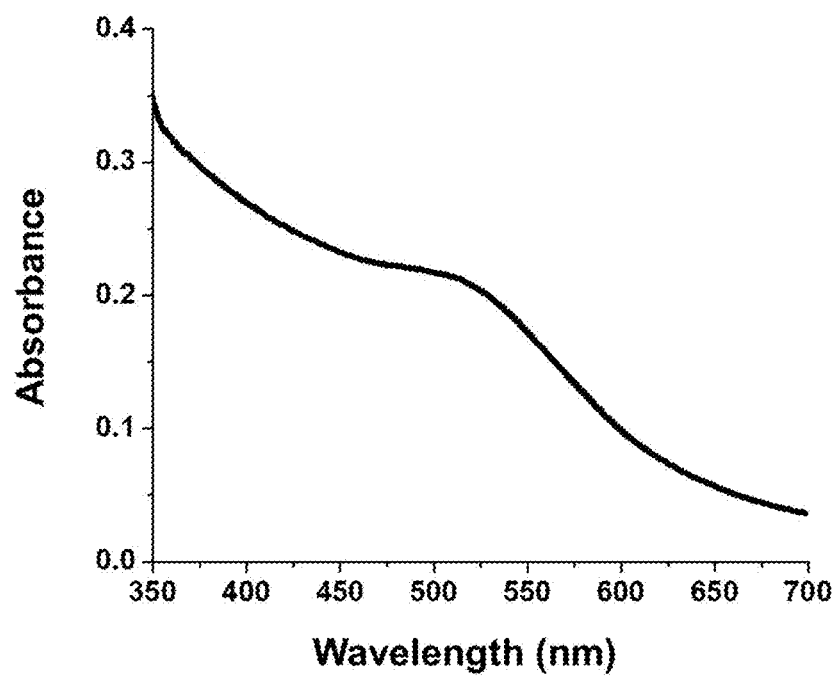

FIG. 43 depicts a SPR-induced absorbance peak at 520 nm of Au—NHC NPs.

Figure 44:
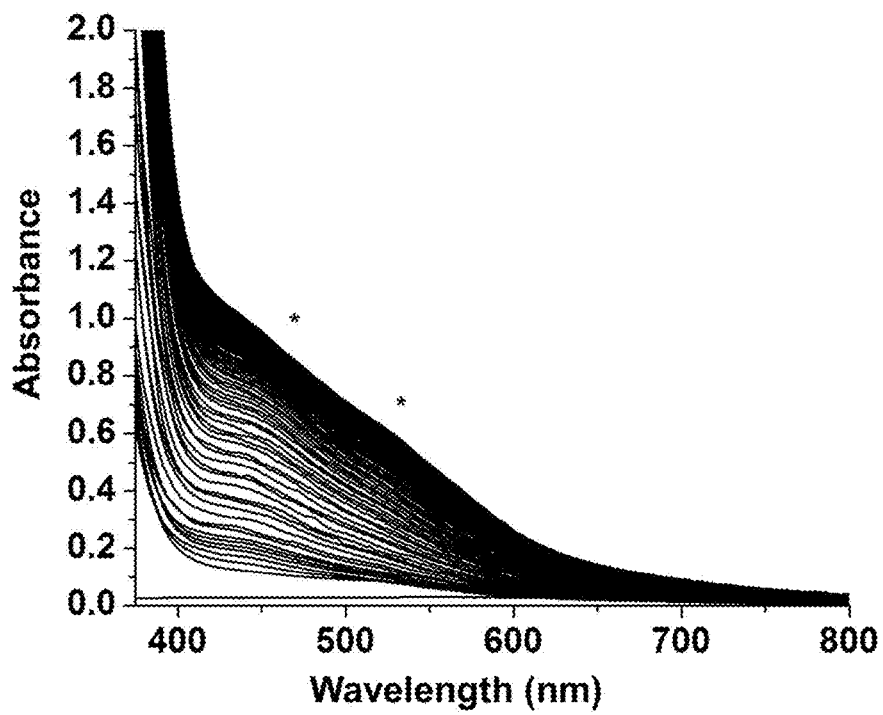

FIG. 44 depicts UV-vis spectra of Cu NCs and shows evolution of multiple absorbance bands (*) over 16 h reaction time.

Figure 45:
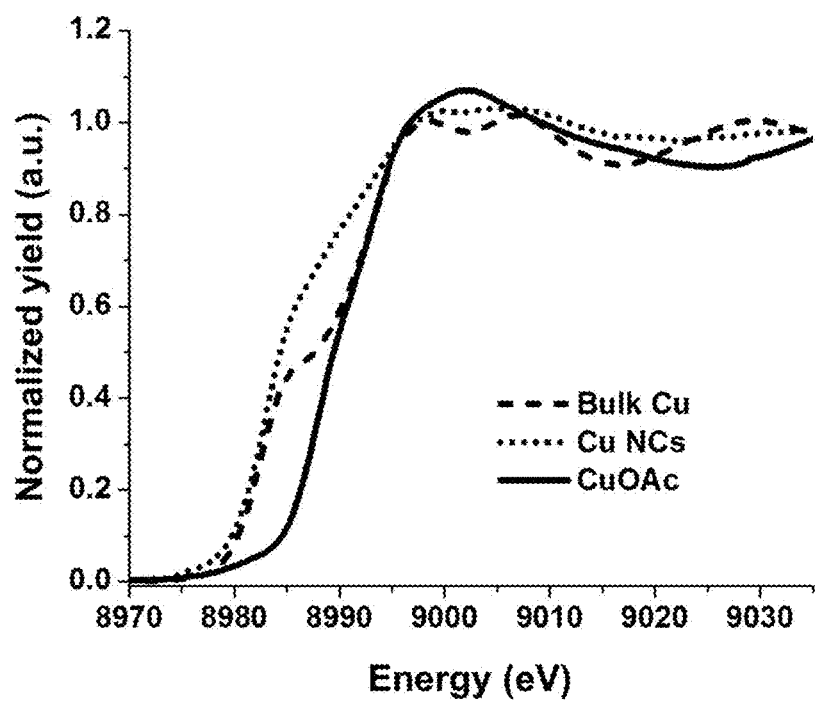

FIG. 45 depicts Cu K-edge XANES of Cu NCs, CuOAc, and bulk Cu; Cu NCs ( . . . ) and bulk Cu ( - - - ) shared similar features indicating similar overall metallic structure, while spectrum of CuOAc (–) was different from both.

Figure 46:
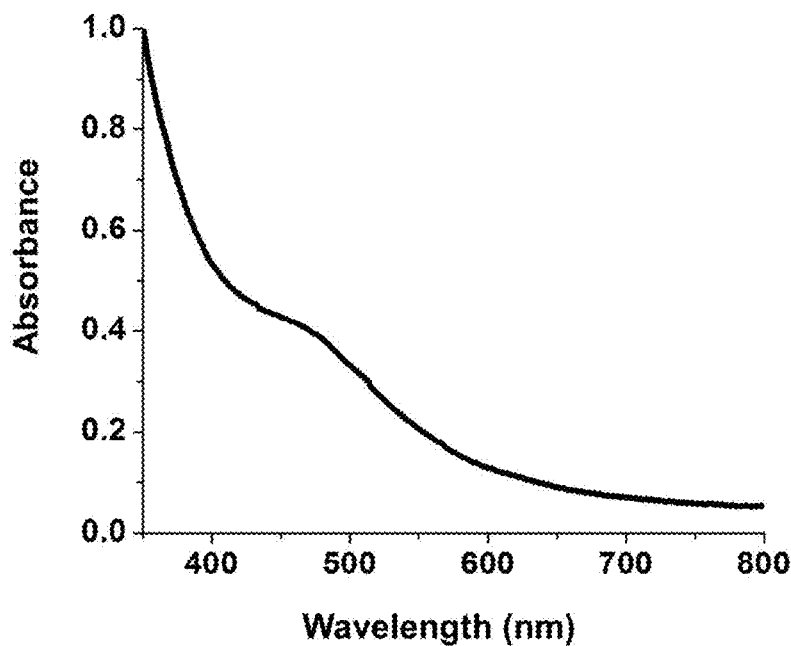

FIG. 46 depicts UV-Vis spectrum of Ag NPs and shows an SPR-induced absorbance feature around 400 nm of larger Ag NPs.

Figure 47:
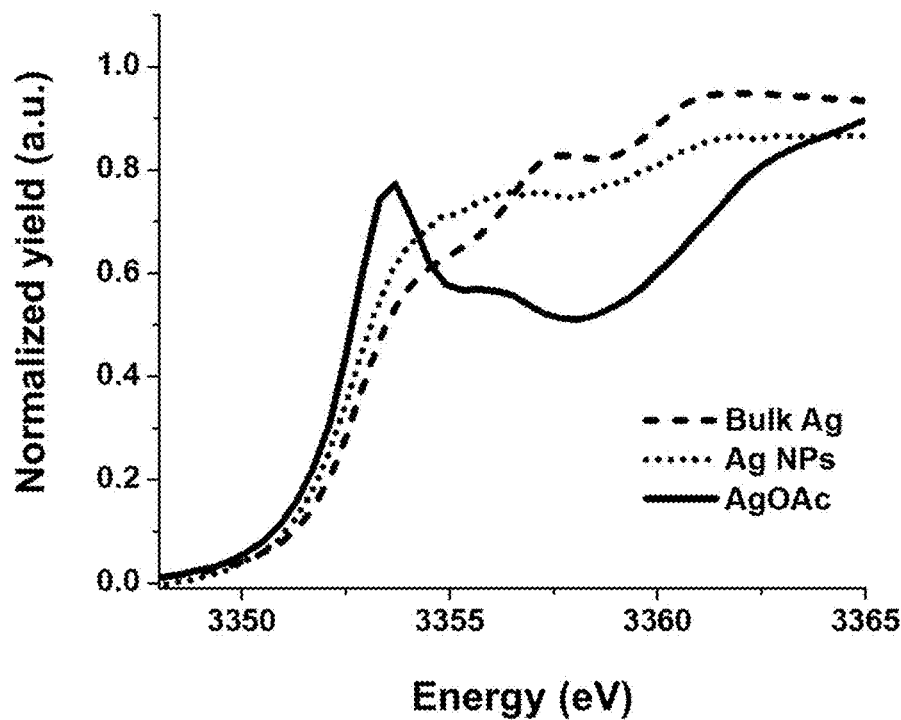

FIG. 47 depicts Ag L$_3$-edge XANES of Ag NPs, AgOAc, and bulk Ag; the first feature of Ag NP ( . . . ) spectrum indicated that Ag was reduced from AgOAc (–) to an oxidation state more similar to bulk Ag ( - - - ).

Figure 48:
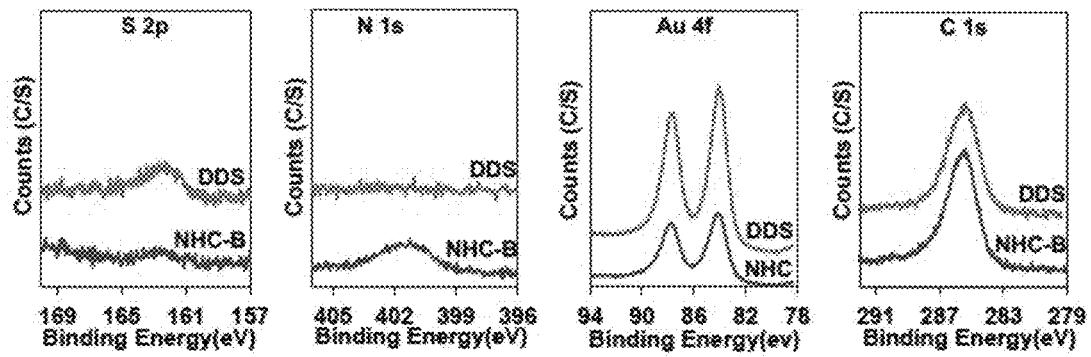

FIG. 48 depicts XPS spectra of bidentate Au—NHC NPs prepared from ligand exchange (NHC—B with bidentate n=4 ligand (bottom)), and Au-DDS NPs (top).

Figure 49:
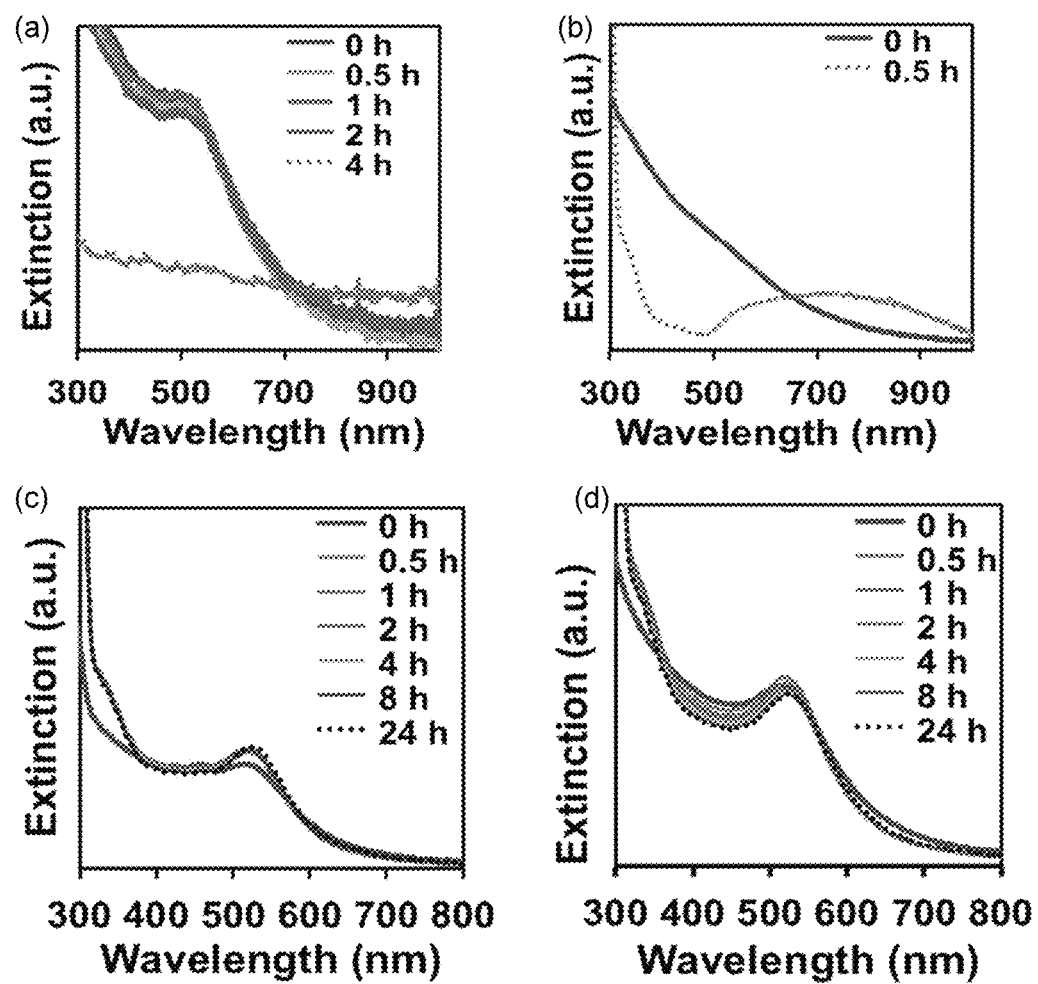

FIG. 49 depicts UV-Vis spectra of (a) Au-DDS NPs heated in toluene at 90° C.; (b) Au-DDT NPs heated in xylene at 130° C.; (c) monodentate Au—NHC NPs heated in xylene at 130° C.; (d) bidentate Au—NHC NPs heated in xylene at 130° C.

Figure 50:
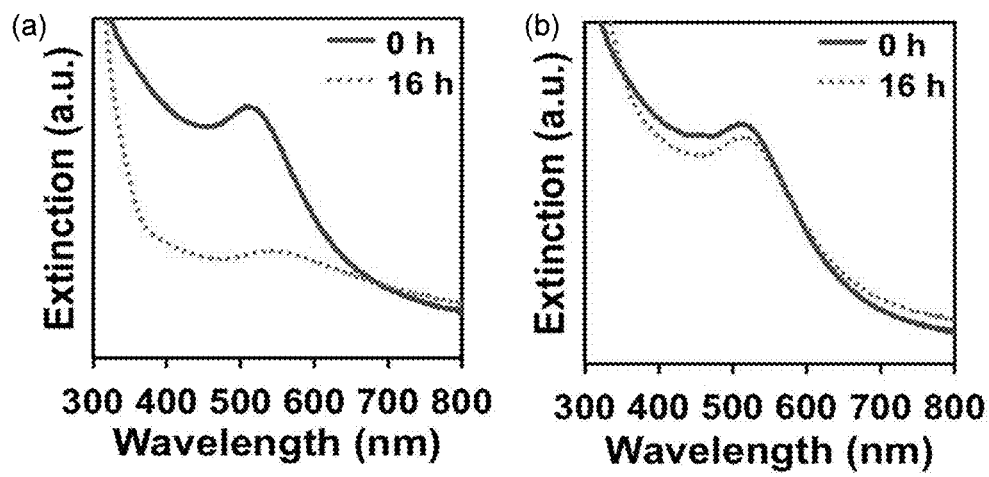

FIG. 50 depicts UV-Vis spectra of (a) monodentate Au—NHC NPs treated with 1 mM thiophenol in THF; (b) bidentate Au—NHC NPs treated with 1 mM thiophenol in THF.

Figure 51:
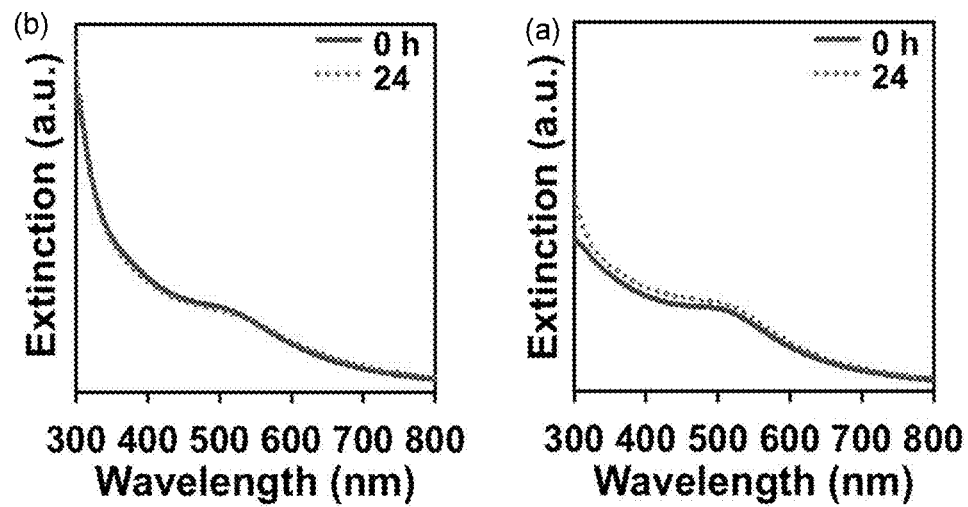

FIG. 51 depicts UV-Vis spectra of (a) monodentate Au—NHC NPs treated with 1 mM DTBP in THF; (b) bidentate Au—NHC NPs treated with 1 mM DTBP in THF.

Figure 52:
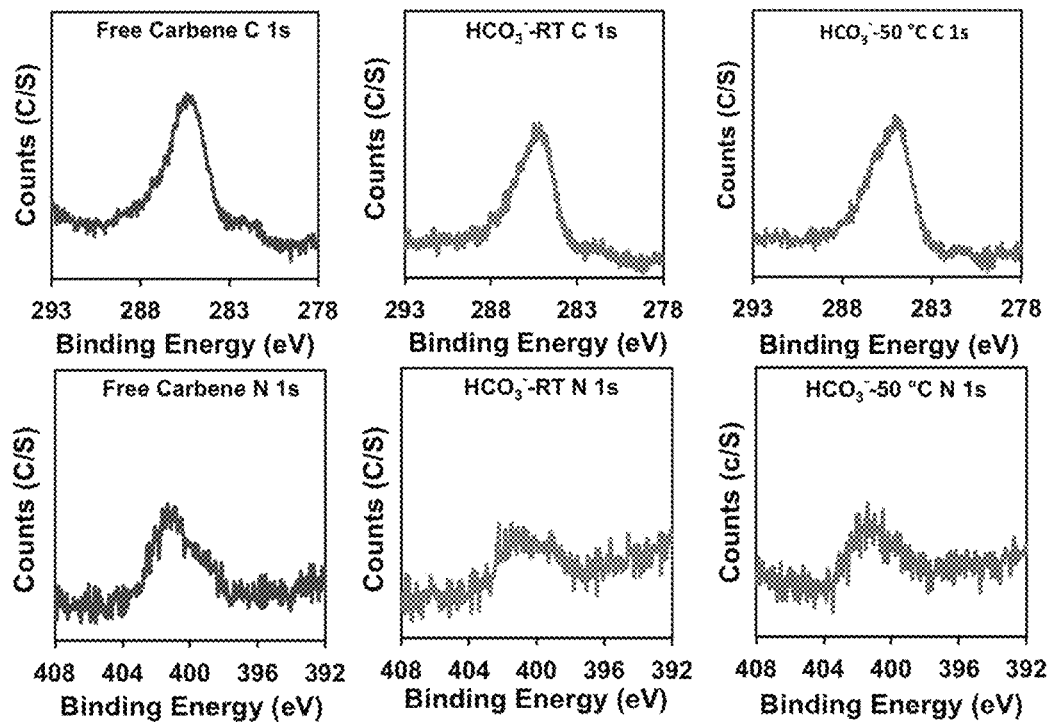

FIG. 52 depicts XPS spectra of aNHC-functionalized Au surfaces generated from: 1,3-diethylimidazo[1,2-a]pyridinium bromide (Free Carbene); and, 1,3-diethylimidazo[1,2-a]pyridinium hydrogen carbonate salt at room temperature (HCO$_3$-RT), and at 50° C. (HCO$_3$— 50° C.).

Figure 53:
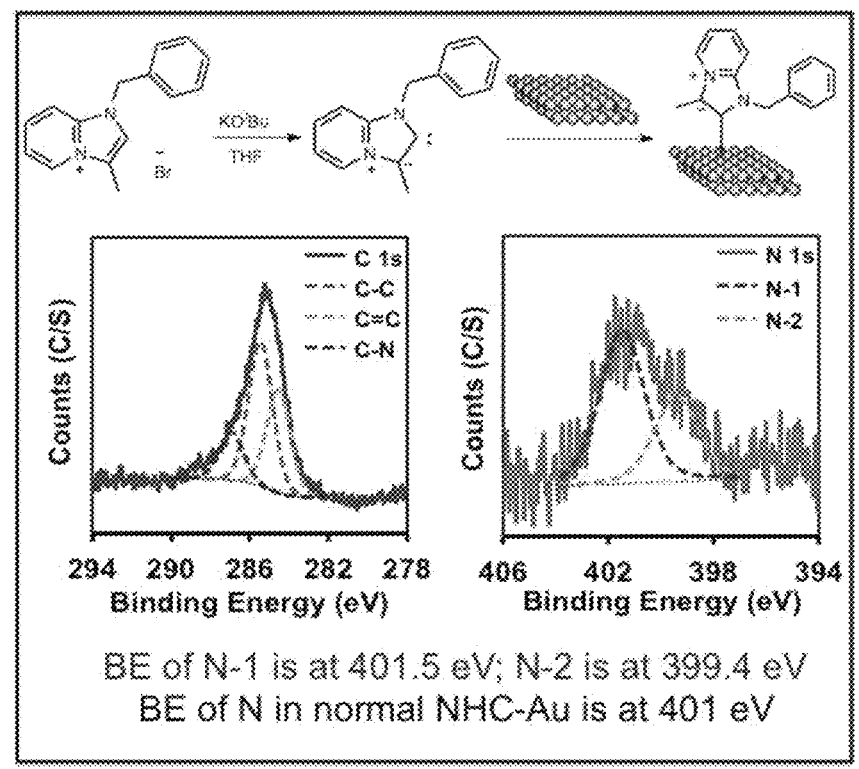

FIG. 53 depicts a free carbene deposition of 1-ethyl-3-benzylimidazo[1,2-a]pyridinium bromide on Au, and characterization thereof.

Figure 54:
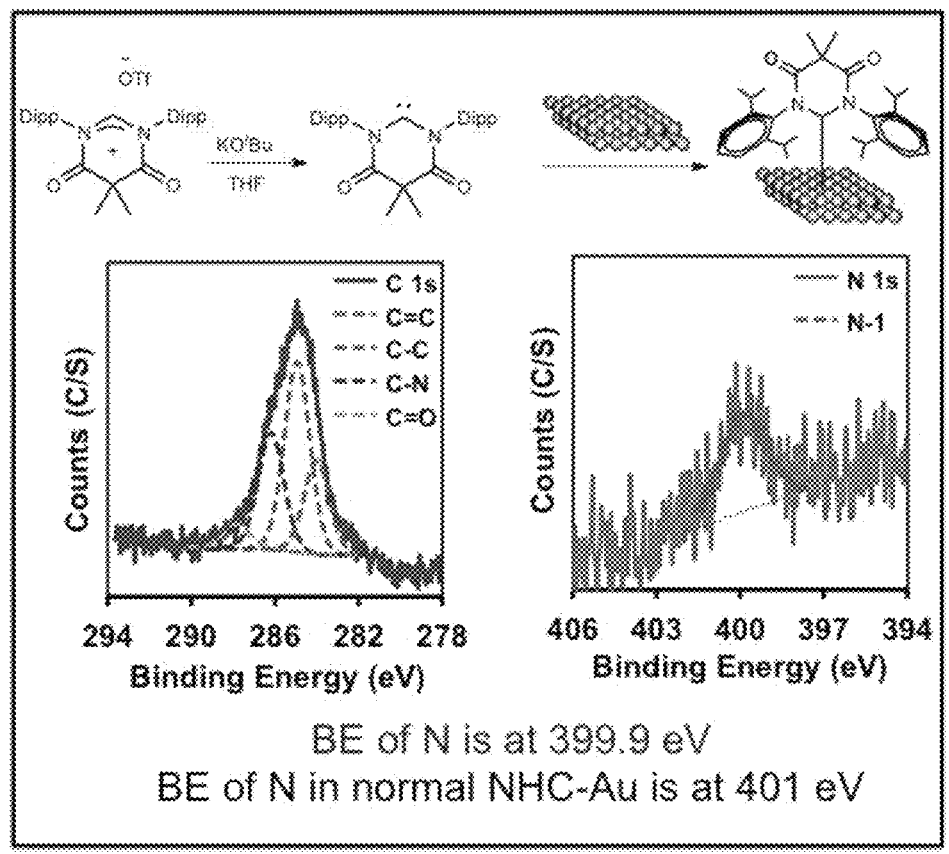

FIG. 54 depicts a free carbene deposition of a diamidocarbene (DAC)-triflate salt on Au, and characterization thereof.

Figure 55:
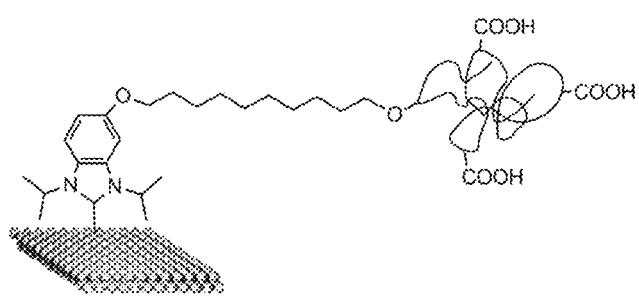

FIG. 55 depicts a schematic of carboxymethyldextran-coated NHC-based chip.

Figure 56:
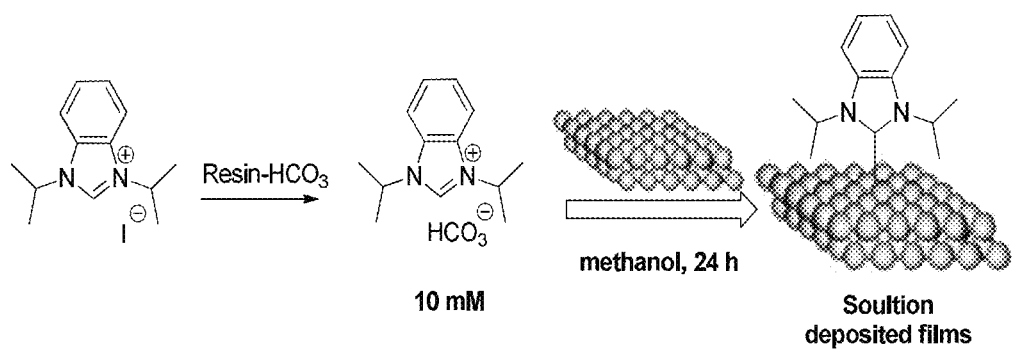

FIG. 56 depicts preparation of a self-assembled carbene monolayer on Au from 1,3-diisoproplylbenzimidazolium iodide.

Figure 57:
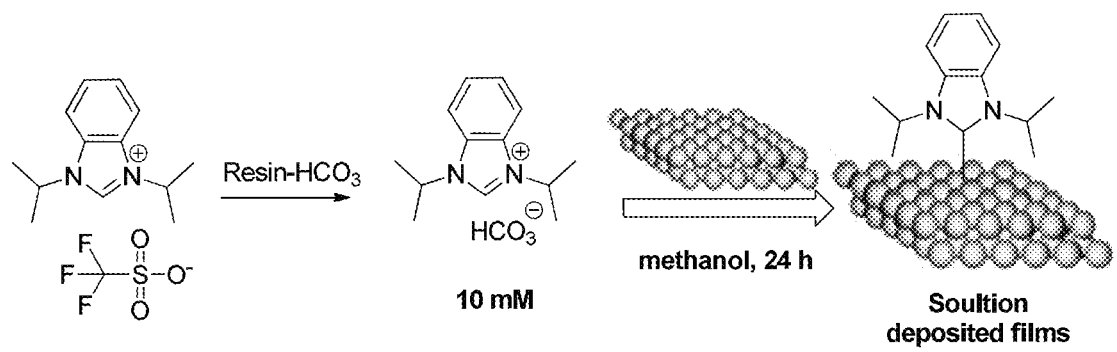

FIG. 57 depicts preparation of a self-assembled carbene monolayer on Au from 1,3-diisopropylbenzimidazolium triflate.

Figure 58:
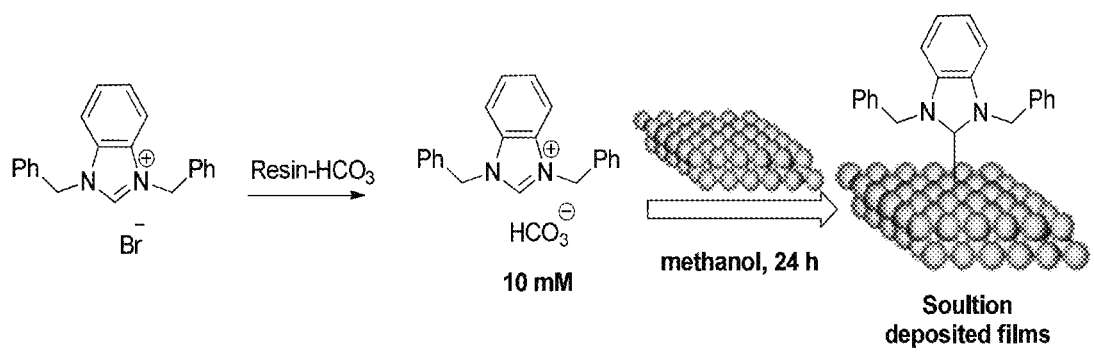

FIG. 58 depicts preparation of a self-assembled carbene monolayer on Au.

DETAILED DESCRIPTION OF THE INVENTION

Definitions

Unless defined otherwise, all technical and scientific terms used herein have the same meaning as commonly understood by one of ordinary skill in the art to which this invention belongs.

As used in the specification and claims, the singular forms "a", "an" and "the" include plural references unless the context clearly dictates otherwise.

The term "comprising" as used herein will be understood to mean that the list following is non-exhaustive and may or may not include any other additional suitable items, for example one or more further feature(s), component(s) and/or ingredient(s) as appropriate.

As used herein, the term "substituted" means having one or more substituent moieties whose presence either facilitates or improves the desired reaction, or does not impede the desired reaction. A "substituent" is an atom or group of bonded atoms that can be considered to have replaced one or more hydrogen atoms attached to a parent molecular entity; and, whose presence either facilitates or improves desired reactions and/or functions of the invention, or does not impede desired reactions and/or functions of the invention. Examples of substituents include alkyl, alkenyl, alkynyl, aryl, polycyclic aryl, benzyl, polycyclic benzyl, fused aromatic rings, aryl-halide, heteroaryl, cycloalkyl (non-aromatic ring), Si(alkyl)$_3$, Si(alkoxy)$_3$, halo, alkoxyl, amino, alkylamino, alkenylamino, amide, amidine, hydroxyl, thioether, alkylcarbonyl, alkylcarbonyloxy, arylcarbonyloxy, alkoxycarbonyloxy, aryloxycarbonyloxy, carbonate, alkoxycarbonyl, aminocarbonyl, alkylthiocarbonyl, phosphate, phosphate ester, phosphonato, phosphinato, cyano, acylamino, imino, sulfhydryl, alkylthio, arylthio, thiocarboxylate, dithiocarboxylate, sulfate, sulfato, sulfonate, sulfamoyl, sulfonamide, nitro, nitrile, azido, heterocyclyl, ether, ester, silicon-containing moieties, thioester, or a combination thereof. The substituents may themselves be substituted. For instance, an amino substituent may itself be mono or independently disubstituted by further substituents defined above, such as alkyl, alkenyl, alkynyl, aryl, aryl-halide and heteroaryl cycloalkyl (non-aromatic ring).

As used herein, "aliphatic" refers to hydrocarbon moieties that are linear, branched or cyclic, may be alkyl, alkenyl or alkynyl, and may be substituted or unsubstituted. "Alkenyl" means a hydrocarbon moiety that is linear, branched or cyclic and contains at least one carbon to carbon double bond. "Alkynyl" means a hydrocarbon moiety that is linear, branched or cyclic and contains at least one carbon to carbon triple bond.

As used herein, "alkyl" or "alkylene" refers to a linear, branched or cyclic, saturated hydrocarbon, which consists solely of single-bonded carbon and hydrogen atoms, which can be unsubstituted or is optionally substituted with one or more substituents, for example a methyl or ethyl group. Examples of saturated straight or branched chain alkyl groups include, but are not limited to, methyl, ethyl, 1-propyl, 2-propyl, 1-butyl, 2-butyl, 2-methyl-1-propyl, 2-methyl-2-propyl, 1-pentyl, 2-pentyl, 3-pentyl, 2-methyl-1-butyl, 3-methyl-1-butyl, 2-methyl-3-butyl, 2,2-dimethyl-1-propyl, 1-hexyl, 2-hexyl, 3-hexyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl and 2-ethyl-1-butyl, 1-heptyl and 1-octyl. As used herein the term "alkyl" encompasses cyclic alkyls, or cycloalkyl groups.

The term "cycloalkyl" as used herein refers to a non-aromatic, saturated or partially saturated, monocyclic, bicyclic or tricyclic hydrocarbon ring system containing at least 3 carbon atoms. Examples of $C_3$-$C_n$ cycloalkyl groups include, but are not limited to, cyclopropyl, cyclobutyl, cyclopentyl, cyclohexyl, cycloheptyl, cyclooctyl, norbornyl, adamantyl, bicyclo[2.2.2]oct-2-enyl, and bicyclo[2.2.2]octyl.

As used herein, "alkenyl" or "alkenylene" means a hydrocarbon moiety that is linear, branched or cyclic and comprises at least one carbon to carbon double bond which can be unsubstituted or optionally substituted with one or more substituents. "Alkynyl" or "alkynylene" means a hydrocarbon moiety that is linear, branched or cyclic and comprises at least one carbon to carbon triple bond which can be unsubstituted or optionally substituted with one or more substituents.

As used herein, "aryl" and/or "aromatic ring" refers to hydrocarbons derived from benzene or a benzene derivative that are unsaturated aromatic carbocyclic groups from 6 to 100 carbon atoms, or from which may or may not be a fused ring system, in some embodiments 6 to 50, in other embodiments 6 to 25, and in still other embodiments 6 to 15. The aryls may have a single or multiple rings. The term "aryl" and/or "aromatic ring" as used herein also includes substituted aryls and/or aromatic rings. Examples include, but are not limited to, phenyl, naphthyl, xylene, phenylethane, substituted phenyl, substituted naphthyl, substituted xylene, substituted 4-ethylphenyl and the like.

As used herein, the term "Au(111)" refers to a single crystal of gold, either alone or supported on a substrate (e.g. mica) that has a particularly flat orientation of its atoms on the surface of the crystal. (111) refers to a dominant arrangement of exposed surface atoms to form a 1,1,1 crystal plane (Miller indices $x=y=z=+1$).

As used herein, "polycrystalline gold" refers to a gold sample that has many small crystals of the same or different crystal structure adhered to a substrate, such as, but not limited to, a silicon wafer (the silicon wafer may be pre-coated with a chromium or titanium layer for improved adhesion). Such polycrystalline gold can be used for electrochemical applications. The surface texture of polycrystalline gold can be rougher than the smooth Au(111) referred to above; however, polycrystalline gold's dominant arrangement of exposed surface atoms is typically (111). The rms-roughness (rms=root mean squared) of the polycrystalline samples used herein was less than 2.5 nm As used herein, "cycle" refers to an aromatic or nonaromatic monocyclic, bicyclic, or fused ring system of carbon atoms, which can be substituted or unsubstituted. Included within the term "cycle" are cycloalkyls and aryls, as defined above.

As used herein, "heteroaryl" or "heteroaromatic" refers to an aryl (including fused aryl rings) that includes heteroatoms selected from oxygen, nitrogen, sulfur and phosphorus. A "heteroatom" refers to an atom that is not carbon or hydrogen, such as nitrogen, oxygen, sulfur, or phosphorus. Heteroaryl or heteroaromatic groups include, for example, furanyl, thiophenyl, pyrrolyl, imidazoyl, benzamidazoyl, 1,2- or 1,3-oxazolyl, 1,2- or 1,3-diazolyl, 1,2,3- or 1,2,4-triazolyl, and the like.

As used herein, a "heterocycle" is an aromatic or non-aromatic monocyclic or bicyclic ring of carbon atoms and heteroatoms selected from oxygen, nitrogen, sulfur and phosphorus. Included within the term "heterocycle" are heteroaryls, as defined above. Also included within this term are monocyclic and bicyclic rings that include one or more double and/or triple bonds within the ring. Examples of 3- to 9-membered heterocycles include, but are not limited to, aziridinyl, oxiranyl, thiiranyl, azirinyl, diaziridinyl, diazirinyl, oxaziridinyl, azetidinyl, azetidinonyl, oxetanyl, thietanyl, piperidinyl, piperazinyl, morpholinyl, pyrrolyl, oxazinyl, thiazinyl, diazinyl, triazinyl, tetrazinyl, imidazolyl, benzimidazolyl, tetrazolyl, indolyl, isoquinolinyl, quinolinyl, quinazolinyl, pyrrolidinyl, purinyl, isoxazolyl, benzisoxazolyl, furanyl, furazanyl, pyridinyl, oxazolyl, benzoxazolyl, thiazolyl, benzthiazolyl, thiophenyl, pyrazolyl, triazolyl, benzodiazolyl, benzotriazolyl, pyrimidinyl, isoindolyl and indazolyl.

As used herein, the term "mesoionic" refers to a dipolar five- or six-membered heterocyclic compounds in which both a negative and a positive charge are delocalized, for which a totally covalent structure cannot be written, and which cannot be represented satisfactorily by any one polar structure.

As used herein, the term "mesityl" refers to the substituent derived from mesitylene, or 1,3,5-trimethylbenzene.

As used herein, "diisopropylphenyl" is the substituent

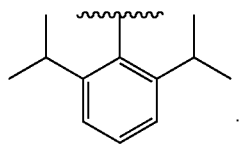 [SMILES: *c1c(C(C)C)cccc1C(C)C]

As used herein, "MIC" refers to meso-ionic carbene.

As used herein, the term "resin" or "ion exchange resin" refers to a polymer(s) that is capable of exchanging particular ions within the polymer with ions in a solution that is passed through them.

As used herein, the term "TEM" refers to Transmission Electron Microscopy.

As used herein, a "chemically derivatizable group" is any functional group capable of participating in a chemical reaction, such as, but not limited to, electrophilic/nucleophilic substitution, addition, elimination, acid/base, reduction, oxidation, radical, pericyclic, Diels-Alder, metathesis or click chemistry reactions.

As used herein, the term "unsubstituted" refers to any open valence of an atom being occupied by hydrogen. Also, if an occupant of an open valence position on an atom is not specified then it is hydrogen.

As used herein, a "functional group" is a specific group of atoms within a molecule that are responsible for characteristic chemical reactions. Thus functional groups are moieties within a molecule that are likely to participate in chemical reactions.

As used herein, "NHC" or "carbene" refers to a N-heterocyclic carbene. Structural formulae of certain NHCs and NHCs on metal surfaces are presented herein.

As used herein, carbene is an electronically neutral species comprising a carbon having two nonbonding electrons (i.e., form a lone pair), which is referred to as the "carbene carbon." In the carbenes used in the method and materials of the present application, this carbon having the two nonbonding electrons is the carbon that will be bound to a metal surface and is divalent; in other words, this carbon is covalently bonded to two substituents of any kind, and bears two nonbonding electrons that may be spin-paired (singlet state), such that the carbon is available for formation of a dative bond. As used herein, N-heterocyclic carbene refers to heterocyclic moiety that includes a carbene, as defined above, which is electronic and/or resonance stabilized, typically by the presence of one or more carbene-adjacent heteroatoms, and/or is sterically stabilized by substituents adjacent to the carbene. A non-limiting example of such a stabilized carbene is provided below:

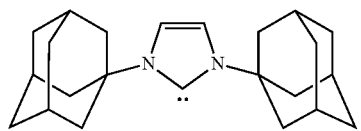

As would be well appreciated by a worker skilled in the art, there are many alternative substituents that would stabilize the carbene. Furthermore, as would be readily apparent to a worker skilled in the art, in the case of two stabilizing substituents, it is not necessary for the two substituents to be the same.

As used herein, a "carbene precursor" or "carbene salt" refers to a non-carbenic salt that, under appropriate conditions, will generate a carbene in situ, such as an N-heterocyclic carbene, as defined above, either directly, or indirectly through a transient or intermediate species.

As used herein, a "self-assembled monolayer" is a molecular assembly formed spontaneously, from the vapour or liquid phase, onto surfaces by adsorption or chemisorption, and are organized into large, essentially ordered domains.

As used herein, a 'carbene monolayer' or 'carbene self-assembled monolayer' or 'self-assembled carbene monolayer' is a molecular assembly derived from carbenes that forms spontaneously from at least one carbene precursor, from the vapour or liquid phase, onto surfaces by adsorption or chemisorption, and are organized into large, essentially ordered domains.

The term 'film', when used herein in the context of carbenes or carbene precursors (e.g., NHC film), is synonymous with monolayer.

As used herein, the term "composite material" or "carbene-functionalized composite material" refers to materials made from two or more constituent materials (i.e., metal surfaces, carbenes, carbene precursors) having different physical or chemical properties. Such materials may be preferred for many reasons, such as materials, which are stronger, lighter or less expensive when compared to traditional materials. In a non-limiting example, composite materials may be generally but not exclusively used for buildings, bridges and structures such as boat hulls, automotive and aircraft bodies, and storage tanks. Advanced examples perform on spacecraft in demanding environments.

As used herein, the term "dative bond" refers to a bond (a shared pair of electrons) forms between two atoms wherein both of the electrons that make up the bond came from the same atom.

As used herein, the term "uniform" when used to refer to a monolayer, as defined above, indicates that the monolayer is generally consistent, or without significant variation, across substantially the entirety of the functionalized surface.

As used herein, the term "stability" refers to both the physical and chemical stability of the herein described carbene monolayers. "Physical stability" refers to retention of improved physical properties of carbene monolayers on a timescale of their expected usefulness in the presence of air, moisture or heat, and under the expected conditions of application. This physical stability is relative to other self-assembled monolayer-functionalized surfaces, such as thio-functionalized surfaces. "Chemical stability" refers to thermodynamic stability of the carbene monolayers upon exposure to different chemicals or mixtures of chemicals, including but not limited to air, oxygen, water, acid, base, oxidant, reductant, etc. It may refer to a lack of undesired chemical reactivity exhibited by the carbene monolayers in the environment, or under the conditions, of normal use. That is, it retains its useful properties on the timescale of its expected usefulness in the presence of air, moisture or heat, and under the expected conditions of application. This chemical stability may be defined relative to other self-assembled monolayer-functionalized surfaces, such as thio-functionalized surfaces.

As used herein, the term "contaminant" or "contamination" refers to any elemental, atomic or molecular species, or combination thereof; whose presence impedes the desired reactions to form the herein described composite materials, or impedes the desired purity, stability, or properties of the final composite materials.

As used herein, a "metal film" refers to a metal layer that has lateral dimensions (i.e., thickness) in the range of 0.1-100 nm, or alternatively 0.1-100 μm, or alternatively >100 μm.

As used herein, "Au(NP)" or "Au11-NP" or "Au—X NP" where X is DDS, DDT, NHC refers to gold nanoparticles. As used herein, a "nanoparticle" is a plurality of metal atoms, with at least one dimension less than 100 nm, that together form a nano-scale geometric shape that is optionally multi-faceted. Properties of a metal nanoparticle typically deviate from the properties of a bulk metal.

The term "nanoclusters" or "NCs" as used herein refers to a subset of nanoparticles that are atomically precise; consisting of a few metal atoms or tens of metal atoms protected by ligands; and have at least one dimension is less than 10 nm in length.

As used herein, a "single crystal metal" refers to an entire metal sample in which a crystal lattice is continuous and unbroken to the edges of the sample.

The term "immersing" or "immersion" as used herein will be understood to mean any method of contacting a metal-containing material with carbenes, as described herein, and/or carbene precursors, as described herein, in such a manner that a metal surface of the metal-containing material is fully or partially covered by the carbenes and/or carbene precursors. Immersing can include, but is not limited to, dipping a metal material into a solution, pouring or flowing a solution over a metal surface, spraying a metal surface with a solution, or roll coating a surface.

As used herein, the term "vapour depositing" refers to deposition of a film, coating, or self-assembled monolayer onto a surface in a vacuum environment, at temperatures ≤0° C., or alternatively between 0-25° C., or alternatively between 25-100° C., or alternatively ≥100° C.

As used herein, "microelectronic devices" refers to very small electronic designs and/or components that are made from semiconducting materials and manufactured on the micrometer scale, or smaller. Examples of such devices include, but are not limited to, transistors, capacitors, inductors, resistors, diodes, insulators, conductors or combinations thereof.

As used herein, the term "surface properties" refers to properties imparted to a surface as a result of being functionalized by heterocyclic carbenes, as described herein. Examples of said surface properties include, but are not limited to, hydrophobicity/hydrophilicity, conductivity, electrical impedance, piezoelectricity, absorbance, radiance, fluorescence, chemical or biochemical reactivity, or luminescence.

As used herein, the term "sensing applications" refers to systems, methods, procedures, and/or instruments that use sensors to receive and respond to signals and/or stimuli. Examples of sensors can include, but are not limited to, optical sensors (based on, for example, absorbance, reflectance, luminescence, fluorescence, or light scattering effects); electrochemical sensors (based on, for example, voltammetric, amperometric, and potentiometric effects, chemically sensitized field effect transistors, or potentiometric solid electrolyte gas sensors); electrical sensors (based on, for example, metal oxide semiconductors or organic semiconductors); mass-sensitive sensors (based on, for example, piezoelectric or surface acoustic wave effects); magnetic sensors (based on, for example, paramagnetic properties); thermometric sensors (based on, for example, heat effects of a specific chemical reaction, or adsorption); radiation sensitive sensors (based on, for example, absorbance or radiation emission); biosensors (based on, for example, signal transduction, biological recognition elements, or an analyte being sensed) (D. Buenger, et al., *Progress in Polymer Science* 37, 1678 (2012)). Specific sensing applications can include, but are not limited to, surface plasmon resonance.

As used herein the abbreviation "XPS" is used to refer to X-ray photoelectron spectroscopy. A typical XPS spectrum is a plot of number of electrons detected as a function of the binding energy of detected electrons. Each element produces a characteristic set of XPS peaks at characteristic binding energy values. The peaks identify each element, and often its oxidation state, that exists on, or some 100 nm below, a surface being analyzed. XPS reveals the number of detected electrons in each of the characteristic peaks. This number is related to the amount of an element within the sample, and it reveals whether contamination, if any, exists at the surface or in the bulk of the sample.

As used herein, the term 'metal chip' refers to a composite material in which a substrate (e.g., glass) has had a metal film deposited on it, comprising appropriate connections such that it can be incorporated into a commercial surface plasmon resonance instrument.

As used herein in relation to carbene precursors, the term 'starting anion' refers to a non-carbonate anion of a carbene precursor.

As used herein, the term 'metal salt' refers to a compound comprising a metal ion and a counter ion.

As used herein, the term 'elevated temperature' refers to a temperature that is above ambient temperatures.

As used herein, the term 'material' refers to a thing made from matter. In some embodiments, a 'material' may compose at least two components. In other embodiments, a 'material' may compose multiple components.

As used herein, the term 'metal complex' refers to a chemical species that has a metal atom or ion with a number of other molecules or ions surrounding it.

As used herein, the term "1a" refers to 1,3-Diisoproplyl-benzimidazolium iodide. As used herein, the term "1b" refers to 1,3-dimethylbenzimidazolium iodide. As used herein, the term "1c" refers to 5-((12-(4-(Ferrocenyl)-1H-1,2,3-triazol-1-yl)dodecyl)oxy)-1,3-diisopropyl-1H-benzo[d]imidazol-3-ium iodide.

As used herein, the term "1d" refers to 5-(Dodecyloxy)-1,3-diisopropyl-1H-benzo[d]imidazol-3-ium iodide.

As used herein, the term "iPr$_2$bimy" or 2a refers to 1,3-dihydro-1,3-bisisopropylbenzimidazol-2-ylidene), see structural formulae in Example 10.

As used herein, the term "iPr$_2$bimy(H)[HCO$_3$]" or 3a refers to 1,3-diisopropylbenzimidazolium hydrogen carbonate, see structural formulae in Example 10.

As used herein, the term "Me$_2$bimy(H)[HCO$_3$]" or 3b refers to 1,3-dimethylbenzimidazolium hydrogen carbonate).

As used herein, the term "3c" refers to 5-((12-(4-(Ferrocenyl)-1H-1,2,3-triazol-1-yl)dodecyl)oxy)-1,3-diisopropyl-1H-benzo[d]imidazol-3-ium hydrogen carbonate. See structural formulae in Example 1.

As used herein, the term "3d" refers to 5-(Dodecyloxy)-1,3-diisopropyl-1H-benzo[d]imidazol-3-ium hydrogen carbonate (see structural formulae in Example 1).

As used herein, the term "UHV" refers to ultra-high vacuum.

As used herein, the term "TPD" refers to temperature programmed desorption.

As used herein, the term "LEED" refers to low energy electron diffraction.

As used herein, the term "STM" refers to scanning tunneling microscopy.

As used herein, the term "SAM" refers to self-assembled monolayer.

As used herein, the term "SPR" refers to surface plasmon resonance.

As used herein, the term "THF" refers to tetrahydrofuran.

As used herein, the term "NMR" refers to nuclear magnetic resonance.

As used herein, the term "gs-COSY" refers to gradient selected correlation spectroscopy.

As used herein, the term "gs-HSQC" refers to gradient selected heteronuclear single-quantum correlation.

As used herein, the term "gs-HMBC" refers to gradient selected heteronuclear multiple bond correlation.

As used herein, the term "SUVs" refers to Small Unilamellar Vesicles.

As used herein, the term 'XANES' refers to X-ray absorption near edge structure

As used herein, the term 'EXAFS' refers to extended x-ray absorption fine structure.

DESCRIPTION

Method:

Recently, a first example of highly robust N-heterocyclic carbene (NHC)-based SAMs were reported with high chemical and electrochemical stability, providing an organic-to-metal linkage with significantly greater robustness than traditional thiol-based SAMs (C. M. Crudden et al., *Nature Chem.* 6, 409-414 (2014)). Compared with diazo-based films (J. Pinson et al., *Chem. Soc. Rev.* 34, 429-439 (2005)), NHC systems showed no evidence of multilayer formation.

However, it was found that the quality (e.g., purity, uniformity, etc.) of carbene monolayers sourced from a carbene precursor and formed on a metal surface were affected by precursor-derived impurities. In some embodiments, the impurities were a starting anion of the carbene precursor. In some embodiments, the impurities physisorbed to the metal surface through weak physical bonding (e.g., van der Waal's interactions); or, chemisorbed to the metal surface (e.g., chemically bonded to a surface atom of the metal surface). As such, methods described herein were developed to remove such sources of impurity or comtamination from a carbene precursor before said precursor is used to generate carbene monolayers.

An aspect of the present application provides a method, comprising oxidizing an anion of a carbene precursor in the presence of water and $CO_2$; or exchanging a starting anion of a carbene precursor via a hydrogen carbonate-anion exchange resin; and forming a purified carbene precursor comprising a final hydrogen carbonate anion, the purified carbene precursor being substantially free of the starting anion.

In an embodiment of the method, the starting anions of the carbene precursor comprise chloride, bromide, iodide, tetrafluoroborate, triflate, or hexafluorophosphate.

In an embodiment of the method, the purified hydrogen carbonate carbene precursor is formed by exchanging a starting anion of a carbene precursor via a hydrogen carbonate-anion exchange resin.

In yet another embodiment of the method, the purified hydrogen carbonate carbene precursor is formed by oxidizing a starting anion of a carbon precursor in the presence of water and $CO_2$. In another embodiment, oxidizing comprises exposing the starting anion of a carbene precursor to hydrogen peroxide. In another embodiment, the anion is iodide, wherein the iodide precipitates as molecular iodine once oxidized. In another embodiment, wherein the starting anion is iodide, the carbene precursor is relatively water soluble (e.g., relatively hydrophilic). It was found that hydrophobic iodide carbene precursors were relatively insoluble in water, and that changing reaction (i.e., oxidation) solvents from water to organic solvents, such as methanol, increased solubility of any precipitated molecular iodine, and facilitated its disproportionation back to iodides and/or iodates.

In further embodiments of the method, there is provided a purified hydrogen carbene precursor that comprises ≤10% of the starting anion; or, ≤5%; or, ≤2%; or, ≤1%; or, ≤0.5%; or, ≤0.1%. As would be understood by one skilled in the art, however, the method provided herein oxidizes or exchanges the starting anion of a carbene precursor to afford a purified hydrogen carbene precursor that is substantially free of the starting anion; but, may not, in all embodiments, remove other impurities if they exist.

Crudden et al. have previously described carbene-functionalized composite materials comprising a material having a metal surface, and a carbene monolayer that is uniform, contaminant-free (metal oxide, etc), and more stable than thiol-functionalized monolayers (see International Patent Application No. PCT/CA2014/050794, publication No. WO2015/024120, entitled Carbene Functionalized Composite Materials). However, Crudden et al. do not teach or disclose methods for forming purified hydrogen carbonate carbene precursors as described herein; or, methods of forming carbene-functionalized composite materials sourced from the purified hydrogen carbonate carbene precursors.

Figure 2:
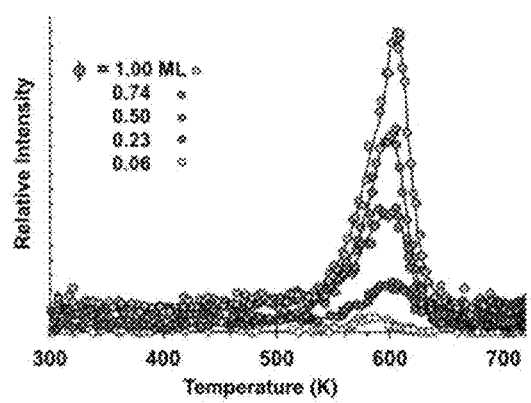
FIG. 2 graphically demonstrates temperature programmed desorption studies of 3a-based NHCs showing a maximum desorption temperature of 605K.

The present application further provides a method for formation of self-assembled carbene monolayers on metal surfaces (i.e., NHC monolayers) from a single source, high stability, purified carbene precursor, under conditions including in undried solvents open to air, and in the vapor phase from the solid state. In some embodiments, films formed from said robust and readily formed self-assembled carbene monolayers were effectively applied to SPR-based biosensing. A single source precursor (i.e., a precursor that requires no additional components (e.g., additional base) to form a free carbene) was prepared from readily available materials, not requiring the use of strong bases or inert atmosphere. Films can be prepared directly from this precursor without pre-generation of the carbene by thermal or other methods. Films prepared from this precursor show high chemical and electrochemical robustness, along with unprecedented film quality for monolayers deposited from the vapor phase (e.g., FIGS. 7a-g). Thermal desorption of NHC films from Au surfaces occurs at >125 K higher than thiol-based monolayers (FIG. 2). When employed in SPR-based biosensing, NHC films were superior in terms of ease-of-use, reproducibility, longevity, and repeated use. Considering the wide application of SPR-based biosensors, these new monolayers/films may have a relatively large impact. Also described herein, are many novel carbene structures and their corresponding carbene metal complexes. Some carbene metal complexes are nanoparticles, nanoworms, nanoparticles comprising carbene and gold, and/or nanoworms comprising carbene and gold.

Certain embodiments of the present application provide carbene precursors having a general structural formulae of Formula (I) or Formula (Ia) as shown below:

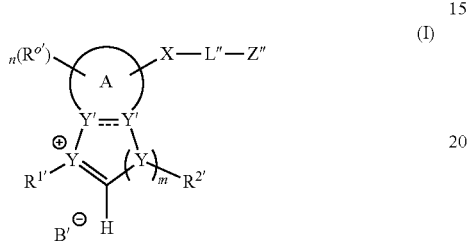
(I)

wherein:
n is an integer from 1 to 8, or from 1 to 4;
m is an integer from 0 to 4;
B' is a counter ion that optionally acts as a base;
A is optionally absent, an aliphatic cycle, a heterocycle, an aromatic ring, a fused aromatic ring system, a heteroaromatic ring, and/or a fused heteroaromatic ring system, each of which is optionally substituted;
X-L"-Z" is optionally absent,
X is C or a heteroatom,
L" is a divalent moiety, such as $C_1$-$C_{10}$ alkylene, $C_{10}$-$C_{20}$ alkylene, $C_1$-$C_{10}$ alkenylene, $C_{10}$-$C_{20}$ alkenylene, alkynylene, $C_{10}$-$C_{20}$ alkynylene, or dextran, a simple sugar, complex sugar, carbohydrate, ether, thioether, amine, polyamine, polyether, and/or polythioether, each of which is optionally substituted;
Z" is H, an aliphatic cycle, a heterocycle, an aromatic ring, a fused aromatic ring system, a heteroaromatic ring, a fused heteroaromatic ring system, an organometallic complex, a transition-metal catalyst, a metal-oxide catalyst, a simple sugar, a complex sugar, a carbohydrate, or a chemically derivatizable group, such as —OH, azide, carboxylic acid, carbonyl chloride, anhydride, ester, aldehyde, alcohol, amine, halogen, epoxide, thiirane, aziridine, amino acid, nucleic acid, alkene, alkyne, conjugated diene, thiol, or thioester, each of which is optionally substituted;
Y and Y' are independently C or a heteroatom;
$R^{o'}$ is independently H, halogen, the substituent X-L"-Z" as defined above, $C_1$-$C_{10}$ alkyl, $C_{10}$-$C_{20}$ alkyl, $C_1$-$C_{10}$ alkenyl, $C_{10}$-$C_{20}$ alkenyl, $C_1$-$C_{10}$ alkynyl, $C_{10}$-$C_{20}$ alkynyl, $C_1$-$C_{10}$ alkoxyl, $C_{10}$-$C_{20}$ alkoxyl, $C_3$-$C_{20}$ cyclic aliphatic moiety, aryl, heteroaryl, ether, thioether, amine, polyamine, polyether, or polythioether, each of which is optionally substituted; or, two of $R^o$, together with the atoms to which they are attached, are connected to form a cycle, or heterocycle, each of which is optionally substituted; and
$R^{1'}$, $R^{2'}$, $R^{3'}$, and $R^{4'}$ are independently optionally absent, at least one lone pair of electrons, H, $C_1$—$C_{10}$ alkyl, $C_{10}$-$C_{20}$ alkyl, $C_1$-$C_{10}$ alkenyl, $C_{10}$-$C_{20}$ alkenyl, $C_1$-$C_{10}$ alkynyl, $C_{10}$-$C_{20}$ alkynyl, $C_3$-$C_{20}$ cyclic aliphatic moiety, aryl, heteroaryl, ether, thiol, thioether, amine, polyamine, polyether, the substituent X-L"-Z" as defined above, polythioether, or polythiol, each of which is optionally substituted; or, one of $R^1$ or $R^2$, with one of $R^o$, together with the atoms to which they are attached, are connected to form a cycle, or heterocycle, each of which is optionally substituted;

wherein, when A is absent or non-aromatic, the dashed line represents an optional double bond; and/or
when A is absent, each Y' is independently bonded to $R^o$ or X-L"-Z", as defined above.

In accordance with an another embodiment of this method, the carbene precursor is of formula Ia

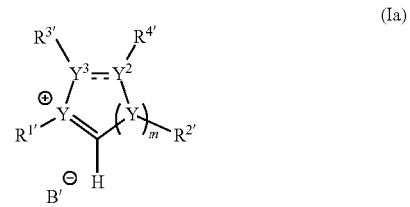
(Ia)

wherein the terms are as defined for formula (I).

Other embodiments of the present application provide carbene precursors having general structural formulae of Formula (III) or Formula (IIIa) as shown below:

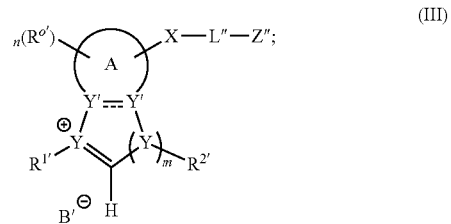
(III)

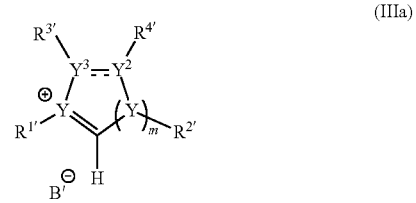
(IIIa)

wherein the terms are as defined for Formulas (I) and (Ia).

In some embodiments of formulas (I), (Ia), (III) and (IIIa), $R^{1'}$ and $R^{2'}$ are independently methyl, ethyl, propyl, butyl, isopropyl, phenyl, mesityl, or 1,3-diisopropylphenyl, each of which may be optionally substituted.

Such carbene precursors have been prepared herein as air stable hydrogen carbonate salts. A salt is thus provided that was substantially free of contaminates, such as iodide, bromide, triflate. Details regarding this synthesis and preparation are provided in the working examples herein (e.g., see Example 1). For example, by using an ion exchange resin on 1,3-diisoproplylbenzimidazolium iodide, it was possible to form purified carbene precursor 1,3-diisopropylbenzimidazolium hydrogen carbonate of substantially all iodide impurities sourced from the 1,3-diisopropylbenzimidazolium iodide. Such contaminant-free carbene precursors have been used in the deposition of carbenes on representative examples of metal surfaces (e.g., gold, nickel, silver, copper) and have been shown to provide protection against oxidation and corrosion. Details of this protection are provided in the Working Examples and Figures.

Figure 1A:
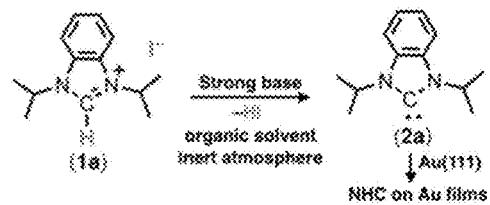
FIG. 1a is a schematic showing a strong base method previously employed for generation of NHCs.

In embodiments of the present application, the purified carbene precursors are N-heterocyclic (NHC) carbene precursors. Free NHCs are typically prepared by deprotonation of corresponding imidazolium salts with strong bases including KOtBu, NaH, and KHMDS (HMDS=hexamethyldisilazane), LiHMDS, or NaHMDS; a process that must be carried out under inert atmosphere, with rigorous exclusion of air and moisture (see FIG. 1a) (A. J. Arduengo, III et al., *Angew. Chem., Int. Ed.* 37, 1963-1965. (1998), and E. Aldeco-Perez et al., *Science* 326, 556-559 (2009)). Depending on the base, contamination of the metal surface has been observed [V. Zhukhovitskiy, et al. *J. Am. Chem. Soc.* 135, 7418 (2013)]. As an alternative, embodiments of the present application used single source air stable purified NHC precursors that did not require external reagents. In particular, hydrogen carbonate salts (3a) (M. Fèvre et al., *J. Am. Chem. Soc.* 134, 6776-6784 (2012)) were employed, in which the counter anion served as a base to deprotonate an imidazolium cation. Through use of such purified carbene precursors under such mild conditions, it was possible to form monolayers from carbenes that had functional groups (e.g., OH) that would have been susceptible to deprotonation if a strong base were used. This approach provides for more breadth and diversity in the range of carbenes that can be used in self-assembled monolayer formation. Carbon dioxide and water were the only byproducts.

In some embodiments, preparation of imidazolium hydrogen carbonates began with the corresponding iodide salts, introducing the basic anion via exchange with $KHCO_3$, as described (M. Fèvre et al., *J. Am. Chem. Soc.* 134, 6776-6784 (2012)). However, this procedure gave highly variable levels of exchange of iodide for hydrogen carbonate. A high affinity of certain metals (e.g., gold) for iodide posed a problem for creation of clean (e.g., iodide-free) NHC films. Thus, two synthetic procedures have been developed and described herein that provided carbene precursors (e.g., NHC hydrogen carbonate salts) that were at least iodide-free within the limits of combustion analysis (see Example 1, section 'Preparation of 1,3-Diisopropylbenzimidazolium hydrogen carbonate, [$iPr_2bimy$ (H)][$HCO_3$] (3a)). The first synthetic procedure involved oxidative removal of an iodide counterion in the presence of hydrogen peroxide, water, and $CO_2$, and the second synthetic procedure involved an ion exchange resin (Z. J. Wang, et al., *Green Chem.* 17, 3407-3414 (2015)). Once purified, diisopropylbenzimidazolium hydrogen carbonate (3a) was effective in generating high quality NHC monolayers either in solution or in the gas phase that showed no contamination by iodide as determined by XPS analysis. Compound 3a was an odorless, bench-stable, free-flowing (e.g., non-clumped) solid that formed an NHC monolayer on Au(111) by simply immersing the Au surface in an alcohol (e.g., methanol) solution of 3a in air without any special precautions. Such monolayers have identical chemical and electrochemical stability to monolayers deposited using a free carbene method (C. M. Crudden et al., *Nature Chem.* 6, 409-414 (2014)), resisting refluxing solvents, water, acid, base and oxidant. See Example 4, and FIGS. 7a-7g which depict XPS spectra of NHC self-assembled monolayers on gold, both before and after various treatment regimes (extremes of pH, exposure to oxidizing solutions, etc.). The spectra remained unchanged following treatment, indicating that the NHC SAM was stable under those conditions.

Benzimidazolium hydrogen carbonates 3a/b (R=iPr or Me) were also used to generate films in vacuo from the solid state providing clean formation of a monolayer with substantially no physisorbed species (e.g., hydrogen carbonate; imidazolium ions, etc.).

Figure 3A:
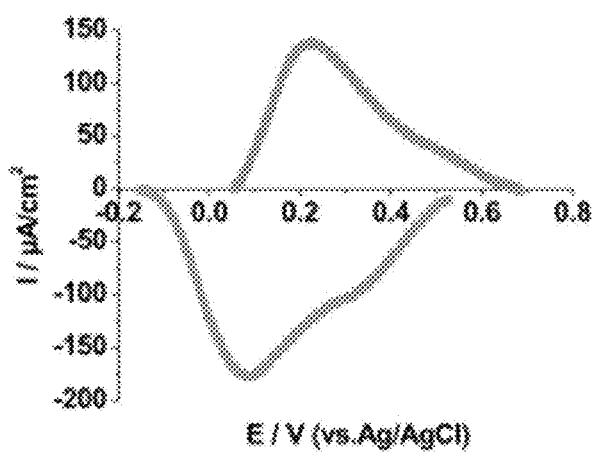
FIG. 3a depicts a cyclic voltamogram with background subtraction of 3c-based films showing asymmetric electron transfer (scan rate 1 $Vs^{-1}$).
Figure 3B:
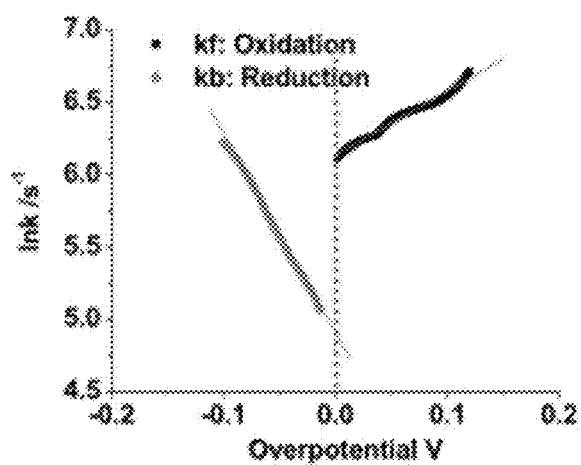
FIG. 3b graphically presents current vs. scan rate showing a linear dependence, which confirms that ferrocene conjugate was immobilized on the surface.
Figure 3C:
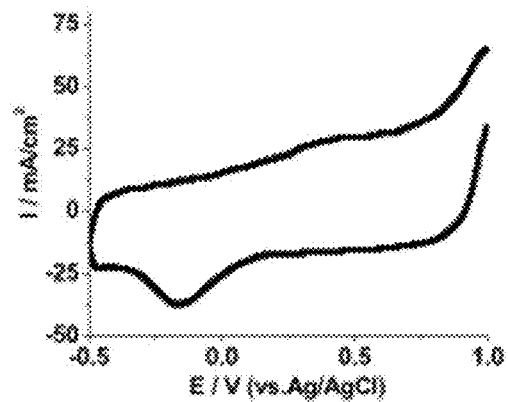
FIG. 3c depicts a cyclic voltamogram measured at 200 $Vs^{-1}$ with background subtraction of 3c-based films.

Surface coverage (film density) was probed quantitatively using electrochemical techniques, since the Fc redox signal from 3c can be directly related to molecular density (FIGS. 3a-c). Surface molecular density was determined to be $3.92\pm0.12$ molecules/$nm^2$, consistent with previous calculation of 3.5 molecules/$nm^2$ for free carbene-based films (C. M. Crudden et al., *Nature Chem.* 6, 409-414 (2014). The cyclic voltammogram was asymmetric with regard to reduction and oxidation, with the reduction peak larger than oxidation (FIG. 3a), an effect enhanced at faster scan rates (FIG. 3c). Without wishing to be bound by theory, this may be interpreted as oxidized ferrocenyl groups forming a more ordered configuration, and thus accepting electrons more quickly through the film. Tafel plots showed the same effect (FIG. 3b). The average electron transfer rate of 9.1 $s^{-1}$ was remarkably similar to films prepared from $FcCONH(CH_2)_{17}SH$, with substantially the same overall number of atoms separating the gold and the ferrocene unit (9 s-1). Finally, the current density was linear with scan rate, indicating that the ferrocene moieties were immobilized (see Examples 1 and 2).

Composite Materials:

Described herein is a new method for functionalizing metal surfaces that results in substantially impurity-free (e.g., free of starting anions), stable monolayer films. Further, described herein are carbene-functionalized composite materials comprising a material having at least a metal surface, and a self-assembled carbene monolayer sourced from a purified carbene precursor, wherein said carbene monolayer interacts with the metal surface and is uniform, stable and substantially free of contamination. The carbene-functionalized composite materials are prepared by forming a metal-carbon dative bond with carbenes that are derived from carbene precursors (i.e., purified hydrogen carbonate carbene salts), the carbene precursors having been purified such that the precursors comprise substantially no contaminants (e.g., starting anions iodine, bromide, triflate). Accordingly, this results in carbene-functionalized composite materials comprising stable monolayers that are substantially free of impurities (e.g., starting anions) derived from said carbene precursors.

In some embodiments, the carbene-functionalized composite materials are prepared using said purified (e.g., non-iodide, non-bromide, non-triflate containing) carbene precursors, the precursors comprising one or more chemically derivatizable groups. Composite materials prepared using such carbene precursors comprise a carbene monolayer that can be chemically modified by treatment of the chemically derivatizable groups, for example, to obtain desired composite material properties.

In embodiments of the present application, the purified (e.g., non-iodide, non-bromide, non-triflate containing) carbene precursors are N-heterocyclic carbene precursors.

As above, the carbene-functionalized composite materials are prepared using a material that comprises at least a metal surface. The material can comprise, for example, a solid metal, a metal film, a metal sheet, metal nanoparticles, or metal nanoclusters (pure or mixed metal). By way of further example, the metal surface can be a metal film or layer on a support material, a surface of a metal particle or nanoparticle, a surface of a metal nanocluster, a surface of a solid metal or a surface of a single crystal metal. A metal surface can comprise an alloy such as steel (including stainless steel), brass, bronze, tungsten carbide, or any combination thereof. Alternatively, or in combination, a metal surface can comprise Mg, Ga, Al, Ti, Fe, Rh, Ir, Ni, Pd, Pt, Cr, Cu, Ag, Au, W, Ta, Nb, Re, Mo, Ru, Co, or any combination or alloy thereof. In an example, in which the material comprising at least a metal surface is a metal film or a layer on a solid support, the solid support can comprise, for example, mica, alumina, silica, titania, silicon, glass, gallium arsenide, PbS, CdSe, or indium tin oxide. Gold, nickel, copper and silver have been used as representative metals in the studies described herein and were used merely as examples of metals that can be coated with carbenes; they are not meant to be limiting.

Gold was chosen most frequently for surface studies since it does not react quickly with $O_2$ and forms an oxide which can be easily removed and because it can be obtained as single crystals with clean surfaces. Gold is also interesting because it is a biocompatible metal and is relatively inert as a bulk metal. Further, it was observed that, when Au is the metal surface of the carbene-functionalized composite materials described herein, the carbene-carbon selects for a-top gold atoms. Although not wishing to be bound by theory, it has been suggested that this selection of a-top gold atoms means that the resultant functionalized surfaces are characterized by a novel bonding mode and ligand class, and are more stable in air, solvents, and higher temperatures than current metal-alkanethiol systems (for example, in the gas phase Au—C is 557 kJ/mol, and Au—S is 295 kJ/mol).

A limitation of using such alkanethiols systems is that they can be unstable; they are expected to desorb from a bulk Au or thin Au film surfaces at temperatures of 70° C. or higher. They are particularly unstable in hydrophobic solvents at higher temperatures (C. D. Bain, et al. *J. Am. Chem. Soc.* 111, 321 (1989)), and they are known to begin decomposing in air at room temperature within a week. They can also be susceptible to exchange with amines or other thiols. This can pose a particular challenge if amino acid or protein species are to be bound to the surface and in in vivo biological systems where thiols abound. Thiol monolayers have been shown to begin decomposing by oxidation in air at room temperature after as little as 1-2 weeks (C. Vericat, et al. *J. Phys. Condens. Matter* 20, 184004 (2008); Y. Li, et al. *J. Am. Chem. Soc.*, 114, 2428 (1992); M. H. Schoenfisch, et al. *J. Am. Chem. Soc.* 120, 4501 (1998); J. B. Schlenoff, et al. *J. Am. Chem. Soc.* 117, 12528 (1995)). This limits the stability of such surfaces and thus the ability of thiol monolayers to protect surfaces. Furthermore, an Au—S bond can be a poor conductor where compared to certain Au—C bonding configurations (J. M. Seminario, et al. *J Am. Chem. Soc.* 123, 5616 (2001)).

Applications of Composite Materials:

Carbene-functionalized composite materials of the present application are useful for, or can be configured for use in, various applications. For example, coupling a hydrocarbon-based compound to a metal via a carbon-metal bond, particularly one adjacent to a delocalised electronic system as is exhibited by the carbenes derived from the carbene precursors described herein, could be useful in maintaining a high conductivity at any metal/organic interface used in an electronic device. Further, functionalizing pure metal surfaces has some advantages, as it allows for binding of a ligand (or analyte) to be detected electrochemically. In general, the process and materials described herein may be used to modify the properties of a metal surface of a material. For example, it may be desirable to modify a metal surface of a material by changing its surface properties (e.g., its surface wettability), by protecting the metal surface, by chemically activating or deactivating the metal surface to make it reactive or unreactive to a selected reagent or combination of reagents, or by displacing existing chemical groups or moieties from the metal surface (e.g., phosphine-containing, or sulfur-containing compounds or groups). In other embodiments, the presently described process and materials can be used in the following, non-limiting, examples of applications:

- making nano-patterns on semi-conducting surfaces;
- fabricating electronic or microelectronic devices;
- drug delivery;
- electrochemically detecting molecules including biomolecules such as DNA, proteins, lipids or glucose, via, for example, non-specific adsorption;
- electrochemically biosending;
- surface plasmon resonance for detecting molecules, or specifically biomolecules such as DNA, proteins, lipids or glucose via, for example, non-specific adsorption;
- making electrochemical sensors;
- catalysis;
- generating a catalyst;
- sensing applications;
- colorimetric analysis of molecules, such as biomolecules;
- antibacterial/antimicrobial application; or
- protecting metal surfaces from, for example, oxidation or corrosion.

As above, one factor to many technological applications, such as nano-patterned semiconducting surfaces, drug delivery, and biomolecule detection, is surface functionalization, wherein a single layer of molecules is chemically bound to a surface to change its physical and chemical properties. For example, alkylidenes generally form stable monolayers on substrates that are good conductors (non-limiting examples include Ru or MoC). However, unlike gold and copper, Ru and MoC are not materials that are routinely incorporated as part of the microelectronic fabrication industry. Diazo compounds are known to form films on Au, however the high reactivity of these species leads to frequent formation of multilayers, while there is no evidence for formation of multilayers under any conditions with N-heterocyclic carbenes derived from purified carbene precursors, as described herein. Instead these N-heterocyclic carbene precursors have given clean (e.g., stable, uniform, and free of contamination) monolayer formation under conditions examined herein.

Further, alkylidene monolayers are primarily utilized as catalytic platforms for metathesis reactions, in which the carbon-meal bond itself takes part in the reaction. On MoC, the Mo=C double bond of alkylidene monolayers appears to be stable up to approximately 600° C. in vacuum. Stability of alkylidene monolayers on Ru under ambient conditions is similar to self-assembled carbene monolayers on gold, as described herein; for example, alkylidene monolayers on Ru are stable at room temperature in non-aqueous solvents. However, self-assembled carbene monolayers on gold described herein are stable at higher temperatures in such solvents, and are also stable in boiling water for at least 24 hours. These are conditions that a SAM must be able to withstand if it were to act, for example, as a structural support for catalytic reactions on a surface. The herein described self-assembled carbene monolayers on gold, by contrast, have been specifically designed to be stable as defined herein, and unreactive (e.g., relative to alkylidene monolayers, as described above); they can therefore act as a structural platform to support other functional groups that will be able to modify various properties of the metal surface, including its catalytic activity, and thus should support a much wider range of applications. In addition, the purified carbene precursors described herein are more general in terms of the type of metal they bond to.

Surface plasmon resonance (SPR) is an application in which self-assembled monolayers on Au are used routinely on a commercial basis. In SPR, a thin Au film functionalized with an appropriate protein or antibody is used to detect biomolecules in solution: as analytes from solution are adsorbed onto a film, reflectance of the film changes, and the quantity of analyte adsorbed can be detected optically. Currently, thiol SAMs are used to functionalize Au films, which are subject to degradation, have to be stored in a freezer under $N_2$ to preserve functionality, and have a shelf life of 6-12 months. An N-heterocyclic carbene monolayer could substitute for the thiol, in principle forming a more stable film with a longer detector lifetime. As described previously, it has been demonstrated that substitution of thiol SAMs with NHC SAMs provided detectors that can be stored under ambient conditions, with longer shelf lives. It has been further demonstrated that the NHC-functionalized metal surface will adsorb a lipid overlayer film, as measured using SPR, with stability and reproducibility greater than that of a commercially available alkanethiol-based Au film.

Figure 4A:
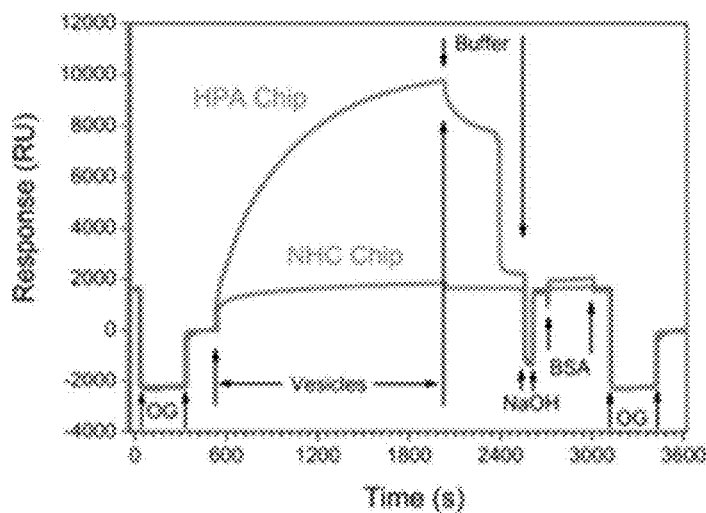
FIG. 4a demonstrates monitoring of supported hybrid bilayer formation on NHC and HPA chips.
Figure 4B:
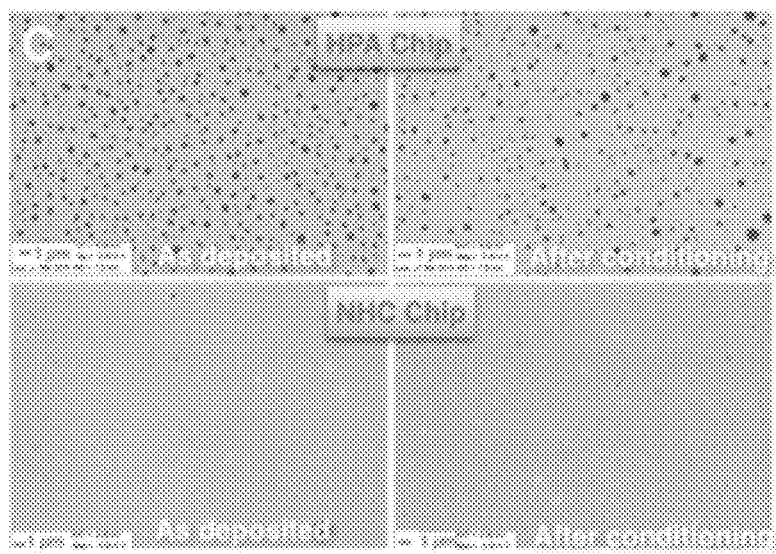
FIG. 4b depict SEM images of the chips of FIG. 4a, indicating presence of vesicles on HPA chips even after conditioning.

As further described below, with access to carbene-functionalized composite materials comprising stable self-assembled carbene (i.e., NHC) monolayers that are high quality and prepared easily in solution or in vacuo from purified carbene precursors, the behavior of such monolayers in SPR-based biosensing was examined. 5-(Dodecyloxy)-1,3-diisopropyl-1H-benzo[d]imidazol-3-ium hydrogen carbonate (3d) was deposited on a clean gold SPR chip (NHC chip) and benchmarked against an equivalent thiol-derived HPA chip. Commercial HPA chips are typically employed to create supported hybrid bilayers between hydrophobic lipids and surface-bound thiol monolayers, and the resulting bilayers then interrogate receptor-analyte interactions in a membrane-like environment. When commercial HPA chips were treated with phosphatidyl choline vesicles (FIG. 4a), a large signal with substantial curvature was observed, attributed to an adsorption of a large excess of lipid, which is typical behavior for this chip (M. A. Cooper et al., *Biochim. Biophys. Acta* 1373, 101-111 (1998)). Excess lipid was removed with a buffer rinse and base conditioning. In the NHC chips (FIG. 4a), complete monolayer formation was observed with almost no extraneous lipid adsorbed. SEM analysis also showed a significant number of vesicles on the thiol-based chip, even after conditioning (FIG. 4b, top), while said NHC chip gave clean, vesicle-free hybrid bilayers directly. Without wishing to be bound by theory, it was considered that this may result from a greater spacing of NHC compared to the thiol, permitting efficient interdigitation of the phosphatidyl choline, while dense packed thiol SAMs require desorption before interdigitation can occur.

Figure 4C:
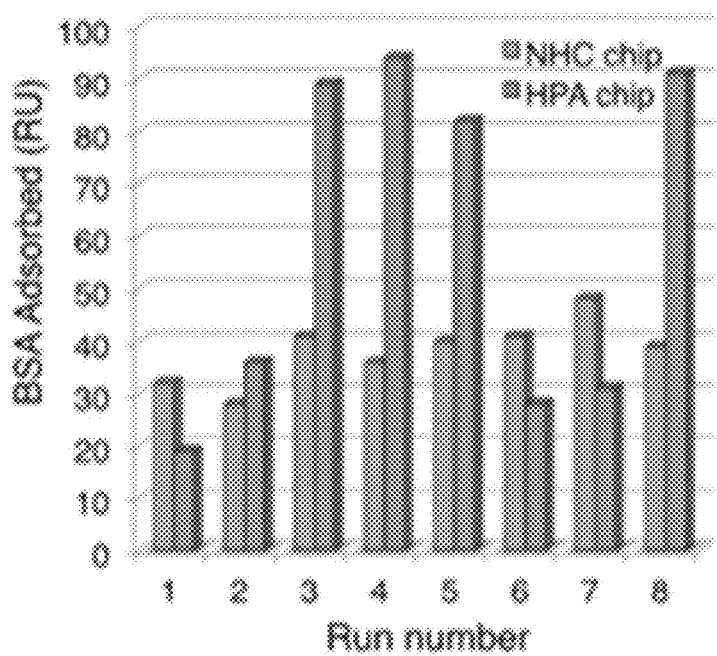

The quality of the thus-formed bilayers was tested using bovine serum albumin (BSA) absorption, a benchmark for monolayer quality since it is known to adsorb at defects. Between each run, the chip was regenerated and a new lipid layer adsorbed, such that BSA adsorption data reflected run-to-run variability of bilayer formation and monolayer quality under essentially identical conditions. In PBS buffer (pH=7.4), the HPA chip demonstrated a BSA adsorption of 59±33 RU (33% deviation) over 8 runs, while the total BSA adsorption for the NHC chip was 38±6 RU (16% deviation) (FIG. 4c). Similar results were obtained in citrate (pH=5.0, HPA=274±85 RU, NHC=102±9 RU) and other buffers, where NHC chips showed improved or equivalent performance to the HPA chip under virtually all conditions (see Tables 2 and 3). The NHC chips outperformed the HPA chips at the extremes of pH.

NHC chips were stable after heating at 65° C. at pH 7.4 for 24 hours, and in a variety of buffers (see Table 3). The NHC chip was fully functional after 9 months of use while the commercial chip showed decreased performance after less than 2 months.

Figure 4D:
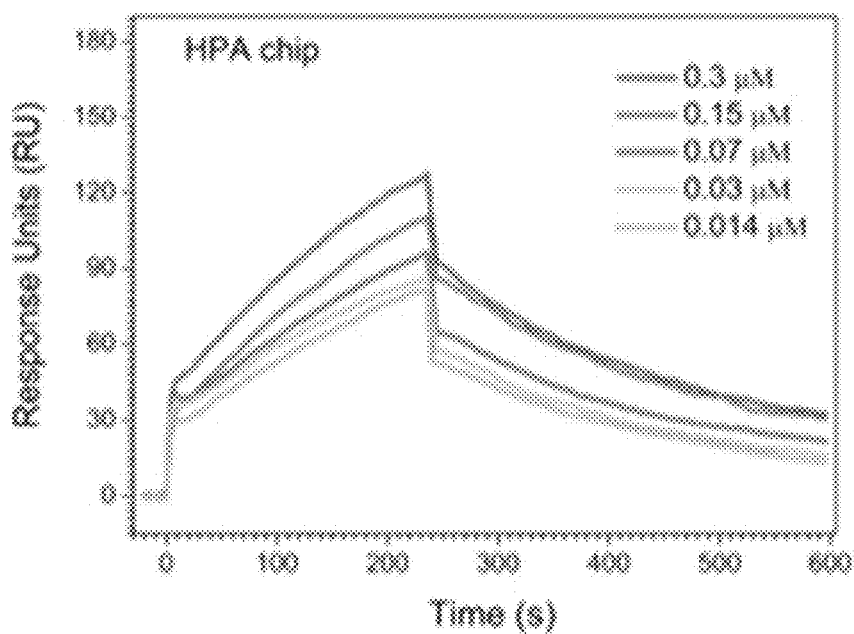
FIG. 4d graphically presents quantitative melittin sensing on the HPA chip.
Figure 4E:
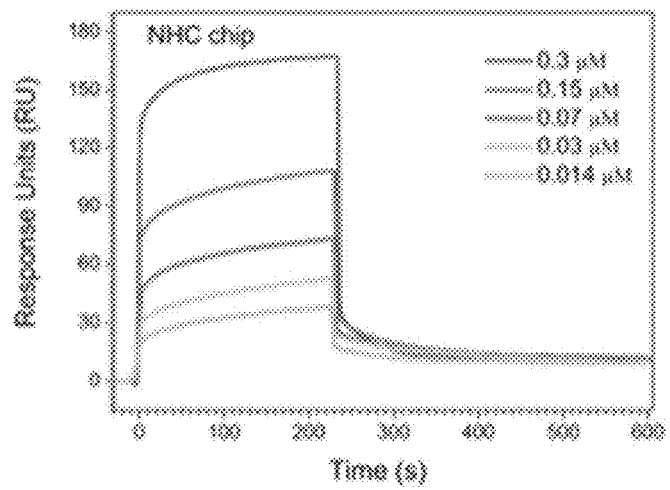
FIG. 4e graphically presents quantitative melittin sensing on NHC chip.

Adsorption of lytic peptide melittin illustrated key differences in the monolayers during actual protein sensing experiments. For the HPA chip, the correlation between melittin concentration and response was poor and proper equilibration was not achieved even after multiple attempts. By contrast, the NHC chip showed a proportionate and reliable response to melittin concentration, permitting facile and accurate measurement of affinity constants (FIGS. 4d and 4e).

Colorimetric analysis is another application where the herein described composite materials may be applied, given that functionalized gold nanoparticles have also demonstrated promise in the detection or analysis of molecules via colorimetric analysis (J. Liu, et al. *Agnew. Chem., Int. Ed.* 45, 90, (2006)). Nanoparticles are functionalised with a DNA aptamer, which is designed to bind an analyte. Once bound, the nanoparticles aggregate, changing colour.

Opportunities exist in other applications that are less commercially developed, such as use of functionalized Au nanoparticles for cancer treatment (B. Kang, et al. *J. Am. Chem. Soc.* 132, 1517, (2010)). In this case, use of a relatively more stable N-heterocyclic carbene functionalised surface, sourced from a herein described purified carbene, may prolong shelf life of drug compounds formed. Coupling organic molecules to metals is also an important step in building novel electronic devices. An ability to form stable patterns on a surface could potentially be an important step in bottom-up approaches for the semiconductor industry (R. K. Smith, et al. *Prog. Surf Sci.* 75,1, (2004); Rahul Bhure, et al. *ACS Symposium Series*, Vol. 1054 Chapter 4 (2010); A. Kumar, et al. *Langmuir* 10, 1498 (1994)). See Example 14 regarding competitive displacement studies that may be used for patterning metal surfaces.

Further, the herein described self-assembled carbene monolayers can be used to aid in selectively functionalizing materials containing both metal and non-metal surfaces. For example, the carbene-monolayer can be applied as a nano-scale protecting group, coating a metal surface to allow selective etching or functionalization of a non-metal surface, after which the carbene SAM can be selectively removed.

Other applications include use of carbene-functionalized composite materials in the field of supported catalysis, including electrocatalysis, wherein the self-assembled carbene monolayer on the metal surface is itself further functionalized with active metal catalysts. It has been demonstrated previously that this compound will successfully catalyze the reproducible and repeatable decomposition of ceric ammonium nitrate in aqueous acidic solution, which may occur through water oxidation. Carbene-functionalized surfaces can be employed to immobilized or bind catalysts useful for catalytic reactions, such as in $H_2$ production or CO oxidation. As would be readily within the skill of a worker skilled in the art, selection of the appropriate catalyst, such as a transition metal catalyst, will be based on the type of reaction to be catalyzed.

Thus, the herein described method using purified carbene precursors to prepare carbene-functionalized composite materials for surface functionalization has been developed and demonstrated (see below and Working Examples). Various metal surfaces have been amenable to this functionalization, such as bulk metal, thin films, atomically ordered surfaces, metal nanoparticles, and metal nanoclusters.

Nanoparticles and Nanoclusters:

As above, an aspect of the present application provides a carbene-functionalized composite material comprising a material having at least a metal surface; and a carbene monolayer that is uniform, stable, and substantially free of contamination, the monolayer being sourced from a purified carbene precursor; wherein the monolayer interacts with the metal surface; and the purified precursor is sourced from a carbene precursor having a starting anion that is exchanged for hydrogen carbonate such that the purified precursor and the monolayer is substantially free of the starting anion. In an embodiment of the aspect, the composite material comprises carbene-functionalized nanoclusters.

A further aspect of the present application provides a method for forming a carbene-functionalized composite material, comprising forming a carbene precursor by
(i) oxidizing a starting anion of a carbene precursor in the presence of water and $CO_2$, or
(ii) exchanging a starting anion of a carbene precursor via a hydrogen carbonate-anion exchange resin, and forming a purified precursor comprising a final hydrogen carbonate carbene anion that is substantially free of the starting anion; reducing a metal salt in the presence of the purified precursor; and forming a carbene-functionalized composite material, the composite material comprising carbene-functionalized nanoclusters.

Nanoclusters are considered to bridge a gap between molecules and materials. Although nanoclusters are nanomaterials with size dependent properties, they are known to have discrete electronic transitions due to well-defined molecular orbitals, and can be characterized by techniques usually reserved for molecules. Use of single crystal X-ray diffraction to characterize the $Au_{102}SR_{44}$ cluster illustrated nanoclusters' molecular behaviour. Also demonstrated was the complexity of gold-thiolate interfaces, which was shown to be made up of staple-like RS—Au—SR structures supporting an Au(0) core. This structure provided support for a super atom model of bonding, which explains why certain cluster sizes are "magic"—why certain cluster numbers are over represented among known, stable species.

Research into magic number nanoparticles has featured different thiolates, different metals, and different core sizes and configurations; however, the thiol linkage has remained largely invariant across the large majority of identified clusters. A smaller number of clusters has been prepared featuring phosphine ligands, however with lower diversity of structure. Distinguishingly, herein described are carbene-functionalized (e.g., NHC-stabilized) nanoclusters, which have been shown to have increased stability relative to phosphine clusters (for example, see Examples 22 and 24) and unique photophysical properties (e.g., UV-vis absorption bands of the NHC-modified nanoclusters were slightly shifted from the phosphine-stabilized clusters).

As described herein, ligand replacement reactions of phosphine-stabilized clusters $[Au_{11}(PPh_3)_8Cl]Cl_2$ and $[Au_{11}(PPh_3)_7Cl_2]Cl$ were examined. A phosphine cluster was chosen since both NHC and phosphine ligands were neutral and required no change in oxidation state or charge for the exchange. The herein described purified hydrogen carbonate carbene precursors were employed as the NHC source. Treatment of phosphine-stabilized clusters with 1,3-diisopropylbenzimidazolium hydrogen carbonate resulted in decomposition for the less stable $[Au_{11}(PPh_3)_7Cl_2]Cl$ cluster during the reaction, as observed by the disappearance of characteristic $^1H$, $^{31}P$-NMR peaks of the cluster; however, nanoclusters as described herein (e.g., Au11-NHC(iPr)) were observed in high yield when the more stable $[Au_{11}(PPh_3)_8Cl]Cl_2$ was employed as a starting material.

When the purified carbene precursor 1,3-diiethyl-1H-benzo[d]imidazol-3-ium hydrogen carbonate was used, it was also found to react cleanly $[Au_{11}(PPh_3)_8Cl]Cl_2$; and, $[Au_{11}(PPh_3)_n(NHC-Me)_mCl_2]Cl$ 'Au11-NHC(Me)' was synthesized. Further, it was found that herein described NHC-functionalized (e.g., stabilized) nanoclusters, such as Au11-NHC(iPr), were readily formed from herein described purified hydrogen carbonate carbene precursors generated from either iodide carbene precursors or triflate carbene precursors. It was found that nanoclusters derived from iodide carbene precursors or triflate carbene precursors were the same.

UV/vis spectra of the herein described nanoclusters were characterized by fine structure indicative of individual transitions and an absence of plasmon resonance bands. Mass spectroscopy gave molecular weights of the nanoclusters, and showed that the reactions were relatively clean, particularly in regard to Au11-NHC(iPr). Further, it was observed that nanocluster distribution was essentially the same before and after purification by silica chromatography, which removed byproducts (e.g., $[Au(NHC)_2]^+$, [NHC—Au—PPh_3] and $[Au(PPh_3)_2]$). The clusters were also characterized by nuclear magnetic resonance (NMR) spectroscopy, examining $^1H$, $^{31}P$ and $^{13}C$ nuclei, the latter employing a NHC precursor isotopically enriched (prepared from an enriched starting material) at the central carbon to facilitate characterization.

A further aspect of the present application provides a method for forming a carbene-functionalized composite material, comprising forming a carbene precursor by
(i) oxidizing a starting anion of a carbene precursor in the presence of water and $CO_2$, or
(ii) exchanging a starting anion of a carbene precursor via a hydrogen carbonate-anion exchange resin, and forming a purified precursor comprising a final hydrogen carbonate carbene anion that is substantially free of the starting anion; reducing a metal salt in the presence of the purified precursor; and forming a carbene-functionalized composite material, the composite material comprising carbene-functionalized nanoclusters. In an embodiment of the aspect, the composite material comprises carbene-functionalized nanoparticles.

Herein described carbene-functionalized (e.g., stabilized) nanoparticles were formed via a direct method that avoided use of air or moisture sensitive reagents, use of high pressure or flammable gases, or a required use of long alkyl-chained substituents on the carbene or carbene precursor. In contrast, earlier examples of NHC-stabilized nanoparticles required hydrogenative decomposition (under 4 atm $H_2$) of a metal precursor in the presence of a NHC to generate nanoparticles [Lara, P.; et al. Angew. Chem., Int. Ed. 2011, 50, 12080-12084]. In other examples, NHC-stabilized nanoparticles were generated through ligand exchange of thioether protected nanoparticles [Hurst, E. C.; et al. New J. Chem. 2009, 33, 1837-1840]; however, these nanoparticles aggregated in solution after 12 hours. A direct reduction of a NHC—Au—Cl complex using 9-BBN (9-borabicyclo[3.3.1]nonane) was also demonstrated [Vignolle, J.; et al. Chem. Commun. 2009, 7230-7232], but required use of long alkyl-chained substituents on the NHC to provide nanoparticle stability in solution. However, not one of the above-referenced examples taught or disclosed a method by which metal nanoparticles were formed by reducing a metal salt in the presence of the purified precursor as described herein.

Further, as per A. V. Zhukhovitskiy, et al. [Chem. Rev. 2015, 115, 11503-11532] little progress has been made toward stabilization of Ag nanoparticles with NHCs. For example, reports of NHC-stabilized Ag nanoparticles derived from NHC—Ag(I) complexes were either not stable or never isolated in pure form, the NHC binding to the nanoparticle was not confirmed, or the NHC was verified to be absent in the resulting nanoparticles. A. V. Zhukhovitskiy, et al. also reported that there were no examples of preparing NHC-stabilized copper NPs, with the exception of one example of CuSe nanodiscs. Distinguishingly, as per Example 24, NHC-functionalized (i.e., stabilized) Ag nanoparticles were successfully synthesized and characterized, as described herein.

In embodiments of the above aspects, the purified hydrogen carbonate carbene precursor from which the carbene-functionalized nanoparticles and nanoclusters are derived are compounds of (i) Formula II:

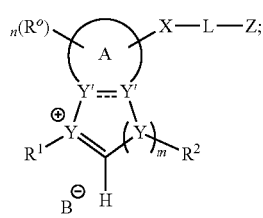

(II)

(ii) Formula IIa

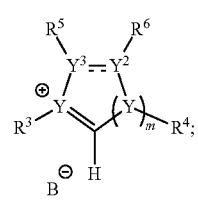

(IIa)

(iii) Formula V

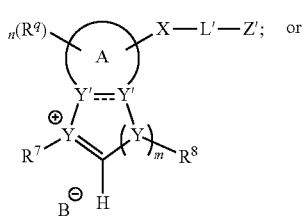

(V)

(iv) Formula Va

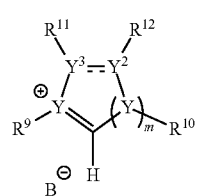

(Va)

as defined herein.

In an aspect of the present application, there is provided a method for forming carbene-functionalized nanoparticles comprising exposing a non-hydrogen carbonate carbene precursor to a base under inert conditions to generate a free carbene; and, exposing pre-formed nanoparticles to the free carbene. In some embodiments, the nanoparticle is a gold nanoparticle. In particular embodiments, the carbene-functionalized nanoparticle is:

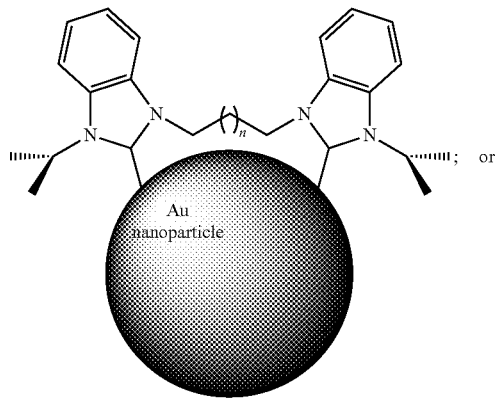

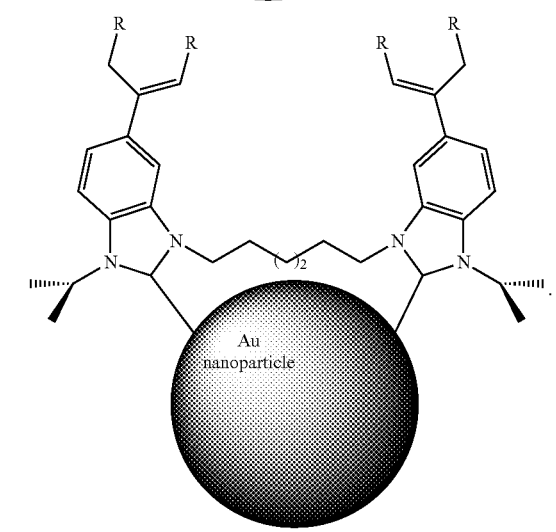

n = 1, 4, 10
R = $C_{11}H_{23}$

In another aspect of the present application, there is provided a method for forming carbene-functionalized composite materials comprising exposing a non-hydrogen carbonate carbene precursor to a base under inert conditions to generate a free carbene; and, exposing a metal surface to the free carbene. In some embodiments, the metal surface is a gold metal surface.

In an embodiment of the above two aspects, the non-hydrogen carbonate carbene precursor is a compound of Formulae:

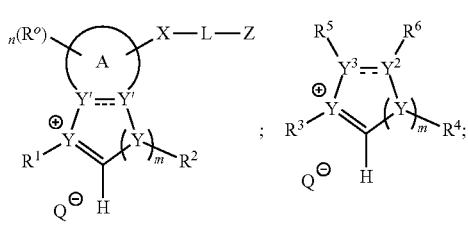

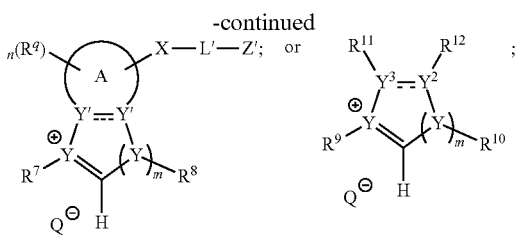

wherein Q is a non-hydrogen carbonate anion, and the other variables are as defined herein.

In embodiments of the present application, the herein described carbene-functionalized nanoparticles may be used in applications such as, but not limited to, catalysis, biomedical, and semiconducting applications. Without wishing to be bound by theory, it was considered that the herein described Au nanoparticles may be useful in biomedical applications owing to the biocompatibility and unique optical properties (e.g., absorbing/scattering light; producing heat as energy from absorbed light dissipates, etc.) of Au nanoparticles in general.

Abnormal or Mesoionic Carbenes

Normal N-heterocyclic carbenes (NHCs) are characterized by a N—C—N arrangement at their bonding site. Electronic communication from the NHC to a metal is expected to be altered by modifying atoms adjacent to the carbene carbon that bonds to a metal surface. For example, "abnormal" NHCs (aNHC), or mesoionic carbenes, are an interesting class of NHCs that are typically prepared by blocking (e.g., derivatizing) the carbon (e.g., with alkyl or aryl groups) between the two nitrogens to prevent reaction at that site [Aldeco-Perez, E.; et al. Science 2009, 326, 556-559]. It has been shown that aNHCs are stronger σ-donors than normal NHCs, where a calculated strength of aNHC-Au⁰ bond (~189 kJ/mol) was found to be ~33 kJ/mol higher than that of a normal NHC-Au⁰ bond (~158 kJ/mol). As such, without wishing to be bound by theory, it has been considered that SAMs formed by bonding at this site (e.g., new bonding site that is not between the two N-atoms) may have an even higher stability relative to normal NHC-based monolayers; that NHCs with different electronic properties may bind more tightly to a surface; and/or that NHCs with different electronic properties may have different effects on, for example, the work function of gold or other electronic properties.

In contrast to the amine groups of normal NHCs, diamidocarbenes (DAC) have two amide groups directly bonded to the carbenic carbon. Consequently, electron-withdrawing effects of the amide groups result in DACs being weaker σ-donors compared to normal NHCs. Thus, different NHC classes can be generally arranged in the following order with respect to their decrease in electron-donation ability: aNHC>normal NHC>DAC.

As such, to investigate NHCs' electronic variation effects on properties of resulting SAMs, initially 1,3-diethylimidazo[1,2-a]pyridinium bromide (aNHC) and its corresponding hydrogen carbonate analog, 1,3-diethylimidazo[1,2-a]pyridinium hydrogen carbonate, were considered as described herein due to their structural similarities to normal NHCs in the present application. Further precursors investigated included 1-ethyl-3-benzylimidazo[1,2-a]pyridinium bromide and a diamidocarbene (DAC)-triflate salt.

Stability:

Stability of the herein described self-assembled carbene monolayers, comprised by the herein described carbene-functionalized composite materials and sourced from the herein described purified carbene precursors, has been demonstrated.

As described previously, carbenes bound to gold surfaces were resistant to exchange by sulphur ligands, indicating that the Au—C bond is more stable than the Au—S bond. Thus functionalized nanoparticles were stable for at least 15 weeks under ambient conditions, and surfaces were stable in non-aqueous solvents such as THF at temperatures of up to 70° C. for 24 hours. By way of further example, surfaces modified by self-assembled carbene monolayers were stable after boiling in water in air for 24 hrs, they were stable to pH 2 and pH 12 at room temperature, and, 85% of the film has been shown to survive overnight in 1% hydrogen peroxide. Further, the composite materials were electrochemically stable (C. M. Crudden, et al. Nature Chem. 6, 409-414 (2014), which is incorporated herein in its entirety). The ability of previously described carbene monolayer-functionalized metal surfaces to adjust surface properties has been demonstrated by modifying the carbene precursor's backbone to impart hydrophobic or hydrophilic properties to a surface. The ability to modify said carbene monolayers and affect surface properties can be relevant to sensing applications.

NHCs necessary to be implemented effectively in the herein described self-assembled carbene monolayers and composite materials, and to affect the herein described surface modified/functionalization, are stable relative to other carbenes, which decompose, often violently, under non-cryogenic conditions or when exposed to a variety of simple chemicals. Comparatively, NHCs used in the herein described self-assembled carbene monolayers and composite materials are stable enough to be bottled, crystallized, and even distilled. It has been shown that NHCs can be stored in a regular freezer, under nitrogen without any evidence of decomposition for upwards of four years.

Additionally, herein described purified NHC precursors are stable under ambient conditions; and, conversion to the desired carbenes does not require external reagents. In particular, for the herein described NHC hydrogen carbonate carbene precursors, the counter anion serves as a base to deprotonate an imidazolium cation. Resulting solutions can be used directly in the formation of self-assembled carbene monolayers on metal; or, the carbene precursor can be used directly from the solid state under vacuum in the formation of self-assembled carbene monolayers on metal. In some embodiments, monolayer formation has been shown to occur in just a few hours or less at room temperature by immersing, for example, a gold substrate in a solution of the desired carbene (see Example 3). Thus, preparation of a stable monolayer on gold can be simple and readily accomplished.

Removal:

As described previously, self-assembled carbene monolayers can be removed from a metal surface by various means. For example, carbene monolayers were removed from a surface by being physically abraded, together with some or all of the underlying metal film; or, by being exposed to strong oxidizing conditions such as, but not limited to, exposure to 3% $H_2O_2$ for 24 hours. Further, it was shown that carbene monolayers can be removed with heat (186° C.) and decalin, or the like, as solvent.

Discussion:

As described herein, NHC films derived from bench stable, easily handled purified benzimidazolium hydrogen carbonates have high thermal, chemical and electrochemical stability. The desorption temperature of the NHC monolayers from the surface (600 K) provides an estimate of the NHC—Au bond strength at 158±10 kJ/mol (FIG. 2). Scanning tunneling microscopy (STM) studies on solution and vapor-deposited SAMs indicated a higher propensity for reconstruction, pitting and islanding when depositing from solution, with very high quality SAMs being obtained from vapor deposition. Electrochemical measurements put NHC density at 3.8 molecules/nm$^2$.

As described above, NHC-based films provided advantages relative to thiol analogs in SPR-based biosensing, including more reliable and reproducible bilayer formation, and faster, more consistent protein sensing results. To illustrate the behavior of such films, gold chips designed for surface plasmon resonance-based biosensing were coated with alkylated NHCs, resulting in a biosensor with more reproducible responses to analytes, more stability to harsh conditions, improved equilibration times and greater longevity compared to state-of-the-art thiol-based systems (see FIGS. 4a and 4b).

Successful depositions of self-assembled carbene monolayers were achieved using purified carbene hydrogen carbonate species that excluded contaminates such as, for example, iodide, bromide, and triflate ions. Iodide is a typical contaminant in carbene salts/precursors when synthesized using state-of-the-art methods. A method is described for eliminating substantially all contamination (e.g., starting anions iodide, bromide, and triflate) during synthesis of carbene hydrogen carbonate species. Carbenes (either as a free carbene for comparison purposes, or as hydrogen carbonate carbene precursor) were deposited to form intact monolayers on the surface of some industrially relevant metals, and demonstrated that such monolayers protect these metals against oxidation. It was demonstrated that such carbenes deposit to form an intact monolayer on Ni which protects this metal from oxidation. Such carbenes were also deposited to form an intact monolayer on Cu, and increase its protection to oxidation. Deposition of such carbenes on silver was also demonstrated.

A range of hydrogen carbonate carbene precursors (R=methyl, ethyl, isopropyl) were deposited from the vapour phase by mildly heating the hydrogen carbonate carbene precursor under vacuum conditions. Scanning tunnelling microscopy (STM) and thermal programmed desorption (TPD) were used to show that, on both gold and copper, an ordered self-assembled monolayer formed that was intact and upright on the surface.

As above, improvements of an NHC-based surface plasmon resonance (SPR) sensor chip relative to a commercially available HPA SPR chip have been demonstrated. Specifically, improved (by a factor of 10) baseline drift stability, improved stability following exposure to a range of common regeneration solutions, and improved sensitivity to detection of peptide adsorption within a supported lipid layer on the chip surface. The commercial HPA chip gave irreproducible results to adsorption of the peptide mellitin while the NHC chip showed sensitivity, and approached adsorption equilibrium within a reasonable experimental timescale, allowing adsorption coefficients for the peptide to be determined.

In the working examples, means for modifying an SPR chip is described, and the results appear to be comparable to commercially available chips; and, superior performance of an NHC chip described herein is described and is compared with commercially available chips (for example, see Examples 8, 15, 17-19). Therein, a NHC-functionalized Au surface served as a platform for surface modification. In some examples, the NHC functionalizing the Au surface comprised a carboxymethylated dextran maxtrix, wherein COOH groups of the matrix were modified using known methods to create a surface that was active towards detection of biomolecules. Other examples (protein A, SA, his-tagged etc.) were based on subsequent surface modification of a carboxymethylated dextran NHC chip. The NHC-functionalized chips demonstrated a performance that was at least equivalent to equivalently-modified commercial CM3 products, though the surface coating procedure was not optimized (e.g. not in a clean room, limited exploration of NHC deposition parameters, etc.). The carboxymethylated NHC chips were also found to be more resistant to non-specific protein adsorption, and more resistant to heating to 65° C. than commercial chips.

Referring to FIGS. 16A-C, sensorgrams are shown to indicate an example of an NHC-SA chip, specifically NHC-CM3 6 KDa, interacting with biotinylated DNA, followed by interaction with his-tagged protein. Referring to FIGS. 17A-C, sensorgrams are shown to indicate an example of CM3-SA chip (specifically CM3) interacting with biotinylated DNA, followed by interaction with his-tagged protein.

Referring to FIGS. 16A-C and 17A-C, as shown, both NHC-SA and CM3-SA chips performed SA—biotinylated DNA—histagged protein interactions. Because of the higher capacity of SA on the CM3-SA chip, there was higher biotinylated DNA density and his-tagged protein level under the same immobilization condition. However, maintaining a SPR sensor surface's capacity as low as possible minimizes mass transport, steric hindrance, crowding and aggregation. In this perspective, NHC-SA chips may have improved sensing ability relative to commercially-available chips. As shown herein, as less protein was adsorbed on the CM3-SA chip, the relative change in response is notable.

Referring to FIGS. 18A-F and Example 18, a method to prepare NHC-Protein A chip to bind IgG type anti-body is presented. Based on results from two kinds of anti-body tests, the NHC-Protein A chip gave reasonable sensing signals. Following treatment with regeneration solutions, NHC-Protein A chips were shown to provide reproducibility and robustness. The density of protein A was controlled, indicating that different NHC-Protein A chips based on different immobilization levels of protein A can be produced.

Referring to FIGS. 19A-D and Example 19, using a Biacore SPR analysis system, NHC-NTA chips have been shown to detect histidine-tagged proteins via Ni2+ chelation of nitrilotriacetic acid (NTA). It was found to have a comparable ability relative to the Biacore NTA chip. Capture stability varied between his-tagged proteins, which was dependent on the protein's nature and its tag's microenvironment. Other factors that may have affected the capture stability are quality of the capturing surface and amount of captured protein. Lower capture levels of protein usually give a more stable signal level.

Referring to FIG. 20 and Example 20, studies described herein have shown that BSA can be immobilized on a NHC-CM5 (500 KDa) surface using an amine coupling method. A BSA pre-immobilized surface (NHC-CM5) can sense ferulic acid (FA) and show appropriate reproducibility of replicate tests (association and dissociation phases).

Figure 21:
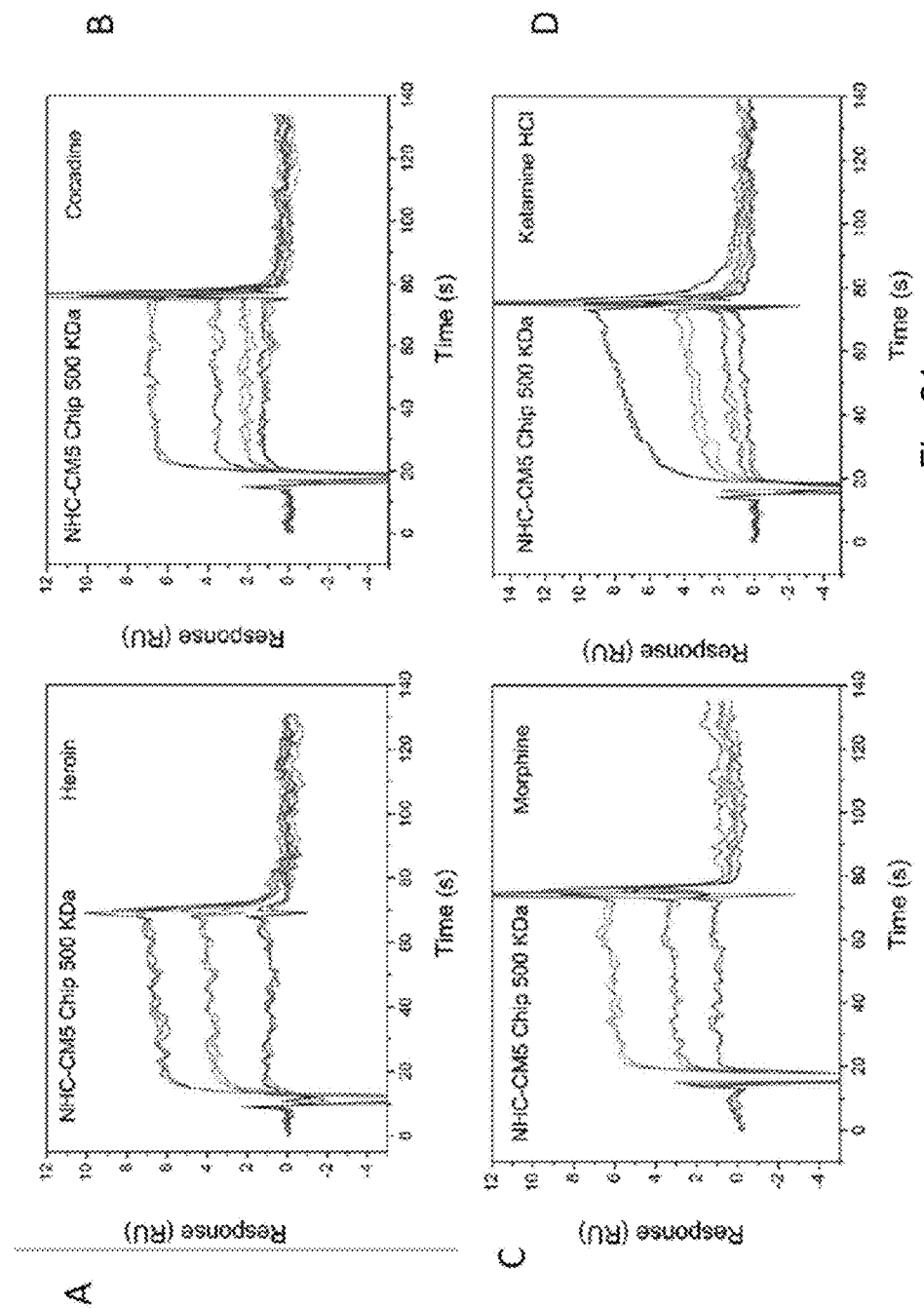

Referring to FIG. 21(A-D), NHC-CM5 chips (see Example 15 regarding preparation) have been shown useful for detection of opioids such as cocaine, heroin, ketamine and morphine. Signals for repeated runs overlap one another, while the different concentrations are spaced from one another with the higher concentration having the higher signal. For heroin and morphine, as shown in FIGS. 21A and 21C, only three levels are shown since the lowest concentration was not detectable. As shown in FIG. 22, such chips have been shown to have relatively excellent thermal stability.

While there have been studies of reactive carbenes (alkylidenes) on metal surfaces, which bind via a reactive metal-carbon double bond, [E. M. Zahidi, et al., Nature 409, 1023 (2001); G. S. Tulevski, et al., Science 309(5734), 591-594 (2005)) there have been few reports on the use of stable, bottleable NHC-type carbenes for the formation of single bonds to metal surfaces resulting in non-reactive surfaces.

In terms of NHC-type carbenes on flat metal surfaces, there are reports by Weidner et al. [T. Weidner et al., Aust. J. Chem. 64, 1177 (2011)] and Zhukhovitskiy et al. [A. V. Zhukhovitskiy, et al. J. Am. Chem. Soc. 135, 7418 (2013)].

In the 2013 report, a NHC containing an appended reactive metal alkylidene was prepared on gold by deprotonation using HMDS derived bases; however, only a 20% monolayer coverage was achieved under these conditions due to contamination by the base. Alternative methods employing carboxylate salts were reported, however these also required the use of strong base for their generation and required heating to pregenerate the free carbene before deposition, also requiring specialized equipment and inert atmosphere. In both cases, no stability or ordering was demonstrated. In the 2011 report of NHCs on flat Au surfaces, an ordered NHC film was inferred from NEXAFS C K-edge spectroscopy, but no stability studies were performed and no potential for derivatization illustrated. With respect to nanoparticles (curved metal surfaces), examples of NHC—Au species have been described [J. Vignolle, et al. Chem. Commun. 7230 (2009); E. C. Hurst, et al. New J. Chem. 33, 1837 (2009); R. T. W. Huang, et al. Dalton Trans. 7121 (2009)]. In these reports, the stability of the functionalized surface was either determined to be low, to require aging via multiple dissolution/precipitation cycles, or was not largely assessed.

Further, Johnson et al. previously described articles and methods comprising persistent carbenes and related compositions (see International Patent Application No. PCT/US2014/026752, filed 2013). In some embodiments of Johnson et al.'s work, persistent carbenes were derived from carbene precursors. In other embodiments, articles comprising persistent carbenes were carbene-functionalized composite materials, the materials having at least one metal surface. In other embodiments, the articles were carbene-functionalized nanoparticles.

However, not one of the foregoing suggest, teach, or disclose a method for producing carbene-functionalized composite material comprising a self-assembled carbene monolayer sourced from a purified carbene precursor, wherein the carbene monolayer is uniform, stable and substantially free of contamination, and the carbene precursor has been purified such that it contains substantially no contaminating staring anions (e.g., iodine, bromide, triflate) and that the carbene-functionalized composite materials are substantially free of contaminating starting anions derived from the carbene precursors. Further, not one of the foregoing suggest, teach, or disclose a method of producing carbene-functionalized nanoparticles formed by reducing a metal salt in the presence of a purified hydrogen carbonate carbene precursor, as described herein.

To gain a better understanding of the invention described herein, the following examples are set forth. It should be understood that these examples are for illustrative purposes only. Therefore, they should not limit the scope of this invention in any way.

WORKING EXAMPLES

Materials, Instruments and Calculations

Materials

Solvents were used without purification except where stated. THF was distilled from sodium, and DriSolv® methanol was purchased from EMT and used as received. All other reagents were purchased from chemical suppliers and used as received. Reactions requiring an inert atmosphere were carried out in a nitrogen-filled glovebox (M. Braun) with oxygen and water levels ≤2 ppm.

STM measurements were also performed in UHV at room temperature using a lab-built Pan-style STM (B. Drevniok et al., Review of Scientific Instruments 83, (2012)) on molecules added from solution to commercial Au(111) on mica surfaces. Mechanically formed platinum-iridium tips were used for all experiments. GXSM (P. Zahl et al., J. Vac. Sci. Technol. B 28 (2010)) was used as control software using the Signal Ranger A810 DSP and Nanonis HVA4 high-voltage amplifier.

All electrochemical measurements were performed with three-electrode configuration electrochemical cell, which was in an enclosed Faraday cage, and a CHI-660b potentiostat (CH Instruments, Austin, Tex.). A reference electrode (Ag/AgCl/3.0 M KCl), a platinum counter electrode and a salt bridge were used for all the experiments. The salt bridge was filled with agar solution, prepared by dissolving 2 grams of agar and 10.1 g $KNO_3$ in 100 mL of water. The solutions were always purged thoroughly with argon for 20-30 minutes and all the experiments were carried out in an Argon protected environment. Two types of electrolytes have been used. An aqueous solution of 0.1 M $NaClO_4$ and an aqueous solution of 5 mM/5 mM $Fe(CN)_6^{3-/4-}$ with 1 M $NaClO_4$ as supporting electrolyte were used as the electrolytes for electrochemistry on Fc-labeled films and electrochemical cycling tests respectively.

Instruments $^1H$ and $^{13}C$ NMR, spectra were recorded on Bruker Avance-400, 500 or 600 MHz spectrometers. Chemical shifts are reported in delta (δ) units, expressed in parts per million (ppm) downfield from tetramethylsilane, using residual protonated solvent as an internal standard ($^1H$ NMR $CDCl_3$: 7.26, methanol-$d_4$: 3.31 ppm; $^{13}C$ NMR $CDCl_3$: 77.16, methanol-$d_4$: 49.00 ppm). All 2D spectra (gs-COSY, gs-HSQC, gs-HMBC) were acquired in the phase-sensitive mode. All data were acquired, processed, and displayed using BrukerXWinNMR and MestReNova software and a standard pulse-sequence library. All measurements were carried out at 298 K.

IR spectra were collected on a Bruker ALPHA Platinum ATR as neat solids and absorption bands are given in $cm^{-1}$. Melting points were recorded on an Electrothermal MEL-TEMP apparatus connected to a Fluke 51 II Thermometer. Temperatures are given in degree Celsius (° C.) and are uncorrected. Mass-spectrometry was carried out using a Micromass Platform LCZ 4000 system. Elemental analyses were performed using Flash 2000 CHNS-O analyzer or Carlo Erba EA 1108 CHNOS Elemental Analyzer.

A plasma cleaner (Harrick Plasma Cleaner/Sterilizer PDC-32G, Ossining, N.Y.) was used. TGA experiments were performed using TGA Q500 with platinum crucibles. A constant heating rate of 5° C./min and gas purging ($N_2$) at a flow rate of 60 mL/min were used. The amount of samples used for TGA was between 10 and 11 mg.

XPS measurements were performed using a Thermo Microlab 310F UHV surface analysis instrument using Al Kα X-rays (1486.6 eV) or Mg Kα (1253.4 eV) at 15 kV anode potential and 20 mA emission current with a surface/detector take off angle of 75°. The binding energies of all spectra were calibrated to the Au 4f line at 84.0 eV. A Shirley algorithm was used as the background subtraction method for all peaks. The Powell peak-fitting algorithm was used, with peak areas normalized between different elements using the relative XPS sensitivity factors of Scofield (J. H. Scofield Journal of Electron Spectroscopy and Related Phenomena 8, 129-137 (1976)). In cases where absolute peak intensities for a single element were compared between different samples, care was taken to ensure a standard sample size and orientation with respect to the X-ray source and detector within the analysis chamber. Calibration of our system using Au thiol SAMs of known surface concentration gave peak areas reproducible within ±5% between sample runs.

Calculations

Frequency calculations of an NHC—Au—Cl complex related to 2a were performed using Kohn-Sham density functional theory (W. Kohn et al., Phys Rev 140, 1133-& (1965), P. Hohenberg et al., Phys Rev 136, B864-B871 (1964)) with the M06-2X exchange-correlation functional (Y. Zhao et al., Theor Chem Acc 120, 215-241 (2008)) in conjunction with the TZVP basis set (A. Schafer et al., Journal of Chemical Physics 100, 5829-5835 (1994)) for C, N, Cl, and H and the SDD basis set/effective core potential combination (D. Andrae, et al., Theor Chim Acta 77, 123-141 (1990), M. Dolg, et al., Journal of Chemical Physics 86, 866-872 (1987) for Au. The calculated frequencies were shifted using a scaling factor of 0.97 (I. M. Alecu, et al., J. Chem. Theory Comput. 6, 2872-2887 (2010). The components of the dipole moment derivatives along the direction of the Au—C bond were required for each normal mode and used to generate the simulated infrared spectrum of 2a residing perpendicular to an Au surface.

The inventors wish to acknowledge the Collaborative Innovation Center of Judicial Civilization of the Chinese University of Political Science and Law, China, who made its in-house SPR and Biocore instruments available for tests to be conducted.

Example 1. Preparation of Compounds

Preparation of 1,3-Diisoproplylbenzimidazolium iodide (1a) and 1,3-dimethylbenzimidazolium iodide (1b)

1,3-Diisoproplylbenzimidazolium iodide, 1a, and 1,3-dimethylbenzimidazolium iodide, 1b, were prepared according to literature procedures (Chen, W. C. et al., (2014) *Chemistry—a European Journal* 20, 8099-8105).

Figure 1B:
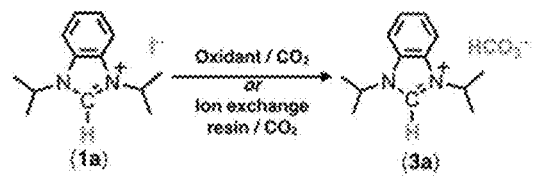
FIG. 1b is a schematic showing synthesis of benzimidazolium hydrogen carbonate (3a).

Preparation of 1,3-Diisopropylbenzimidazolium hydrogen carbonate, [iPr$_2$bimy (H)][HCO$_3$] (3a; FIG. 1b)

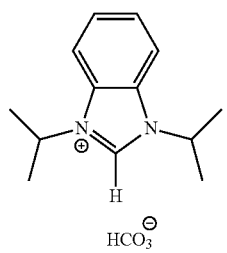

(3a)

1,3-Diisopropylbenzimidazolium hydrogen carbonate, [iPr$_2$bimy (H)][HCO$_3$] (3a) was prepared using a hydrogen peroxide oxidation in presence of carbon dioxide. Specifically, a 50 mL round bottom flask capped with a rubber septum and containing a needle for ventilation and a glass pipette for addition of gaseous carbon dioxide was charged with a clear colorless solution of 1,3-diisoproplylbenzimidazolium iodide (1a) (990.6 mg, 3 mmol) in deionized water (30 mL) (pH=6). CO$_2$ was bubbled through this solution for 1 min, after which time hydrogen peroxide (193 µL (30% w/v), 2.25 mmol in 0.5 mL water) was injected. Vigorous CO$_2$ bubbling was maintained for 1 h under stirring during which time the solution turned yellow and then brown until the formation of a purple precipitate was detected. The mixture was filtered by vacuum filtration and washed with 3 mL of water resulting in a clear colorless filtrate solution (pH=8), leaving the insoluble iodine as a violet solid precipitate. Water was removed by flushing air overnight over the surface of the solution then the product was dried under high vacuum for 2 h to give a white solid. The resulting solid was triturated and sonicated in acetone (3×3 mL), which was then decanted off. Subsequent drying under vacuum afforded the desired product as a white powder (478 mg, 66% yield).

To test for complete removal of iodine, a qualitative silver nitrate test was performed where one drop from the reaction aliquot was mixed with excess aqueous silver nitrate (1 M) solution. In cases where incomplete exchange was observed, a yellow precipitate of silver iodide formed that persisted upon the addition of nitric acid. When iodide was completely exchanged, a white precipitate of silver bicarbonate formed that became colorless upon addition of a solution of 1M nitric acid. Quantitatively, the removal of iodide was assessed by elemental analysis in house looking at CHN and also externally analyzing for iodide content. Mp: 123-124° C. (dec.).

$^1$H NMR (400 MHz, CD$_3$OD): δ 8.07 (dd, J=6.3, 3.2 Hz, 2H, Ar—H), 7.75 (dd, J=6.3, 3.1 Hz, 2H, Ar—H), 5.11 (hept, J=6.7 Hz, 2H, NCHiPr), 1.77 (d, J=6.7 Hz, 12H, CH$_3$iPr). The N$_2$CH and HCO$_3$ protons could not be observed due to their rapid exchange with the deuterated solvent on the NMR time scale.

$^{13}$C ($^1$H) NMR (100 MHz, CD$_3$OD): 161.42 (s, HCO$_3^-$), 138.96 (s, N$_2$CH), 132.59 (s, C$_q$), 128.19 (s, C$_{Ar}$), 114.97 (s, C$_{Ar}$), 52.83 (s, CHiPr), S 22.11 (s, CH$_3$iPr).

ATR-IR: strong peaks for CO$_2$ asym. str. at 1622 cm$^{-1}$ and sym. str. at 1367 cm$^1$ Anal. Calc. for C$_{14}$H$_{20}$N$_2$O$_3$: C, 63.62; H, 7.63; N, 10.60. Found: C, 63.63; H, 7.83; N, 10.38, I<0.2. HRESI-MS (m/z) for C$_{13}$H$_{19}$N$_2^+$ [M-HCO$_3$]$^+$: 203.1543, Calc.: 203.1543.

Hydrogen Carbonate-Anion Exchange Resin

Firstly, a hydrogen carbonate exchange resin was prepared from commercial (Sigma Aldrich) Amberlyst A26 hydroxide resin. To accomplish the conversion, 10 g (0.8 meq/mL) of the resin was suspended in 10 mL deionized water (pH=8) and carbon dioxide bubbled through the solution for 0.5 h (pH=6, as measured by a pH strip). To test the conversion of the resin, aqueous KI (0.2 mL, 0.4 M) was added to 0.2 mL of resin before and after CO$_2$ bubbling. The mixtures were sonicated for 10 min and to one drop of the aliquots, excess aqueous silver nitrate (1 M) was added. The fresh (hydroxide) resin gave a dark brown precipitate of silver oxide, while the bicarbonate resin gave a white precipitate of silver bicarbonate. Both precipitates gave a clear colourless solution after addition of nitric acid. After this, the resin was used to treat several iodide salts as described below.

Resin-HCO₃ suspended in water was measured out in a graduated cylinder (3.8 mL, 3 equiv., prepared as described above) and transferred to a 20 mL vial where the resin was allowed to settle and water was decanted. The resin was washed with methanol (3×2 mL). 1,3-Diisoproplylbenzimidazolium iodide (1a) (320 mg, 1 mmol) was dissolved in 5 mL methanol and transferred to the resin. The mixture was stirred for 30 min. The silver nitrate test indicated the completeness of the exchange reaction. The hydrogen carbonate solution was passed through a cotton plug to remove any resin beads and the resin was washed with methanol (3×2 mL), which was then added to the original filtrate. Solvent was evaporated and the residual solid was triturated and sonicated in acetone (3×3 mL), which was then decanted off via syringe and discarded. Subsequent drying of the white powder under vacuum afforded the desired product as a white powder (198 mg, 75% yield). Mp: 123-125° C. (dec.). Anal. Calc. for $C_{14}H_{20}N_2O_3$: C, 63.62; H, 7.63; N, 10.60. Found: C, 63.34; H, 7.70; N, 10.71

Preparation of 1,3-Dimethylbenzimidazolium hydrogen carbonate, [Me₂bimy(H)][HCO₃] (3b)

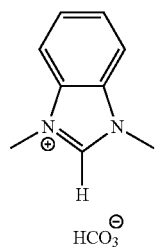

(3b)

Hydrogen Peroxide Oxidation in Presence of Carbon Dioxide

A 50 mL round bottom flask that was capped with a rubber septum and containing a needle for ventilation and a glass pipette for addition of gaseous carbon dioxide, was charged with a clear colorless solution of 1,3-dimethylbenzimidazolium iodide (1b) (274.1 mg, 1 mmol) in deionized water (7 mL) (pH=6). Carbon dioxide was bubbled for 1 min followed by addition of hydrogen peroxide (65 μL (30% w/v), 0.75 mmol in 0.5 mL water, 1.5 equiv). Vigorous $CO_2$ bubbling was maintained for 1 h under stirring during which time the solution turned yellow and then brown until the formation of a purple precipitate was detected. The mixture was filtered and washed with water (3×2 mL) resulting in a clear colorless filtrate solution (pH=8). Water was removed by flushing air overnight over the surface of the solution then it was dried under high vacuum for 2 h to give a white solid. The residual solid was triturated and sonicated in acetone (3×2 mL), which was then decanted off. Subsequent drying under vacuum afforded the desired product as a white powder (123 mg, 59% yield) Mp: 137-138° C. (dec.).

¹H NMR (400 MHz, CD₃OD): δ 7.96 (dd, J=6.2, 3.1 Hz, 2H, Ar—H), 7.74 (dd, J=6.3, 3.1 Hz, 2H, Ar—H), 4.15 (s, 6H, CH₃). The N₂CH and HCO₃ protons could not be observed due to their rapid exchange with the deuterated solvent on the NMR time scale. ¹³C (¹H) NMR (100 MHz, CD₃OD): δ 161.38 (s, HCO₃⁻), 143.94 (s, N₂CH), 133.54 (s, $C_q$), 128.18 (s, $C_{Ar}$), 114.15 (s, $C_{Ar}$), 33.65 (s, CH₃).

ATR-IR: strong peaks for $CO_2$ asym. str. at 1626 cm⁻¹ and sym. str. at 1367 cm⁻¹.

Anal. Calc. for $C_{10}H_{12}N_2O_3$: C, 57.68; H, 5.81; N, 13.45. Found: C, 57.72; H, 5.75; N, 13.03. HRESI-MS (m/z) for $C_9H_{11}N_2^+[M-HCO_3]^+$: 147.0913, Calc.: 147.0917.

Hydrogen Carbonate-Anion Exchange Resin

Resin-HCO₃ (5.7 mL, 3 equiv.) suspended in water was measured in a graduated cylinder. The resin was transferred to 50 mL round bottom flask and water was removed by decantation. The resin was washed with methanol (3×4 mL). 1,3-Dimethyl-benzimidazolium iodide (1b) (411 mg, 1.5 mmol) was dissolved in 7.5 mL methanol and transferred to the resin. The mixture was stirred for 30 min. The silver nitrate test indicated the completeness of the exchange reaction. The bicarbonate solution was passed through a cotton plug to remove any resin beads and the resin was washed with methanol (3×2 mL). Solvent was evaporated using rotavap at 40° C. then in vacuo. The residual solid was triturated and sonicated in acetone (3×3 mL), which was then decanted off. Subsequent drying under vacuum afforded the desired product as a white powder (233 mg, 75% yield). Mp. 135-138° C. (dec.). Anal. Calc. for $C_{10}H_{12}N_2O_3$: C, 57.68; H, 5.81; N, 13.45. Found: C, 57.69; H, 5.77; N, 13.10.

Preparation of 5-((12-(4-(Ferrocenyl)-1H-1,2,3-triazol-1-yl)dodecyl)oxy)-1,3-diisopropyl-1H-benzo[d]imidazol-3-ium iodide (1c)

5-((12-(4-(Ferrocenyl)-1H-1,2,3-triazol-1-yl)dodecyl)oxy)-1,3-diisopropyl-1H-benzo[d]imidazol-3-ium iodide (1c) was prepared via the method reported in Crudden, C. et al., *Nature Chemistry* 6, 409 and 553 (2014).

Preparation of 5-((12-(4-(Ferrocenyl)-1H-1,2,3-triazol-1-yl)dodecyl)oxy)-1,3-diisopropyl-1H-benzo[d]imidazol-3-ium hydrogen carbonate (3c)

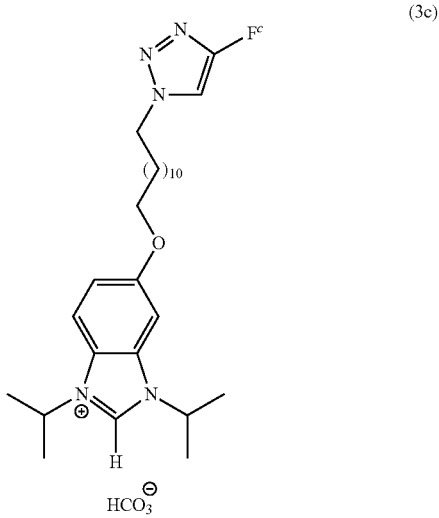

(3c)

Hydrogen Carbonate-Anion Exchange Resin

Resin-HCO₃ (0.3 mL, 3 equiv.) suspended in water was measured in a graduated cylinder and transferred to 20 mL vial where the resin was allowed to settle and water was decanted off. The resin was washed with methanol (3×1 mL). 5-(12-(4-(Ferrocenyl)-1H-1,2,3-triazol-1-yl)dodecyloxy)-1,3-diisopropyl-1H-benzo[d]imidazol-3-ium iodide (1c) (56 mg, 0.07 mmol) as dissolved in 5 mL methanol and transferred to the resin. The mixture was stirred for 30 min. The red solution was passed through a cotton plug. Solvent was evaporated using a rotary evaporator at 40° C. then in vacuo for 2 h to give an orange solid (35 mg, 71%).

$^1$H NMR (400 MHz, CD$_3$OD): 8.01 (s, 1H, triazole), 7.88 (d, 1H, J$_{HH}$=9.0 Hz, ArH), 7.42 (s, 1H, ArH), 7.28 (d, 1H, J$_{HH}$=8.6 Hz, ArH), 5.00 (m, 2H, CH—(CH$_3$)$_3$), 4.73 (s, 2H, ferrocene), 4.40 (t, 2H, J$_{HH}$=6.8 Hz, ferrocene), 4.30 (m, 2H, N—CH$_2$), 4.11 (t, J$_{HH}$=6.4 Hz, O—CH$_2$), 4.02 (m, 5H, ferrocene), 1.93 (m, 2H), 1.82 (m, 2H), 1.70 (m, 12H, —CH$_2$—), 1.49 (m, 2H), 1.31 (m, br, 16H). $^{13}$C ($^1$H) NMR (CD$_3$OD): δ 161.35 (s, HCO$_3^-$), 160.39 (s, Cq), 147.94 (s, Cq), 139.39 (s, N—CH═N), 133.80 (s, Cq), 126.52 (s, Cq), 121.36 (s, triazole), 118.69 (s, Ar), 115.63 (s, Ar), 97.46 (s, Ar), 76.19 (s, Ar), 70.53 (s, ferrocene), 70.24 (s, CH$_2$—O), 69.77 (s, ferrocene), 67.60 (s, ferrocene), 52.80 (s, CH$_3$—CH—CH$_3$), 52.24 (s, CH$_3$—CH—CH$_3$), 51.32 (s, CH$_2$-triazole), 31.16 (s), 30.60 (s), 30.56 (s), 30.48 (s), 30.46 (s), 30.38 (s), 30.18 (s), 29.95 (s), 27.79 (s), 27.09 (s), 22.17 (s, CH$_3$), 22.11 (s, CH$_3$).

ATR-IR: strong peaks for CO$_2$ asym. str. at 1661 cm$^{-1}$ and sym. str. at 1288 cm$^{-1}$ HRESI-MS (m/z) for C$_{37}$H$_{52}$FeN$_5$O$^+$[M-HCO$_3$]$^+$: 638.3491, Calc.: 638.3516.

Preparation of 5-(Dodecyloxy)-1,3-diisopropyl-1H-benzo[d]imidazol-3-ium iodide (1d)

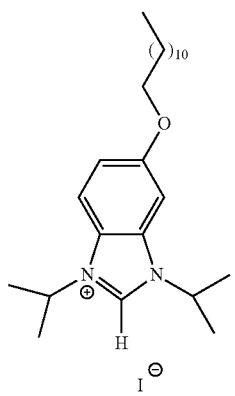

(1d)

5-(Dodecyloxy)-1,3-diisopropyl-1H-benzo[d]imidazol-3-ium iodide (1d) was prepared using a similar method as described in a literature procedure [C. M. Crudden et al., Nature Chem. 6, 409-414 (2014)]. with a slight modification where 2-iodopropane (1.6 mL, 16 mmol, 5 equiv.) was slowly added to a suspension of 5-(dodecyloxy)-1H-benzo[d]imidazole (971 mg, 3.2 mmol) and Cs$_2$CO$_3$ (1.04 g, 3.2 mmol) in acetonitrile (16 mL). The mixture was heated to 90° C. in a two-necked round bottom flask under an argon atmosphere for 48 h. The reaction mixture was allowed to cool to room temperature. Water (20 mL) was added to the reaction mixture. The reaction mixture was then extracted with dichloromethane (3×30 mL). The combined organic layers were dried over anhydrous magnesium sulfate, filtered and then concentrated in vacuo. The crude solid was triturated and sonicated in diethyl ether (3×6 mL). Subsequent drying under high vacuum afforded the desired product as an off-white powder (1.30 g, 78% yield).

$^1$H NMR (400 MHz, CDCl$_3$) δ 10.81 (s, 1H, N—CH═N), 7.64 (d, 1H, J$_{HH}$=9.2 Hz, ArH), 7.21 (dd, 1H, J$_{HH}$=9.2, 2.0 Hz, ArH), 7.09 (d, 1H, J$_{HH}$=1.9 Hz, ArH), 5.10 (m, 2H, CH—(CH$_3$)$_3$), 4.05 (t, 2H, J$_{HH}$=6.4 Hz, O—CH$_2$), 1.84 (m, 14H), 1.48 (m, 2H), 1.26 (m, 16H), 0.87 (t, 3H, J$_{HH}$=6.6 Hz). Spectra were consistent with literature reports.

Preparation of 5-(Dodecyloxy)-1,3-diisopropyl-1H-benzo[d]imidazol-3-ium hydrogen carbonate (3d)

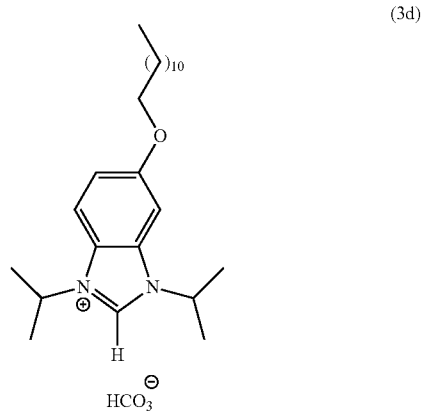

(3d)

Hydrogen Carbonate-Anion Exchange Resin

Resin-HCO$_3$ (9.4 mL, 10 equiv.) suspended in water was measured in a graduated cylinder and then transferred to 50 mL round bottom flask, allowed to settle and water was decanted. 5-(Dodecyloxy)-1,3-diisopropyl-1H-benzo[d]imidazol-3-ium iodide (358.5 mg, 0.75 mmol) was dissolved in 7.5 mL acetonitrile and transferred to the resin suspension. Water (7.5 mL) was added to the resin. The mixture was stirred for 30 min. The bicarbonate solution was passed through a cotton plug to remove any resin beads and the resin was washed with (3×2 mL 1:1 water:acetonitrile). Solvents were removed overnight under a stream of air. The resulting yellow oily solid was triturated and sonicated in 10% acetone/diethyl ether (3×4 mL), which was then decanted off. Subsequent drying under vacuum afforded the desired product as an off-white powder (206 mg, 61% yield). Mp. 68-71° C. (dec.).

$^1$H NMR (400 MHz, CD$_3$OD): δ 7.89 (d, J=9.2 Hz, 1H, CH$_{Ar}$), 7.44 (d, J=2.1 Hz, 1H, CH$_{Ar}$), 7.30 (dd, J=9.2, 2.2 Hz, 1H, CH$_{Ar}$), 5.10-4.92 (m, 2H, CH—(CH$_3$)$_2$), 4.13 (t, J=6.4 Hz, 2H, —O—CH$_2$), 1.85 (m, 2H), 1.71 (dd, J=6.7, 2.5 Hz, 12H, CH—(CH$_3$)$_2$), 1.53 (s, 2H), 1.29 (s, 16H), 0.90 (t, J$_{HH}$=6.8 Hz, 3H, CH$_3$). The N$_2$CH and HCO$_3$ protons could not be observed due to their rapid exchange with the deuterated solvent on the NMR time scale.

$^{13}$C ($^1$H) NMR (CD$_3$OD): δ161.43 (s, HCO$_3$), 160.43 (C$_q$—O—CH$_2$), 137.96 (C$_{Ar}$, N$_2$CH), 133.83 (C$_q$), 126.54 (C$_q$), 118.71 (C$_{Ar}$), 115.62 (C$_{Ar}$), 97.41 (C$_{Ar}$), 70.23 (CH$_2$-0), 52.80 (CH(CH$_3$)$_2$), 52.23 (CH(CH$_3$)$_2$), 33.07 (CH$_2$), 30.76 (CH$_2$), 30.75 (CH$_2$), 30.70 (CH$_2$), 30.47 (CH$_2$), 30.23 (CH$_2$), 27.15 (C$_1$-12), 23.73 (CH$_2$), 22.17 (CH(CH$_3$)$_2$), 22.11 (CH(CH$_3$)$_2$), 14.43 (CH$_3$)

ATR-IR: strong peaks for CO$_2$ asym. str. at 1620 cm$^1$ and sym. str. at 1371 cm$^{-1}$.

Anal. Calc. for C$_{26}$H$_{44}$N$_2$O$_4$: C, 69.61; H, 9.89; N, 6.24. Found: C, 69.14; H, 9.71; N, 6.24. HRESI-MS (m/z) for C$_{25}$H$_{43}$N$_2$O$^+$[M-HCO$_3$]$^+$: 387.3370, Calc.: 387.3370.

Example 2. Cleaning of Metal Surfaces and Chip Surfaces

Vapor deposition experiments were conducted in three separate stainless steel UHV chambers hosting an Ar ion sputtering gun and annealing facilities for sample cleaning. TPD data were collected in a UHV chamber (base pressure P=1×10$^9$ mbar) equipped with a quadrupole mass spectrometer (SPECTRA, Microvision Plus) in direct line-of-sight with the crystal, and a LEED/Auger spectrometer (Specta-LEED, Omicron). STM images were recorded in a third chamber (base pressure=1×10$^{-10}$ mbar) equipped with a variable temperature scanning tunneling microscope (Omicron), and LEED optics. An electrochemically etched W tip was used for STM imaging typically employing bias voltages of ±0.6 V and tunneling currents of 300 pA. Image processing and filtering have been applied to the STM data using WSxM.

An Au (111) single crystal was cleaned by 10 cycles of annealing at 775 K and Ar ion sputtering (1.25 kV). Each cleaning cycle was terminated by annealing to 775 K for 15 minutes before the crystal was cooled down to room temperature. Annealing was done by direct or resistive heating of the sample, and the temperature monitored by means of a type-K thermocouple. Cleanliness of the sample was assessed either by monitoring the TPD traces during the final annealing cycle until no desorbing species were observed, or by STM and LEED until the 22×√3 reconstruction[14] was visible.

Au(111) on Mica

Prior to functionalization the Au(111) films were cleaned by washing the films in 3×2 mL of methanol, drying them under an argon gas (4.8 Praxair) stream for 1 minute, then cleaning them with plasma generated from room air at a medium RF level and a pressure kept between 300 and 500 mtorr for 1 minute. The films were then used immediately for functionalization.

Au/Si for Electrochemical Cycling

NHC films prepared for electrochemical cycling with 3d using Au/Si substrates, which were prepared by electron-beam deposition at a thickness of 200 nm Au on a Si wafer with 20 nm of Ti as the adhesion layer (Nanofabrication Facility at University of Western Ontario).

Au Microelectrodes: Synthesis and Cleaning

Homemade gold microelectrodes were used for electrochemistry using NHC derivative 3c. The microelectrodes were manufactured by sealing gold wire with diameter of 25 μm into a glass capillary. After this, the microelectrodes were polished with 3-micron lapping films to expose the cross-section of Au wires and then the Au surfaces was polished down with 0.3-micron and 0.05-micron $Al_2O_3$ lapping films. The microelectrodes were sonicated in deionized water, ethanol and deionized water for 20 minutes respectively. The microelectrodes were electrochemically cleaned prior to each experiment by running a cyclic voltammetry immersed in a 0.5 M KOH solution between −2 V and 0 V for 100 cycles, followed by 0.5 M $H_2SO_4$ solutions between 0 V and +1.4 V for 100 cycles at a scan rate of 0.5 V·s$^{-1}$. The electrodes were always rinsed with deionized water thoroughly between steps.

Preparation of SPR Biosensing Chip Surfaces

Gold sensor surfaces (SIA kit Au, GE Healthcare) were stored at 4° C. Prior to use, initial cleaning of these sensor surfaces was performed by immersion in a mixture of $NH_4OH:H_2O_2:H_2O$ (1:1:5) at 80° C. for 0.5 h, rinsed thoroughly with milliQ-water, and drying under a stream of nitrogen. Additional cleaning was performed at 60 W for 15 min with a Harrick Plasma Cleaner/Sterilizer (PDG-32G), followed by immediately immersing the gold sensor surfaces into a 10 mM solution of NHC molecules dissolved in dry methanol (48 h, room temperature, without light). The sensor surfaces were then rinsed with methanol to remove excess adsorbate, dried under nitrogen, and then mounted on a support for insertion into the cartridge. Special care was taken to prevent artificial scratches or impurities from depositing onto the hydrophobic NHC sensor surfaces.

Example 3. Preparation of SAMs

Hydrogen Carbonate Salt (Carbene Precursor) Method

Figure 1C:
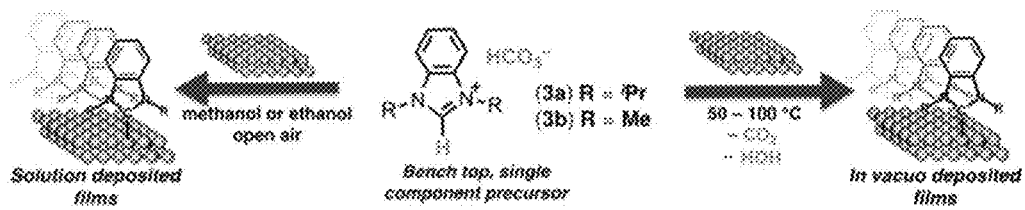
FIG. 1c is a schematic showing preparation of NHC films from 3a and 3b in solvent at 293K or by heating neat solid in vacuo.

Self-assembled monolayers were prepared by immersion of Au(111) on mica substrates in 1 to 10 mM solutions of the corresponding benzimidazolium hydrogen carbonate salt (carbene precursor) in methanol for 24 hours at room temperature in air (FIG. 1c). Substrates were then rinsed in methanol (5×2 mL) and dried under an argon gas (4.8 Praxair) stream for 1 minute.

Free Carbene Method

Self-assembled monolayers were prepared by immersion of Au(111) on mica substrates in a 1 mM solution of the corresponding free carbene dissolved in dry toluene at room temperature in the glove box. Substrates were then rinsed in toluene (10×2 mL) and dried under an argon gas (4.8 Praxair) stream for 1 minute.

Example 4. Chemical Stability Tests

All films were prepared using the hydrogen carbonate salt (carbene precursor) 3a and the solution deposition method previously described. Data for stability measurements are given in Chemical Stability Results. See FIGS. 7a-g.

pH Stability Tests

NHC films derived from iPr$_2$bimy(H)[HCO$_3$] (3a) were submerged in freshly prepared unbuffered solutions of varying pH (pH 2 or pH 12) in Ace Glass pressure tubes at 25° C. for 24 h. Experiments were conducted under $N_2$ gas to minimize the possibility of pH change due to adsorption of atmospheric $CO_2$. After this time, functionalized surfaces were rinsed in deionized water (3×2 mL) and dried in an $N_2$ gas stream. The pH values of the solutions were adjusted using concentrated NaOH and HCl solutions in deionized water. Unbuffered solutions were employed in order to avoid potential adsorption effects of buffer ions from solution.

Tetrahydrofuran Stability Tests

NHC films derived from iPr$_2$bimy(H)[HCO$_3$] (3a) were placed in Ace Glass pressure tubes and 3 mL of freshly distilled tetrahydrofuran (THF) was added. The tube was purged with nitrogen gas, sealed and heated to 68° C. for 24 h. After this time, the sample was cooled to RT, rinsed in THF (2×5 mL), and dried under a nitrogen gas stream.

Decalin Stability Tests

NHC films derived from iPr$_2$bimy(H)[HCO$_3$] (3a) were placed in Ace Glass pressure tubes and 2 mL of decalin were added. The tubes were purged with nitrogen gas, sealed and heated to either 100° C. or 190° C. for 24 h. After this time, the samples were cooled to RT, rinsed with hexane (2×5 mL), ether (2×5 mL), and ethanol (2×5 mL), and dried under a nitrogen gas stream.

Water Stability Tests

NHC films derived from iPr$_2$bimy(H)[HCO$_3$] (3a) were placed in freshly deionized (resistivity 18.2 MΩ·cm) water (3 mL) in Ace Glass pressure tubes at left at 25° C. or heated to 100° C. for 24 h. A separate slide was left at 25° C. for one month to assess long-term stability. Experiments were conducted under nitrogen gas. After this time, functionalized surfaces were rinsed in DI water (3×3 mL) and dried in a nitrogen gas stream.

Peroxide Stability Tests

NHC films derived from iPr$_2$bimy(H)[HCO$_3$] (3a) were placed in a freshly prepared 1% solution of hydrogen peroxide and left at RT for 24 h. After this time, the surfaces were rinsed in DI water (3×3 mL) and dried in a nitrogen gas stream.

Example 5. SPR Protocols

Preparation of Small Unilamellar Vesicles (SUVs)

SUVs were prepared in PBS buffer (100 mM Na$_2$HPO$_4$/NaH$_2$PO$_4$, 150 mM NaCl, pH 7.4). The general protocol was as follows: Egg yolk L-☐-phosphatidylcholine (9.0 mg, 2 mM) was dissolved in chloroform/methanol (2/1, v/v) in a vial. The solvent mixture was evaporated under a steam of nitrogen for at least 30 min, yielding a thin lipid film on the bottom of the vial. The lipid films were then thoroughly dried by connecting the vial to a vacuum pump for 2 h in order to remove organic solvents. The dried lipid films were hydrated by adding 6.0 mL of the running buffer to be used in the assays. The vial was then vortexed thoroughly until all lipid films were removed from the wall of vial, resulting in a milky suspension. The lipid suspension was then frozen in a dry ice/acetone bath for 8 min, followed by thawing in a hot water bath (80° C., 8 min). This freeze-thaw cycle was repeated 8 times. The solution was then sonicated until the suspension changed from milky to nearly transparent, yielding a uniform suspension of SUVs with a predominant size range between 30 and 35 nm.

Formation and Regeneration of Lipid Monolayer on NHC Sensor Chip

Formation and regeneration of lipid monolayer test was carried out using Biacore 3000 (GE Healthcare) and NHC sensor chips (see Preparation of SPR Biosensing Chip Surfaces). Following equilibration of each sensor chip to room temperature, they were docked into a Biacore 3000 and primed with running buffer. All solutions for injections were prepared freshly, filtered through a 0.2 μm pore filter, and thoroughly degassed prior to use.

The sensor surface was preconditioned by a 5-min injection of 40 mM n-Octylβ-D-glucopyranoside (OG) at a flow rate of 1 mL/min. SUVs were injected immediately for a period of 25 min, followed by a 5 min dissociation period with buffer. To remove loosely bound vesicles, the flow rate was increased to 100 mL/min for a 1 min buffer rinse followed by a 1-min wash with 50 mM sodium hydroxide at 10 mL/min. The result was a stable baseline, presumably corresponding to the lipid monolayer. The degree of the surface coverage for the lipid was evaluated by injecting 0.1 mg/mL BSA at flow rate of 10 mL/min for 5 min to assess the quantity of non-specific binding. After each binding cycle, the sensor surface was regenerated by 40 mM OG for 5 min. The stability of the sensor chip performance was assayed by repeated cycles of binding with egg PC SUV and regenerating with OG. Sensor chips were stored at 4° C. in 50 mL centrifuge tubes, which contained a small portion of moist tissue for maintaining hydration environment.

A range of buffers and pHs were tested to evaluate egg phosphatidyl choline (PC) lipid binding capacity and reproducibility over multiple binding cycles, and non-specific binding of lipid monolayer formation. The buffers with pHs including 100 mM Citric acid/200 mM Na$_2$HPO$_4$ (Citrate) pH 5.0, (100 mM Na$_2$HPO$_4$/NaH$_2$PO$_4$, 150 mM NaCl) PBS pH7.4, (10 mM N-(2-hydroxyethyl) 1-piperazine-N'-(2-ethanesulphonic acid), 100 mM NaCl) HEPES pH8.0, (10 mM Tris-HCl, 1 mM EDTA) TE pH 8.0, and (10 mM 3-(cyclohexylamino)-1-propanesulfonic acid, 150 mM NaCl) CAPS pH 10.0.

Thermal Stability of NHC Sensor Chip

Gold sensor surfaces (SIA kit Au, GE Healthcare) coated with the NHC (3d)-based SAM was baked at a constant 65° C. for 24 h, then cooled in air and mounted onto the inner support of a sensor chip (SIA kit Au, GE Healthcare). Performance of the 65° C.-exposed NHC sensor chip was evaluated by 4 cycles of lipid (egg PC, SUV) monolayer formation and regeneration in PBS buffer, as described above for the non-exposed NHC sensor chip.

Example 6. XPS Analysis of Deposition of Hydrogen Carbonate Salt (Carbene Precursor)

Metal samples were fixed using copper tape, mounted in a XPS instrument antechamber, and subjected to high vacuum overnight before being introduced into an ultra-high vacuum analysis chamber. XPS data were acquired using a Thermo Microlab 310F ultrahigh vacuum (UHV) surface analysis X-ray photoelectron spectrometer operating at 15 kV anode potential and 20 mA emission current with a surface/detector take off angle of 75°. See Table 1 for XPS data. A Mg Kα X-ray source (1253.4 eV) was used in the case of Au and Ag experiments, while an Al KαX-ray source (1486.6 eV) was used in the case of Ni and Cu experiments. In the case of gold and silver studies, binding energies of all spectra were calibrated to Au (4f, 84 eV) and Ag (3d, 368.3 eV) lines, respectively, while binding energies in nickel and copper studies were calibrated to C (1s, 284.5 eV).

Example 7. STM Results for Films Prepared in Solution

Figure 5:
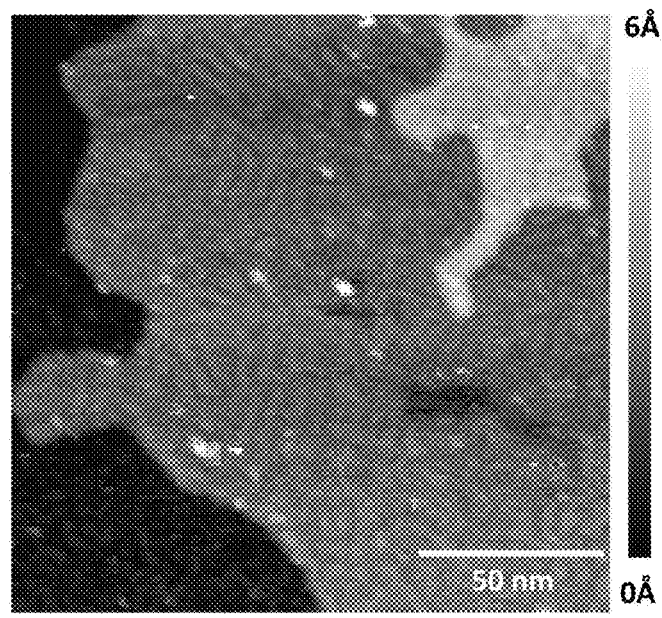
FIG. 5 depicts an STM image of an altered herringbone reconstruction on Au(111) due to adsorption of NHC 2b on the surface from solution grafting of 3b, 160 nm×160 nm, bias voltage=0.5 V and set current 5 pA.

Carbene-induced changes to the Au(111) herringbone reconstruction were studied. As with surfaces prepared in ultra-high vacuum, a remnant of the herringbone reconstruction was observed on some carbene films prepared from solution deposition of NHC precursor (3b). In both cases it was determined that the adsorbed molecules reduced the number of kinks in the Au(111) herringbone reconstruction (FIG. 5).

Figure 6:
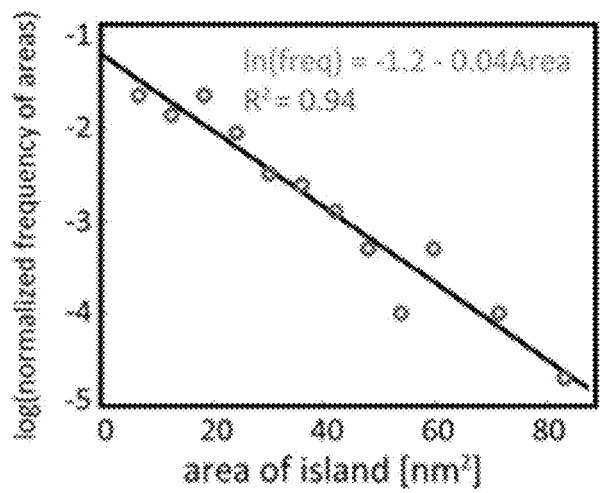
FIG. 6 graphically presents results of a threshold analysis for 3a on Au(111) and mean island size across different samples.

Image threshold analysis (see FIG. 6) was performed using MATLAB (MATrixLABoratory) to count the number and area of pits on a surface. Images were converted to a binary image where islands were set to low and all other areas were set to high. Images were chosen to contain a single atomic terrace to allow for simplified thresholding. Human inspection was used for each thresholded image to determine quality of the procedure. Adjustments to data leveling and threshold settings can be made to obtain an ideal binary image.

A histogram of pit size frequency and a mean pit size was calculated for each image. Pit density ($A_{pit}/A_{total}$ image) for each image was also calculated. Pit density seems to collect in two ranges, one around 0.10±0.05 and another around 0.35±0.01.

Example 8. SPR Results

Reproducibility of the NHC-derived sensor chip (NHC (3d) chip) was benchmarked against the commercial HPA chip under a range of pH conditions. Table 2 demonstrates that reproducibility of the phosphatocholine hybrid lipid bilayer loading was similar for both HPA and NHC under most pH conditions. However, adsorption of BSA, which probes the quality of the surface, showed much higher variability on the HPA chip under all but the highest pH conditions, such that the NHC chip demonstrates more reproducible film quality. Furthermore, the absolute quantity of BSA adsorbed was higher on the HPA chip at both extremes of pH, suggesting that a more complete hybrid lipid bilayer was formed on the NHC chip over a much wider range of pH conditions. The effect of heating the NHC-modified SPR chip is shown in Table 3 and discussed in more detail herein.

Example 9. Mesoionic Carbenes

The following experiment describes surface-functionalization of Au on mica with a mesoionic carbene ("MIC"). An in-situ approach was used where isolation of free carbene (1,3-diphenyl-1H-1,2,3-triazolylidene) can be avoided by reacting 1,3-diphenyl-1H-1,2,3-triazolium tetrafluoroborate with a suitable base to result in carbene-formation in the presence of a clean, unfunctionalized Au-surface (the term mesoionic accounts for the fact that no neutral canonical Lewis-formula can be drawn for this family of carbenes. All contributing resonance formulas have a separated negative and positive charge). $NaBF_4$ formed during the reaction as well as any remaining starting materials were removed by washing the MIC-functionalized Au-chips with THF and MeOH. XPS analysis suggested that incorporation of the MIC carbene occurred and that $BF_4$-salts (absence of F-signal) and fragments from the base (absence of Si-signal) did not interfere with the Au-surface. However, measured C/N ratios deviated slightly from calculated values for both bases used: calc 14:3, NaH 14:1.9; NaHMDS 14.9:2.3.

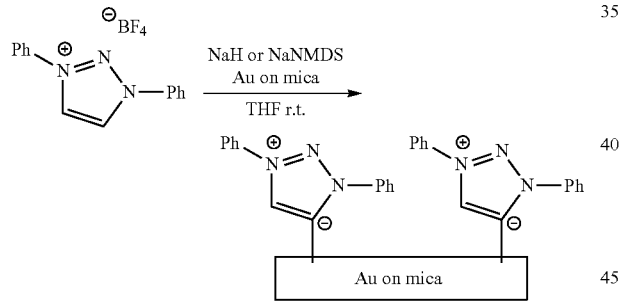

In a nitrogen filled glove box 1,3-diphenyl-1H-1,2,3-triazolium tetrafluoroborate and base were placed in a large 4-dram vial equipped with a very small stir bar. The Au-chip (cleaned with MeOH and plasma) was carefully placed in the vial and THF was added. The mixture was stirred carefully such that the stir bar was not agitating the Au-chip over night at ambient temperature. In the morning the supernatant liquid was removed and the chip was repeatedly washed with THF. The Au-chip was removed from the glove box and rinsed several times with MeOH and dried in a stream of argon. The chip was subjected to XPS analysis to establish elemental ratios.

Reagent Quantities:
A) Au-mica chip (1 cm×1 cm), 1,3-diphenyl-1H-1,2,3-triazolium tetrafluoroborate (3.0 mg, 9.7 μmop, NaHMDS (1.9 mg, 10.3 μmol) in dry, degassed THF (5 mL).
B) Au-mica chip (1 cm×1 cm), 1,3-diphenyl-1H-1,2,3-triazolium tetrafluoroborate (3.4 mg, 11.0 mol), NaH (0.4 mg, 16.6 μmop in dry, degassed THF (5 mL).

Example 10. Self-Assembled Monolayers on Various Metal Surfaces

Preparation of Silver Substrate

Clean silver surfaces were prepared by thermal deposition of silver onto a Si(111) substrate. Bare silver was prepared for surface analysis as a blank glass slides were cut to approximately 0.7 $cm^2$. Cut glass slide pieces were coated with a UV adhesive and spread evenly, excess adhesive was pipetted off the cut slide. Non-UV adhesive is recommended to avoid introduction of thiols.) The slide was then placed on the silver and cured under 365 nm light for 10 minutes. The edges around the glass slide on the silver was then scored with a clean razor blade. The glass slide and silver was then carefully pulled and stripped from the silicon wafer.

Hydrogen Carbonate Salt Method

Self-assembled monolayers were prepared by immersion of Cu and Ni foil (purity: 99.99%) and Ag substrates in a degassed solution of 3a in a suitable solvent for approximately 24 hours at room temperature in air. Substrates were then rinsed and dried under an argon gas.

Free Carbene Method

Self-assembled monolayers were prepared by immersion of Cu and Ni foil (purity: 99.99%) in a solution of 2a dissolved in dry suitable solvent at room temperature in the glove box for approximately 24 hours. Substrates were then rinsed and dried under an argon gas.

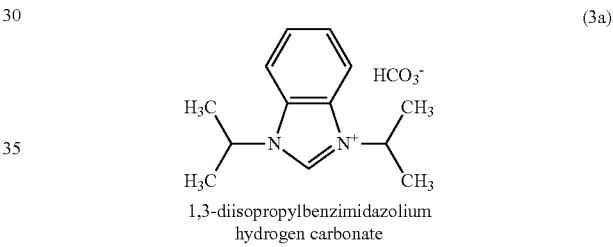

1,3-diisopropylbenzimidazolium hydrogen carbonate

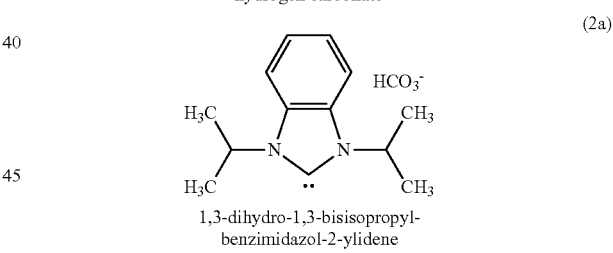

1,3-dihydro-1,3-bisisopropyl-benzimidazol-2-ylidene

XPS measurements were performed using a Thermo Microlab 310F ultrahigh vacuum (UHV) surface analysis instrument using Al Kα X-rays (1486.6 eV) or Mg Kα (1253.4 eV) at 15 kV anode potential and 20 mA emission current with a surface/detector take off angle of 75°. The binding energies of all spectra were calibrated to the C 1s line at 284.5 eV.

Self-Assembled Monolayer on Copper

A formed monolayer on copper was characterized using XPS. High resolution XP and Auger spectra for the blank Cu and NHC (3a and 2a-coated Cu surfaces are shown in FIGS. 8a and 8b. No shake-up peaks were observed in the Cu(2p) region. Cu(2p), and Cu(LMM) regions indicate a decrease in the peaks intensities for NHC-coated Cu. O (1s), C(1s), and N(1s) spectra are shown in FIG. 9a-c. The intensity of 0 (Is), C(1s), and N(1s) peaks were increased compare to the blank sample. The presence of the NHC monolayers was indicated by a large increase in the nitrogen intensity, and a decrease in the copper peak intensities. No significant difference was observed for coating copper using 3a or 2a. FIG. 10a-c illustrates the Cu (2p), Cu(LMM) region, O(1s), C(1s), and N(1s) peaks for freshly prepared Cu coated with 3a or 2a and after a week in air. A slight decrease was observed in the Cu(2p), Cu(LMM), and N(1s) peaks intensity after one week. Cu(LMM) region indicates that the Cu(0) surface was partially oxidized to Cu(+1), meaning that the NHC layer partially protects the copper surface from oxidation.

Self-Assembled Monolayer on Nickel

The formed monolayer on nickel was characterized using XPS. The high resolution XP spectra for the blank Ni and NHC (3a and 2a)-coated Ni surfaces are shown in FIG. 11a. No shake-up peaks were observed in the Ni(2p) region. FIG. 11b shows O (1s), C(1s), and N(1s) spectra. The intensity of O (1s), C(1s), and N(1s) peaks were increased compare to the blank sample. The presence of the monolayers was indicated by a large increase in the nitrogen intensity, and a decrease in the nickel peaks intensities. No significant difference was observed for coating nickel using 3a or 2a. FIG. 11c illustrates the Ni (2p), O(1s), C(1s), and N(1s) peaks for freshly prepared Ni coated with 3a or 2a and after a week in air. A slight decrease in the N(1s) intensity for 3a on Ni after one week, while N(1s) intensity remains stable for 2a on Ni after one week. This demonstrates that the NHC layer fully protects the Ni from oxidation over this time period.

Self-Assembled Monolayer on Silver

The formed monolayer on silver was characterized using XPS. The high resolution XP spectra for the NHC-coated Ag surfaces is shown in FIG. 12. O (1s), C(1s), and N(1s) spectra are shown in FIG. 13. The increase in N signal indicates formation of the NHC monolayer on the surface.

Example 11. Nanoworms

In most instances, rapid reduction of gold(I) complexes renders nanoparticles with spherical morphology, however imidazole based complexes give "ribbon like" gold nanoworms (see FIG. 14). Potential benefits of such non-spherical metallic nanostructures stem from their ability to be used in device fabrication without the close-packing that renders much of a particle's surface inaccessible in close-packed structures.

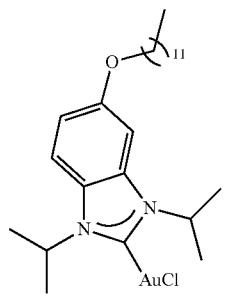

In a typical nanoworm synthesis reaction procedure, 309 mg (0.0075 mmol) of an imidazolium gold(I) complex (see three compounds above as examples) in 2 mL of EtOH was stirred vigorously with hydrazine monohydrate (0.5 ml, 13.2 mmol) for 48 h. Resulting particles were collected by centrifugation and washed with ethanol 4 times.

Direct Reduction of NHC—Au(I) Complexes to Give NHC Gold Nanoworms

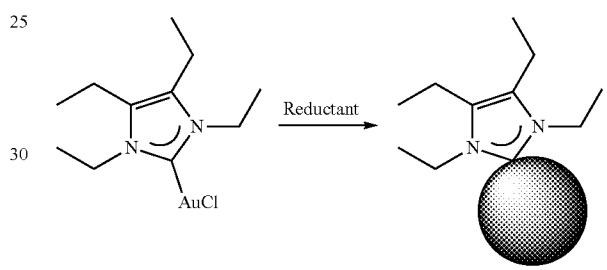

Mild reduction conditions of gold(I) NHC imidazolium based precursors (see above) resulted in elongation of the particle along its z-axis to give NHC-nanoworms with ribbon-like particle morphology. Use of stronger reducing conditions (either higher temperature or stronger reductant) resulted in less elongation until spherical morphology was attained.

Conversely, salts based on benzimidazole gold(I) complexes exhibited spherical morphology even under mild conditions. Although particle morphologies appear the same, the presence of the greasy side chain drastically reduced agglomeration of the particles.

Example 12 Nanoparticles

Synthesis of $C_3H_6$—, $C_6H_{12}$—, and $C_{12}H_{24}$-linked dibenzimidazolium bromide salts

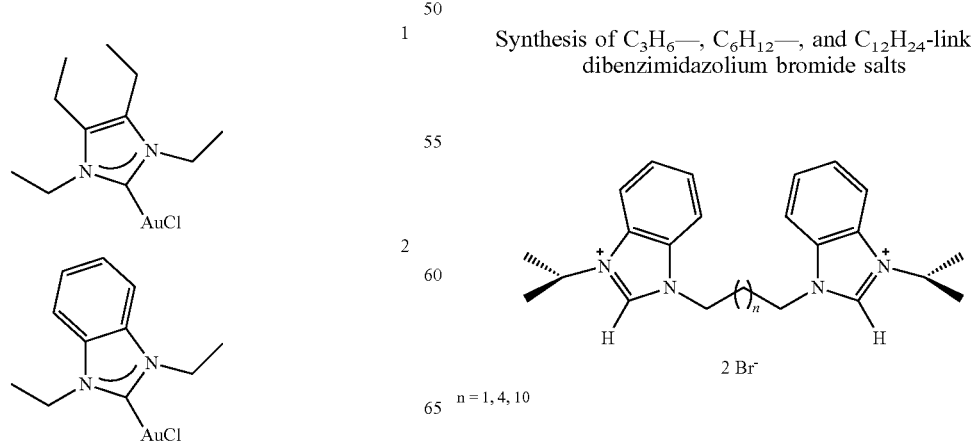

A sample of isopropylbenzimidazole (2 equiv.) was added to a pressure tube equipped with a stirbar and was dissolved in THF (12.0 mL). Alkyldibromide (1 equiv) was injected slowly to the stirring solution via dropwise addition. The pressure tube was subsequently sealed tightly and heated at 80° C. for 18 h, at which point the solution was allowed to cool to room temperature. A brown residue was washed with THF and Et$_2$O before collection in a Buchner funnel. A sticky powder was re-dissolved in minimal MeOH and recrystallized via slow diffusion of pentane at −35° C. In the case of the C$_{12}$H$_{24}$-linked system, recrystallization from pure pentane produced the most purified product. A crystalline white powder was collected via Büchner filtration and washed with pentane before drying in vacuo.

Preparation of C$_3$H$_6$, C$_6$H$_{12}$, C$_{12}$H$_{24}$-Linked Di-NHC-Protected Au Nanoparticles

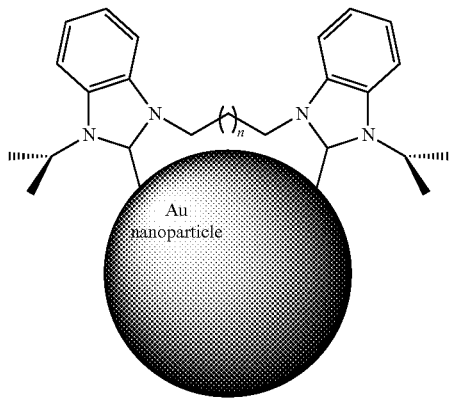

n = 1, 4, 10

In an inert-atmosphere glovebox, a sample of dibenzimidazolium salt (1 equiv.) was added to a 4-dram sample vial equipped with a stir bar and was suspended in THF (3.0 mL). In a separate 1-dram vial, a basic solution of KO$^t$Bu (2.9 equiv.) in THF (1.5 mL) was prepared and added dropwise to the 4-dram vial. A second wash of THF (1.5 mL) was used to ensure all the KO$^t$Bu was extracted from the small vial. The 4-dram vial was sealed with an aluminum-lined cap and stirred for 3.0 h, at which point solvent was removed in vacuo. The carbene was extracted with benzene (6.0 mL) and passed through a bed of Celite into a new 4-dram vial containing 2-3 mg of dodecylsulfide (DDS)-protected Au nanoparticles (11% DDS, 89% Au). The solution was stirred for 50 h and the vial removed from the glovebox, at which point volatiles were removed in vacuo, and the residue extracted with EtOH (4×1.5 mL). The resulting solution subjected to centrifugation to collect the desired nanoparticles at the bottom of plastic test tubes. Incomplete exchange (approx. 50:50) was observed for the C$_3$H$_6$-linked system, as evidenced by a significant S (2s) peak in the XPS spectrum, attributed to residual coordinated DDS, in addition to the expected N (1s) and C (1s) peaks in 1:10 ratios (expected N:C=1:5.75) characteristic of coordinated carbene. In the case of the C$_6$H$_{12}$— and C$_{12}$H$_{24}$-linked systems, complete exchange was observed as evidenced by N (1s) and C (1 s) peaks in 1:19 (expected N:C=1:6.5) and 1:13 (expected N:C=1:8) ratios by XPS, respectively, along with no observable S (2s) peak. Without wishing to be bound by theory, the larger than expected N:C ratios were considered a consequence of the XPS instrument being contaminated by carbon.

Preparation of C$_2$H$_4$, C$_3$H$_6$-Linked di-NHC-Protected Au Surfaces

In an inert-atmosphere glovebox, a sample of dibenzimidazolium salt (1 equiv.) was added to a 4-dram sample vial equipped with a stirbar and was suspended in TI-IF (3.0 mL). In a separate 1-dram vial, a basic solution of KO$^t$Bu (2.9 equiv.) in THF (1.5 mL) was prepared and added dropwise to the 4 dram vial. A second wash of THF (1.5 mL) was used to ensure all KO$^t$Bu was extracted from the small vial. The 4-dram vial was sealed with an aluminum-lined cap and stirred for 3.0 h, at which point solvent was removed in vacuo. The carbene was extracted with benzene (6.0 mL) and passed through a bed of Celite into a new 4-dram vial containing an Au chip. After 50 h of immersion in the carbene solution, the Au chip was removed from the vial and washed with benzene (5×1.5 mL). Monolayer formation of —C$_2$H$_4$— and C$_3$H$_6$-linked dicarbenes was evident from N (1s) and C (1s) peaks in 1:6.5 (expected N:C=1:5.5) and 1:6 (expected N:C=1:5.75) ratios by XPS, respectively, along with no observable Br (3d) peak.

Preparation of Olefinic Tail-Equipped C$_6$H$_{12}$-Linked Dibenzimidazolium Bromide Salt

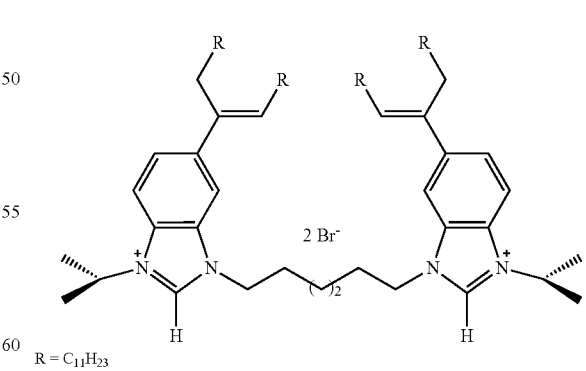

R = C$_{11}$H$_{23}$

This dication was prepared as described above using (E)-1-isopropyl-5-(pentacos-12-en-13-yl)-1H-benzo[d]imidazole.

Preparation of Olefinic Tail-Equipped C$_6$H$_{12}$-Linked Di-NHC-Protected Au Nanoparticles

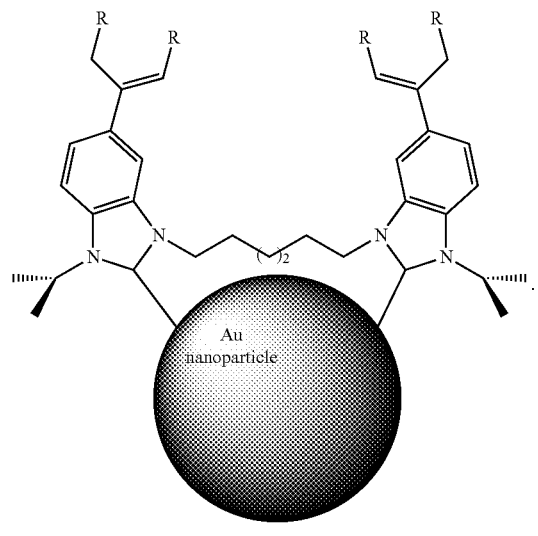

R = C$_{11}$H$_{23}$

These nanoparticles were prepared as described above using the olefinic tail-equipped C$_6$H$_{12}$-linked dibenzimidazolium bromide salt. Complete exchange was observed as evidenced by N (1s) and C (1s) peaks in a 1:19 (expected N:C=1:19) ratio by XPS, respectively, along with no observable S (2s) peak. See FIG. 15B for a TEM image of specified nanoparticles. No drastic etching/recombination of nanoparticles was observed. For the left hand side TEM image, average NP size 2.27 nm, polydispersity 22%. For the right hand side image, average NP size 2.4 nm, polydispersity 25%.

Example 13. Ditopic Carbene Precursors

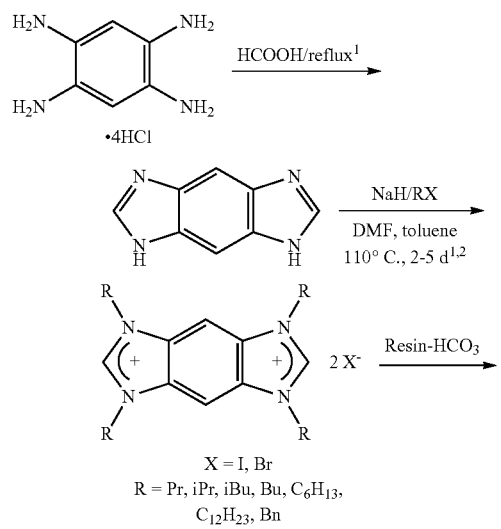

X = I, Br
R = Pr, iPr, iBu, Bu, C$_6$H$_{13}$, C$_{12}$H$_{23}$, Bn

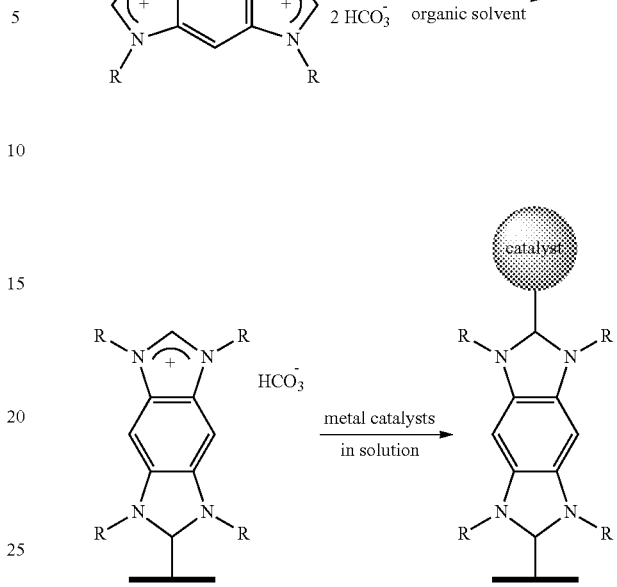

Preparation of Benzo-bis(imidazole)

1,2,4,5-Benzenetetraamine tetrahydrochloride (284 mg, 1.00 mmol) was poured into a round bottom flask was charged with a magnetic stir bar. Formic acid (88-99%) was added and the flask was fitted with an air-jacketed condenser. The reaction carried out in an oil bath at 100° C. for 36 h. The reaction mixture was then allowed to cool, decanted into ice-cold water (equal volume to formic acid) and neutralized with K$_2$CO$_3$. Neutralization caused precipitation of the product which was collected via vacuum filtration, washed with cold water, and dried under vacuum. The desired product as a light brown solid: $^1$H NMR (250 MHz, DMSO-d6, D2O) δ 7.651 (s, 2H), 8.156 (s, 2H); $^{13}$C NMR (250 MHz, DMSO-d6) δ 99.67, 135.38, 143.01. See Karimi, B. et al. *Inorg. Chem.*, 2011, 50, 6063.

General Procedure for Formation of Tetraalkyl or tetraaryl benzo-bis(imidazolium) halide In a well-dried two necked Schlenk flask, bis(imidazole) was added to a solution of NaH (2 equiv) in PhCH$_3$ under argon atmosphere. The resulting solution was heated to 110° C. for 1 h, after cooling the solution to room temperature, alkyl or aryl halide (6 equiv.) was added via syringe. The suspension was placed in an oil bath at 110° C. for 1 h, then dry DMF was added via syringe and the reaction was maintained at 110° C. for 6 h, then 60° C. for 4 h. Upon completion, the suspension was allowed to cool, diluted with PhCH$_3$ and the solids were collected by vacuum filtration, rinsed with water and THF successively, and dried under vacuum.

Anion exchange can be done using the Resin-HCO$_3$ method to generate the corresponding hydrogen carbonate followed by solution deposition in an organic solvent on different metal surfaces. Surface may be, for example, functionalized by different metal catalysts using the free hydrogen carbonate end. See Schmidtendorf, M. et al., Dalton Trans., 2013, 42, 16128.

Example 14. Competitive Deposition of Dodecanethiol Versus NHC on Au(111)

Dodecanethiol was deposited onto a 1 cm³ gold film, Au(111) on mica, by solution deposition. The film was immersed in a 1 mM solution of dodecanethiol in anhydrous ethanol and left to stand for 24 h at room temperature. The ethanol solution was decanted and the film was washed repeatedly with ethanol. The film was then immersed in a solution of benzimidazole carbene (1a) (1.4 mM) in toluene for 24 h after which the solution was decanted and the film washed with toluene.

Oxidation of the mixed thiol/NHC SAMs on gold was carried out in a 0.5 weight % aqueous solution of hydrogen peroxide kept in the dark. The film stood for 24 h in the oxidizing solution before the peroxide was decanted and the film washed with distilled water and THF. A second oxidation of the same film was carried out according to the same procedure.

Deposition of dodecanethiol on the Au(111) surface was observed by the XPS carbon C(1s) and sulfur S(2p) signals, giving a $C_xS_y$ ratio consistent with that of dodecanethiol. No nitrogen N(1s) signal was observed. After treatment with the carbene solution, the sulfur signal decreased by approximately 43% and a nitrogen signal appeared, indicating displacement of thiol molecules by the benzimidazole carbene. The nitrogen:sulfur signal ratio indicated the presence of 1 molecule of carbene on the surface per 3 molecules of thiol.

Exposure of the mixed thiol/NHC SAMs on gold to 0.5 wt % hydrogen peroxide caused the carbon and sulfur signals to decrease, while the nitrogen signal remained constant. This result supports that thiol groups were leached from the surface while the carbenes remained intact. The nitrogen:sulfur ratio estimated 3 molecules of carbene on the surface per molecule of thiol. A second exposure of the mixed film to 0.5 wt % hydrogen peroxide showed a decrease in the carbon signal, but the sulfur signal was still observed, indicating that a stronger technique would be required to completely remove thiol groups from the surface.

Example 15. Preparation of a Carboxymethyldextran-Coated NHC-Based Biosensing SPR Chip Herein is described the preparation of a carboxymethyldextran-coated NHC-based chip.

See FIG. 55 for a schematic of carboxymethyldextran-coated NHC-based chip referred to herein as "NHC-CM5" (for Dextran 500 KDa) and "NHC-CM3" (for Dextran 6 KDa).

Synthesis of the hydroxyl-terminated NHC(H) $HCO_3$ [(5-((11-hydroxyundecyl)oxy)-1,3-diisopropyl-1H-benzo[d]imidazol-3-ium hydrogen carbonate)]

Synthesis of 2-nitro-4-(undec-10-en-1-yloxy)aniline

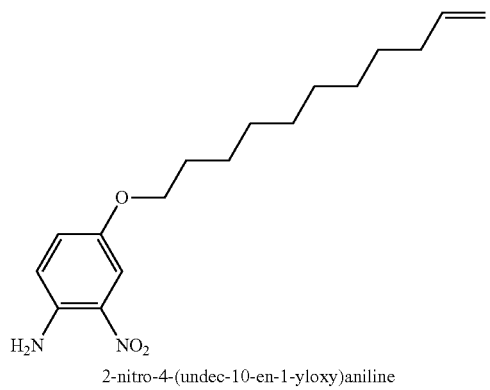 [SMILES: C=CCCCCCCCCCOc1ccc(N)c([N+](=O)[O-])c1]

2-nitro-4-(undec-10-en-1-yloxy)aniline

To a solution of 4-amino-3-nitrophenol (1.000 g, 6.5 mmol) and 11-bromo-1-undecane (1.644 g, 1.55 mL, 7.1 mmol) in anhydrous acetonitrile (50 mL), potassium carbonate (0.986 g, 7.1 mmol) was added. The mixture was stirred at 80° C. for 17 h under argon. Then the solvent was evaporated and a residue was dissolved in dichloromethane and filtered. Dichloromethane was evaporated and the crude product was separated by flash-chromatography using hexane-ethyl acetate gradient mixtures. Yield: 2.444 g (85%). Anal. Calc. for $C_{17}H_{26}N_2O_3$: C, 66.64; H, 8.55; N, 9.14. Found: C, 66.68; H, 8.58; N, 9.10. TOF MS (m/z) for $C_{17}H_{26}N_2O_3$: 306.1929, Calc.: 306.1943. ¹H NMR (400 MHz, $CDCl_3$) δ 7.53 (d, 1H, J=2.8 Hz), 7.06 (dd, 1H, J=9.1, 2.8 Hz), 6.75 (d, 1H, J=9.1 Hz), 5.88 (s, 2H, $NH_2$), 5.81 (m, 2H, —CH=$CH_2$), 4.96 (m, 2H, —CH=$CH_2$), 3.91 (t, 2H, J=6.5 Hz, —O—$CH_2$—), 2.04 (m, 2H, —$CH_2$—CH=$CH_2$), 1.76 (m, 2H, —$CH_2$—$CH_2$O—) 1.45-1.26 (m, 12H). Reference: C. M. Crudden et al., *Nature Chem.* 6, 409-414 (2014).

Synthesis of 5-(undec-10-en-1-yloxy)-1H-benzo[d]imidazole

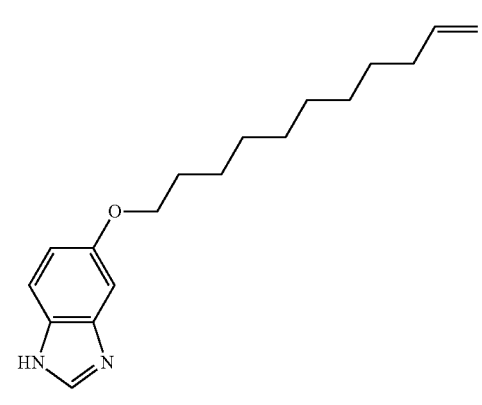

5-(undec-10-en-1-yloxy)-1H-benzo[d]imidazole

Formic acid (25 mL) was added to a mixture of 2-nitro-4-(undec-10-en-1-yloxy)aniline (1.532 g, 5 mmol), iron powder (2.790 g, 50 mmol), and ammonium chloride (2.670 g, 50 mmol) in isopropyl alcohol (50 mL). The resulting mixture was stirred at 80° C. for 3.5 h, then cooled to room temperature and filtered through sintered glass filter. The solid was washed with isopropyl alcohol (3×5 mL). The filtrate was evaporated to dryness and 30 mL of saturated sodium bicarbonate solution was added carefully to avoid significant foaming. Then sodium bicarbonate (powder) was added portion-wise until pH 6 was achieved. Then the suspension was extracted with dichloromethane (5×30 mL). The combined organic layers were dried over anhydrous magnesium sulfate, filtered and evaporated to give 1.407 g of product. Yield 98%. TOF MS (m/z) for $C_{18}H_{26}N_2O$: 286.2045, Calc.: 286.2056. $^1$H NMR (400 MHz, CDCl$_3$) δ 7.98 (s, 1H), 7.53 (d, 1H, J=8.8 Hz), 7.07 (d, 1H, J=1.7 Hz), 6.93 (dd, 1H, J=8.8, 2.2 Hz), 5.81 (m, 1H, —CH=CH$_2$), 4.95 (m, 2H, —CH=CH$_2$), 3.91 (t, 2H, J=6.6 Hz, —O—CH$_2$—), 2.04 (m, 2H, —CH$_2$—CH=CH$_2$), 1.79 (m, 2H, —CH$_2$—CH$_2$O—), 1.49-1.27 (m, 12H). Reference: C. M. Crudden et al., *Nature Chem.* 6, 409-414 (2014)

Synthesis of 1,3-diisopropyl-5-(undec-10-en-1-yloxy)-1H-benzo[d]imidazol-3-ium iodide

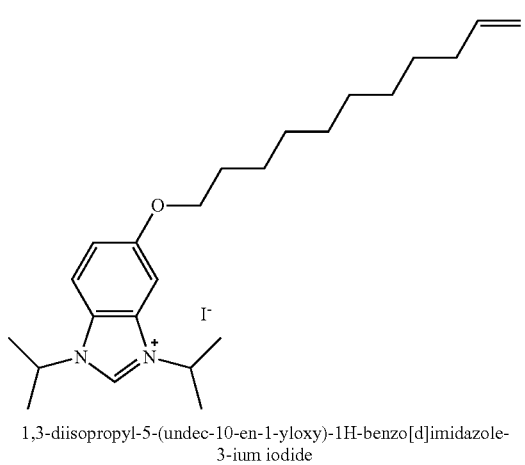 [SMILES: C=CCCCCCCCCCOc1ccc2c(c1)[n+](C(C)C)cn2C(C)C ; [I-]]

1,3-diisopropyl-5-(undec-10-en-1-yloxy)-1H-benzo[d]imidazole-3-ium iodide

To a suspension of 5-(undec-10-en-1-yloxy)-1H-benzo[d]imidazole (286.4 mg, 1 mmol) and Cs$_2$CO$_3$ (325.8 mg, 0.11 mmol) in acetonitrile (5 mL), 2-iodopropane (499 μL, 5 mmol) was slowly added. The mixture was stirred at 90° C. in a sealed pressure tube under an argon atmosphere for 48 h. The reaction mixture was allowed to cool to room temperature. Water (20 mL) was added to the reaction mixture which was then extracted with dichloromethane (3×15 mL). The combined organic layers were dried over anhydrous magnesium sulfate, filtered and then concentrated in vacuo. The crude solid was triturated and sonicated in diethyl ether (5×5 mL). Subsequent drying under high vacuum afforded the desired product as a yellow powder (411 mg, 82% yield). TOF MS (m/z) for $C_{24}H_{39}N_2O$: 371.3069, Calc.: 371.3057. $^1$H NMR (300 MHz, CDCl$_3$): δ 10.77 (s, 1H), 7.63 (d, 1H, J=9.1 Hz), 7.21 (dd, 1H, J=9.2, 1.7 Hz), 7.08 (d, 1H, J=1.6 Hz), 5.81 (m, 1H, —CH=CH$_2$), 5.12 (m, 2H, 2H, CH—(CH$_3$)$_2$), 4.95 (m, 2H, —CH=CH$_2$), 4.05 (t, 2H, J=6.3 Hz, —O—CH$_2$—), 2.04 (m, 2H, —CH$_2$—CH=CH$_2$), 1.85 (m, 14H, —CH$_2$—CH$_2$O—, CH—(CH$_3$)$_2$), 1.40 (m, 12H).

Synthesis of 5-((11-hydroxyundecyl)oxy)-1,3-diisopropyl-1H-benzo[d]imidazol-3-ium iodide

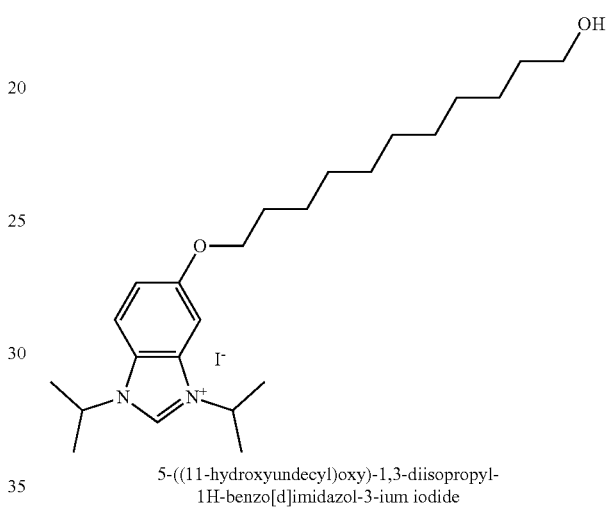

5-((11-hydroxyundecyl)oxy)-1,3-diisopropyl-1H-benzo[d]imidazol-3-ium iodide

A Schlenck flask equipped with 1,3-diisopropyl-5-(undec-10-en-1-yloxy)-1H-benzo[d]imidazol-3-ium iodide (99.7 mg, 0.2 mmol) was cooled to 0° C. (ice bath), and hydroboration was initiated by dropwise addition of a 1.0 M solution of borane-THF (0.67 mL) and then 1.3 mL dry THF was added. The mixture was stirred at room temperature for 2 h. Water (2 mL) and sodium perborate (199.6 mg, 2 mmol) were added sequentially to the flask, and the mixture was vigorously stirred at room temperature for 2 h. Water (20 mL) was added to the reaction mixture which was then extracted with dichloromethane (3×20 mL). The combined organic layers were dried over anhydrous magnesium sulfate, filtered and then concentrated in vacuo. The crude solid was triturated and sonicated in diethyl ether (3×4 mL). Subsequent drying under high vacuum afforded the desired product as a yellow powder (95 mg, 95% yield). $^1$H NMR (400 MHz, CDCl$_3$+D$_2$O): δ 10.73 (s, 2H), 7.62 (d, 1H, J=9.2 Hz), 7.22 (dd, 1H, J=8.9, 1.5 Hz), 7.08 (d, 1H, J=1.6 Hz), 5.11 (m, 2H, 2H, CH—(CH$_3$)$_2$), 4.05 (t, 2H, J=6.4 Hz, —O—CH$_2$—), 3.62 (t, 2H, J=6.6 Hz, —CH$_2$—OH), 1.85 (m, 14H, —CH$_2$—CH$_2$O—, CH—(CH$_3$)$_2$), 1.56 (—CH$_2$—OH, D$_2$O-exchangeable), 1.52 (m, 4H), 1.30 (m, 12H). Reference: G. W. Kabalka et al., *Org. Chem.* 54, 5930-5933 (1988)

Synthesis of 5-((11-hydroxyundecyl)oxy)-1,3-diisopropyl-1H-benzo[d]imidazol-3-ium hydrogen carbonate

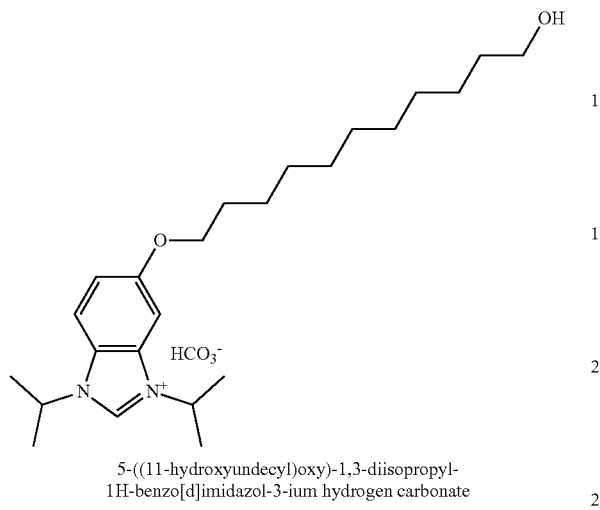

5-((11-hydroxyundecyl)oxy)-1,3-diisopropyl-1H-benzo[d]imidazol-3-ium hydrogen carbonate Resin-HCO$_3$ (0.4 mL, 3 equiv.) suspended in water was measured in a graduated cylinder and transferred to 20 mL vial where the resin was allowed to settle and water was decanted off. The resin was washed with methanol (3×2 mL). 5-((11-hydroxyundecyl)oxy)-1,3-diisopropyl-1H-benzo[d]imidazol-3-ium iodide (52 mg, 0.1 mmol) was dissolved in 1 mL methanol and transferred to the resin. The mixture was stirred for 15 min. The solution was passed through a cotton plug. Solvent was evaporated using a rotavap at 40° C. then in vacuo to give an brown solid (44 mg, 97%). $^1$H NMR (400 MHz, CD$_3$OD): δ 7.86 (d, J=9.2 Hz, 1H), 7.41 (d, 1H, J=1.6 Hz), 7.26 (dd, J=9.2, 1.6 Hz, 1H), 4.98 (m, 2H, 2H, CH—(CH$_3$)$_2$), 4.10 (t, 2H, J=6.3 Hz, —OCH$_2$—), 3.50 (t, 2H, J=6.6 Hz, —CH$_2$OH), 1.82 (m, 2H, —CH$_2$—CH$_2$O—), 1.68 (m, 12H, CH—(CH$_3$)$_2$), 1.48 (m, 4H), 1.29 (m, 12H).

Deposition of Hydroxyl-Terminated Carbene on Gold Surface and Surface Reactions

Sensors were first cleaned by placing them in a boiling H$_2$O$_2$ (30%):NH$_3$:H$_2$O (1:1:5) solution for 10 min, washed thoroughly with ultrapure water, washed with methanol, dried under an argon gas for 1 min, then cleaned with plasma generated from room air at a medium RF level and pressure kept between 300 and 500 mtorr for 10 minute. Hereafter, the sensors were immersed in a solution of 10 mM 5-((11-hydroxyundecyl)oxy)-1,3-diisopropyl-1H-benzo[d]imidazol-3-ium hydrogen carbonate in a methanol solution (2 mL) for 24 h. XPS data showed the formation of a hydroxyl-terminated NHC-based SAM with a reasonable C/N ratio (C/N Ratio Predicted 24:2, Observed 26:2). The sensors were then allowed to react for 3 h with epichlorohydrin (2% v/v) in 0.1 M NaOH, rinsed with water, transferred to a 300 g/L solution of dextran in 0.1 M NaOH, and left to react for 24 h. After this the sensors were washed thoroughly with ultrapure H$_2$O and immersed in 2.0 M bromoacetic acid in 2 M NaOH for 24 h, after which the sensors were thoroughly washed with ultrapure H$_2$O and stored at +4° C. Reference: N. Granqvist et al., *Langmuir* 30, 2799-2809 (2014).

Example 16. Hydrogen Carbonate-Anion Exchange Resin with Triflate Starting Material Synthesis of 1-Isopropylbenzimidazole

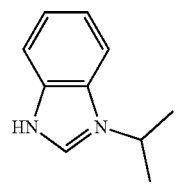

A mixture of benzimidazole (1.0 g, 8.7 mmol), anhydrous Cs$_2$CO$_3$ (4.4 g, 13.6 mmol) and 2-bromopropane (2.2 mL, 23.4 mmol) in acetonitrile (60 mL) was refluxed overnight with stirring. After cooling to RT, solvent was removed. Dichloromethane was added to the residue and the resulting mixture was filtered by suction through a pad of Celite and washed a few times with dichloromethane. Solvent was removed in vacuo yielding a yellowish liquid, which was further purified by silica column chromatography with dichloromethane-MeOH 95:5 mixture (R$_f$=0.59 in dichloromethane-MeOH 9:1). The product was obtained as pale yellow liquid (1.3 g, 92%). Spectra were consistent with the literature (see Starikova, O. V. et al. Synthesis of 1,3-dialkylimidazolium and 1,3-dialkylbenzimidazolium salts. *Russ. J. Org. Chem.* 39, 1467-1470 (2003).

Synthesis of 1,3-Diisopropylbenzimidazolium triflate

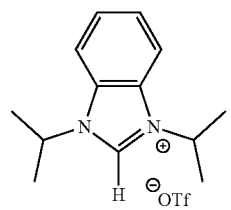

To a stirred solution of anhydrous 2-propanol (0.43 mL, 5.6 mmol) and anhydrous pyridine (0.45 mL, 5.6 mmol) in dry dichloromethane (10 mL) at −20° C. under argon was slowly added triflic anhydride (0.92 mL, 5.6 mmol), which resulted in a formation of white precipitate. The reaction mixture was stirred at −20° C. for 30 minutes and then at RT for additional 30 minutes. Pentane (10 mL) was added to further precipitate the formed salts and reaction mixture was then filtered by suction through a pad of Celite to a solution of 1-isopropylbenzimidazole (0.6 g, 3.8 mmol) in dry dichloromethane (10 mL). Reaction mixture was stirred under argon at −10° C. for 1 hour and then at RT overnight. Dichloromethane was removed in vacuo to yield slightly pink viscous oil. The product was purified either by silica column chromatography (dichloromethane-MeOH, 95:5) or by trituration depending on the impurities. The crude product was dissolved in small amount of dichloromethane and cooled to −10° C. Diethyl ether was slowly added to the stirred solution to precipitate product as white solid. The product was collected and washed with diethyl ether and dried in air (0.9 g, 69%).

¹H NMR (400 MHz, CDCl₃): δ 9.84 (s, 1H, N—CH═N), 7.81 (dd, J=6.4, 3.2 Hz, 2H, Ar—H), 7.66 (dd, J=6.4, 3.1 Hz, 2H, Ar—H), 5.04 (m, 2H, NCHiPr), 1.79 (d, J=6.7 Hz, 12H, CH₃iPr). ¹³C (¹H) NMR (101 MHz, CDCl₃): δ 139.14 (s, N₂CH), 131.13 (s, $C_q$), 127.25 (s, $C_{Ar}$), 114.01 (s, Cm), 52.46 (s, CHiPr), S 22.91 (s, CH₃iPr). ¹⁹F NMR (376, CDCl₃): δ −78.23. Spectra were consistent with the literature (see Fernandez-Rodriguez, M. A., Andina, F., Garcia-Garcia, P., Rocaboy, C. & Aguilar, E. Multicomponent Cascade Reactions Triggered by Cycloaddition of Fischer Alkoxy Alkynyl Carbene Complexes with Strained Bicyclic Olefins. *Organometallics* 28, 361-369 (2009)).

Hydrogen Carbonate-Anion Exchange

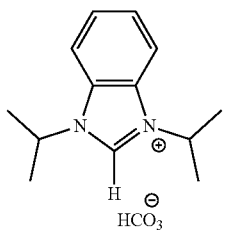

Amberlyst A26 resin in water was bubbled with CO₂ gas for 15 minutes to regenerate the resin with HCO₃⁻ anions. An aliquot of resin-HCO₃ (3.2 mL, 2.6 mmol) was taken to a 20 mL-vial and water was pipetted off. Resin-HCO₃ was washed three times with MeOH (2 mL) and solution of 1,3-diisopropylbenzimidazolium triflate (0.3 g, 0.85 mmol) in MeOH (5 mL) was added and the mixture was stirred at RT at medium speed for 30 minutes. Solution was collected and filtered through a cotton plug, and solvent was removed by rotary evaporation. The resulting oily residue was dried under vacuum affording white solid. The crude product was washed successively with acetone and dried under vacuum (0.2 g, 75%).

Spectra matched those shown of Example 1 above. Anal. Calc. for C₁₄H₂₀N₂O₃: C, 63.62; H, 7.63; N, 10.60. Found: C, 63.74; H, 7.74; N, 10.55.

Synthesis of 1-isopropyl-5-propoxy-1H-benzo[d]imidazole and 1-isopropyl-6-propoxy-1H-benzo[d]imidazole

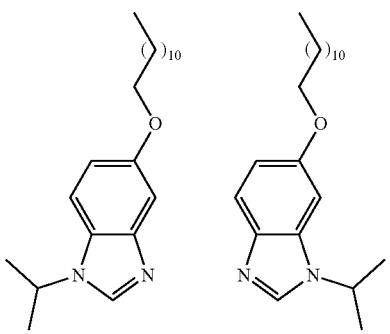

A mixture of 5-propoxy-1H-benzo[d]imidazole (0.917 g, 3.03 mmol), anhydrous Cs₂CO₃ (1.480 g, 4.55 mmol) and 2-bromopropane (0.854 mL, 9.09 mmol) in acetonitrile (21 mL) was stirred at 90° C. in a two-neck round bottomed flask attached to a reflux condenser under an argon atmosphere for 14 h. After cooling to RT, the resulting mixture was filtered by suction and washed with dichloromethane (30 mL), then solvents were removed. The resulting crude mixture was purified by silica column chromatography using hexane-ethyl acetate 1:2 mixture (R_f=0.19) yielding a yellow liquid (0.673 g, 64%) of the products as a 1:1 mixture of the two regioisomers.

¹H NMR (400 MHz, CDCl₃) δ 7.91, 7.87 (s, 2H, N—CH═N), 7.67 (d, J=9.2 Hz, 1H, $CH_{AT}$), 7.28 (m, 2H, $CH_{Ar}$), 6.90 (m, 3H, $CH_{Ar}$), 4.54 (m, 2H, CH—(CH₃)₂), 4.00 (t, J=6.4 Hz, 4H, —O—CH₂), 1.81 (m, 4H), 1.58 (m, 12H), 1.48 (m, 4H), 1.27 (m, 32H), 0.88 (t, $J_{HH}$=6.6 Hz, 6H, CH₃). ¹³C (¹H) NMR (101 MHz, CDCl₃): δ 156.03, 155.51, 144.84, 140.23, 139.30, 138.52, 133.89, 127.82, 120.70, 113.40, 111.67, 110.34, 103.31, 94.61, 77.16, 68.81, 68.68, 47.74, 47.44, 31.92, 29.67, 29.64, 29.61, 29.44, 29.35, 26.12, 22.69, 22.57, 22.47, 14.11. EI-MS (m/z) for C₂₂H₃₆N₂O 344.2813, Calc.: 344.2828.

5-(dodecyloxy)-1,3-diisopropyl-1H-benzo[d]imidazol-3-ium trifluoromethanesulfonate

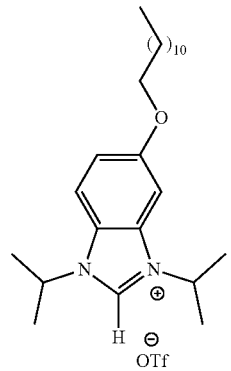

In an oven-dried Schlenk flask, triflic anhydride (0.50 mL, 3.0 mmol) was slowly added to a stirred solution of anhydrous 2-propanol (0.23 mL, 3.0 mmol) and anhydrous pyridine (0.24 mL, 3.0 mmol) in dry dichloromethane (5 mL) at −20° C. under argon resulting in the formation of white precipitate. The reaction mixture was stirred at −20° C. for 30 minutes and then at RT for additional 30 minutes. Dry pentane (5 mL) was added to further precipitate the formed salts and the reaction mixture was then filtered through a pad of CELITE™ directly to a solution of 1-isopropyl-5-propoxy-1H-benzo[s]imidazole and 1-isopropyl-6-propoxy-1H-benzo[d]imidazole (0.344 g, 1.0 mmol) in dry dichloromethane (5 mL). After stirring for 10 min at −10° C. and then at RT for 14 h under argon, the reaction mixture was quenched with a saturated solution of NaHCO₃ (15 mL). The layers were separated, and the aqueous layer was extracted twice with dichloromethane (2×15 mL). The combined organic layer was dried over MgSO₄, filtered and concentrated in vacuo. The residue was triturated and sonicated in diethyl ether (2×5 mL), which was then decanted off. Subsequent drying under vacuum afforded the desired product as an off-white powder (0.537 g, 82% yield).

¹H NMR (400 MHz, CDCl₃): δ 9.75 (s, 1H, N—CH═N), 7.63 (d, 1H, $J_{HH}$=9.2 Hz), 7.22 (dd, 1H, $J_{HH}$=9.2, 2.0 Hz, ArH), 7.09 (s, 1H), 4.95 (m, 2H, CH—(CH₃)₃), 4.05 (t, 2H, $J_{HH}$=6.5 Hz, —O—CH₂—), 1.85 (m, 2H), 1.77 (m, 12H), 1.49 (m, 2H), 1.26 (m, 16H), 0.87 (t, 3H, $J_{HH}$=6.8 Hz). ¹³C (1H) NMR (CDCl$_3$): δ 158.88 (C$_q$, C$_{Ar}$—O—CH$_2$—), 137.95 (C$_{Ar}$, N=CH—NH), 132.25 (C$_q$), 124.92 (C$_q$), 117.45 (C$_{Ar}$), 114.41 (C$_{Ar}$), 96.53 (C$_{Ar}$), 69.30 (—CH$_2$—O—), 52.29 (CH—(CH$_3$)$_2$), 51.80 (CH—(CH$_3$)$_2$), 31.91, 29.66, 29.63, 29.59, 29.55, 29.36, 29.34, 29.04, 25.98, 22.68, 21.85 (CH—(CH$_3$)$_2$), 21.72 (CH—(CH$_3$)$_2$), 14.10 (CH$_3$). $^{19}$F NMR (376, CDCl$_3$): δ −78.71. HRESI-MS (m/z) for C$_{25}$H$_{43}$N$_2$O$^+$[M-CF$_3$O$_3$S]$^+$: 387.3371, Calc.: 387.3370.

Hydrogen Carbonate-Anion Exchange

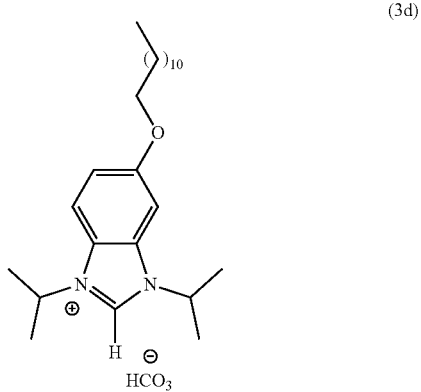

(3d)

Resin-HCO$_3$ (1.5 mL, 3 equiv.) suspended in water was measured in a graduated cylinder and transferred to 20 mL vial where the resin was allowed to settle and water was decanted off. The resin was washed with methanol (3×2 mL). 5-(dodecyloxy)-1,3-diisopropyl-1H-benzo [d]imidazol-3-ium trifluoromethanesulfonate (215 mg, 0.4 mmol) was dissolved in 2 mL methanol and transferred to the resin. The mixture was stirred for 15 min. The solution was passed through a cotton plug. Solvent was evaporated under vacuum and the crude oily product was triturated and sonicated in hexane (2×4 mL). Subsequent drying under high vacuum afforded the desired product as an off-white powder (153 mg, 85% yield). Spectra matched those shown above. Anal. Calc. for C$_{26}$H$_{44}$N$_2$O$_4$: C, 69.61; H, 9.89; N, 6.24. Found: C, 68.98; H, 10.10; N, 6.10.

Example 17. Validation of CM3-SA Chip and NHC-SA Chip (6 KDa)

HBS-EP buffer (0.01 M (4-(2-hydroxyethyl)-1-piperazineethanesulfonic acid) (HEPES), 0.15 M NaCl, 3 mM EDTA, 0.005% P20, pH 7.4) was used as the running buffer. CM (carboxymethylated) type chip (on Flow Cell 4) was first activated with 0.2 Ml-ethyl-3-(3-dimethylaminopropyl)carbodiimide (EDC)/0.05 M N-hydroxysuccinimide (NHS) for 10 min at a flow rate of 5 ul/min by modification of the carboxymethyl groups to NHS-esters. Then, 0.1 mg/ml Streptavidin in 10 mM Sodium Acetate pH 4.7 was injected for 10 min. Finally, the unreacted NHS-esters were deactivated by 10-min 1 M ethanolamine (pH 8.5). For this study, Flow cell 3 was activated by EDC/NHS, and then followed by blocking with ethanolamine to be used as a reference surface. It is better to treat the reference surface with the same immobilization conditions used for the reaction surface (D. G. Myszka. Improving biosensor analysis. J. Mol. Recognit. 1999, 12, 279-284; M. A. Cooper, Label-free biosensors: Techniques and applications. Cambridge University Press). This is to ensure the similar environment between flow cells and improve the quality of the binding data. The resultant immobilization level of streptavidin for NHC-CM3 and CM3 chips were 2000 RU and 3000 RU, respectively. Then change flow rate to 10 ul/min and 2.5 ng/ml biotinylated DNA (140 bp) was injected over the SA and reference surfaces for 5-min on the two chip surfaces, giving rise to the immobilization level of 310 RU and 690 RU, respectively. Three start-up cycles of running buffers injections were carried out to further equilibrium the baseline. His-tagged protein was injected over the biotinylated DNA and reference surfaces from 6 µg/ml to 100 µg/ml for 3 min followed by 5-min dissociation phase. 1-min injection of 2 M NaCl and 5 M NaCl were used as regeneration solutions on NHC-CM3 chip and CM3 chip, respectively. The data was processed by subtracting from reference flow cell and blank injections—double referencing method. See FIGS. 16A-C and 17A-C for results.

biotinylated DNA (MW. 91 KDa, from synechocystis)
his-tagged protein (MW. 35 KDa, from synechocystis)

Example 18. NHC-Protein a Chip

Sensor Chip Protein A's surface was pre-immobilized with a recombinant Protein A variant binding antibodies for protein interaction analysis using Biacore systems (GE Healthcare Life Sciences, Instructions 29-1383-04 AA Biacore™ and Protein interaction analysis Biacore™ Sensor Chip Protein A. GE Healthcare Life Sciences. Application note 29-1466-99 AA).

This recombinant variant on the surface of Sensor Chip Protein A binds the heavy chain only within the Fc region of antibodies from several mammalian species, most notably human antibodies of the subclasses IgG1, IgG2, and IgG4. It is ready-to-use with high binding capacity offering a wide dynamic range and high convenience, reproducibility and robustness. Sensor Chip Protein A is an excellent surface choice for antibody concentration analysis in biopharmaceutical process development and in manufacturing QC. The sensor chip is also suitable for comparability studies and other types of characterization work involving kinetic analysis.

Protocol for Preparation of Protein a Chip on NHC-CM5 Chip

NHC-CM5 (Dextran 500 KDa) chip was used for this study. HBS-EP buffer (0.01 M HEPES, 0.15 M NaCl, 3 mM EDTA, 0.005% P20, pH 7.4) was used as the running buffer. Protein A was immobilized to the sensor surface (FC2) using amine-coupling chemistry. The surface was activated for 7 min with a 1:1 mixture of 0.2 M EDC/0.05 M NHS at a flow rate of 10 µl/min. Protein A at a concentration of 25 µg/ml in 10 mM Sodium Acetate pH 4.2 was injected for 10 min. Then, the surface was blocked with a 7-min injection of 1 M ethanolamine, pH 8.5. The resultant Protein A immobilization level was around 980 RU. FC1 was activated by EDC/NHS, followed by blocking with ethanolamine, which can be used as a reference flow cell. FC1 and FC2 are flow channels on the SPR sensor chip, wherein typically FC1 is a reference channel and FC2 is an active channel.

Validation of NHC-Protein a Chip with Antibodies

Antibodies and antigen were dissolved in HBS-EP buffer. A 30-second injection of sample was suitable for concentration measurements in the range 1 to 50 µg/ml, and the contact time could also be used to adjust to different measuring ranges. One injection of 30-second to 1-min of 10 mM Glycine-HCl pH1.5 was suitable to remove the analyte from the Protein A chip surface. Avoided using basic regeneration solution, as in some cases, exposuring surface to basic conditions might impair assay performance by introducing a slight drift in the assay.

NHC-Protein a with Anti-BSA Followed by BSA

Flow rate was changed to 5 µl/min, and different concentrations were injected with anti-BSA (3 min) and BSA (0.5 min) on FC2 and FC1. One injection of 30-second 10 mM Glycine-HCl pH1.5 was used as regeneration solution.

Usage of anti-BSA and BSA for each cycle were as following:

| Cycle 1: | anti-BSA 100 µg/mL | BSA 100 µg/mL |
| Cycle 2: | anti-BSA 50 µg/mL | BSA 50 µg/mL |
| Cycle 3: | anti-BSA 25 µg/mL | BSA 25 µg/mL |
| Cycle 4: | anti-BSA 12 µg/mL | BSA 12 µg/mL |
| Cycle 5: | anti-BSA 6 µg/mL | BSA 6 µg/mL |

See FIGS. 18A-F.

Example 19. NHC-NTA Chip

Sensor Chip NTA was designed to bind histidine-tagged biomolecules for interaction analysis in Biacore systems (GE Healthcare Life Sciences. Instruction 22-0519-97 AF Biacore™, Approaches for capture of histidine-tagged proteins in Biacore™ systems. GE Healthcare Life Sciences. Application note 29-0079-29 AA, The ProteOn™ HTG sensor chip: Novel surface for stable capture of histidine-tagged proteins for protein-protein interaction analysis. BIO-RAD Tech Note 6132, and L. Nieba, et al., BIACORE analysis of histidine-tagged proteins using a chelating NTA sensor chip. Anal. Biochem. 1997, 252, 217-228). The surface consisted of a carboxymethylated dextran matrix pre-immobilized with nitrilotriacetic acid (NTA). His-tagged ligands are thus captured on NTA chip by chelation of $Ni^{2+}$ by NTA and histidine residues in the ligand tag. Other amino acid side chains in the ligand might participate in chelation, but these interactions tend to be weak in comparison to those involving poly-histidine tags.

Protocol for Preparation of NHC-NTA Sensor Chip

NHC-CM3 (Dextran 6 KDa) chip was used for this study. PBS (10 mM phosphate, 138 mM NaCl, 2.7 mM KCl, pH 7.4) was used as the running buffer. NTA was immobilized to the sensor surface using amine-coupling chemistry. The surface was activated for two consecutive 10-min with a 1:1 mixture of 0.2 M EDC/0.05 M NHS at a flow rate of 10 µl/min. NTA at a concentration of 10 mM in PBS buffer was injected for 30 min. Then, the surface was blocked with a 10-min injection of 1 M ethanolamine, pH 8.5. The resultant NTA immobilization level was around 140 RU per flow cell. See FIG. 19A for results of this study.

When working with NTA chip, the reference surface should be a non-activated flow cell that has not been subjected to $Ni^{2+}$ ions. So for the next step, change FC1-2 to FC2 alone, leaving FC1 as the reference surface. The surface (FC2) was activated with 2-min 0.5 mM $NiSO_4$ (prepared in MiliQ water) at a flow rate of 10 µl/min. Then change FC2 to FC1-2 and flow rate to 30 µL/min, followed by a 1 to 3-min injection of his-tagged protein and subsequently a buffer dissociation phase. An injection of 1-min 350 mM EDTA strips all the his-tagged protein and $Ni^{2+}$, which can be demonstrated by the return of the baseline before the injection of $NiSO_4$. See FIGS. 19B and 19C for results of this study.

Example 20. Protein/Drug Interaction: Ferulic Acid and Bovine Serum Albumin

Ferulic acid (4-hydroxy-3-methoxycinnamic acid, FA) is a phenolic acid commonly found in foods and plants. It has antioxidant, antimicrobial, anti-cancer and anti-inflammatory properties ((Protein/Drug Interaction: Ferulic Acid and Bovine Serum Albumin. Application Note 105, Biosensing Instrument Inc., Y. Zhang, et al., Electrophoresis, 2007, 28, 1839-1845, and H. Ojha, et al., *Thermochim Acta*, 2012, 548, 56-64). NHC-CM5 (500 KDa) was used to study FA BSA interaction.

NHC-CM5 (500 KDa) chip was used for this study. Bovine Serum Albumin (BSA) was immobilized (covalently bound to the sensor surface) using amine-coupling chemistry. PBS (10 mM phosphate, 138 mM NaCl, 2.7 mM KCl, pH 7.4) was used as running buffer. The surface (FC2) was activated by two consecutive 7 min with a 1:1 mixture of 0.2 M EDC/0.05 M NHS at a flow rate of 20 ul/min. Injections of BSA (10 min) at a concentration of 200 ug/ml in 10 mM sodium acetate, pH 4.2, were repeated until desired immobilization level was reached. Then, the surface was blocked with a 10-min injection of 1 M ethanolamine, pH 8.5. Final immobilization level of BSA of this study was around 3500 RU. Unmodified dextran surface was used as a reference surface (FC1).

Ferulic acid was first serially diluted into running buffer to final concentrations of 100, 200, 400, 800 µM. To test data quality and further equilibrate the surfaces, four warm-up buffer cycles were performed at a flow rate of 30 µl/min. Then, ferulic acid was injected over the reference and BSA surfaces at a flow rate of 30 Each cycle consisted of a 2-min waiting period for monitoring of the baseline stability. Then the ferulic acid/BSA complex was allowed to associate and dissociate for 3-min and 3-min, respectively, and 20 mM NaOH (30 s) was used as the regeneration solution. The data was processed by subtracting from reference flow cell and blank injections—double referencing method.

Example 21A Immobilization of HSA on NHC-CM5 Chip

NHC-CM5 chip was used for this study. HSA was immobilized using amine-coupling chemistry. PBS (10 mM phosphate, 138 mM NaCl, 2.7 mM KCl, pH 7.4) was used as the running buffer. The surface was activated by two consecutive 7 min with a 1:1 mixture of 0.2 M EDC/0.05 M NHS at a flow rate of 20 µl/min. HSA at a concentration of 200 µg/ml in 10 mM sodium acetate, pH 5.2, was injected for 10 min twice. Then, the surface was blocked with a 10-min injection of 1 M ethanolamine, pH 8.5. Three 30s-injections of 50 mM NaOH was used to wash off non-covalently bound HSA and to further stabilize the baseline. Final immobilization levels of HSA on NHC-CM5 chip and CM3 chip were 4200. Unmodified dextran surface was used as a reference surface.

Example 21B. Opioid/Protein Interactions

Opioids were first serially diluted into running buffer to final concentrations of 50, 100, 200, 400 µM. To test data quality and further equilibrate the surfaces, 4 warm-up buffer cycles were performed at a flow rate of 30 µl/min. Opioids samples were injected over the reference and HSA surfaces at a flow rate of 30 µl/min. Replicate injections of each drug concentration were analyzed. Each cycle consisted of a 1-min waiting period for monitoring of the baseline stability. Then the drug/HSA complex was allowed to associate and dissociate for 60 s and 30 s, respectively. No regeneration of the surface was required between injections. Data obtained in the reference flow cell was subtracted from that obtained in the HSA immobilized flow cell. Double referencing method was used to improve the quality of the sensorgrams (R. L. Rich, et al., Anal. Biochem. 2001, 296, 197-207, Å. Frostell-Karlsson, et al., J. Med. Chem. 2000, 43, 1986-1992, and Biacore Application Note 30, Characterization of drug-plasma protein interactions using surface plasmon resonance. BR-9002-99 December 2002 Version 1.0). As shown in FIG. 21A-D, herion, cocaine, morphine and ketamine samples of opioids were successfully detected using the NHC-CM5 chip. Signals for repeated runs overlap one another, while the different concentrations are spaced from one another with the higher concentration having the higher signal. For heroin and morphine, as shown in FIGS. 21A and 21C, only three levels are shown since the lowest concentration was not detectable.

Example 22: Synthesis of Stable N-Heterocylic Carbene-Phosphine Mixed Ligand-Protected Au Clusters Using a NHC Hydrogen Carbonate Exchange Method Isopropyl and ethyl air-stable NHC—$HCO_3$ derivatives were used as single sources of NHCs to synthesize NHC-phosphine Au nanoclusters via an exchange procedure under ambient conditions. Resulting clusters were characterized using mass spectrometry, UV-vis, NMR and XPS. Results suggested an increased stability relative to fully phosphine-protected Au nanoclusters. It was considered that the NHC-phosphine Au nanoclusters may be suitable for electrocatalytic $CO_2$ reduction and other catalytic applications. Without wishing to be bound by theory, this was considered due to the clusters' increased electron density, originating from their highly electron-donating NHCs and small size, thus resulting in a high surface electric field enhancement.

Nanocluster $[Au_{11}(PPh_3)_7(NHC\text{-}iPr)Cl_2]Cl$ (Au11-NHC(iPr))

Synthesis and Characterization

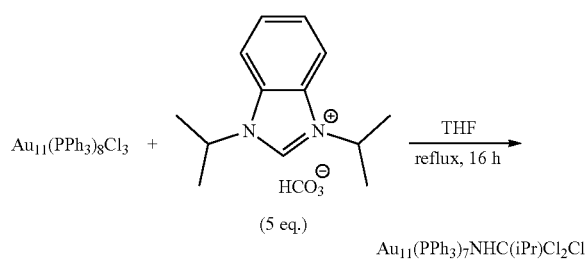

$[Au_{11}(PPh_3)_8Cl_2]Cl$(Au11-TPP8) was synthesized as previously described by Hutchison, J. E. et al. J. Am. Chem. Soc. 2014, 136, 13426-13435. Au11-TPP8 (68.7 mg, 0.0157 mmol, 1 eq) and 1,3-diisopropyl-1H-benzo[d]imidazol-3-ium hydrogen carbonate [NHC(iPr)$HCO_3$] (20.8 mg, 0.0786 mmol, 5 eq; synthesized as per section 'Example 1-Preparation of 1,3-Diisopropylbenzimidazolium hydrogen carbonate, [iPr2bimy (H)][$HCO_3$] (3a)-Hydrogen carbonate-anion exchange resin' and 'Example 16—Synthesis of 1,3-Diisopropylbenzimidazolium triflate—Hydrogen carbonate-anion exchange') were added to a round bottom flask and THF (68.7 mL) was added. A reflux condenser was attached and the mixture was heated at reflux under air for 16 h. The reaction mixture was cooled and solvent was removed in vacuo to give a red/orange oily residue. $Et_2O$ (5 mL) was added to the flask which resulted in precipitation of a red solid. Solvent was carefully decanted and the resulting solid was washed with $Et_2O$ (5 mL) and hexane (2×5 mL). A resulting crude sample was then dried in vacuo to give a red solid. 30 mg of the crude sample was purified by a column chromatography ($CH_2Cl_2$/MeOH 95:5→90:10) to give a red solid (21 mg). $^1$H-, $^{13}$C-, $^{31}$P-NMR ($CD_2Cl_2$) and UV-vis ($CH_2Cl_2$) analysis of the purified Au11-NHC(iPr) clusters was as follows: $^1$H-NMR ($CD_2Cl_2$, 500 MHz) δ 7.70-6.65 (m, ArH for $Ph_3P$ and NHC), 6.20 (m, —NH($CH_3$)$_2$), 1.70-0.75 (m, —NH($CH_3$)$_2$). $^{13}$C-NMR ($CD_2Cl_2$, 126 MHz) δ 134.90, 133.07, 132.65, 130.63, 130.56, 129.22, 123.78, 114.58, 32.15, 23.22, 21.22, 20.63, 14.44. $^{31}$P-NMR ($CD_2Cl_2$) δ 53.82 and 53.58. UV-vis spectrum ($CH_2Cl_2$); characteristic absorbance at 286, 307, and 370, 412 nm.

A concentration of 0.2 mg/ml, $CH_2CL_2$: $CH_3CN$ (1:1) was used in an electrospray ionization mass spectrometry (ESI-MS) analysis (analyzed in Prof. Tsukuda lab, Tokyo University, Japan). In view of the $^1$H-, $^{13}$C-, and $^{31}$P-NMR, the ESI-MS results further indicated a high product purity for the Au11-NHC(iPr) cluster: only mass peaks corresponding to the ionized product/product fragments were observed, and the isotope pattern confirmed the cluster's molecular formula based on isotopic speciation (FIG. 23).

XPS analysis was performed to further study the Au11-NHC(iPr) cluster's atomic composition. XPS analysis of Au11-TPP8 was also undertaken for comparative purposes. As per Table 4 below, XPS analysis of Au11-TPP8 indicated an absence of a nitrogen peak (i.e., lack of NHC moiety) with a good ratio of Au:P that was close to theoretical predictions. As per Table 5 below, XPS analysis of Au11-NHC(iPr) indicated the presence of an NHC moiety. Any variations in measured values was within error of the method.

Stability Tests

Di-Tert-Butylperoxide Oxidation in DCM:

24 eq. of Di-tert-butylperoxide (98% in DCM) was added to separate DCM solutions of Au11-NHC(iPr) and Au11-TPP8 (final concentration was 0.05 mg/ml). Initially, both solutions were clear and orange colored. After 43 h, the solution of Au11-NHC(iPr) remained clear and orange colored, while the solution of Au11-TPP8 was clear and colorless, suggesting decomposition. UV-Vis analysis further indicated that the Au11-TPP8 cluster decomposed due to a loss of any features in its UV-Vis spectrum; in contrast, the UV-Vis spectrum of the Au11-NHC(iPr) cluster indicated that it had retained its molecular features (i.e., transitions/molecular characteristic observed in the UV spectrum at 286, 307, and 370, 412 nm) even after 5 days (FIG. 24). These results suggest that the herein described nanoclusters may experience increased longevity and shelf life relative to incumbent clusters, as well as possess an ability to be used in air, and for oxidative catalysis.

Triphenylphosphine Etching in Boiling THF:

Separate THF solutions of Au11-NHC(iPr) and Au11-TPP8 (4 ml, 0.05 mg/ml) was used to dissolve 0.57 mg, 24 eq. of $PPh_3$. The resulting solutions were refluxed and analyzed by UV-Vis spectroscopy. Initially, both solutions were clear and orange colored. After 30 min, the Au11-NHC (iPr) solution remained colored, and its UV-Vis spectrum was unchanged (within experimental error). After 30 min, the Au11-TPP8 solution was colorless, and its UV-Vis spectrum showed no absorption peaks, both of which indicated decomposition (FIG. 25). These results provide general information as to the stability of the herein described nanoclusters, and their potential use in catalysis.

[Au$_{11}$(PPh$_3$)$_{6-7}$(NHC-Et)$_{1-2}$Cl$_2$]Cl (Au11-NHC(Et))

Preparation of 1,3-Diethyl-1H-benzo[d]imidazol-3-ium hydrogen carbonate, [Et$_2$bimy (H)][HCO$_3$]

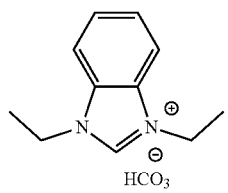

1,3-Diethyl-1H-benzo[d]imidazol-3-ium iodide was according to literature procedures ((Chen, W. C. et at, (2014) Chemistry—a European Journal 20, 8099-8105)).

Resin-HCO$_3$ suspended in water was measured out in a graduated cylinder (6.62 mL, 2 equiv., prepared as described above) and transferred to a 20 mL vial where the resin was allowed to settle and water was decanted. The resin was washed with methanol (3×4 mL). 1,3-diethyl-1H-benzo[d]imidazol-3-ium iodide (1 g, 3.31 mmol) was dissolved in 17 mL methanol and transferred to the resin. The mixture was stirred for 30 min. The silver nitrate test indicated the completeness of the exchange reaction. The hydrogen carbonate solution was passed through a cotton plug to remove any resin beads and the resin was washed with methanol (3×4 mL), which was then added to the original filtrate. Solvent was evaporated and the residual solid was triturated and sonicated in acetone (3×10 mL), which was then decanted off via syringe and discarded. Subsequent drying of the white powder under vacuum afforded the desired product as a white powder (662 mg, 85% yield). Anal. Calc. for C$_{14}$H$_{20}$N$_2$O$_3$: C, 61.00; H, 6.83; N, 11.86. Found: C, 61.19; H, 6.83; N, 11.92. $^1$H NMR (300 MHz, CD$_3$OD): δ 7.99 (dd, J=6.3, 3.1 Hz, 2H, Ar—H), 7.71 (dd, J=6.3, 3.1 Hz, 2H, Ar—H), 4.56 (q, J=7.3 Hz, 4H, NCH$_2$CH$_3$), 1.65 (t J=7.3 Hz, 6H, —CH$_2$H$_3$). The N$_2$CH and HCO$_3$ protons were not observed due to their rapid exchange with the deuterated solvent on the NMR time scale. $^{13}$C ($^1$H) NMR (75 MHz, CD$_3$OD): 129.90 (s, C$_q$), 125.20 (s, C$_{Ar}$), 111.51 (s, C$_{Ar}$), 40.73 (s, CH$_2$CH$_3$), S 11.74 (s, CH$_2$CH$_3$).

Synthesis and Characterization of Nanocluster

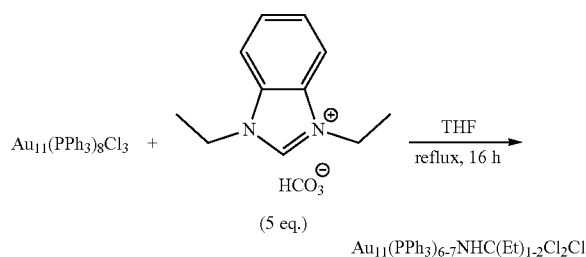

Au11-TPP8 (70.1 mg, 0.0160 mmol, 1 eq) and 1,3-diethyl-1H-benzo[d]imidazol-3-ium hydrogen carbonate [NHC(Et)HCO$_3$] (18.9 mg, 0.08 mmol, 5 eq) were added to a round bottom flask and THF (70.1 mL) was added. A reflux condenser was attached to the flask and the mixture was heated at reflux temperatures under air for 16 h. The reaction mixture was cooled and solvent was removed in vacuo to give a red/orange oily residue. Et$_2$O (5 mL) was added to the flask, which resulted in precipitation of a red solid. Solvent was carefully decanted and the resulting solid was washed with Et$_2$O (5 mL) and hexane (2×5 mL). The resulting solid was then dried in vacuo to give a crude red solid. The crude was purified by a column chromatography (CH$_2$Cl$_2$/MeOH 95:5→90:10) to give a purified red solid (44.3 mg). $^1$H-, $^{13}$C-, $^{13}$P-NMR (CD$_2$Cl$_2$) and UV-vis (CH$_2$Cl$_2$) analysis of the purified clusters is as follows: $^1$H-NMR (CD$_3$OD, 400 MHz) δ 7.60-6.70 (m, ArH for Ph$_3$P and NHC), 3.90-4.25 (2 m, —NH$_2$CH$_3$), 1.00-0.70 (m, —NH$_2$CH$_3$). $^{31}$P-NMR (CD$_3$OD) of Au$_{11}$—NHC(Et) δ 54.46 and 54.36. $^{13}$C-NMR (CD$_3$OD, 101 MHz) δ 134.24, 130.00, 129.92, 128.48, 124.48, 123.52, 111.38, 30.18, 14.54. UV-vis spectrum (CH$_2$Cl$_2$) with characteristic absorbance at 286, 308, 416 and 425 nm.

A concentration of 0.2 mg/ml, CH$_2$Cl$_2$:CH$_3$CN (1:1) was used in an electrospray ionization mass spectrometry (ESI-MS) analysis (analyzed in Prof. Tsukuda lab, Tokyo University, Japan). ESI-MS results indicated the exchange product formed mainly from NHC-mono and disubstituted clusters (FIG. 26). While two exchange products was not expected in view of the results for Au11-NHC(iPr) (see above), without wishing to be bound by theory, it was considered a result of NHC(Et) being smaller than NHC (iPr). With reference to FIG. 26, two peaks corresponding to the two exchange products were observed (peak 1=disubstituted cluster; peak 2=monosubstituted cluster), with each isotope pattern confirming the respective cluster's molecular formula based on isotopic speciation.

Stability Tests

Thermal Stability in Pentanol at 90° C.:

Clusters Au11-TPP8 and Au11-NHC(Et) were separately heated to 90° C. in pentanol. Au11-NHC(Et) demonstrated higher thermal stabilities relative to Au11-TPP8, as evidenced by UV-Vis analysis (FIG. 27). The UV-Vis spectrum of Au11-TPP8 depicted a complete loss of molecular transitions after 1 h, while the UV-Vis spectrum of Au11-NHC (Et) continued to depict molecular transitions after >4 h. These results provide general information as to the stability of the herein described nanoclusters, that they may experience increased longevity and shelf life relative to incumbent clusters, and may possess an ability to be used in air, and for oxidative catalysis.

Nanocluster [Au$_{11}$(PPh$_3$)$_n$ (NHC-Me)$_m$Cl$_2$]Cl (Au11-NHC(Me))

Synthesis and Characterization:

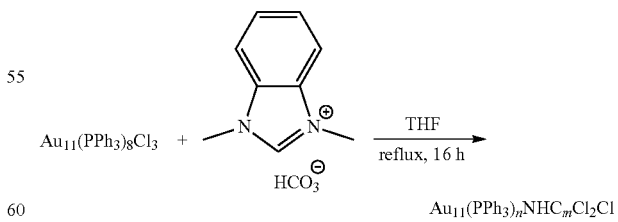

1,3-Dimethylbenzimidazolium iodide was according to literature procedures ((Chen, W. C. et al., (2014) Chemistry—a European Journal 20, 8099-8105)). 1,3-dimethylbenzimidazolium hydrogen carbonate was synthesized via a Resin-HCO$_3$ suspended in water, as described above.

[Au$_{11}$(PPh$_3$)$_8$Cl$_2$]Cl (10.9 mg, 0.00249 mmol, 1 eq) and bicarbonate salt 1,3-dimethylbenzimidazolium hydrogen carbonate, [Me$_2$bimy(H)][HCO$_3$] (10.3 mg, 0.01247 mmol, 5 eq) were added to a round bottom flask and THF (11 mL) was added. A reflux condenser was attached and the mixture was heated at reflux under air for 16 h. The reaction mixture was cooled and the solvent was removed in vacuo to give a red oily residue. The residue was washed with Et$_2$O (2×5 mL) and hexane (2×5 mL). The resulting solid was then dried in vacuo to give a crude red solid product. The crude product was purified by a column chromatography (CH$_2$Cl$_2$/MeOH 90:10). A minor red cluster (1.8 mg, R$_f$=0.5) and a major red cluster (6.1 mg, R$_f$=0.12) were isolated from the column. The major cluster at R$_f$=0.12 was characterized as the following: $^1$H-NMR (CD$_2$Cl$_2$, 400 MHz) δ 7.80-6.45 (m, ArH for Ph$_3$P and NHC), 3.00-4.50 (m, —NCH$_3$); $^{31}$P-NMR (CD$_2$Cl$_2$) of Au$_{11}$—NHC(Me) δ 53.70, 53.57, and 54.36; UV-vis spectrum (CH$_2$Cl$_2$) with characteristic absorbance at 289, 305, 416 and 427 nm.

Example 23: Versatility of Resin-HCO$_3$ Method to Form NHC—HCO$_3$ from Precursors Containing Different Counter Anions 1,3-Diisoproplylbenzimidazolium iodide, 1,3-diisopropylbenzimidazolium triflate, and a benzimidazolium bromide were synthesized as indicated below. From each, a hydrogen carbonate carbene precursor was formed via the ion-exchange resin procedure outlined in Example 1 (Hydrogen carbonate-anion exchange resin), and deposited via the procedure in Example 3 (Hydrogen Carbonate Salt (Carbene Precursor) Method.

Iodide:

1,3-Diisoproplylbenzimidazolium iodide was prepared according to literature procedures (Chen, W. C. et al., (2014) Chemistry—a European Journal 20, 8099-8105).

The self-assembled carbene monolayer on Au shown in FIG. 56 was analyzed by XPS to determine the presence of iodide. As per FIG. 28, no iodide was detected—indicating that the carbene precursor had been successfully purified of iodide, and that its resultant carbene-functionalized composite material (e.g., self-assembled carbene monolayer on Au) was free of iodide that would have been derived from the precursors.

It was noted, however, that irreproducible traces of iodide were detected in other samples; for example: upon immersing a bare gold chip in regular methanol solvent only, iodide was detected by XPS analysis. This was a consequence of the extremely high iodophilicity of gold, and high sensitivity of XPS techniques.

Triflate:

1,3-Diisopropylbenzimidazolium triflate was synthesized as shown in FIG. 57 (Example 16). The self-assembled carbene monolayer on Au as shown in FIG. 57 was analyzed by XPS to determine the presence of fluoride. As per FIG. 29, no fluoride was detected—indicating that the carbene precursor had been successfully purified of triflate ions, and that its resultant carbene-functionalized composite material (e.g., self-assembled carbene monolayer on Au) was free of triflate ions that would have been derived from the precursors.

Bromide:

The self-assembled carbene monolayer on Au as shown in FIG. 58 was analyzed by XPS to determine the presence of bromide. As per FIG. 30 (wide scan), bromide at (Br 3d5/2 at 68 eV) was not detected—indicating that the carbene precursor had been successfully purified of bromide, and that its resultant carbene-functionalized composite material (e.g., self-assembled carbene monolayer on Au) was free of bromide that would have been derived from the precursors.

Preparation of 1,3-dibenzyl-1H-benzo[d]imidazol-3-ium hydrogen carbonate [Bn$_2$bimy (H)][HCO$_3$]

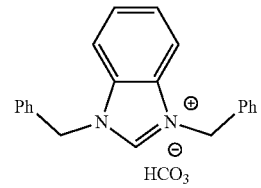

First 10 mL of activated resin was rinsed with HPLC grade methanol three times and then resuspended in 10 mL of methanol. Then 1.000 g of dibenzylbenzimidazolium bromide salt (prepared as described in M. Millen et. al, Synthetic Communications, 40: 2291-2301, 2010) was added to the solution and left to stir at room temperature for thirty minutes. Then the solution was filtered through glass wool and concentrated at 40° C. on a rotary evaporator. To further dry the resulting white solid, it was left under high vacuum overnight. To wash the solid, ether and hexanes were used three times each. The solid was again allowed to dry under high vacuum to obtain 0.7142 g of product, a white solid. $^1$H NMR (CD$_3$OD): 7.86 (s, 1H), 7.65 (s, 1H), 7.44 (s, 5H), 5.75 (s, 2H). EA expected: N: 7.77, C: 73.32, H: 5.59; observed: N: 7.81, C: 73.13, H: 5.60.

Example 24: NHC-Protected Metal Nanoclusters (NCs) and Metal Nanoparticles (NPs)

Various NHC-protected metal nanoclusters (NCs) and metal nanoparticles (NPs) were designed and studied. A ligand replacement reaction of phosphine-protected Au11 NCs with bicarbonate-NHCs was studied, in addition to a replacement reaction of didodecyl sulfide (DDS) protected Au NPs with bicarbonate-NHCs. Due to an observed incomplete replacement of ligands in these systems, more direct synthesis methods were designed in order to prepare NHC-protected Au NPs, Cu NCs, and Ag NPs. These methods avoid a need to prepare the NCs/NPs with another protecting ligands first (such as phosphines or DDS) and overall demonstrate a relatively facile method to prepare metal NPs/NCs using bicarbonate-NHCs. Transmission electron microscopy (TEM), UV-visible spectroscopy (UV-vis), X-ray photoelectron spectroscopy (XPS), and X-ray absorption spectroscopy (XAS) were used to characterize NPs/NCs atomic and electronic structures and overall impact of NHC adsorption on the NPs/NCs.

Synthesis

NHC-Protected Au11-NCs Prepared by Ligand Replacement:

Approximately 40 mg of Au11 NCs protected by diisopropylated bezimidizole derived NHCs (Au11-NHC(iPr)) was prepared and detailed in section 'Example 22; Nanocluster [Au$_{11}$(PPh$_3$)$_7$(NHC-iPr)Cl$_2$]C$_1$ {Au11-NHC(iPr)}'. In addition, approximately 40 mg of the original phosphine-protected Au11 NCs {[Au$_{11}$(PPh$_3$)$_8$Cl$_2$]Cl (Au11-TPP8)} was also prepared according to Hutchison, J. E. et al. J. Am. Chem. Soc. 2014, 136, 13426-13435, and used as a reference sample.

NHC-Protected Au-NPs Prepared by Ligand Replacement:

NHC-protected Au nanoparticles (NPs) were synthesized using a ligand replacement method, where initial Au NPs were prepared with didodecyl sulfide (DDS, Au-DDS NPs), and then DDS was replaced with NHC while in solution (Au—NHC NPs). First, 0.05 mmoles of hydrogen tetrachloroaurate ($HAuCl_4$, Aldrich, 99%) was added to 0.15 mmoles of tetraoctylammonium bromide (TOAB, Aldrich, 98%) in 25 mL of toluene (Aldrich, 99.9%). The mixture was sonicated briefly until all solids were dissolved, and then 0.25 mmoles of DDS was added. The mixture was degassed with argon for 10 minutes and then added to a mixture of 0.5 mmoles of sodium borohydride ($NaBH_4$, Aldrich, 99%) in 5 mL of toluene. Finally, 20 µL of deionized water was added to facilitate reduction of $HAuCl_4$ by $NaBH_4$. The mixture was then allowed to stir for 2 hours under magnetic stirring and argon. After this, the Au-DDS NPs were purified by successive ethanol precipitation accelerated by centrifugation; toluene was first removed via rotary evaporation at a temperature of 30° C., and then 20 mL of ethanol (Commercial Alcohols, anhydrous) was added to the dried samples and then centrifuged at 4000 g to collect Au NPs at the bottom of the centrifuge tubes. Remaining ethanol with excess reagents and impurities was discarded, and the sample was dispersed in another 20 mL of ethanol. This process was repeated a total of three times and then finally dispersed in 20 mL of dichloroethane (DCE, Aldrich, 99.9%) in order to carry out ligand replacement. To half of this mixture, 0.125 mmoles of diisoprolyated bicarbonate-NHC (3a; synthesis detailed in Example 1) was added, and then the mixture was degassed with argon for 10 minutes, sealed, and allowed to stir for 16 h. After the reaction time, the resulting Au—NHC NPs were purified using the same methods described above.

NHC-Protected Au NPs by Direct Synthesis:

Au NPs protected by diisopropylated bicarbonate-NHCs were prepared by a direct reduction method, whereby $HAuCl_4$ (Aldrich, 99%) was reduced in various solvents by $NaBH_4$ (Aldrich, 99%) in the presence of bicarbonate-NHCs. Toluene (EMD Millipore, 99.8%), tetrahydrofuran (THF, Aldrich, 99.9%), ethanol (Commercial Alcohols, anhydrous), methanol (Aldrich, 98%) and dichloroethane (DCE, Aldrich, 99.9%) were used as main solvents, along with either deionized water or ethanol as $NaBH_4$-delivery co-solvents to give 10 different solvent combinations (i.e., 5 main solvents and 2 co-solvents each). For each combination, 0.05 mmoles of $HAuCl_4$ was added to 10 mL of each respective main solvent in a 30 mL sealable sample vial and sonicated until completely dissolved. Then, 0.25 mmoles of diisopropylated bicarbonate-NHC (3a; synthesis detailed in Example 1) was added to each solution and mixed with a magnetic stir-bar while degassing with argon for 30 minutes. To these mixtures, 0.5 mmoles of $NaBH_4$ in 1 mL of freshly prepared, cold (ice-bath) deionized water or ethanol (also degassed for 10 minutes with argon) was added dropwise while magnetically stirring under argon flow. The solutions were sealed and then allowed to stir for 2 hours to complete the reaction. Of the combinations described above, it was found that THF and water/$NaBH_4$ was a successful solvent combination for preparation of stable Au NPs, based on the distinctive ruby-red colour (from surface plasmon resonance, SPR) of the as-prepared sample after the reaction time. While preparations using solvent combinations of toluene, ethanol, methanol underwent various SPR-related colour changes (indicating formation of Au NPs), after the full reaction time they formed insoluble precipitates. The other solvent combination besides THF and water/$NaBH_4$ that was successful in forming Au NPs was the DCE and water/$NaBH_4$ combination, which produced a pale blue solution colour, typically indicating larger NPs (e.g., greater than 50 nm in diameter). Therefore, the sample that underwent further purification and characterization was the sample of Au NPs prepared with THF and water/$NaBH_4$. The THF/water was first removed from this sample by via rotary evaporation at a temperature of 40° C., and then 20 mL of ethanol (Commercial Alcohols, anhydrous) was added and then centrifuged at 4000 g to collect Au—NHC NPs at the bottom of the centrifuge tubes. Remaining ethanol with excess reagents and impurities was discarded, and the sample was dispersed in another 20 mL of ethanol. This process was repeated a total of three times and then finally dispersed in 20 mL of toluene for UV-vis and TEM measurements.

NHC-Protected Cu NCs by Direct Synthesis:

NHC-protected Cu NCs (Cu—NHC NCs) were prepared by a thermal reduction method, whereby copper acetate (CuOAc, Aldrich, 98%) was reduced in hot toluene (EMD Millipore, 99.8%, at 90° C. or 115° C.) in the presence of bicarbonate-NHCs (3a; synthesis detailed in Example 1). In this way, 0.05-0.1 mmoles of CuOAc was dispersed in 20 mL of toluene by sonication in 100 mL round-bottom flask. The solution was degassed with argon for 10 minutes, whereupon 0.25-0.5 mmoles of diisopropylated bicarbonate-NHC (3a; synthesis detailed in Example 1), maintaining at least a 1Cu:5NHC molar ratio, was added and magnetically stirred while under argon for 10 minutes. The mixture was then heated in a reflux apparatus at either 90° C. or 115° C. while magnetically stirring for 16 h. The reflux apparatus was covered by a rubber septum with a needle to minimize outside exposure. The solution was then allowed to cool and small aliquots were removed for TEM and UV-vis characterization, while the rest of the solution was completely dried by vacuum, sealed under argon, and put into a freezer for storage. The Cu—NHC NCs were identified as nanoclusters based on size (usually under 2-3 nm), as well as a lack of SPR related features (e.g. for Cu, SPR occurs around 570-600 nm).

A reference sample was also prepared whereby 0.05 mmoles of CuOAc was added to a round-bottom flask with toluene and then heated at 115° C. for 16 h. This solution was observed to qualitatively assess any changes in colour during the reaction time.

NHC-Protected Ag NPs by Direct Synthesis:

The same thermal decomposition procedure as described in 'NHC-protected Cu NCs by direct synthesis' was used to prepare Ag NPs (Ag—NHC NPs). However, in this case, the reaction was carried out with 1,2-dichlorobenzene (DCB, Acros Organics, 99%, B. P. 180.5° C.) as use of toluene (at 110° C.) appeared to be unable to significantly reduce Ag. First, 0.05-0.1 mmoles of silver acetate (AgOAc, Aldrich, 98%) was dispersed in 20 mL of DCB in a 100 mL round-bottom flask by sonication and then degassed with argon for 10 minutes. Then, 0.25-0.5 mmoles of diisopropylated bicarbonate-NHC (3a; synthesis detailed in Example 1), maintaining at least a 1 Ag:5NHC molar ratio, was added and magnetically stirred while under argon for 10 minutes. The mixture was then heated by a reflux apparatus with rubber septum at 180.5° C. while stirring. The sample solution was then allowed to cool and small aliquots were removed for TEM and UV-vis characterization, while the rest of the solution was dried by ultra-high vacuum, sealed under argon, and put into a freezer for storage. A reference solution was also prepared whereby 0.05 mmoles of AgOAc was added to a round-bottom flask with 20 mL DCB and then heated at 180° C. for 16 h. This solution was observed to qualitatively assess any changes in colour during the reaction time.

Instrumentation

XAS Measurements and Data Processing:

XAS measurements were conducted at Soft X-ray Microcharacterization beamline (SXRMB, 06B1-1, Canadian Light Source, Saskatoon, SK, Canada), Spherical Grating Monochromator beamline (SGM, HID-1, Canadian Light Source, Saskatoon, SK, Canada), and Sector 20-BM beamline at the Advanced Photon Source (APS, Argonne National Lab, Argonne, IL, USA). For Au $L_3$-edge XAS measurements at Sector 20-BM, including extended X-ray absorption fine structure (EXAFS) and X-ray absorption near edge structure (XANES), samples were packaged into kapton film pouches and placed in a cryostatic sample holder at 20 K while Au $L_3$-edge XANES and EXAFS were collected using a 32-element Ge fluorescence detector. Au $L_3$-edge XANES/EXAFS data for Au foil was also collected simultaneously using standard gas-ionization chamber detectors. For P K-edge, Cl K-edge, Cu K-edge, and Ag $L_3$-edge measurements, samples were dispersed onto double-sided carbon tape which was affixed to a sample holder plate. The sample plate was then mounted inside the chamber at 45° to an incident X-ray beam and allowed to reach ultra-high vacuum. The XANES/EXAFS measurements were then collected via Fluorescence mode (FLY) with a four-element silicon drift detector, while simultaneously collecting total electron yield (TEY). All of XANES experimental measurements were processed with Athena, part of the IFEFFIT® software package while EXAFS measurements were processed with the WinXAS® (version 3.2) using standard analysis and refinement procedures. Raw EXAFS data were converted to k-spaces and then Fourier-transformed into R-spaces using data ranges between $k=2.5-16$ $A^{-1}$ depending on quality of the data. The R-spaces were then refined with WinXAS using bonding paths from ab initio simulations of known structures that include correct bonding paths using the FEFF® program (version 8.2). Refinements calculated structural information such as coordination number of nearest neighbors (CN), bond length, and Debye-Waller factors (2) along with energy shift parameter, $\Delta E0$, which helps account for refinement assumptions. For Au11-TTP8 and Au11-NHC(iPr) NCs described in 'NHC-protected Au11 NCs prepared by ligand replacement', all of the R-spaces underwent refinements with Au—P, Au—$Au_1$ (shorter), and Au—$Au_2$ (longer) bonding paths within the R-space range of 1.5-3.5 Å. For the Au $L_3$-edge EXAFS measurements of the Au NPs described in 'NHC-protected Au NPs prepared by ligand replacement', all of the R-spaces underwent refinements with Au—S and Au—Au bonding paths within the R-space range of 1.5-3.3 Å. For all of the R-space refinements throughout this herein described work, $\Delta E0$ values for all of the paths were correlated in order to reduce number of free running parameters to number of independent points. Refinement uncertainties reported were calculated from off-diagonal elements of the correlation matrix of each fit, weighted by square root of reduced chi-squared value, taking into account experimental noise for each R-space spectrum from 15 to 25 Å.

Simulated Au $L_3$-edge XANES spectra of Au11-TTP8 and Au11-NHC(iPr) described in 'NHC-protected Au11 NCs prepared by ligand replacement' were calculated using the FEFF program (version 8.2) with atomic coordinates of the crystallized Au11-cluster obtained by Hutchison, J. E. et al. J. Am. Chem. Soc. 2014, 136, 13426-13435. The coordinates for the Au11-NHC(iPr) cluster were predicted by replacing one phosphine ligand with one NHC ligand. It should be noted that all H atoms, as well as non-bonding C atoms relative to Au and P were removed (except for the NHC ligand) during simulations in order to reduce computational cost of the calculations. Therefore, the simulations are not experimentally accurate, and were only used for comparative purposes to demonstrate simulated data trends. For each simulation, a full multiple scattering (FMS) diameter of 30 Å and a self-consistent field (SCF) radius of 6 Å was used for each individual Au site in order to account for all atoms in the structure.

UV-Vis, TEM, and XPS Analysis Methods:

UV-visible spectroscopy (UV-vis) was carried out using a Varian Cary 100 Bio UV-visible spectrophotometer by adding 0.25 mL of each sample to 2.50 mL of solvent in a quartz cuvette and then scanned from 300-700 nm. An automatic background subtraction was carried out by first running a background solvent scan before samples. Samples described in 'NHC-protected Cu NCs by direct synthesis' were also characterized by in situ UV-vis, whereby the same 1Cu:5NHC molar ratios were dispersed into 3 mL of toluene and then heated and magnetically stirred at 90° C. UV-vis scans from 300-700 nm were then recorded every 5 minutes for 16 h. Transmission electron microscopy (TEM) was carried out using a FEI Osiris TEM operated at 200 kV. TEM samples were prepared by placing a drop of NP solutions on formvar/carbon-coated TEM grids. Films on the TEM grids were allowed to dry while covered for 16 h at room temperature before analysis. Images were taken with the TEM and later analyzed with the ImageJ® program (version 1.50i). XPS measurements were performed using a Thermo Microlab 310F surface analysis instrument using Al Kα X-rays (1486.6 eV) or Mg Kα (1253.4 eV) at 15 kV anode potential and 20 mA emission current with a surface/detector take off angle of 75°. Solutions of samples were drop-casted onto copper substrates and allowed to dry prior to being placed in the XPS chamber.

Results and Discussion

NHC-Protected Au11 NCs Prepared by Ligand Replacement:

XANES spectra of Au11-TPP8/Au11-NHC(iPr) shown in FIG. 31 depicted a decrease in first peak intensity, indicating less Au d-orbital vacancies (more d-electrons), which implies a greater electron donating capacity of the NHC ligand compared to phosphine. The minimal decrease in this feature for Au11-NHC(iPr) relative to Au11-TPP8 also implied a lower degree of substitution, and this was later confirmed by ESI-MS which demonstrated a single phosphine replacement with NHC. Corresponding simulated Au $L_3$-edge XANES data (FIG. 32) corroborated a semi-proportional relationship between the decrease in this feature with replacement of phosphines by NHCs.

FIG. 33($a$) shows Au $L_3$-edge k-space EXAFS spectra of Au11-TPP8, Au11-NHC(iPr), and bulk Au for reference. The k-space demonstrated a relatively large difference between Au11-TPP8/Au11-NHC(iPr) and bulk Au, and overall demonstrated a non-fcc nature of Au11-TPP8/Au11-NHC(iPr) consistent with small Au NCs. Structural similarities of Au11-TPP8 and Au11-NHC(iPr) was also demonstrated by the k-space of each, with relatively minor changes in oscillatory intensity and phase, consistent with subtle differences in coordination of nearest neighbors and bond lengths relative to Au, respectively. The R-space spectra in FIG. 33($b$-$c$) of each NC further indicated a slight change in bonding environment of Au atoms within Au11-NHC(iPr).

The R-space spectra were then refined to yield parameters given in Table 6. A single Au—P path and two Au—Au paths were used for the refinements based on analysis of bonding within the Au11-TPP8 crystal structure from Hutchison, J. E. et al. *J. Am. Chem. Soc.* 2014, 136, 13426-13435. and the predicted structure of Au11-NHC(iPr) (results of this analysis are shown in FIG. 34). The Au—Au$_1$ path was used to characterize core Au—Au bonding, while the Au—Au$_2$ path was used to simulate surface Au—Au bonding within Au11-TPP8 and Au11-NHC(iPr)NHC. Bonding paths of Au—Cl and Au—C(for Au11-NHC(iPr)NHC) were also included in preliminary refinements; however, they yielded entirely unphysical results, likely a result of their small contribution to the overall Au coordination (i.e., Au—Cl=0.18, Au—C=0.09). In both cases, the CN values for each path were fixed to those which were calculated from the Au11-TPP8 crystal structure (from Hutchison, J. E. et al. *J. Am. Chem. Soc.* 2014, 136, 13426-13435), and the predicted Au11-NHC(iPr) structure, while the bond lengths were allowed to run free during the refinements. Both refinements carried out using this method demonstrated good agreement to experimental data. The Au11-NHC(iPr)NHC demonstrated an observable relaxation of Au—P, Au—Au$_1$, and Au—Au$_2$ bond lengths. Overall, it was considered that these Au L$_3$-edge XANES/EXAFS results indicated a relatively large electronic and structural impact of replacing a single phosphine ligand for an NHC ligand.

The surface structures of Au11-TPP8 and Au11-NHC(iPr) also contained P and Cl; as such, P and Cl K-edge XANES experiments were carried out to determine the effect of ligand replacement on those particular components. Au11-TPP8, Au11-NHC(iPr), as well as diethylated benzimidazole derived NHCs Au clusters (Au11-NHC(Et)) were examined, which based on ESI-MS results described in Example 22 demonstrated greater NHC adsorption, and thus may further understanding of the NHC-surface interactions. The overlapped Cl K-edge XANES spectra in FIG. 35(a) show two major peaks for each sample. The first peak at approximately 2821 eV is interpreted as a pre-edge feature associated with Cl(s)→Au(d) transitions, and the second peak at 2149 eV is associated with Cl(s)→(p) transitions. A relatively large decrease in the pre-edge feature with increasing substitution was considered to describe the overall donating effect of NHC ligand. For example, the NHC ligands on Au11-NHC(iPr) induced an overall greater amount of electron transfer to the Au; therefore, the pre-edge feature was smaller because there are less Au(d) orbital vacancies. As noted above, a corresponding effect of a decreasing Au L$_3$-edge was also described for the Au11-NHC(iPr), which implied a greater overall donating effect of the NHC. For the P K-edge XANES shown in FIG. 35(b), the first feature at 2146 eV for all samples was also attributed as a pre-edge feature related to P(s)→Au(d) transitions, while the second feature at 2149 eV was associated with P(s)→(p) transitions. It was noted that there was a similar pre-edge decreasing trend with an increase in NHC substitutions, although not as intense a change. It was considered that this smaller change between the P K-edge for the samples may be due to donation/backdonation mechanism which could replenish Au(d) vacancies. Without wishing to be bound by theory, this type of mechanism was considered more likely to be in effect with phosphine ligands, as this type of mechanism does not occur for Cl, and hence the greater change between samples.

NHC-Protected Au-NPs Prepared by Ligand Replacement:

TEM results shown in FIG. 36(a) and FIG. 36(b) indicated that Au-DDS and Au—NHC NPs are 2.0±0.5 nm and 2.4±0.6 nm, respectively. Au—NHC NPs also appeared to be dispersed more consistently and closer together, which implied a greater surface ordering between the NPs as a result of ligand exchange. UV-Vis results also demonstrated relatively large differences in their surface plasmon (SPR) features (FIG. 37). For example, the SPR peaks were centered at 504 nm and 510 nm for the Au-DDS to Au—NHC NPs, respectively. In addition, the SPR feature for Au—NHC was more intense than for Au-DDS, which was considered to be due to a combination of the removal of the less electronegative S on the surface of the Au NPs and a slight increase in size.

XPS results demonstrated a slight reduction of the S 2p peak (FIG. 38(a)) and an increase in the N 1s peak (FIG. 38(b)), which was considered consistent with the replacement of DDS with NHC ligands. However, there was still a relatively large amount of S within the Au—NHC sample, indicating that DDS ligands were not fully replaced. In addition, the N 1s peak of DDS-NPs also indicated that there were N impurities in the sample or substrate, although the much larger N 1s peak for the Au—NHC NP sample was indicative of the replacement of DDS by NHC.

XANES spectra of Au-DDS and Au—NHC NPs shown in FIG. 39 demonstrated a decrease in the first peak intensity, indicating a greater electron donating capacity of the NHC ligands compared to DDS, and supporting a possibility of ligand exchange. TEM and UV-vis results for these samples suggested (by qualitative comparison) that there may have also been a slight increase in size during ligand replacement; it was considered that this change in size could partially account for the less intense XANES feature (from an increase of s-p-d hybridization in the Au with an increase in size). However, it was considered that the change of magnitude observed (relative to the change between Au-DDS and Au foil) was more likely due to a change in surface structure.

FIG. 40 depicts the Au L$_3$-edge k-space EXAFS spectra of Au-DDS NPs, Au—NHC NPs, and Au foil (Au bulk) for reference. Structural similarities of the NPs to the Au foil was evident from the same oscillatory features in the spectra, and demonstrated that bulk-type Au—Au bonding dominates the EXAFS signal for each sample. However, the intensity of features decreases from the foil to the NPs, which was considered consistent with lower overall coordination numbers. Oscillatory features for Au-DDS NPs were smaller than those of Au—NHC NPs, which is typically attributed to a smaller particle size, and is consistent with UV-Vis and TEM results described above.

The R-space spectra were refined with Au—S and Au—Au paths (refinement of Au-DDS shown in FIG. 41(a) and refinement of Au—NHC shown in FIG. 41(b)) and yielded parameters in Table 7. Both refinements carried out using this method demonstrated good agreement to experimental data. The main difference between the two samples was the Au—S bond length, which for the Au—NHC sample was elongated compared to the original Au-DDS sample. This suggests a structural rearrangement at the surface of the NPs with addition of NHC, corroborating the TEM and UV-Vis results described above. Refinements including Au—C bonding paths were also conducted, however, unphysical results were obtained when the path was added. In this case, it was proposed that low substitution coupled with low backscattering of C atoms may have prevented elucidation of specific Au—C bonding information. Nonetheless, similar to the case of Au-iPr NCs described above, addition of NHCs can be characterized by its influence on other structural features within the NC or NP, such as remaining metal-ligand and metal-metal bonding. Overall, in both reactions involving replacement of existing ligands (either P- or S-based) with NHCs, there were observable changes in the bond lengths of remaining original ligands.

NHC-Protected Au-NPs Prepared by Direct Synthesis:

THF, DCE, ethanol, methanol, and toluene were used as the main solvents to prepare Au—NHC NPs and all syntheses typically resulted in various SPR-related solution colours (e.g., red, purple, blue), indicating various sizes of colloidal Au—NHC NPs. However, the methanol, ethanol, and toluene containing solutions produced insoluble black precipitates by the end of the reaction time; therefore, these solvents were not used for further syntheses. Contrastingly, solvent combinations with TI-IF/water and DCE/water produced more stable Au—NHC NPs solutions, based on stability of solution colour after the full reaction time, as well as a lack of insoluble precipitates for both combinations. For example, the combination of THF and water/NaBH$_4$ resulted in a stable, dark ruby-red solution, which is generally consistent with smaller Au—NHC NPs in solution. The DCE/water combination appeared to stabilize Au—NHC NPs at the interphases of DCE/water bubbles, and resulted in an overall pale purple-blue solution generally indicative of larger Au NPs in solution. Without wishing to be bound by theory, the success of these combinations in preparing stable Au—NHC NPs was considered a result of the mild solubility of bicarbonate-NHC in THF and DCE, as well as solubility of the final NPs in those solutions. For example, the bicarbonate-NHCs were found to be highly soluble in water; it was considered, therefore, that the bicarbonate-NHC likely did not transfer significantly to the toluene phase that contained Au, and hence could not stabilize the NPs effectively. For the ethanol and methanol solutions in which the bicarbonate-NHCs were soluble, it was considered that the final Au—NHC NPs were not soluble enough in ethanol or methanol, and thus were precipitated from the solution as they were formed. Although the qualitative results of these syntheses indicate Au—NHC NPs were formed to some degree, only Au—NHC NPs prepared with the THF/water combination were further studied. The Au—NHC NPs had average diameters of 3.5±0.5 nm according to the TEM results (FIG. 42), and also exhibited the typical SPR induced absorbance feature of Au NPs at 520 nm (FIG. 43).

NHC-Protected Cu NCs Prepared by Direct Synthesis:

The direct synthesis method, as depicted above, with all solvent combinations was applied to the preparation of Cu—NHC NCs; however, the syntheses typically resulted in severe aggregation and precipitation, irrespective of ligand:metal (1:1, 1:2, 1:5, 1:10) and metal:NaBH$_4$ (1:1, 1:5, 1:10) molar ratios. Without wishing to be bound by theory, it was considered that precipitation of the Cu—NHC NCs was a result of the addition of a potentially oxidizing solvent (water or ethanol), and in order to avoid this issue, a one-phase organic system was designed where reduction was provided by heating instead of by NaBH$_4$. Using this technique, reduction of CuOAc in toluene (at 110° C.) in the presence of bicarbonate-NHC resulted in a gradual solution colour change from light blue to light yellow-brown, which indicated the formation of Cu—NHC NCs. The colour of the solution was typically stable by 3 h into the reaction, and no other colour change was observed during the rest of the 16 h reaction time. Without the addition of bicarbonate-NHC, the solution remained light blue, even after the 16 h reaction time. In situ UV-Vis shown in FIG. 44 depicts evolution of multiple non-SPR absorbance features throughout the reaction, consistent with metal NCs, and supports the observed colour change of the solution throughout the reaction. Small clusters were observed by TEM analysis, having an average diameter of 1.7±0.4 nm.

Cu K-edge XANES of the Cu—NHC NCs is shown in FIG. 45, and demonstrated a relatively large structural difference between Cu—NHC NCs (Cu NCs) and CuOAc. Further, features of the Cu—NHC NCs were similar to those of bulk Cu, although less intense, which is consistent with metallic NCs in general.

NHC-Protected Ag-NPs Prepared by Direct Synthesis:

The direct synthesis method described herein, with all solvent combinations, was also applied to the preparation of Ag—NHC NPs; however, the syntheses resulted in aggregation and precipitation irrespective of ligand:metal (1:1, 1:2, 1:5, 1:10) and metal:NaBH$_4$ (1:1, 1:5, 1:10) molar ratios. Therefore, thermal reduction of AgOAc in the presence of bicarbonate-NHC was attempted in toluene; however, no reduction took place as indicated by a lack of colour change (and corresponding absence of any UV-Vis features) in solution after more than 16 h. A higher boiling point solvent, DCB, was then used to provide a higher thermal reduction temperature. Following the same procedure using DCB, a change in solution colour from clear to a characteristic yellow-brown of Ag—NHC NPs was observed within 3 hours, indicating that Ag reduction had taken place. The reference solution with no bicarbonate-NHC did not produce any colour change after more than 16 h at the same temperature. FIG. 46 depicts a corresponding weak UV-Vis feature at around 450 nm consistent with the solution's colour, suggesting that the feature was derived from NP SPR as opposed to more molecular transitions, such as those observed in NCs. Further, TEM analysis indicated that the Ag—NHC NPs were approximately 2.5±0.5 nm, consistent with NPs that exhibit SPR-related features.

Ag L$_3$-edge XANES of the Ag—NHC NCs (Ag NPs) and reference materials (AgOAc/bulk Ag) were also collected (FIG. 47). The intensity of the first feature of the XANES spectrum was associated with Ag d-orbital vacancies in each sample, and correlated to overall oxidation state. Therefore, the decrease of this feature in the Ag—NHC NPs relative to AgOAc indicated a relatively more metallic (reduced) oxidation state, but was still a higher feature than bulk Ag consistent with NPs of this size.

Example 25: Further Synthesis of Monodentate and Bidentate N-Heterocylic Carbene Functionalized Gold Nanoparticles and Stability Studies Thereof

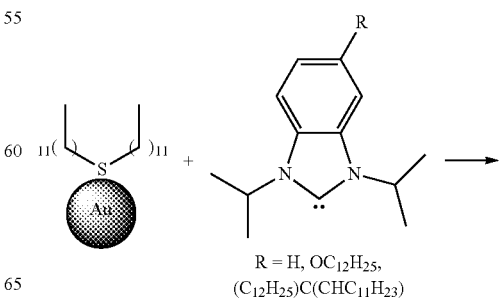

R = H, OC$_{12}$H$_{25}$,
(C$_{12}$H$_{25}$)C(CHC$_{11}$H$_{23}$)

-continued

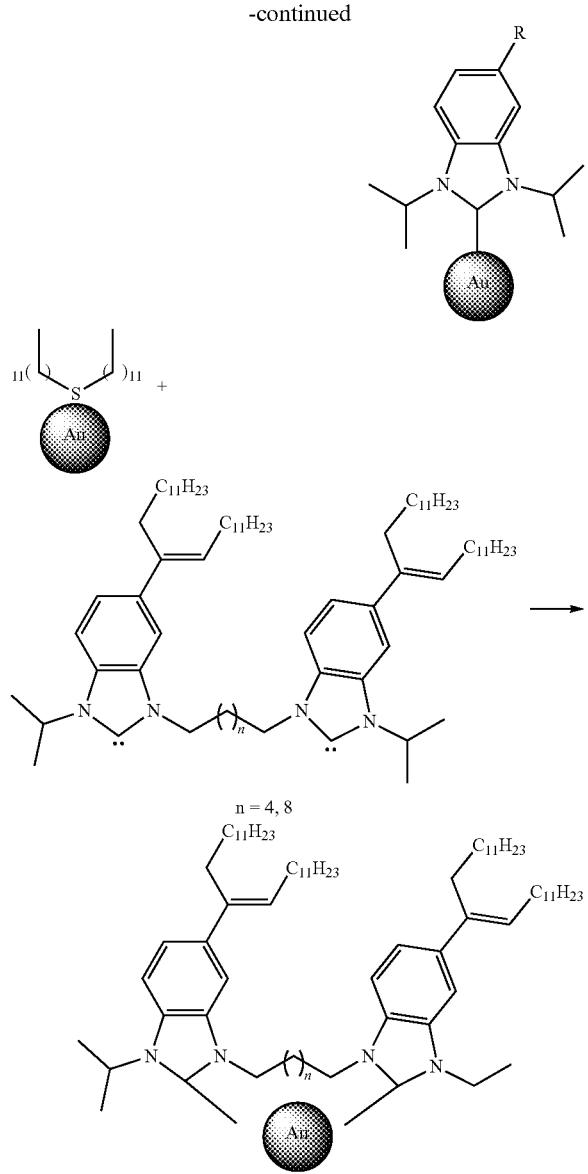

Materials:

Hydrogen tetrachloroaurate (III) trihydrate (HAuCl$_4$.3H$_2$O), sodium borohydride (NaBH$_4$), tetraoctylammonium bromide (TOAB), dodecyl sulfide (DDS), dodecanthiol (DDT), potassium tert-butoxide (K$^t$BuO), and di-tert butyl peroxide (DTBP) were received from Sigma Aldrich.

Synthesis of Dodecyl Sulfide (DDS) Functionalized Gold Nanoparticles (Au-DDS NPs)

Dodecyl sulfide (DDS) functionalized gold nanoparticles (Au-DDS NPs) were synthesized via Brust-Schiffrin method [Brust, M.; et al. J. Chem. Soc., Chem. Commun., 1994, 801-802.]. In a typical synthesis, gold (III) chloride trihydrate (80 mg, 0.2 mmol) was dissolved in water (7.9 mL) and stirred vigorously. To this solution was added tetraoctylammonium bromide (257 mg, 0.47 mmol) in toluene (4.7 mL), and the resulting biphasic mixture was stirred until the aqueous layer became colorless (30 min). The aqueous layer was then removed and the resulting organic layer was allowed to stir for an additional 16 h. A solution of dodecyl sulfide (262 mg, 0.71 mmol) in toluene (17.7 mL) was then added, and the mixture was allowed to stir for 5 min before sodium borohydride (107 mg, 2.8 mmol) in water (27.7 mL) was added in one portion. The reaction vessel was sealed and stirred vigorously for an additional hour, with occasional release of built up gases. The aqueous layer was then separated from the organic layer, and any volatiles were removed from the organic layer at room temperature under high vacuum. The resulting particles were then repeatedly washed by suspending in acetone (50 mL×4) and collected by centrifugation (10 min at 4000 rcf). Resulting Au-DDS NPs (25 mg) were stored as solids at −10° C.

Synthesis of Dodecanethiol Functionalized Gold Nanoparticles (Au-DDT NPs)

Dodecanthiol functionalized gold nanoparticles were synthesized via a modified DDS-Au NPs method. Typically, gold (III) chloride trihydrate (50 mg, 0.125 mmol) was dissolved in water (5 mL) and stirred vigorously. To this solution was added tetraoctylammonium bromide (125 mg, 0.24 mmol) in toluene (2.5 mL), and the resulting biphasic mixture was stirred until the aqueous layer became colorless (30 min). The aqueous layer was then removed and the resulting organic layer was allowed to stir for an additional 16 h. A solution of dodecanethiol (270 mg, 1.3 mmol) in toluene (5 mL) was then added, and the mixture was allowed to stir for 5 min before sodium borohydride (50 mg, 1.4 mmol) in water (10 mL) was added in one portion. The vial was sealed and stirred vigorously for an additional three hours, with occasional release of built up gases. The aqueous layer was then separated from the organic layer, and any volatiles were removed from the organic layer at room temperature under high vacuum. The resulting particles were then repeatedly washed by suspending in acetone (50 mL×4) and collected by centrifugation (20 min at 4000 rpm). Resulting Au-DDT NPs were stored as solids at −10° C. to prevent decomposition.

Monodentate-NHC: Monodentate-NHC was synthesized by modifying a literature method [Ling, X.; et. al. Chem. Mater. 2015, 414-423.].

Bidentate-NHC: Synthesis of bidentate-NHC is described in section 'Preparation of olefinic tail-equipped C$_6$H$_{12}$-finked dibenzimidazolium bromide salt'.

NHC Exchange on DDS Gold Nanoparticles:

The following was performed under nitrogen atmosphere in a glove box. In a typical synthesis, a benzimidazolium salt (0.12 mmol for bidentate-NHC, 0.24 mmol for monodentate-NHC was suspended in THF (2 mL), and potassium tert-butoxide (28 mg, 0.25 mmol) in THF (0.5 mL) was added dropwise over 30 min. The mixture was then allowed to stir at room temperature for 1 h prior to solvent removal under reduced pressure at room temperature. Benzene (3 mL) was then added to the resulting residue and the resulting suspension was filtered into a stirred solution of Au-DDS NPs (7 mg) dissolved in benzene (2 mL). Once addition was complete, the vial was sealed to preserve the nitrogen atmosphere and the vessel was removed from the glove box and placed in an ultrasonic bath for 20 min prior to being stirred at room temperature for 40 h. The vessel was then opened to atmosphere and solvent was removed under reduced pressure at room temperature. The resultant residue was repeatedly suspended and centrifuged against acetone (4×15 mL, for 30 min at 4000 rcf, 10° C.). Resulting particles were stored as solids at −10° C. to prevent decomposition.

Characterizations:

XPS was used to characterize the gold nanoparticles' chemical compositions. Having regard to FIG. 48, the top line represents the Au-DDS NPs and the bottom line represents the bidentate n=4 Au—NHC NPs. As depicted by FIG. 48, a loss of sulfur (S 2p) peaks at ~163 eV, and an appearance of nitrogen (N 1s) peak at ~401 eV indicated an exchange of DDS for NHC ligands on Au-DDS NPs. The Au 4f and C 1 s peaks depicted in FIG. 48 corresponded to the gold nanoparticles and the carbon in both sulfide and NHC ligands. Transmission electron microscopy (TEM) was used to characterize morphology and size of the mono- and bidentate Au—NHC NPs and Au-DDS NPs. The nanoparticles exhibited spherical shape with an average particle size between 1.5 and 5 nm in diameter.

Stability Tests

Thermal Stability:

Separate monodentate and bidentate Au—NHC NP and Au-DDS NP solutions were heated at different temperatures and monitored by UV-Vis spectroscopy. Au-DDS NPs aggregated and precipitated after heating in toluene at 90° C. for 4 h (see FIG. 49(a)). Gold nanoparticles functionalized with dodecanethiol nanoparticles (Au-DDT NPs) remained stable at 90° C. and 110° C. in toluene for 24 h. To further investigate thermal stability of nanoparticles at higher temperatures, solvent was changed from toluene to xylene. However, Au-DDT NPs aggregated and precipitated after heating in xylene at 130° C. for 0.5 h (see FIG. 49 (b)). Regarding the monodentate and bidentate Au—NHC NPs, no precipitation or aggregation of nanoparticles was observed at 130° C. after 24 h. However, the maximum surface plasmon resonance (SPR) band observed in the respective UV-Vis spectra of the monodentate and bidentate Au—NHC NPs red shifted a few nanometers (less than 10 nm and see FIGS. 49 (c) and (d)), indicating that the average size of nanoparticles increase a few nanometers.

Thiol Etching:

Monodentate and bidentate Au—NHC NPs were treated with 1 mM thiophenol in THF and monitored by UV-vis spectroscopy for 16 hours at room temperature. The monodentate Au—NHC NPs exhibited an initial maximum SPR band red shift of ~40 nm, with peak intensity decreasing after 16 h (see FIG. 50 (a)). This result indicated that the monodentate Au—NHC NPs aggregated and precipitated. The bidentate Au—NHC NPs exhibited an initial maximum SPR band red shift of 5 nm, with peak intensity remaining approximately constant after 16 h (see FIG. 50(b)). This result indicated that the bidentate Au—NHC NPs remained stable in the solution. Without wishing to be bound by theory, this was considered a result of an increased the number of NHC binding sites.

Oxidation Stability:

Monodentate and bidentate Au—NHC NPs were treated with 1 mM di-tert butyl peroxide (DTBP) in THF and monitored by UV-Vis spectroscopy for 24 hours at room temperature. For both the monodentate and bidentate Au—NHC NPs, the maximum SPR band and peak intensity remained constant as depicted in FIG. 51, which indicated both monodentate and bidentate NHC—Au NPs remained stable.

Example 26: Abnormal (Mesoionic) Carbenes (aNHC) on Gold Surfaces

Synthesis 1,3-diethylimidazo[1,2-a]pyridinium bromide

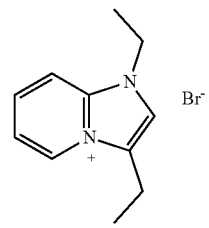

3-Ethylimidazo[1,2-a]pyridine [Krówczyński, A.; Kozerski, L. *Heterocycles* 1986, 24, 1209] (0.50 g, 3.4 mmol, 1.0 equiv.) and bromoethane (7.4 g, 68 mmol, 20 equiv.) were dissolved in acetonitrile (20 mL). The resulting mixture was heated at 50° C. for 16 hrs. At this point, all volatiles were removed under reduced pressure to give the product as a light yellow solid in 91% yield (0.75 g, 3.1 mmol). $^1$H NMR (300 MHz, MeOD): 8.72 (d, J=6 Hz, 1H), 8.15-8.00 (m, 2H), 7.99 (s, 1H), 7.54 (t, J=9 Hz, 1H), 4.50 (q, J=9 Hz, 2H), 3.03 (q, J=9 Hz, 2H), 1.57 (t, J=9 Hz, 3H), 1.48 (t, J=9 Hz, 3H).

1,3-diethylimidazo[1,2-a]pyridinium hydrogen carbonate

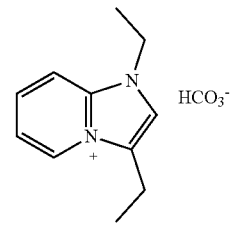

Resin-HCO$_3$ suspended in water was measured out in a graduated cylinder (0.85 mL, 3.0 equiv.) and transferred to a 20 mL vial where the resin was allowed to settle. Water was then decanted and the resin was washed with methanol (3×2 mL). 1,3-diethylimidazo[1,2-a]pyridinium bromide (90 mg, 0.35 mmol) was dissolved in methanol (5 mL) and transferred to the resin. The mixture was stirred for 30 min. The hydrogen carbonate solution was passed through a cotton plug to remove the resin beads and the resin was washed with methanol (3×2 mL). Solvent was removed under reduced pressure to give the desired product as a brown solid in 86% yield (71 mg, 0.30 mmol). $^1$H NMR (300 MHz, CD$_3$OD): 8.71 (d, J=6 Hz, 1H), 8.15-8.00 (m, 2H), 7.98 (s, 1H), 7.54 (t, J=9 Hz, 1H), 4.50 (q, J=9 Hz, 2H), 3.03 (q, J=9 Hz, 2H), 1.57 (t, J=9 Hz, 3H), 1.48 (t, J=9 Hz, 3H). $^{13}$C NMR (75 MHz, CD$_3$OD): 161.31, 140.39, 134.29, 130.57, 127.97, 122.01, 118.22, 111.96, 43.56, 17.68, 15.05, 11.02.

Synthesis of 1-ethyl-3-benzylimidazo[1,2-a]pyridinium bromide: Synthesized and characterized according to previously published procedures [Song, G.; Zhang, Y.; Li, X. *Organometallics* 2008, 27, 1936-1943].

Synthesis of diamidocarbene (DAC)-triflate salt: Synthesized and characterized according to previously published procedures [Hudnall, T. W.; Bielawski, C. W. *J. Am. Chem. Soc.* 2009, 131, 16039-16041].

Deposition of Abnormal Carbene (aNHC) on Gold Surfaces

Prior to functionalization, Au(111) films were cleaned by washing the films in 3×2 mL of methanol, drying them under an argon gas (4.8 Praxair) stream for 1 minute, then cleaning them with plasma generated from room air at a medium RF level and a pressure kept between 300 and 500 mtorr for 1 minute. The films were then used immediately for functionalization.

A) Free carbene method: A free carbene was obtained by dissolving 1,3-diethylimidazo[1,2-a]pyridinium bromide (7.6 mg, 30 µmol) in 6 mL of anhydrous tetrahydrofuran (THF) in a 20 mL vial in a glove box. Separately, potassium tert-butoxide (3.4 mg, 30 µmop was dissolved in 0.3 mL of anhydrous THF and was subsequently added to the carbene precursor solution dropwise at room temperature. The reaction was stirred for an additional 2 hrs at the same temperature. The mixture was then filtered through celite. A self-assembled monolayer was prepared by immersion of the gold substrate in this solution for 24 hrs at room temperature in a glove box. Substrate was then rinsed with methanol (5×2 mL) and hexane (5×2 mL) and dried under a nitrogen gas stream. The free carbene deposition method was also used for 1-ethyl-3-benzylimidazo[1,2-a]pyridinium bromide and the diamidocarbene (DAC)-triflate salt (see FIGS. 53 and 54).

B) In situ carbene formation via hydrogen carbonate method: Self-assembled monolayers were prepared by immersion of Au(111) on mica substrates in 10 mM solution of 1,3-diethylimidazo[1,2-a]pyridinium hydrogen carbonate salt in methanol for 24 hrs in air both at room temperature and at 50° C. Substrates then were rinsed in methanol (5×2 mL) and hexane (5×2 mL) and dried under an argon gas (4.8 Praxair) stream for 1 minute.

Analysis

XPS analysis of gold surfaces functionalized by using 1-ethyl-3-benzylimidazo[1,2-a]pyridinium bromide or diamidocarbene (DAC)-triflate salt indicated that both precursors were successfully used to functionalize a metal surface.

XPS analysis of the gold surface functionalized by using 1,3-diethylimidazo[1,2-a]pyridinium bromide via the free carbene method showed successful anchoring of the aNHC (see FIG. 52). Two peaks at binding energies of 402.9 and 400.4 eV were observed in the N 1s spectrum, indicating the existence of two different nitrogens in the carbene backbone. It is noteworthy that these peaks appeared at binding energies different from those of the normal NHCs (N 1s peak at 400 eV for normal NHCs).

XPS analysis also indicated that gold surfaces were successfully functionalized by using 1,3-diethylimidazo[1,2-a]pyridinium hydrogen carbonate in methanol, both at room temperature and at 50° C. (FIG. 52). Using XPS analysis, similar patterns were observed in the corresponding N 1s spectra confirming deposition on gold surface. However, XPS analysis showed higher degrees of surface coverage at 50° C. (N/Au=0.042) compared to room temperature (N/Au=0.0058), indicating that, unlike normal NHC—$HCO_3$ precursors, aNHC—$HCO_3$ precursors require slightly elevated temperatures for improved deposition on gold surface.

All publications, patents and patent applications mentioned herein are indicative of the level of skill of those skilled in the art to which this invention pertains and are herein incorporated by reference to the same extent as if each individual publication, patent, or patent applications was specifically and individually indicated to be incorporated by reference.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

TABLE 1

XPS Analysis of select hydrogen carbonate salts deposited on Au(111)

| Molecule | Predicted C:N(:Ir) | Observed C:N(:Ir) |
|---|---|---|
| $iPr_2bimy(H)[HCO_3]$ (3a) | 13:2 | 13:2 |
| $Me_2bimy(H)[HCO_3]$ (3b) | 9:2 | 10:2 |
| 5-((12-(4-(ferrocenyl)-1H-1,2,3-triazol-1-yl)dodecyl)oxy)-1,3-diisopropyl-1H-benzo[d]imidazol-3-ium hydrogen carbonate (3c) | 37:5:1 | 34:5:5 |
| 5-(dodecyloxy)-1,3-diisopropyl-1H-benzo[d]imidazol-3-ium hydrogen carbonate (3d) | 25:2 | 27:2 |

TABLE 2

Effect of pH conditions on hybrid lipid bilayer formation on both the commercial HPA SPR sensor chip and our NHC-derived SPR sensor chip.

| Buffer[a] | pH | Sensor chip | Initial loading (RU) | Loading after NaOH wash (RU) | BSA bound (RU) |
|---|---|---|---|---|---|
| Citrate[b] | 5.0 | HPA | 3924 ± 222 (6%) | 2598 ± 145 (6%) | 274 ± 85 (31%) |
| | | NHC | 1893 ± 50 (3%) | 1449 ± 31 (2%) | 101 ± 9 (9%) |
| PBS[c] | 7.4 | HPA | 9577 ± 365 (4%) | 1596 ± 29 (2%) | 59 ± 33 (56%) |
| | | NHC | 1712 ± 53 (3%) | 1344 ± 50 (4%) | 52 ± 8 (15%) |
| HEPES[b] | 8.0 | HPA | 2600 ± 543 (21%) | 1348 ± 24 (2%) | 22 ± 12 (55%) |
| | | NHC | 1244 ± 26 (2%) | 909 ± 32 (4%) | 79 ± 4 (5%) |
| TE[b] | 8.0 | HPA | 804 ± 33 (4%) | 516 ± 40 (8%) | 212 ± 13 (6%) |
| | | NHC | 937 ± 30 (3%) | 592 ± 27 (5%) | 96 ± 4 (4%) |
| CAPS[b] | 10.0 | HPA | 846 ± 32 (4%) | 451 ± 14 (3%) | 309 ± 9 (3%) |
| | | NHC | 1366 ± 18 (1%) | 939 ± 33 (4%) | 42 ± 5 (12%) |

[a]Buffer abbreviations are as follows: Citrate: 100 mM citric acid monohydrate, 200 mM $NaH_2PO_4$; PBS: 100 mM $Na_2HPO_4$/$NaH_2PO_4$, 150 mMNaCl; HEPES: 10 mM N-(2-hydroxyethyl) 1-piperazine-N'-(2-ethanesulphonic acid), 100 mMNaCl; TE: 10 mMTris (hydroxymethyl)aminomethane, 1 mM disodium ethylenediaminetetraacetate; CAPS: 10 mM 3-(Cyclohexylamino)-1-propanesulfonic acid, 150 mMNaCl.
[b]Values given as response units with standard deviations and relative standard deviations for n = 4.
[c]Values given as response units with standard deviations and relative standard deviations for n = 8.

TABLE 3

Effect of heating our NHC-derived SPR sensor chip at 65° C. in air for 24 hours on hybrid lipid bilayer formation.[a]

| Buffer | pH | NHC chip | Initial loading (RU) | Loading after NaOH wash (RU) | BSA bound (RU) |
|---|---|---|---|---|---|
| PBS | 7.4 | before heating | 1671 ± 41 (2.5%) | 1325 ± 34 (2.6%) | 54 ± 8 (15%) |
|  |  | after heating | 1880 ± 22 (1.2%) | 1364 ± 54 (4.0%) | 61 ± 9 (15%) |

[a]Values given as response units with standard deviations and relative standard deviations for n = 4.

TABLE 4

XPS analysis of Au11-TPP8 cluster with an absence of a nitrogen peak and a good ratio of Au:P.

| | Element ratio | | | | |
|---|---|---|---|---|---|
| | Au | P | N | Cl | C |
| Theoretical | 11 | 8 | 0 | 3 | 108-126 |
| Found | 11 (reference) | 7.9 | 0 | 2.1 | 171 |

TABLE 5

XPS analysis of Au11-NHC(iPr) cluster showing presence of an NHC moiety.

| | Element ratio | | | | |
|---|---|---|---|---|---|
| | Au | P | N | Cl | C |
| Theoretical | 11 | 6-7 | 2-4 | 3 | 108-126 |
| Found | 11 (reference) | 6.7 | 4.9 | 2.1 | 372 |

TABLE 6

EXAFS refinement parameters of Au11 and Au11-NHC(iPr); standard deviation in refinement values are given in parentheses, except for CN values (in bold) which were held constant.

| Sample | Bond | CN | R (Å) | $\sigma^2$ (Å$^2$) | $\Delta E_0$ (eV) |
|---|---|---|---|---|---|
| Au11 | Au—P | 0.91 | 2.282 (5) | 0.002 (1) | 1 (1) |
|  | Au—Au1 | 0.91 | 2.666 (3) | 0.001 (1) | 1 (1) |
|  | Au—Au2 | 4.7 | 2.910 (3) | 0.008 (2) | 1 (1) |
| Au11-NHC(iPr)NHC | Au—P | 0.82 | 2.304 (2) | 0.002 (1) | 2 (1) |
|  | Au—Au1 | 0.91 | 2.670 (2) | 0.001 (1) | 2 (1) |
|  | Au—Au2 | 4.7 | 2.921 (4) | 0.008 (2) | 2 (1) |

TABLE 7

EXAFS refinement parameters of Au-DDS and Au-NHC NPs; standard deviation in refinement values are given in parentheses

| Sample | Bond | CN | R (Å) | $\sigma^2$ (Å$^2$) | $\Delta E_0$ (eV) |
|---|---|---|---|---|---|
| Au-DDS | Au—S | 0.7 (2) | 2.364 (8) | 0.002 (1) | 1 (1) |
|  | Au—Au | 5.9 (5) | 2.869 (3) | 0.004 (1) | 1 (1) |
| Au-NHC | Au—S | 0.4 (2) | 2.42 (2) | 0.002 (1) | 1 (1) |
|  | Au—Au | 7.1 (8) | 2.868 (3) | 0.003 (1) | 1 (1) |

We claim:

1. A carbene-functionalized composite material, comprising:
   a material having at least a metal surface; and
   a monolayer that is uniform and stable,
   wherein the composite material comprises carbene-functionalized nanoclusters that consist essentially of [Au$_{11}$(PPh$_3$)$_7$(NHC-iPr)Cl$_2$]Cl, [Au$_{11}$(PPh$_3$)$_{6-7}$(NHC-Et)$_{1-2}$Cl$_2$]Cl; or 1,3-diisopropylbenzimidazolylidene-functionalized Cu nanoclusters.

2. A nanocluster comprising [Au$_{11}$(PPh$_3$)$_7$(NHC-iPr)Cl$_2$]Cl; [Au$_{11}$(PPh$_3$)$_{6-7}$(NHC-Et)$_{1-2}$Cl$_2$]Cl; or 1,3-diisopropylbenzimidazolylidene-functionalized Cu nanocluster.

3. The nanocluster of claim 2, wherein the nanocluster is a catalyst.

\* \* \* \* \*